US007902252B2

(12) United States Patent
Heffernan et al.

(10) Patent No.: US 7,902,252 B2
(45) Date of Patent: Mar. 8, 2011

(54) INHIBITORS OF D-AMINO ACID OXIDASE

(75) Inventors: Michele L. R. Heffernan, Worcester, MA (US); Qun Kevin Fang, Wellesley, MA (US); Robert J. Foglesong, Durham, NC (US); Seth C. Hopkins, Clinton, MA (US); Cyprian O. Ogbu, Durham, NC (US); Mustapha Soukri, Raleigh, NC (US); Kerry L. Spear, Concord, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 12/506,204

(22) Filed: Jul. 20, 2009

(65) Prior Publication Data

US 2010/0029737 A1    Feb. 4, 2010

Related U.S. Application Data

(63) Continuation-in-part of application No. 12/016,954, filed on Jan. 18, 2008.

(60) Provisional application No. 60/885,588, filed on Jan. 18, 2007.

(51) Int. Cl.
*A61K 31/403* (2006.01)
*C07D 209/02* (2006.01)

(52) U.S. Cl. ........................................ 514/423; 548/531
(58) Field of Classification Search .................. 548/531; 514/423
See application file for complete search history.

(56) References Cited

U.S. PATENT DOCUMENTS

| | | | |
|---|---|---|---|
| 4,540,690 A | 9/1985 | Szmuszkovicz | |
| 4,587,258 A | 5/1986 | Gold et al. | |
| 4,738,709 A | 4/1988 | Nielsen | |
| 4,751,231 A | 6/1988 | Halczenko et al. | |
| 4,981,870 A | 1/1991 | Koe | |
| 5,373,018 A | 12/1994 | Cugola et al. | |
| 5,374,649 A | 12/1994 | Cugola et al. | |
| 5,523,278 A | 6/1996 | Wepplo | |
| 5,550,255 A | 8/1996 | Urbach et al. | |
| 5,578,627 A | 11/1996 | Takeda et al. | |
| 5,620,997 A | 4/1997 | Bolton et al. | |
| 5,668,162 A | 9/1997 | Domagala et al. | |
| 5,686,461 A | 11/1997 | Cugola et al. | |
| 5,859,042 A | 1/1999 | Lee et al. | |
| 5,962,496 A | 10/1999 | Cugola et al. | |
| 5,965,591 A | 10/1999 | Kojima et al. | |
| 6,096,771 A | 8/2000 | Kojima et al. | |
| 6,100,289 A | 8/2000 | Cugola et al. | |
| 6,331,636 B1 | 12/2001 | Romero et al. | |
| 6,372,919 B1 | 4/2002 | Lippa et al. | |
| 6,399,601 B1 | 6/2002 | Du Bois | |
| 6,479,527 B1 | 11/2002 | Barker et al. | |
| 6,576,653 B2 | 6/2003 | Du Bois | |
| 6,589,949 B1 | 7/2003 | Moriwaki et al. | |
| 6,603,000 B2 | 8/2003 | Yee et al. | |
| 6,828,460 B2 | 12/2004 | Browning et al. | |
| 6,995,144 B2 | 2/2006 | Ozaki et al. | |
| 7,166,725 B2 | 1/2007 | Fang et al. | |
| 7,226,938 B2 | 6/2007 | Cai et al. | |
| 7,488,747 B2 | 2/2009 | Fang et al. | |
| 7,579,370 B2 | 8/2009 | Heffernan et al. | |
| 7,615,572 B2 | 11/2009 | Fang et al. | |
| 2002/0010198 A1 | 1/2002 | Jerussi et al. | |
| 2002/0085976 A1 | 7/2002 | Elomari | |
| 2002/0123490 A1 | 9/2002 | Howard, Jr. | |
| 2002/0183369 A1 | 12/2002 | Du Bois | |
| 2003/0087803 A1 | 5/2003 | Yatvin et al. | |
| 2003/0171440 A1 | 9/2003 | Senanayake et al. | |
| 2003/0195361 A1 | 10/2003 | Du Bois | |
| 2003/0215523 A1 | 11/2003 | Ozawa et al. | |
| 2004/0048878 A1 | 3/2004 | Cai et al. | |
| 2004/0092605 A1 | 5/2004 | Jerussi et al. | |
| 2004/0106681 A1 | 6/2004 | Rao et al. | |
| 2004/0220229 A1 | 11/2004 | Bussolotti et al. | |
| 2005/0020645 A1 | 1/2005 | Ohta et al. | |
| 2005/0089935 A1 | 4/2005 | Cai et al. | |
| 2005/0143434 A1 | 6/2005 | Fang et al. | |
| 2005/0143443 A1 | 6/2005 | Fang et al. | |
| 2006/0019944 A1 | 1/2006 | Wu et al. | |

(Continued)

FOREIGN PATENT DOCUMENTS

BE    616646    5/1962

(Continued)

OTHER PUBLICATIONS

Bobosik et al. Synthesis of *N*-Phenylsulfonyl Protected Furo[3,2-*b*] Pyroles, *Collect. Czech. Chem. Commun.* (vol. 59) pp. 499-502 (1994).

Cyranski et al. "Aromaticity of dihertero analogues of pentalene dianion. X-ray and ab initio studies of eight methyl furo[3,2-*b*]pyrrole-5-carboxylate derivatives and five methyl furo[2,3-*b*]pyrrole-5-carboxylate derivatives" *Tetrahedon* 57 8867-8873 (2001).

Dandarova, et al. "C NMR Spectra of Some Substituted Furo[3,2-*b*] pyrroles" *Magnetic Resonance in Chemistry*, vol. 28, 830-831 (1990).

Ferguson et al. "N-Acetyl-5,6-Dihydrofuro[3,2-*b*]Pyrid-2-One, $C_9H_9NO_3$" *Cryst. Struct. Comm.* 5, 911 (1976).

(Continued)

*Primary Examiner* — Susannah Chung
*Assistant Examiner* — Janet L Coppins
(74) *Attorney, Agent, or Firm* — Morgan, Lewis & Bockius, LLP

(57) ABSTRACT

The present invention provides novel inhibitors of the enzyme D-amino acid oxidase. The compounds of the invention are useful for treating or preventing diseases and/or condition, wherein modulation of D-serine levels, and/or its oxidative products, is effective in ameliorating symptoms. The invention further provides methods of enhancing learning, memory and/or cognition. For example, the invention provides methods for treating or preventing loss of memory and/or cognition associated with neurodegenerative diseases, such as Alzheimer's disease. The invention further provides methods for preventing loss of neuronal function characteristic of neurodegenerative diseases. In addition, methods are provided for the treatment or prevention of neuropsychiatric diseases (e.g., schizophrenia) and for the treatment or prevention of pain and ataxia.

12 Claims, No Drawings

U.S. PATENT DOCUMENTS

| | | | |
|---|---|---|---|
| 2006/0229286 A1 | 10/2006 | Kakigami et al. |
| 2006/0235002 A1 | 10/2006 | Nagai et al. |
| 2007/0100135 A1 | 5/2007 | Riggs et al. |
| 2007/0142452 A1 | 6/2007 | Banner et al. |
| 2007/0197588 A1 | 8/2007 | Shao et al. |
| 2007/0203111 A1 | 8/2007 | Shao et al. |
| 2008/0004327 A1 | 1/2008 | Heffernan et al. |
| 2008/0004328 A1 | 1/2008 | Dorsey et al. |
| 2008/0058395 A1 | 3/2008 | Heffernan et al. |
| 2009/0005456 A1 | 1/2009 | Shao et al. |
| 2009/0099248 A1 | 4/2009 | Heffernan et al. |
| 2009/0149549 A1 | 6/2009 | Zhao et al. |
| 2010/0016397 A1 | 1/2010 | Fang et al. |
| 2010/0022612 A1 | 1/2010 | Dorsey et al. |
| 2010/0029741 A1 | 2/2010 | Dorsey et al. |
| 2010/0120740 A1 | 5/2010 | Heffernan et al. |

FOREIGN PATENT DOCUMENTS

| | | |
|---|---|---|
| CA | 2066593 A1 | 2/1992 |
| CA | 2410077 A1 | 11/2001 |
| CA | 2474451 A1 | 8/2003 |
| CA | 2498152 A1 | 3/2004 |
| CA | 2498175 A1 | 3/2004 |
| CA | 2565852 A1 | 11/2005 |
| CA | 2566094 A1 | 12/2005 |
| CN | 1106386 A | 8/1995 |
| CN | 1709871 A | 12/2005 |
| CN | 1962656 A | 5/2007 |
| DE | 1124485 A | 3/1962 |
| DE | 3431541 A1 | 3/1986 |
| EP | 0101786 A1 | 3/1984 |
| EP | 0396124 * | 7/1990 |
| EP | 0 396 124 A | 11/1990 |
| EP | 1136071 A2 | 9/2001 |
| EP | 1219603 A2 | 7/2002 |
| EP | 1262181 A1 | 12/2002 |
| EP | 1362864 A1 | 11/2003 |
| EP | 1088824 B1 | 1/2004 |
| EP | 1391460 A1 | 2/2004 |
| EP | 1420028 A2 | 5/2004 |
| ES | 2081747 A1 | 3/1996 |
| JP | S54-059269 A | 5/1979 |
| JP | H01-016786 A | 1/1989 |
| JP | H01-172388 A | 7/1989 |
| JP | H04-077476 A | 3/1992 |
| WO | WO 86/00896 A1 | 2/1986 |
| WO | WO 95/17381 A1 | 6/1995 |
| WO | WO 98/42709 A1 | 10/1998 |
| WO | WO 99/10343 A1 | 3/1999 |
| WO | WO 99/18065 A1 | 4/1999 |
| WO | WO 99/40913 A | 8/1999 |
| WO | WO 99/40914 A1 | 8/1999 |
| WO | WO 99/48868 A2 | 9/1999 |
| WO | WO 00/25770 A1 | 5/2000 |
| WO | WO 01/02427 A1 | 1/2001 |
| WO | WO 01/27103 A1 | 4/2001 |
| WO | WO 01/79208 A1 | 10/2001 |
| WO | WO 02/12249 A2 | 2/2002 |
| WO | WO 02/20530 A1 | 3/2002 |
| WO | WO 02/31128 A1 | 4/2002 |
| WO | WO 03/016302 A1 | 2/2003 |
| WO | WO 03/039540 A2 | 5/2003 |
| WO | WO 03/063797 A2 | 8/2003 |
| WO | WO 03/074531 A1 | 9/2003 |
| WO | WO 03/074532 A1 | 9/2003 |
| WO | WO 03/091213 A1 | 11/2003 |
| WO | WO 03/092670 A1 | 11/2003 |
| WO | WO 2004/022537 A2 | 3/2004 |
| WO | WO 2004/031193 A1 | 4/2004 |
| WO | WO 2004/031194 A1 | 4/2004 |
| WO | WO 2004/039787 A1 | 5/2004 |
| WO | WO 2004/041780 A2 | 5/2004 |
| WO | WO 2004/089470 A2 | 10/2004 |
| WO | WO 2004/113345 A1 | 12/2004 |
| WO | WO 2005/013981 A1 | 2/2005 |
| WO | WO 2005/018637 A1 | 3/2005 |
| WO | WO 2005/020986 A1 | 3/2005 |
| WO | WO 2005/020987 A1 | 3/2005 |
| WO | WO 2005/046575 A2 | 5/2005 |
| WO | WO 2005/066135 A2 | 7/2005 |
| WO | WO 2005/066143 A2 | 7/2005 |
| WO | WO 2005/089753 A2 | 9/2005 |
| WO | WO 2005/123677 A | 12/2005 |
| WO | WO 2006/001958 A2 | 1/2006 |
| WO | WO 2006/004040 A1 | 1/2006 |
| WO | WO 2006/021000 A2 | 2/2006 |
| WO | WO 2006/077412 A1 | 7/2006 |
| WO | WO 2007/039773 A1 | 4/2007 |
| WO | WO 2007/068621 A1 | 6/2007 |
| WO | WO 2007/081542 A2 | 7/2007 |
| WO | WO 2007/081857 A2 | 7/2007 |
| WO | WO 2007/115185 A2 | 10/2007 |
| WO | WO 2008/005456 A2 | 1/2008 |
| WO | WO 2008/089453 A2 | 7/2008 |
| WO | WO 2008/151156 A1 | 12/2008 |
| WO | WO 2009/020814 A2 | 2/2009 |
| WO | WO 2010/017418 A1 | 2/2010 |

OTHER PUBLICATIONS

Fisera et al. "Correlation of Kinetic Data of 1,3-Dipolar Cycloadditions of C-Benzoyl-N-Phenylnitrones With the Homo Energies of Furan Derivatives" Collect. Czech. Chem. Commun. Vol. 46, 1504-1512 (1981).

Fisera et al. "Cycloadditions of C-Benzoyl-N-Phenylnitrone with Furocondensed Derivatives" Collect. Czech. Chem. Commun. vol. 48, 2421-2427 (1981).

Flaugh, et al., "Synthesis of Porphyrins. Deoxophylloerythroetioporphyrin," J. Am, Chem. Society, 90(24):6877-6879 (1968).

Fukuda, et al. "Tensidols, New Potentiators of Antifungal Miconazole Activity, Produced by Aspergillus niger FKI-2342" J. Antibiot 59(8): 480-485 (2006).

Gross et al. "Direct Observation of 1-Azafulven-6-one and Annelated Derivatives" J. Chem. Soc. Chem. Commun. p. 360-361 (1982).

Hu, et al., "Synthesis of Porphyrin With Fused Five- and Seven-Membered Exocyclic Rings from a Cross-Conjugated Tetracyclic Dipyrrole," Synlett, 11:909-910, Example 6 (1994).

Ilyin et al. "Synthesis of Annelated Azaheterocycles Containing a 5-Carbamoylpyrazin-3-one Fragment by a Modification of the Four-Component Ugi Reaction" Eur. J. Org. Chem. 4670-4679 (2005).

Java et al. "Chimie Organique—Synthese de selnolo, furo et pyrrolpyrroles" C.R. Acad. Sc. Paris, t. 281 (Nov. 10, 1975) Serie C—793-795.

Kralovicova et al., "Electrophilic Substitution Reactions of Furo[3,2-b]Pyrrole Derivatives" Collect. Czech. Chem. Commun. (vol. 51) 106-111 (1986).

Krutosikova et al. "Addition and Cycloaddition Reactions of Furo[3,2-b]-Pyrroles and Their Benzo[b] Analogues: an NMR Study of Structure of Products" Collect. Czech. Chem. Commun. (vol. 53) 1770-1778 (1988).

Krutosikova et al. "Effect of microwave irradiation on reaction of furo[3,2-b]pyrrole and furo[2,3-b]pyrrole-2-carbeldehydes with some active methylene compounds" ARKIVOC (iii) 409-420 (2000).

Krutosikova et al. "Reactions of Ethyl 2-(4-Chlorophenyl)-4H-Furo[3,2-b]Pyrrole-5-Carboxylate*" Collect. Czech. Chem. Commun. vol. 45, 2949-2957 (1980).

Krutosikova et al. "Reactions of furo[3,2-b]pyrroles and their benzol[b] analogues", Chem Papers 42 (1) 89-95 (1988).

Krutosikova et al. "Reactions of Methyl 2-Formylfuro[3,2-b]pyrrole-5-carboxylates" Chem Papers 50 (2)72-76 (1996).

Krutosikova et al. "Substituted 4-Benzylfuro [3,2-b] Pyrroles" Collect. Czech. Chem. Commun. (vol. 57) 1487-1494 (1992).

Krutosikova et al. "Substituted Vinyl Azides in the Synthesis of Condensed Nitrogen Heterocycles" Chem Papers 48 (4) 268-273 (1996).

Krutosikova et al. "Synthesis and reactions of 4-Oxiranylmethylfuro-[3,2-b]Pyrroles and their benzo derivatives*" Chem. of Heterocyclic Compounds vol. 37, No. 12, 1511-1517 (2001).

Krutosikova et al. "Synthesis and reactions of Furo[2,3-b]pyrroles" Molecules (2) 69-79 (1997).

Krutosikova et al. "Synthesis and Reactions of Furocondensed Derivatives*" *Collect. Czech. Chem. Commun.* (vol. 49) 65-70 (1984).

Krutosikova et al. "Synthesis and Reactions of Substituted Furo[3,2-*b*]Pyrrole Derivatives*" *Collect. Czech. Chem. Commun.* (vol. 46) 2564-2572 (1981).

Lash, et al., "Influence of Carbocyclic Rings on Porphyrin Cyclizations: Synthesis of Geochemically Significant Cycloalkanoporphyrins," *Energy & Fuels*, 4:668-674 (1990).

Lash, et al., "Porphyrins With Exocyclic Rings. Part 3. A Reassessment on the Utility of Cyclopenta[b]pyrroles in the Synthesis of Porphyrin Molecular Fossils. Preparation of Three Type II Porphyrins Related to Deoxophylloerythroetioporphyrin (DPEP)," *Tetrahedron*, 49(20):4159-4172 (1993).

Lash, et al., "Recent Advances in the Synthesis of Porphyrins With Five-Membered Exocyclic Rings," *Energy & Fuels*, 7:172-178 (1993).

Li, et al., "Synthesis of Deoxophylloerythroetioporphyrin (DPEP) and Three Ring Homologs by an Improved b-Bilene Methodology," *Tetrahedron Letters, Elsevier, Amsterdam*, 39(47) 8571-8574 (Nov. 19, 1998).

Martin, et al., "110. Das Diazo-Chinon Von PQQ als mögliches Reagenz für die Kartierung von Chinoproteinen Mittels Photoaffinitätsmarkierung," *Helvetica Chimica Acta*, Abstract Only, 76:1674-1677 (1993).

New et al. "The Thieno [3.2-*c*]pyridine and Furo[3,2-*c*]pyridine rings: New Pharmacophonres with Potential Antipsychotic Activity" *J. Med. Chem* vol. 32, 1147-1156 (1989).

Ogawa et al. "Preparation of Oxygen-Bridged AZA[15]- and AZA[17]Annulene Dicarboxylates by Intramuscular Azide Cyclization" *Tetrahedon Letters*, vol. 29, No. 2, pp. 219-222, 1988.

Puterova et al. "Reaction of Substituted Furan-2-carboxaldehydes and Furo[*b*]pyrrole Type Aldehydes with Hippuric Acid" *Molecules* vol. 9, 11-21 (2004).

Puterova, et al. "Reactions of Substituted Furan-2-carboxaldehydes and Furo[*b*] pyrrole Type Aldehydes with Benzothiazolium Salts" *Molecules* vol. 9, 241-255 (2004).

Romanova et al. "DC Polarographic and UV Spectrometric Studies of Substituted Furo[3,2-*b*]- and Furo[2,3-*b*]Pyrroles" *Collect. Czech. Chem. Commun.* (vol. 66) 1615-1622 (2001).

Sivy et al. "Structure of a Furo[3,2-*b*]pyrrole Derivative" *Acta. Cryst.* C44, 2032-2033 (1988).

Sleath, et al., "Synthesis of 7, 9-Didecarboxymethoxatin (4,5-dihydro-4,5-dioxo-1H-pyrrolo[2, 3-f ]quinoline-2-carboxylic acid) and Comparison of its Chemical Properties with Those of Methoxatin and Analogous O-Quinones," *J. Am. Chem. Soc.*, 107(11):3328-3338 (1985).

Sleziak et al. "Furo[2,3-*b*]Pyrrole Derivatives, Syntheses and Reactions in the Furan and Pyrrole Ring" *Polish J. Chem.* vol. 74, 207-217 (2000).

Sleziak et al. "Reactions of Furo[2,3-*b*]Pyrrole and Furo[3,2-*b*]Pyrrole-Type Aldehydes" *Collect. Czech. Chem. Commun.* (vol. 64) 1135-1146 (1999).

Sorotskaya et al. "The Series of Substituted Butenolides and Butenolides. IV.* 4-Arylidene (Heteroarylidene)-2-Butenolides" *Zhurnal Organicheskoi Khimii*, vol. 25, No. 1, pp. 175-182 (1989).

Soth et al. "Recherches en série hétérocylique. XXIX. Sur des voies d'accés á des tghiéno, sélénolo, furo et pyrrolopyrroles" *Can. J. Chem.* vol. 56, 1429-1434, (1978).

Welch et al. "Improved Synthesis of [3,2-*b*] and [2,3-*b*]-fused Selenolo-and Thienopyrroles, and of Furo[3,2-*b*]pyrrole" *Heterocyclic Communications* vol. 5, No. 4, 305-310 (1999).

Zhang, et al., "Total Synthesis of the Porphyrin Mineral Abelsonite and Related Petroporphyrins With Five-Membered Exocyclic Rings," *Tetrahedron Letters, Elsevier, Amsterdam*, 44(39):7253-7256 (Sep. 22, 2003).

Abarbri et al., "Les beta-cétonitriles groupes protecteurs de la fonction amine. Préparation d'amino-alcools", Helv. Chim. Acta 1995, 78(1), 109-121.

Aboul-Enein et al., "Synthesis and Antiemetic Profile of N-[1-[(diethylamino)methyl]cyclohexyl]amides ", Sci. Pharm. 1990, 58(3), 273-280.

Alvaro et al., "Preparation and photolysis of diaryl esters of acetylenedicarboxylic acid", Tetrahedron 1992, 48(16), 3437-3444.

Ando et al., "3-(Arylacetylamino)-N-methylbenzamides: A Novel Class of Selective Anti-Helicobacter pylori Agents", J. Med. Chem. 2001, 44(25), 4468-4474.

Arya et al., "Synthesis of New Heterocycles: Part XV. Synthesis of Novel Cyclic and Acyclic Sulfamides", Indian J. Chem., Sec. B, 1976, 14B(10), 766-769.

Ashton et al., "Nonpeptide angiotensin II antagonists derived from 1H-pyrazole-5-carboxylates and 4-aryl-1H-imidazole-5-carboxylates", J. Med. Chem. 1993, 36(23), 3595-3605.

Associated Press, "FDA mulls drug to slow late-stage Alzheimer's", CNN.com, Sep. 24, 2003, URL: <http://www.cnn.com/2003/HEALTH/conditions/09/24/alzheimers.drug.ap/index.html>.

Aubert et al., "New cyclopenta[b]-pyrroles and -pyridines by reaction of 2-azido- and 2- phosphoranylideneaminocyclopent-1-ene-1-carbaldehydes with aliphatic esters", J. Chem. Soc. Perkin Trans. 1 1989(8), 1369-1373.

Azéma et al., "Efficient approach to acyloxymethyl esters of nalidixic acid and in vitro evaluation as intra-ocular prodrugs", Bioorg. Med. Chem. 2006, 14(8), 2569-2580.

Baba et al., "Structure-Based Design of a Highly Selective Catalytic Site-Directed Inhibitor of Ser/Thr Protein Phosphatase 2B (Calcineurin)", J. Am. Chem. Soc. 2003, 125(32), 9740-9749.

Babu et al., "Simple and facile oxidation of aldehydes to carboxylic acids", Org. Prep. Proced. Int. 1994, 26(1), 123-125.

Bagal et al.,"Radicals from Aldehydes: A Convergent Access to Dienes and δ-Lactones", Synlett 2006(10), 1485-1490.

Balsamini et al., "(E)-3-(2-(N-phenylcarbamoyl)vinyl)pyrrole-2-carboxylic acid derivatives. A novel class of glycine site antagonists", J. Med. Chem. 1998, 41(6), 808-820.

Balsamini et al., "An improved route to cycloalka[b]pyrrole 2-carboxylates", Org. Prep. Proced. Int. 1997, 29(4), 471-473.

Bambury et al., "Trifluoromethylfurans II", J. Heterocycl. Chem. 1970, 7(2), 269-273.

Banekovich et al., "Synthesis and biological activities of novel dexibuprofen tetraacetylriboflavin conjugates", Bioorg. Med. Chem. Lett. 2007, 17(3), 683-687.

Banfi et al., "Synthesis of New Imidazole Derivatives as Potential Inhibitors of Thromboxane Synthetase", J. Heterocycl. Chem. 1990, 27, 215-219.

Bardakos et al., "Enhydrazine, 10. Einige aliphatische Enhydrazone", Chem. Ber. 1975, 108(7), 2161-2170.

Bartlett et al., "Evaluation of alternative approaches for the synthesis of macrocyclic bisindolylmaleimides", Org. Biomol. Chem. 2004, 2(19), 2874-2883.

BASF Corp., "Borane-tetrahydrofuran Complex (BTHF)" Product Bulletin, 2002, pp. 1-14.

Baumes et al., "No. 227.—Recherches sur les enehydrazines. VI.— Condensation de methylhydrazones de cetones sur les esters acetyleniques: synthese de carbomethoxypyrroles", Bull. Soc. Chim. Fr. 1974(5-6), 1147-1150.

Beaumont et al., "Design of Ester Prodrugs to Enhance Oral Absorption of Poorly Permeable Compounds: Challenges to the Discovery Scientist", Curr. Drug Metab. 2003, 4(6), 461-485.

Bedford et al., "Quaternary salts of 2-[(hydroxyimino)methyl]imidazole. 2. Preparation and in vitro and in vivo evaluaton of 1-(alkoxymethyl)-2-[(hydroxyimino)methyl]-3-methylimidazolium halides for reactivation of organophosphorus-inhibited acetylcholinesterases", J. Med. Chem. 1989, 32(2), 493-503.

Benson et al., "Aliphatic β-Chlorovinyl Aldoximes", J. Org. Chem. 1965, 30(4), 1126-1129.

Bergauer et al., "Practical ex-chiral-pool methodology for the synthesis of dopaminergic tetrahydroindoles", Tetrahedron 2004, 60(5), 1197-1204.

Bialer et al., "Pharmacokinetic analysis and antiepileptic activity of tetra-methylcyclopropane analogues of valpromide", Pharm. Res. 1996, 13(2), 284-289.

Biggadike et al., "Selective plasma hydrolysis of glucocorticoid gamma-lactones and cyclic carbonates by the enzyme paraoxonase: an ideal plasma inactivation mechanism." J. Med. Chem. 2000, 43(1), 19-21.

Birkofer et al., "The Use of Silylation in Organic Syntheses", Angew. Chem. Int. Ed. 1965, 4(5), 417-429.

Black, D., "Product Class 13: 1H-Pyrroles" in "Science of Synthesis: Houben-Weyl Methods of Molecular Transformations", vol. 9; Maas, G., ed.; Thieme Medical Publishers: Stuttgart, 2001; pp. 441-552.

Blanchfield et al., "The stability of lipidic analogues of GnRH in plasma and kidney preparations: the stereoselective release of the parent peptide", Bioorg. Med. Chem. Lett. 2005, 15(6), 1609-1612.

Bobbitt et al., "Organic Nitrosonium Salts. II. Stability Studies and Oxidations of Some Indole Derivatives", Heterocycles 1990, 30(2), 1131-1140.

Boeshagen et al., "Ueber 3-Acylimino-3H-1.2-benzodithiole", Chem. Ber. 1968, 101(7), 2472-2484.

Borza et al., "Selective NR1/2B N-Methyl-d-aspartate Receptor Antagonists among Indole-2-carboxamides and Benzimidazole-2-carboxamides" J. Med. Chem. 2007, 50(5), 901-914.

Braga et al, "Making crystals from crystals: a green route to crystal engineering and polymorphism", Chem. Commun. 2005(29), 3635-3645.

Bregant et al., "Orthogonally Protected Lanthionines: Synthesis and Use for the Solid-Phase Synthesis of an Analogue of Nisin Ring C", J. Org. Chem. 2005, 70(7), 2430-2438.

Brunner et al., "Asymmetrische Hydrierung von (Z)-α-(Acetylamino)-zimtsäure mit einem Rh/norphos-Katalysator", Angew. Chem. 1979, 91(8), 655-656.

Brunner-Guenat et al., "Esters of L-dopa: structure-hydrolysis relationships and ability to induce circling behaviour in an experimental model of hemiparkinsonism", J. Pharm. Pharmacol. 1995, 47(10), 861-869.

Bueno et al., "Dipeptides as effective prodrugs of the unnatural amino acid (+)-2-aminobicyclo[3.1.0]hexane-2,6-dicarboxylic acid (LY354740), a selective group II metabotropic glutamate receptor agonist" J. Med. Chem. 2005, 48(16), 5305-5320.

Bundgaard et al., "Esters of N,N-disubstituted 2-hydroxyacetamides as a novel highly biolabile prodrug type for carboxylic acid agents", J. Med. Chem 1987, 30(3), 451-454.

Byrn et al., "Solid-State Chemistry of Drugs", 2nd ed.; SSCI, Inc.: West Lafayette, Indiana, 1999; pp. 232-247.

Cai et al., "Synthesis of 2,4,5-Trisubstituted Oxazoles", Synthesis 2005(10), 1569-1571.

Calderon et al., "Novel 1-Phenylcycloalkanecarboxylic Acid Derivatives Are Potent and Selective .sigma.1 Ligands", J. Med. Chem. 1994, 37(15), 2285-2291.

Callis et al., "A Tandem Horner-Emmons Olefination-Conjugate Addition Approach to the Synthesis of 1,5-Disubstituted-6-azabicyclo[3.2.1]octanes Based on the AE Ring Structure of the Norditerpenoid Alkaloid Methyllycaconitine", J. Org. Chem. 1996, 61(14), 4634-4640.

Cartoon et al., "Lithiation reactions of 1-(2'-bromophenyl)pyrrole and related compounds", J. Organomet. Chem. 1981, 212(1), 1-9.

Chakraborty et al., "Synthesis and characterization of Boc-protected 4-amino- and 5-amino-pyrrole-2-carboxylic acid methyl esters", Tetrahedron Lett. 2006, 47(27), 4631-4634.

Chapman et al., "The Analytical Reduction of Porphyrins to Pyrroles", Can. J. Chem. 1971, 49(21), 3544-3564.

Chaubey et al., "Kinetics of the Oxidation of Heterocyclic Aldehydes by Quinolinium Dichromate", Bull. Chem. Soc. Jpn. 2002, 75(10), 2215-2220.

Chen et al., "4,4-Difluoro-4-bora-3a,4a-diaza-s-indacene (BODIPY) Dyes Modified for Extended Conjugation and Restricted Bond Rotations", J. Org. Chem. 2000, 65(10), 2900-2906.

Chen et al., "Studies on the SAR and pharmacophore of milnacipran derivatives as monoamine transporter inhibitors", Bioorg. Med. Chem. Lett. 2008, 18(4), 1346-1349.

Chimichi et al., "New 5-(2-ethenylsubstituted)-3(2H)-furanones with in vitro antiproliferative activity", Tetrahedron 2003, 59(28), 5215-5223.

Cottineau et al., "Synthesis and hypoglycemic evaluation of substituted pyrazole-4-carboxylic acids", Bioorg. Med. Chem. Lett. 2002, 12(16), 2105-2108.

Crane et al., "A Novel Enantioselective Synthetic Route to Omuralide Analogues with the Potential for Species Selectivity in Proteasome Inhibition", Org. Lett. 2001, 3(9), 1395-1397.

Cuevas-Yañez et al., "Rhodium(II) catalyzed intramolecular insertion of carbenoids derived from 2-pyrrolyl and 3-indolyl α-diazo-β-ketoesters and α-diazoketones", Tetrahedron 2004, 60(7), 1505-1511.

Damaslo, A. R., "Alzheimer's Disease and Related Dementias" in "Cecil Textbook of Medicine", 20th ed., vol. 2; W.B. Saunders Co.: Philadelphia, 1996; pp. 1992-1996.

Das et al., "Synthesis of some N-substituted carbazoles and their larvicidal studies", J. Indian Chem. Soc. 2005, 82, 158-160.

Database Beilstein, Beilstein Institute for Organic Chemistry, Frankfurt-Main, DE; Database Accession No. BRN: 10196160 Abstract; and Eur. J. Org. Chem. 2005(21), 4670-4679.

Database Beilstein, Beilstein Institute for Organic Chemistry, Frankfurt-Main, DE; Database Accession No. BRN: 1074598 Abstract; and Can. J. Chem. 1978, 56(10), 1429-1434.

Database Beilstein, Beilstein Institute for Organic Chemistry, Frankfurt-Main, DE; Database Accession No. BRN: 4185621 Abstract; and Collect. Czech. Chem. Commun. 1986, 51(1), 106-111.

Database Beilstein, Beilstein Institute for Organic Chemistry, Frankfurt-Main, DE; Database Accession No. BRN: 4429388 Abstract; and Collect. Czech. Chem. Commun. 1984, 49(1), 65-70.

Database Beilstein, Beilstein Institute for Organic Chemistry, Frankfurt-Main, DE; Database Accession No. BRN: 7812555 Abstract; and Collect. Czech. Chem. Commun. 1997, 62(10), 1612-1622.

Database CAPLUS on STN, Acc. No. 1977:83511, Koe, J. Pharmacol. Exp. Ther. 1976, 199(3), 649-661. [abstract].

De Luca et al., "A New, Simple Procedure for the Synthesis of Formyl Amides", Synlett 2004(14), 2570-2572.

Denmark et al., "Chiral fluoro ketones for catalytic asymmetric epoxidation of alkenes with oxone", J. Org. Chem. 2002, 67(10), 3479-3486.

Denmark et al., "Organocerium additions to SAMP-hydrazones: general synthesis of chiral amines", J. Am. Chem. Soc. 1987, 109(7), 2224-2225.

Dhanak et al., "Studies in the protection of pyrrole and indole derivatives", J. Chem. Soc., Perkin Trans. 1, 1986, 2181-2186.

Durrer et al., "Structure-metabolism relationships in the hydrolysis of nicotinate esters by rat liver and brain subcellular fractions", Pharm. Res. 1991, 8(7), 832-839.

Elghamry, "Synthesis of ethyl pyrrole-2-carboxylates: a regioselective cyclization of enaminones under knorr-type conditions", Synth. Commun. 2002, 32(6), 897-902.

Eliel, "Infelicitous stereochemical nomenclature", Chirality 1997, 9(5-6), 428-430.

El-Nagger et al., "Synthesis and Biological Activity of Some New Aminoacylcarbazole Derivatives. Part I", J. Heterocycl. Chem. 1982, 19, 1025-1028.

English et al., "Orally effective acid prodrugs of the beta-lactamase inhibitor sulbactam", J. Med. Chem. 1990, 33(1), 344-347.

Eras et al., "Reactivity of thienopyrroles. Synthesis of isomeric nitro and bromothienopyrroles", J. Heterocycl. Chem. 1984, 21(1), 215-217.

Estep, "An Efficient Synthesis of 4-Hydroxy-1H-indole-2-carbonitrile and Its Conversion to DPI 201-106", Synth. Commun. 1995, 25(4), 507-514.

Fagan et al., "A new approach to the core of roseophilin", Tetrahedron Lett. 1999, 40(33), 6117-6120.

Fischer et al., "On Benzisothiazolones: A Series with a Wide Range of Bacteriostatic and Fungistatic Activity", Arzneimittel-Forschung 1964, 14(12), 1301-1306.

Fischer et al., "Synthese einiger Pyrrole und ihre Umsetzungen", Justus Liebigs Ann. Chem. 1932, 492(1), 128-155.

Fischer et al., "Synthesen der Opso- und Hämopyrrolcarbonsäure. Neue Synthese von Koproporphyrin. II", Justus Liebigs Ann. Chem. 1928, 462(1), 240-250.

Fischer et al., "Synthesen von Koproporphyrin I und II, sowie Mesoporphyrin II, V und XII", Justus Liebigs Ann. Chem. 1928, 466(1), 147-178.

Foucaud et al., "The [1+4] cycloaddition of isocyanides with 1-aryl-2-nitro-1-propenes. Methyl 2-nitro-3-arylpropenoates and methyl 2-nitro-2,4-pentadienoates. Synthesis of 1-hydroxyindoles of 1-hydroxypyrroles", J. Org. Chem. 1983, 48(21), 3639-3644.
Fraga-Dubreuil et al., "Grafted ionic liquid-phase-supported synthesis of small organic molecules", Tetrahedron Lett. 2001, 42(35), 6097-6100.
Franciò et al., "Asymmetric Catalysis with Chiral Phosphane/Phosphoramidite Ligands Derived from Quinoline (QUINAPHOS)", Angew. Chem. Int. Ed. 2000, 39(8), 1428-1430.
Frisell et al., "Flavoenzyme Catalysis. Substrate-Competitive Inhibition of D-Amino Acid Oxidase", J. Biol. Chem. 1956, 223, 75-83.
Fu et al., "Design and synthesis of novel bis(l-amino acid) ester prodrugs of 9-[2-(phosphonomethoxy)ethyl]adenine (PMEA) with improved anti-HBV activity", Bioorg. Med. Chem. Lett. 2007, 17(2), 465-470.
Gabbutt et al., "A Facile Synthesis of Some Benzothiopyrano[4,3-b]pyrroles", J. Chem. Res. (S) 1997(3), 102-103.
Gale et al., "Preparation and Reactions of 5-Carbethoxythieno[3,2-b]pyrrole and Some of Its Derivatives", J. Org. Chem. 1964, 29(8), 2160-2165.
Garg et al., "Development of an Enantiodivergent Strategy for the Total Synthesis of (+)- and (−)-Dragmacidin F from a Single Enantiomer of Quinic Acid", J. Am. Chem. Soc. 2005, 127(16), 5970-5978.
Gelas-Mialhe et al., "Photochemical heterocyclization of functionalized dienamines", J. Org. Chem. 1987, 52(24), 5395-5400.
Gelas-Mialhe et al., "Réactivité des N-vinylaziridines fonctionnalisées. Synthèse de dérivés des α,β-déhydro α-amino acides", Can. J. Chem. 1982, 60(22), 2830-2851.
Geraldine et al., "How an increase in the carbon chain length of the ester moiety affects the stability of a homologous series of oxprenolol esters in the presence of biological enzymes", J. Pharm. Sci. 1998, 87(7), 880-885.
Grygorenko et al., "Stereoselective synthesis of 2,4-methanoproline homologues", Tetrahedron Asymmetry 2006, 17(2), 252-258.
Guan et al., "Design and synthesis of aminopropyl tetrahydroindole-based indolin-2-ones as selective and potent inhibitors of Src and Yes tyrosine kinase", Bioorg. Med. Chem. Lett. 2004, 14(1), 187-190.
Haginoya et al., "Synthesis and conformational analysis of a non-amidine factor Xa inhibitor that incorporates 5-methyl-4,5,6,7-tetrahydrothiazolo[5,4-c]pyridine as S4 binding element", J. Med. Chem. 2004, 47(21), 5167-5182.
Haj-Yehia et al., "Pharmacokinetic analysis of the structural requirements for forming "stable" analogues of valpromide", Pharm. Res. 1992, 9(8), 1058-1063.
Haj-Yehia et al., "Structure-pharmacokinetic relationships in a series of valpromide derivatives with antiepileptic activity", Pharm. Res. 1989, 6(8), 683-689.
Harada et al., "A Simple Preparation of Chloromethyl Esters of the Blocked Amino Acids", Synth. Commun. 1994, 24(6), 767-772.
Harrak et al., "PtCl2-Catalyzed Cycloisomerizations of 5-En-1-yn-3-ol Systems", J. Am. Chem. Soc. 2004, 126(28), 8656-8657.
Harrison et al., "Cyclopenta[b]indoles. Part 2. Model studies towards the tremorgenic mycotoxins", J. Chem. Soc. Perkin Trans. 1 1995(9), 1131-1136.
Harwood et al., "Tandem generation and intramolecular trapping of chiral stabilised azomethine ylids with alkyne dipolarophiles", Tetrahedron Lett. 1993, 34(41), 6603-6606.
Hauptmann et al., "Beiträge zum Reaktionsverhalten von 2-Aminovinylcarbonylverbindungen", Journal für Praktische Chemie 1972, 314(2), 353-364.
Hauptmann et al., "Eine neue Synthese substituierter Thiophene und Pyrrole", Tetrahedron Lett. 1968, 9(11), 1317-1319.
Hillenweck et al., "Chlorothalonil Biotransformation by Gastrointestinal Microflora: In Vitro Comparative Approach in Rat, Dog, and Human", Pestic. Biochem. Physiol. 1997, 58(1), 34-48.
Hilton et al., "Observations on the reactivity of thiyl radicals derived from 3,6-epidithiodiketopiperazine-2,5-diones and related congeners", Bioorg. Med. Chem. Lett. 2005, 15(9), 2239-2242.
Hoffman, R. V., "Organic Chemistry: An Intermediate Text, Second Edition"; Wiley: Hoboken, 2004; pp. 124 and 138-144.
Holmes et al., "Reactions of N-Benzylthieno[3,2-b]pyrrole. I. Metalation and an Electrophilic Substitution", J. Org. Chem. 1964, 29(8), 2155-2160.

Hori, M., "Syntheses of Analgesics. XIV. Aminocyclohexane Derivatives. 8.", Yakugaku Zasshi 1958, 78, 11-14.
Howarth et al., "Pyrroles and related compounds. Part XXVI. Pyrrole beta-keto-esters", J. Chem. Soc. Perkin Trans. 1 1974, 490-501.
Ikegami et al., "Synthesis and pharmacological activity of O-(5-isoxazolyl)-L-serine", Chem. Pharm. Bull. 2000, 48(2), 278-280.
Ingram et al., "Investigation of enzyme activity by SERRS using poly-functionalised benzotriazole derivatives as enzyme substrates", Org. Biomol. Chem. 2006, 4(15), 2869-2873.
Inukai et al., "ortho-Disubstituted F-Benzenes. III. Preparation of (F-Benzo)heterocyclic Compounds from F-Benzoic Acid and F-Phenol, and the Reactions of Some Intermediary F-Benzoyl- and F-Phenoxy Compounds", Bull. Chem. Soc. Jpn. 1981, 54(11), 3447-3452.
Iranpoor et al., "A Rapid and Facile Conversion of Primary Amides and Aldoximes to Nitriles and Ketoximes to Amides with Triphenylphosphine and N-Chlorosuccinimide", Synth. Commun. 2002, 32(16), 2535-2541.
Isoherranen et al., "New CNS-active drugs which are second-generation valproic acid: can they lead to the development of a magic bullet?", Curr. Opin. Neurol. 2003, 16(2), 203-211.
Jacob et al., "gamma-Aminobutyric acid esters. 2. Synthesis, brain uptake, and pharmacological properties of lipid esters of gamma-aminobutyric acid", J. Med. Chem. 1985, 28(1), 106-110.
Jolicoeur et al., "Pyrrole protection", Tetrahedron 2006, 62(50), 11531-11563.
Katritzky et al., "Efficient Conversion of Carboxylic Acids into N-Acylbenzotriazoles", Synthesis 2003(18), 2795-2798.
Katritzky et al., "Novel Synthesis of Bicycles with Fused Pyrrole, Indole, Oxazole, and Imidazole Rings", J. Org. Chem. 2004, 69(26), 9313-9315.
Katritzky et al., "Regiospecific C-Acylation of Pyrroles and Indoles Using N-Acylbenzotriazoles", J. Org. Chem. 2003, 68(14), 5720-5723.
Katterle et al., "A Heck-Type Coupling for the Synthesis of Novel Bridged Metallochlorin-Fullerene C60 Dyads", European J. Org. Chem. 2006(2), 414-422.
Keener et al., "Synthesis of 6-substituted thieno[3,2-b]pyrroles", J. Org. Chem. 1968, 33(4), 1355-1359.
Kesel, "Synthesis of Novel Test Compounds for Antiviral Chemotherapy of Severe Acute Respiratory Syndrome (SARS)", Curr. Med. Chem. 2005, 12(18), 2095-2162.
Khanna et al., "Evaluation of glycolamide esters of indomethacin as potential cyclooxygenase-2 (COX-2) inhibitors", Bioorg. Med. Chem. 2006, 14(14), 4820-4833.
Kittredge et al., "alpha-Helical Polypeptide Films Grown From Sulfide or Thiol Linkers on Gold Surfaces", Helv. Chim. Acta 2002, 85(3), 788-798.
Kleinspehn et al., "The Synthesis of Some β,β-Dipyrrylpropionic Esters", J. Am. Chem. Soc. 1954, 76(22), 5641-5646.
Koe, "Molecular geometry of inhibitors of the uptake of catecholamines and serotonin in synaptosomal preparations of rat brain", J. Pharmacol. Exp. Ther. 1976, 199(3), 649-661.
Krayushkin et al., "Synthesis of Photochromic 1,2-Dihetarylethene Using Regioselective Acylation of Thienopyrroles", Org. Lett. 2002, 4(22), 3879-3881.
Kren et al., "Clustered ergot alkaloids modulate cell-mediated cytotoxicity", Bioorg. Med. Chem. 2002, 10(2), 415-424.
Krutosikova et al., "Synthesis and Reactions of 8-Hydrazinofuro[2',3':4,5]pyrrolo-[1,2-d][1,2,4]triazines", Collect. Czech. Chem. Commun. 1997, 62(10), 1612-1622.
Kukolja et al., "Orally absorbable cephalosporin antibiotics. 2. Structure-activity studies of bicyclic glycine derivatives of 7-aminodeacetoxycephalosporanic acid", J. Med. Chem. 1985, 28(12), 1896-1903.
Kumar et al., "Synthesis and biological evaluation of thiophene [3,2-b] pyrrole derivatives as potential anti-inflammatory agents", Bioorg. Med. Chem. 2004, 12(5), 1221-1230.
Kuo et al., "G-protein coupled receptors: SAR analyses of neurotransmitters and antagonists", J. Clin. Pharm. Ther. 2004, 29(3), 279-298.

Lamboley et al., "Synthesis and Properties of Conformationally Constrained Analogues of Floral-Type Odorants", Helv. Chim. Acta 2004, 87(7), 1767-1793.

Lash et al., "Normal and Abnormal Heme Biosynthesis. 2.1 Synthesis and Metabolism of Type-III Pentacarboxylic Porphyrinogens: Further Experimental Evidence for the Enzymic Clockwise Decarboxylation of Uroporphyrinogen-III", J. Org. Chem. 1999, 64(2), 478-487.

Lash et al., "Porphyrins with exocyclic rings. 1. Chemistry of 4,5,6,7-tetrahydro-1H-indoles: synthesis of acetoxy derivatives, dihydroindoles, and novel porphyrins with four exocyclic rings", J. Org. Chem. 1992, 57(18), 4809-4820.

Law et al., "The synthesis and chemistry of azolenines. Part 2. A general synthesis of pyrrole-2-carboxylic acid derivatives by the reaction of 2H-azirines with enamines, and the crystal and molecular structure of ethyl 3-phenyl-4,5,6,7-tetrahydroindole-2-carboxylate", J. Chem. Soc. Perkin Trans. 1 1984, 111-118.

Layzer, R. B., "Section Five—Degenerative Diseases of the Nervous System" in "Cecil Textbook of Medicine", 20th ed., vol. 2; W.B. Saunders Co.: Philadelphia, 1996; pp. 2050-2057.

Lee at al., "Amphiphilic amino acid copolymers as stabilizers for the preparation of nanocrystal dispersion", Eur. J. Pharm. Sci. 2005, 24(5), 441-449.

Lee et al., "An Effective and Convenient Esterification of Cephalosporin Derivatives by Using Quarternary Ammonium Salts as Catalysts", Synth. Commun. 1998, 28(23), 4345-4354.

Lerche et al., "Umsetzungen mit Monohydrazonen von Dicarbonylverbindungen, V: Umsetzungen von Hydrazonoethylidenammonium-Salzen und Hydrazonoaldehyden mit Grignard-Verbindungen", Chem. Ber. 1978, 111(3), 1195-1209.

Liederer et al., "Enzymes involved in the bioconversion of ester-based prodrugs", J. Pharm. Sci. 2006, 95(6), 1177-1195.

Liederer et al., "Stability of oxymethyl-modified coumarinic acid cyclic prodrugs of diastereomeric opioid peptides in biological media from various animal species including human", J. Pharm. Sci. 2005, 94(10), 2198-2206.

Liu et al., "Facile construction of the pentacyclic framework of subincanadine B. Synthesis of 20-deethylenylated subincanadine B and 19,20-dihydrosubincanadine B", Org. Lett. 2006, 8(1), 115-118.

Liu et al., "Indole-5-phenylcarbamate derivatives as human non-pancreatic secretory phospholipase A2 inhibitor", Bioorg. Med. Chem. Lett. 2005, 15(20), 4540-4542.

Liu et al., "The synthesis of camostat intermediate", Huaxue Shiji, 2006, 28(6), 371-372.

Ma et al., "Hydrolysis of angiotensin II receptor blocker prodrug olmesartan medoxomil by human serum albumin and identification of its catalytic active sites", Drug Metab. Dispos. 2005, 33(12), 1911-1919.

Majumdar et al., "α-(1H-Imidazol-1-yl)alkyl (IMIDA) carboxylic acid esters as prodrugs of carboxylic acid containing drugs", Tetrahedron Lett. 2007, 48(26), 4609-4611.

Mal et al., "Regioselective synthesis of 1-hydroxycarbazoles via anionic [4+2] cycloaddition of furoindolones: a short synthesis of murrayafoline-A", Tetrahedron Lett. 2006, 47(7), 1071-1075.

Mamber et al., "Tubulin polymerization by paclitaxel (taxol) phosphate prodrugs after metabolic activation with alkaline phosphatase", J. Pharmacol. Exp. Ther. 1995, 274(2), 877-883.

Mandel et al., "Neuroprotective Strategies in Parkinson's Disease: An Update on Progress", CNS Drugs 2003, 17(10), 729-762.

Marrel et al., "L-Dopa esters as potential prodrugs 1. Physicochemical properties", Eur. J. Med. Chem. 1985, 20(5), 459-465.

Marrel et al., "L-Dopa esters as potential prodrugs 2. Chemical and enzymatic-hydrolysis", Eur. J. Med. Chem. 1985, 20(5), 467-470.

Martin et al., "Do structurally similar molecules have similar biological activity?", J. Med. Chem. 2002, 45(19), 4350-4358.

McConnaughie et al., "Novel Acridine-Triazenes as Prototype Combilexins: Synthesis, DNA Binding, and Biological Activity" J. Med. Chem. 1995, 38(18), 3488-3501.

McLaughlin, "Suzuki-Miyaura Cross-Coupling of Benzylic Phosphates with Arylboronic Acids", Org. Lett. 2005, 7(22), 4875-4878.

Medforth et al., "Nonplanar distortion modes for highly substituted porphyrins", J. Am. Chem. Soc. 1992, 114(25), 9859-9869.

Meltzer et al., "The synthesis of bivalent 2β-carbomethoxy-3β-(3,4-dichlorophenyl)-8-heterobicyclo[3.2.1]octanes as probes for proximal binding sites on the dopamine and serotonin transporters", Bioorg. Med. Chem. 2008, 16(4), 1832-1841.

Mergen et al., "Antiepileptic activity of 1,3-dihexadecanoylamino-2-valproyl-propan-2-ol, a prodrug of valproic acid endowed with a tropism for the central nervous system", J. Pharm. Pharmacol. 1991, 43(11), 815-816.

Merisor et al., "Synthesis of New Derivatives in the Izoxazole Class with Potential Antimicrobial Activity", Rev. Chim. (Bucharest, Romania) 2001, 52(4), 206-209.

Miao et al., "Benzamide derivatives as blockers of Kv1.3 ion channel", Bioorg. Med. Chem. Lett. 2003, 13(6), 1161-1164.

Mikhaleva et al., "Expedient synthesis of 1-vinylpyrrole-2-carbaldehydes", Tetrahedron Lett. 2006, 47(22), 3693-3696.

Miki et al., "Synthesis of 3-Methoxyellipticine and Ellipticine by Friedel-Crafts Reaction of Indole-2,3-dicarboxylic Anhydride and Selective Demethylation", Heterocycles 2005, 65(11), 2693-2703.

Milkiewicz et al., "Synthesis of a novel series of tetra-substituted furan[3,2-b]pyrroles", Tetrahedron Lett. 2003, 44(22), 4257-4260.

Mishra et al., "Synthesis, characterization and pharmacological evaluation of amide prodrugs of ketorolac", Eur. J. Med. Chem. 2008, 43(11), 2464-2472.

Mokhallalati et al., "A single-pot synthesis of 1,1,2-trisubstituted 1,2-dihydronaphthalenes in high enantiomeric purity", Tetrahedron Lett. 1994, 35(25), 4267-4270.

Montero et al., "Solid-Phase Combinatorial Synthesis of Peptide-Biphenyl Hybrids as Calpain Inhibitors", Org. Lett. 2004, 6(22), 4089-4092.

Morgan et al., "Synthesis of hydrocarbon-strapped porphyrins containing quinone and phenolic groups", J. Org. Chem. 1987, 52(24), 5364-5374.

Morissette et al., "High-throughput crystallization: polymorphs, salts, co-crystals and solvates of pharmaceutical solids", Adv. Drug Deliv. Rev. 2004, 56(3), 275-300.

Mork et al., "Stereoselective enzymatic hydrolysis of various ester prodrugs of ibuprofen and flurbiprofen in human plasma", Pharm. Res. 1992, 9(4), 492-496.

Muchowski et al., "Protecting groups for the pyrrole and indole nitrogen atom. The [2-(trimethylsilyl)ethoxy]methyl moiety. Lithiation of 1-[[2-(trimethylsilyl)ethoxy]methyl]pyrrole", J. Org. Chem. 1984, 49(1), 203-205.

Murakami et al., "The Friedel-Crafts Acylation of Ethyl Pyrrole-2-carboxylate. Scope, Limitations, and Application to Synthesis of 7-Substituted Indoles", Heterocycles 1988, 27(8), 1855-1860.

Nacci et al., "Polycondensed Heterocycles. I. Synthesis of 11-Oxo-5H,11H-pyrrolo[2,1-c][1,4]benzothiazepine, Derivative of a Novel Ring System", J. Heterocycl. Chem. 1985, 22(2), 259-263.

Nacci et al., "Polycondensed Heterocycles. II. A New Preparative Route to 11-Oxo-5H,11H-pyrrolo[2,1-c][1,4]benzothiazepine", J. Heterocycl. Chem. 1986, 23(3), 769-773.

Nagarathnam et al., "Design and Synthesis of Novel αla Adrenoceptor-Selective Dihydropyridine Antagonists for the Treatment of Benign Prostatic Hyperplasia", J. Med. Chem. 1998, 41(26), 5320-5333.

Nagel et al., "Enantioselektive Katalyse, 4. Synthese N-substituierter (R,R)-3,4-Bis(diphenylphosphino)-pyrrolidine and Anwendung ihrer Rhodiumkomplexe zur asymmetrischen Hydrierung von α-(Acylamino)acrylsäure-Derivaten", Chem. Ber. 1986, 119(11), 3326-3343.

Narasimhan et al., "A QSAR approach for the prediction of stability of benzoglycolamide ester prodrugs", Chem. Pharm. Bull. 2006, 54(8), 1067-1071.

Nelson et al., "Stereoselective Synthesis of a Potent Thrombin Inhibitor by a Novel P2-P3 Lactone Ring Opening", J. Org. Chem. 2004, 69(11), 3620-3627.

Newman-Evans et al., "The influence of intramolecular dynamics on branching ratios in thermal rearrangements", J. Org. Chem. 1990, 55(2), 695-711.

Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", Eur. J. Pharm. Sci. 2005, 24(5), 433-440.

Nielsen et al., "Glycolamide esters as biolabile prodrugs of carboxylic acid agents: Synthesis, stability, bioconversion, and physicochemical properties", J. Pharm. Sci. 1988, 77(4), 285-298.

Nudelman et al., "Novel anticancer prodrugs of butyric acid. 2.", J. Med. Chem. 1992, 35(4), 687-694.

Nudelman et al., "The role of intracellularly released formaldehyde and butyric acid in the anticancer activity of acyloxyalkyl esters." J. Med. Chem. 2005, 48(4), 1042-1054.

Ojida et al., "Highly Enantioselective Reformatsky Reaction of Ketones: Chelation-Assisted Enantioface Discrimination", Org. Lett. 2002, 4(18), 3051-3054.

Ouyang et al., "Steric hindrance is a key factor in the coupling reaction of (acyloxy) alkyl-α-halides with phenols to make a new promoiety for prodrugs", Tetrahedron Lett. 2002, 43(4), 577-579.

Paine et al., "Regioselectivity of pyrrole synthesis from diethyl aminomalonate and 1,3-diketones: further observations", J. Org. Chem. 1987, 52(18), 3986-3993.

Parikh et al., "The Use of Amino Acid Oxidases for the Small-scale Preparation of the Optical Isomers of Amino Acids", J. Am. Chem. Soc. 1958, 80(4), 953-958.

Paxéus et al., "Screening for non-regulated organic compounds in municipal wastewater in Göteborg, Sweden", Water Sci. Technol. 1996, 33(6), 9-15.

Pérez-Balderas et al., "Synthesis of multivalent neoglycoconjugates by 1,3 dipolar cycloaddition of nitrile oxides and alkynes and evaluation of their lectin-binding affinities", Tetrahedron 2005, 61(39), 9338-9348.

Pfeiffer et al., "Synthesen and Eigenschaften von Pyrrolindigo-Verbindungen", Liebigs Ann. Chem. 1980(4), 564-589.

Poszavacz et al., "New Synthesis of Naratriptan", Heterocycles 2006, 68(4), 713-719.

Quizon-Colquitt et al., "Porphyrins with exocyclic rings. Part 4. An improved one step synthesis of cyclopenta[b]pyrroles", J. Heterocycl. Chem. 1993, 30(2), 477-482.

Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery", J. Med. Chem. 2000, 43(8), 1489-1494.

Rodriguez et al., "Conformational and molecular study of the 4-(2-carboxyethyl)-1,2,3,4-tetrahydrocyclopent[b]indole", Tetrahedron 1985, 41(18), 3813-3823.

Rosati et al., "Cephalosporins to carbapenems: 1-oxygenated carbapenems and carbapenams.", J. Med. Chem. 1990, 33(1), 291-297.

Rose et al., "Preclinical antitumor activity of water-soluble paclitaxel derivatives", Cancer Chemother. Pharmacol. 1997, 39(6), 486-492.

Salim et al., "Pharmacokinetic analysis of esteric prodrugs of valproic acid", Pharm. Res. 1990, 7(9), S222.

Sambasivarao et al., "Synthetic approach to pentaleno[2,1-b:5,4-b']diindoles", J. Org. Chem. 1990, 55(12), 3858-3866.

Sandham et al., "Synthesis and biological properties of novel glucocorticoid androstene C-17 furoate esters", Bioorg. Med. Chem. 2004, 12(19), 5213-5224.

Sandler et al., "Organic Functional Group Preparations", vol. 3; Academic Press: New York, 1972; pp. 372-381.

Satake et al., "The Reaction of Electron Excess Aromatic Heterocycle, 1,4-Dihydropyrrolo[3,2-b]pyrrole and Some Related Compounds with Chlorosulfonyl Isocyanate (CSI)"Heterocycles 1996, 43(11), 2361-2365.

Scott et al., "Preparation and Reductive Cyclization of Some Carbon-Alkylated Derivatives of Ethyl 3-Nitro-2-thienylpyruvate", J. Org. Chem. 1964, 29(8), 2165-2168.

Sergievskaya et al., "N-Bis(chloroethyl)amines with Alicyclic and Aromatic Radicals in the Molecules. II.", Zhurnal Obshchei Khimii 1958, 28, 1845-1849.[translation].

Severin et al., "Umsetzungen von Ketonen mit azavinylogen Säureamiden", Chem. Ber. 1975, 108(5), 1756-1767.

Sewald et al., "Synthesis of homochiral camphor annulated pyrrole derivatives", Tetrahedron Asymmetry 1996, 7(5), 1269-1272.

Sha et al., "Synthesis of 2,4-Dihydropyrrolo[3,4-b]pyrroles and 4,6-Dihydro-2H-dipyrrolo[3,4-b:3',4'-d]pyrroles", Heterocycles 1990, 31(4), 603-609.

Shaaya et al., "Anhydride prodrugs for nonsteroidal anti-inflammatory drugs", Pharm. Res. 2003, 20(2), 205-211.

Shek, "Chemical delivery systems and prodrugs of anticonvulsive drugs", Adv. Drug Deliv. Rev. 1994, 14(2-3), 227-241.

Shirai et al., "Reduction of 1-(m-methoxyphenyl )-4-oxocycloalkanecarbonitriles with lithium aluminum hydride ", Nagoya-shiritsu Daigaku Yakugakubu Kenkyu Nenpo 1969, 17, 33-37.

Shirai et al., "Synthesis of spiro[4-hydroxycyclohexane-1,4,2',3'-dihydro-6'-methoxy-1'-substituted-2'-methyl-1'H-isoquinoline]", Chem. Pharm. Bull. 1972, 20(1), 41-46.

Shvedov et al., "Monoarylhydrazones of di- and tricarbonyl compounds in the Knorr synthesis of pyrroles", Khimiya Geterotsiklicheskikh Soedinenii 1972(3), 342-344. [translation].

Silvestri et al., "Simple, short peptide derivatives of a sulfonylindolecarboxamide (L-737,126) active in vitro against HIV-1 wild type and variants carrying non-nucleoside reverse transcriptase inhibitor resistance mutations.", J. Med. Chem. 2004, 47(15), 3892-3896.

Skolnick et al., "Antidepressant-like actions of DOV 21,947: a "triple" reuptake inhibitor", Eur. J. Pharmacol. 2003, 461(2-3), 99-104.

Slawik et al., "Lipophilicity of a series of 1,2-benzisothiazol-3(2H)-ones determined by reversed-phase thin-layer chromatography", J. Chromatogr. A 2002, 952(1-2), 295-299.

Smith et al., "Deacylation and deformylation of pyrroles", J. Org. Chem. 1983, 48(24), 4779-4781.

Snyder et al., "Synthesis of the Thieno [3,2-b]pyrrole System", J. Am. Chem. Soc. 1957, 79(10), 2556-2559.

Sohma et al., "Controlled Drug Release: Design and Application of New Water-soluble Prodrugs" in "Peptide Science 2001"; Aoyagi, H., Ed.; The Japanese Peptide Society, 2002; pp. 249-252.

Sparey et al., "The discovery of fused pyrrole carboxylic acids as novel, potent d-amino acid oxidase (DAO) inhibitors", Bioorg. Med. Chem. Lett. 2008, 18(11), 3386-3391.

STN Registry File No. 67268-37-5. Registry File. Retrieved from STN Mar. 17, 2008. One page.

Stuart et al., "Cobalt-mediated Alkylation of Siloxy Furans", Heterocycles 1991, 32(5), 949-963.

Svahn et al., "Tranexamic acid derivatives with enhanced absorption", J. Med. Chem. 1986, 29(4), 448-453.

Takahashi et al., "Asymmetric α-Substituted Phenethylamines. I. Synthesis of Optically Pure 1-Aryl-N-(2'-hydroxy-1'-isopropylethyl)-2-phenylethylamines", Chem. Pharm. Bull. 1982, 30(9), 3160-3166.

Tammara et al., "Morpholinoalkyl ester prodrugs of diclofenac: synthesis, in vitro and in vivo evaluation", J. Pharm. Sci. 1994, 83(5), 644-648.

Treibs et al., "Über einige Pyrrolderivate mit angegliedertem isocyclischem Ring. Bz-Tetrahydrindole und Cyclopentenopyrrolle", Justus Liebigs Ann. Chem. 1935, 517, 152-169.

Trost et al., "Palladium-Catalyzed Enantioselective C-3 Allylation of 3-Substituted-1H-Indoles Using Trialkylboranes", J. Am. Chem. Soc. 2006, 128(19), 6314-6315.

Ueda et al., "Novel water soluble phosphate prodrugs of taxol® possessing in vivo antitumor activity", Bioorg. Med. Chem. Lett. 1993, 3(8), 1761-1766.

Ueda et al., "Novel, water-soluble phosphate derivatives of 2'-ethoxy carbonylpaclitaxel as potential prodrugs of paclitaxel: Synthesis and antitumor evaluation", Bioorg. Med. Chem. Lett. 1995, 5(3), 247-252.

Urbach et al., "Eine einfache diastereoselektive Synthese von (1SR,3SR,5SR)-2-Azabicyclo [3.3.0] octan-3-carbonsäure", Tetrahedron Lett. 1985, 26(15), 1839-1842.

van Herk et al., "Pyrazole Derivatives as Partial Agonists for the Nicotinic Acid Receptor", J. Med. Chem. 2003, 46(18),3945-3951.

Vicini et al., "Biological studies on 1,2-benzisothiazole derivatives. I. Evaluation of antibacterial, antifungal and DNA-damaging activity", Farmaco 1989, 44(5), 511-517.

Vicini et al., "Sintesi e proprieta antiflogistiche antipiretiche ed analgesiche di 5-(1,2-benzisotiazolil)tetrazoli", Farmaco Sci. 1986, 41(2), 111-118.

Vicini et al., "Sintesi e proprieta antiflogistiche antipiretiche ed analgesiche di acidi 5-benzisotiazolilalcanoici e di loro derivati funzionali", Farmaco Sci. 1984, 39(10), 817-829.

Vippagunta et al., "Crystalline solids", Adv. Drug Deliv. Rev. 2001, 48(1), 3-26.

Viswanathan et al., "Free Radical-Mediated Aryl Amination and Its Use in a Convergent [3 +2] Strategy for Enantioselective Indoline α-Amino Acid Synthesis", J. Am. Chem. Soc. 2003, 125(1), 163-168.

Vitali et al., "Ricerche nella classe dei fitocidi 3-benzisotiazolacetici", Farmaco Sci. 1973, 28(1), 8-18.

Vogel et al., "Cycloalkano-2H-pyrrole als stabile Zwischenstufen bei der Umwandlung von β-Cycloalkenyl-α-azidoacrylestern in Cycloalkano-1H-pyrrole", Angew. Chem. 1993, 105(7), 1116-1117.

Vogel et al., "Cycloalkano-2H-pyrrole as a Stable Intermediate in the Conversion of beta-Cycloalkenyl-alpha-azidoacrylates to Cycloalkano-1H pyrroles", Angew. Chem. Int. Ed. Engl. 1993, 32(7), 1051-1052. [translation of Angew. Chem. 1993, 105(7), 1116-1117.].

Wang et al., "Synthesis of ethyl cyclopenteno- or cyclohexeno[b]pyrrolyl-2-carboxylates", Youji Huaxue 1997, 17(6), 524-528.

Watanabe et al., "Enantioselective addition of chirally modified allylboranes to N-(trimethylsilyl)benzaldehyde imine", Tetrahedron Asymmetry 1995, 6(7), 1531-1534.

Wen et al., "Cell differentiation enhancement by hydrophilic derivatives of 4,8-Dihydrobenzo[1,2-b:5,4-b']dithiophene-4,8-diones in HL-60 leukemia cells", Bioorg. Med. Chem. Lett. 2007, 17(10), 2908-2912.

Wensbo et al., "Indole-3-Acetic Acids and Hetero Analogues by One Pot Synthesis including Heck Cyclisation", Tetrahedron 1995, 51(37), 10323-10342.

Wensbo et al., "Indole-3-pyruvic acid oxime ethers and thieno analogues by Heck cyclisation. Application to the synthesis of thiatryptophans", Tetrahedron 1996, 52(47), 14975-14988.

Wernly-Chung et al., "Structure-reactivity relationships in the chemical hydrolysis of prodrug esters of nicotinic acid", Int. J. Pharm. 1990, 63(2), 129-134.

West, A. R., "Solid State Chemistry and Its Applications"; Wiley: New York, 1988; pp. 358 and 365.

Wright et al., "Derivatives of 11-(1-piperazinyl)-5H-pyrrolo[2,1-c][1,4]benzodiazepine as central nervous system agents", J. Med. Chem. 1980, 23(4), 462-465.

Xue et al., "An Efficient Synthesis of Glycoprotein IIb/IIIa Inhibitor DMP728. A Novel Synthesis of N.alpha.- Methylarginine-Containing Peptide", J. Org. Chem. 1995, 60(4), 946-952.

Yardley et al., "2-Phenyl-2-(1-hydroxycycloalkyl)ethylamine derivatives: synthesis and antidepressant activity", J. Med. Chem. 1990, 33(10), 2899-2905.

Yarovenko et al., "Regioselective acylation of methyl 2-methyl-4H-thieno[3,2-b]pyrrole-5-carboxylate", Russ. Chem. Bull., Int. Ed., 2003, 52(2), 451-456.

Yasuhara et al., "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential", Bioorg. Med. Chem. 2006, 14(12), 4193-4207.

Yevich et al., "Synthesis and biological evaluation of 1-(1,2-benzisothiazol-3-yl)- and (1,2-benzisoxazol-3-yl)piperazine derivatives as potential antipsychotic agents", J. Med. Chem. 1986, 29(3), 359-369.

Yu et al., "The regiospecific C-4 lithiation of 2-(tert-butyldimethylsilyl)-3-furoic acid", J. Chem. Soc., Perkin Trans. 1, 1991(10), 2600-2601.

Yudina et al., "Synthesis and alkylation of indolo[3,2-b]carbazoles", Tetrahedron 2003, 59(8), 1265-1275.

Zani et al., "Biological studies on 1,2-benzisothiazole derivatives. VI. Antimicrobial activity of 1,2-benzisothiazole and 1,2-benzisothiazolin-3-one derivatives and of some corresponding 1,2-benzisoxazoles", Farmaco 1996, 51(11), 707-713.

Zaragoza Dörwald, F., "Side Reactions in Organic Synthesis"; Wiley-VCH: Weinheim, 2005; pp. IX and 41.

Zhang et al., "Synthesize the china 3-pyridyl ester analogs of anaddicted analgesic Epibatidine", Journal of Shangqiu Teachers College (Shangqiu Shifan Xueyuan Xuebao) 2004, 20(5), 90-94.

Zinoune et al., "Aminoalkylation of Aldehydes with Glyoxal N,N-Dimethlmonohydrazone Yields Stable 4-Substituted Pyrrolin-3-ones", Heterocycles 1989, 28(2), 1077-1084.

Zong et al., "A new and efficient synthetic route toward 3,4-alkylenedioxypyrrole (XDOP) derivatives via Mitsunobu chemistry", Tetrahedron Lett. 2006, 47(21), 3521-3523.

Hemetsberger et al., "Synthese and Thermolyse von α-Azidoacrylestern", Monatsh. Chem. 1972, 103(1), 194-204.

STN - Registry file (RN 132857-67-1, RN 109252-80-4, RN 93144-92-4, RN 92321-04-5, RN 83957-46-4, RN 83957-32-8, RN 69740-90-5, RN 69640-94-4, RN 69640-90-0, RN 69640-89-7, RN 69640-88-6, RN 69640-87-5, RN 69640-86-4, RN 69640-85-3, RN 69640-84-2, RN 69640-83-1, RN 69640-82-0, RN 69640-80-8, RN 67313-00-2, RN 67312-99-6, RN 67312-98-5, RN 60068-34-0, RN 60068-33-9, RN 60068-32-8, RN 58379-13-8, RN 57955-60-9, RN 57955-59-6, RN 51074-73-8, RN 51074-72-7, RN 51074-71-6, RN 51074-69-2, RN 36373-65-6, RN 36373-63-4, RN 34779-69-6, RN 34779-67-4, RN 33317-36-1, RN 33317-33-8). [earliest date entered STN Nov. 16, 1984].

* cited by examiner

INHIBITORS OF D-AMINO ACID OXIDASE

CROSS-REFERENCES TO RELATED APPLICATIONS

This application is a Continuation-in-Part of and claims priority under 35 U.S.C. §120 to U.S. patent application Ser. No. 12/016,954 filed on Jan. 18, 2008, which claims priority under 35 U.S.C. §119(e) to U.S. Provisional Patent Application No. 60/885,588 filed on Jan. 18, 2007, all of which are incorporated herein by reference in their entirety for all purposes.

FIELD OF THE INVENTION

This invention relates to enzyme inhibitors, particularly inhibitors of D-amino acid oxidase (DAAO).

BACKGROUND OF THE INVENTION

The enzyme D-amino acid oxidase (DAAO) metabolizes D-amino acids, and in particular, metabolizes D-serine in vitro at physiological pH. DAAO is expressed in the mammalian central and peripheral nervous system. D-Serine's role as a neurotransmitter is important in the activation of the N-methyl-D-aspartate (NMDA) selective subtype of the glutamate receptor, an ion channel expressed in neurons, here denoted as NMDA receptor.

NMDA receptors mediate many physiological functions. NMDA receptors are complex ion channels containing multiple protein subunits that act either as binding sites for transmitter amino acids and/or as allosteric regulatory binding sites to regulate ion channel activity. D-serine, released by glial cells, has a distribution similar to NMDA receptors in the brain and acts as an endogenous ligand of the allosteric "glycine" site of these receptors (Mothet et al., *PNAS*, 97:4926 (2000)), the occupation of which is required for NMDA receptor operation. D-serine is synthesized in brain through serine racemase and degraded by D-amino oxidase (DAAO) after release.

Small organic molecules, which inhibit the enzymatic cycle of DAAO, can be used to control the levels of D-serine, and thus can influence the activity of the NMDA receptor in the brain. NMDA receptor activity is important in a variety of disease states, such as schizophrenia, psychosis, ataxias, ischemia, several forms of pain including neuropathic pain, and deficits in memory and cognition.

DAAO inhibitors can also control production of toxic metabolites of D-serine oxidation, such as hydrogen peroxide and ammonia. Thus, these molecules can influence the progression of cell loss in neurodegenerative disorders. Neurodegenerative diseases are diseases in which CNS neurons and/or peripheral neurons undergo a progressive loss of function, usually accompanied by (and perhaps caused by) a physical deterioration of the structure of either the neuron itself or its interface with other neurons. Such conditions include Parkinson's disease, Alzheimer's disease, Huntington's disease and neuropathic pain. N-methyl-D-aspartate (NMDA)-glutamate receptors are expressed at excitatory synapses throughout the central nervous system (CNS). These receptors mediate a wide range of brain processes, including synaptic plasticity, that are associated with certain types of memory formation and learning. NMDA-glutamate receptors require binding of two agonists to induce neurotransmission. One of these agonists is the excitatory amino acid L-glutamate, while the second agonist, at the so-called "strychnine-insensitive glycine site", is now thought to be D-serine. In animals, D-serine is synthesized from L-serine by serine racemase and degraded to its corresponding ketoacid by DAAO. Together, serine racemase and DAAO are thought to play a crucial role in modulating NMDA neurotransmission by regulating CNS concentrations of D-serine.

Known inhibitors of DAAO include benzoic acid, pyrrole-2-carboxylic acids, and indole-2-carboxylic acids, as described by Frisell, et al., *J. Biol. Chem.*, 223:75-83 (1956) and Parikh et al., *JACS,* 80:953 (1958). Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. Several examples of traumatic events that can result in neurotoxic injury are given, including hypoxia, anoxia, and ischemia, associated with perinatal asphyxia, cardiac arrest or stroke. Neurodegeneration is associated with CNS disorders such as convulsions and epilepsy. U.S. Pat. Nos. 5,373,018; 5,374,649; 5,686,461; 5,962,496 and 6,100,289, to Cugola, disclose treatment of neurotoxic injury and neurodegenerative disease using indole derivatives. None of the above references mention improvement or enhancement of learning, memory or cognition.

WO 03/039540 to Heefier et al. and U.S. Patent Application Nos. 2005/0143443 to Fang et al. and 2005/0143434 to Fang et al. disclose DAAO inhibitors, including indole-2-carboxylic acids, and methods of enhancing learning, memory and cognition as well as methods for treating neurodegenerative disorders. Patent Application No. WO/2005/089753 discloses benzisoxazole analogs and methods of treating mental disorders, such as Schizophrenia. However, a need for additional drug molecules that are effective in treating memory defects, impaired learning, loss of cognition, and other symptoms related to NMDA receptor activity, remains. The present invention addresses this and other needs.

SUMMARY OF THE INVENTION

The invention provides novel inhibitors of D-amino acid oxidase that are useful in the prevention and treatment of a variety of diseases and/or conditions including neurological disorders, pain, ataxia and convulsion.

In a first aspect, the present invention provides a compound having a structure according to Formula (VI):

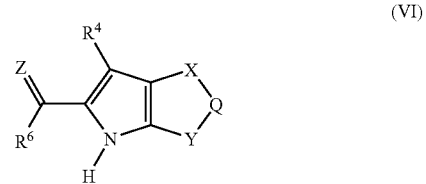

(VI)

In Formula (VI), Z is a member selected from O and S. X, Q and Y are members independently selected from $-CR^1R^2-$, $C=O$, $C=S$, $C=NR^3$ and $C=CR^{40}R^{41}$, with the proviso that at least one of X, Q and Y is other than $-CH_2-$. X and Q are optionally joined to form a 3-, 4- or 5-membered ring. Y and Q are optionally joined to form a 3-, 4- or 5-membered ring. X and Y, together with the atoms to which they are attached, are optionally joined to form a 5- to 7-membered ring thereby forming a bicyclic substructure.

In Formula (VI), $R^3$ is a member selected from H, $OR^{12}$, acyl, $NR^{12}R^{13}$, $SO_2R^{13}$, $SOR^{13}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{12}$ and $R^{13}$ are members independently selected from substituted or unsubstituted alkyl, substituted or unsubstituted heteroalkyl, substituted or unsubstituted aryl, substituted or unsubstituted heteroaryl and substituted or unsubstituted heterocycloalkyl.

In Formula (VI), $R^4$ is a member selected from H, $CF_3$, F, Cl, Br, CN, $OR^{14}$, $NR^{14}R^{15}$, $C_4$-$C_6$ unsubstituted alkyl, substituted or unsubstituted cycloalkyl, substituted or unsubstituted heterocycloalkyl, substituted or unsubstituted arylalkyl, substituted or unsubstituted heteroarylalkyl, cycloalkyl-substituted alkyl and heterocycloalkyl-substituted alkyl. $R^{14}$ and $R^{15}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

In Formula (VI), each $R^1$, each $R^2$, each $R^{40}$ and each $R^{41}$ is a member independently selected from H, halogen, CN, $CF_3$, acyl, $C(O)OR^{14'}$, $C(O)NR^{14'}R^{15'}$, $OR^{14'}$, $S(O)_2OR^{14'}$, $S(O)_pR^{14'}$, $SO_2NR^{14'}R^{15'}$, $NR^{14'}R^{15'}$, $NR^{14'}C(O)R^{15'}$, $NR^{14'}S(O)_2R^{15'}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein p is an integer selected from 0 to 2. Adjacent $R^1$ and $R^2$, together with the atoms to which they are attached, are optionally joined to form a 3-, 4- or 5-membered ring. In one example, $R^1$ and $R^2$ are not joined to form a ring. $R^{14'}$ and $R^{15'}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{14}$ and $R^{15}$, together with the atoms to which they are attached, are optionally joined to form a 5- to 7-membered ring. In one example, when X is C=O, then $R^4$ is other than H. In another example, when X is C=O, then Q and Y are other than —$CH_2$—. In yet another example, when X is $CHR^1$, wherein $R^1$ is ethyl, propyl or butyl, then $R^4$ is other than H. In a further example, when X is $CHR^1$, wherein $R^1$ is ethyl, propyl or butyl, then Q and Y are other than —$CH_2$—. In another example, when X is $CHR^1$, wherein $R^1$ is ethyl, propyl or butyl, then Y is other than C=O and $CR^1R^2$, wherein both $R^1$ and $R^2$ are —O-acyl (e.g., OAc). In a further example, when $R^4$ is H, then X and Y are not both $CR^1R^2$, wherein both $R^1$ and $R^2$ are other than H (e.g., X and Y are not both $C(Me)_2$).

In Formula (VI), $R^6$ is a member selected from OH and $O^-X^+$, wherein $X^+$ is a cation.

Compounds of Formula (VI) include any enantiomer, diastereoisomer, racemic mixture, enantiomerically enriched mixture, and enantiomerically pure forms for each compound.

In one embodiment according to the above aspect, at least one of $R^1$, $R^2$, $R^3$, $R^{40}$ and $R^{41}$ in Formula (VI) has the formula:

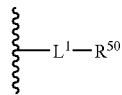

wherein $R^{50}$ is a member selected from substituted or unsubstituted aryl, substituted or unsubstituted heteroaryl, substituted or unsubstituted cycloalkyl, substituted or unsubstituted heterocycloalkyl and a fused ring system; and wherein $L^1$ is a linker moiety, which is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

In one example according to any of the above embodiments, at least one of $R^1$, $R^2$ and $R^3$ has a formula, which is a member selected from:

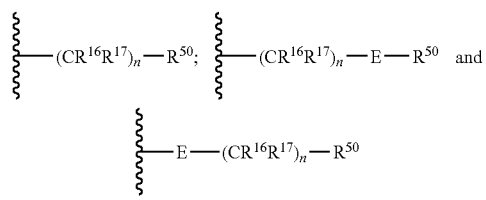

wherein n is an integer from 1 to 5. In the above structures, each E is a member independently selected from —O—, —S—, —$NR^{43}$—, —$C(O)NR^{43}$—, —$NR^{43}C(O)$—, —$S(O)_2NR^{43}$— and —$NR^{43}S(O)_2$—, wherein each $R^{43}$ is a member independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

$R^{16}$ and $R^{17}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, wherein two of $R^1$, $R^{16}$ and $R^{17}$ or two of $R^2$, $R^{16}$ and $R^{17}$, together with the carbon atoms to which they are attached, are optionally joined to form a 3- to 7-membered ring, wherein said ring is a member selected from substituted or unsubstituted cycloalkyl and substituted or unsubstituted heterocycloalkyl, and wherein said ring is optionally fused to $R^{50}$.

In another example according to any of the above embodiments, $(CR^{16}R^{17})_n$ is a member selected from —$CH_2$—, —$CH_2CH_2$— and —$CH_2CH_2CH_2$—.

In another example according to any of the above embodiments, $R^{50}$ is a member selected from substituted or unsubstituted aryl and substituted or unsubstituted heteroaryl.

In another example according to any of the above embodiments, $R^{50}$ is substituted or unsubstituted aryl and has the formula:

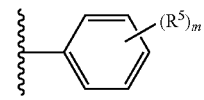

wherein m is an integer from 0 to 5. Each $R^5$ is a member independently selected from H, halogen, CN, $CF_3$ hydroxy, alkoxy, acyl, $C(O)OR^{18}$, $OC(O)R^{18}$, $NR^{18}R^{19}$, C(O)

$NR^{18}R^{19}$, $NR^{18}C(O)R^{20}$, $NR^{18}SO_2R^{20}$, $S(O)_2R^{20}$, $S(O)R^{20}$, substituted or unsubstituted alkyl, substituted or unsubstituted heteroalkyl, substituted or unsubstituted aryl, substituted or unsubstituted heteroaryl and substituted or unsubstituted heterocycloalkyl. Adjacent $R^5$, together with the atoms to which they are attached, are optionally joined to form a ring (e.g., substituted or unsubstituted cycloalkyl, substituted or unsubstituted heterocycloalkyl, substituted or unsubstituted aryl and substituted or unsubstituted heteroaryl). $R^{18}$ and $R^{19}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{20}$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. Two of $R^{18}$, $R^{19}$ and $R^{20}$, together with the atoms to which they are attached, are optionally joined to form a 5- to 7-membered ring.

In another example according to any of the above embodiments, the compound of the invention has a formula, which is a member selected from:

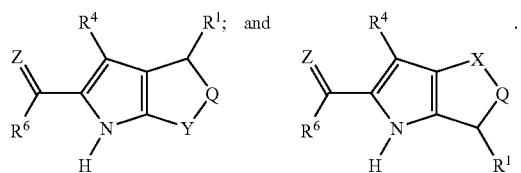

In another example according to any of the above embodiments, the compound of the invention has a formula, which is a member selected from:

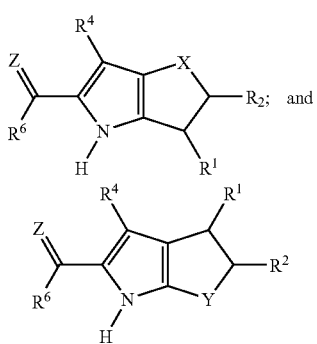

In another example according to any of the above embodiments, the compound of the invention has a structure, which is a member selected from:

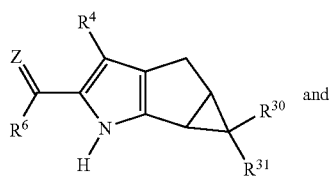

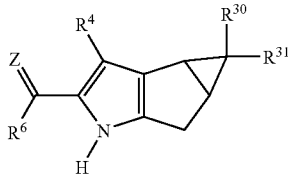

wherein $R^{30}$ and $R^{31}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. For example, $R^{30}$ and $R^{31}$ are not both methyl.

In another example according to any of the above embodiments, at least one of $R^{30}$ and $R^{31}$ has the formula:

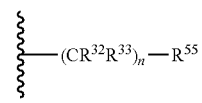

wherein each n is an integer from 0 to 5. $R^{55}$ is a member selected from substituted or unsubstituted aryl, substituted or unsubstituted heteroaryl, substituted or unsubstituted cycloalkyl and substituted or unsubstituted heterocycloalkyl. Each $R^{32}$ and each $R^{33}$ is a member independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{32}$ and $R^{33}$, together with the carbon atom to which they are attached, are optionally joined to form a 3- to 7-membered ring, which is optionally fused to $R^{55}$.

In another example according to any of the above embodiments, the compound of the invention has the formula:

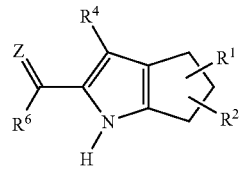

wherein at least one of $R^1$ and $R^2$ is other than H. In the above formula, adjacent $R^1$ and $R^2$, together with the atoms to which they are attached, are optionally joined to form a 3-, 4- or 5-membered ring.

In another example according to any of the above embodiments, the compound of the invention has formula, which is a member selected from:

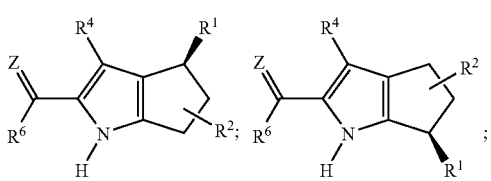

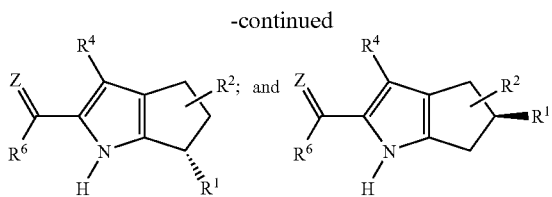

wherein R¹ is other than H and absolute stereochemistry with respect to R¹ is shown.

In another example according to any of the above embodiments, R¹ is substituted or unsubstituted alkyl.

In another example according to any of the above embodiments, R¹ is a member selected from substituted or unsubstituted methyl, substituted or unsubstituted ethyl, substituted or unsubstituted n-propyl, substituted or unsubstituted iso-propyl, substituted or unsubstituted n-butyl and substituted or unsubstituted iso-butyl.

In another example according to any of the above embodiments, R¹ is aryl-substituted alkyl or heteroaryl-substituted alkyl.

In another example according to any of the above embodiments, R¹ is alkyl substituted with a member selected from substituted or unsubstituted cycloalkyl and substituted or unsubstituted heterocycloalkyl.

In another example according to any of the above embodiments, Z is O.

In another example according to any of the above embodiments, R¹ and R² are members independently selected from H, F, methyl, ethyl, n-propyl, iso-propyl, n-butyl, iso-butyl, substituted or unsubstituted arylalkyl, substituted or unsubstituted heteroarylalkyl, cycloalkyl-substituted alkyl and heterocycloalkyl-substituted alkyl, wherein a cycloalkyl or heterocycloalkyl group is optionally substituted.

In another example, the invention provides a pharmaceutical composition including a compound of the invention (e.g., any of the compounds described in any of the above embodiments), or a pharmaceutically acceptable salt thereof, and a pharmaceutically acceptable carrier.

In another example, the invention provides a composition including a first stereoisomer and at least one additional stereoisomer of a compound of the invention (e.g., any of the compounds described in any of the above embodiments) wherein the first stereoisomer is present in an enantiomeric or diastereomeric excess of at least 80% relative to the at least one additional stereoisomer.

In a second aspect, the invention provides a method for treating or preventing a condition which is a member selected from a neurological disorder, pain, ataxia and convulsion. The method includes administering to a subject in need thereof a therapeutically effective amount of a compound according to Formula (I):

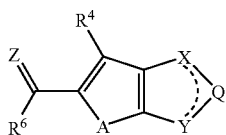

(I)

wherein Z is a member selected from O and S. A is a member selected from NR⁷, S and O.

X, Q and Y are members independently selected from O, S, NR³, CR¹, —(CR¹R²)_q—, C=O, C=S, C=NR³ and C=CR⁴⁰R⁴¹, wherein q is an integer selected from 1 and 2. In Formula (I), the ring, which includes Q, X and Y is a non-aromatic ring. X and Q are optionally joined to form a 3- to 7-membered ring. Y and Q are optionally joined to form a 3- to 7-membered ring. X and Y, together with the atoms to which they are attached, are optionally joined to form a 5- to 7-membered ring thereby forming a bicyclic substructure.

In Formula (I), R³ and R⁷ are members independently selected from H, OR¹², acyl, NR¹²R¹³, SO₂R¹³, SOR¹³, substituted or unsubstituted alkyl, substituted or unsubstituted heteroalkyl, substituted or unsubstituted aryl, substituted or unsubstituted heteroaryl and substituted or unsubstituted heterocycloalkyl, wherein R¹² and R¹³ are members independently selected from substituted or unsubstituted alkyl, substituted or unsubstituted heteroalkyl, substituted or unsubstituted aryl, substituted or unsubstituted heteroaryl and substituted or unsubstituted heterocycloalkyl.

In Formula (I), R⁴, each R¹, each R², each R⁴⁰ and each R⁴¹ are members independently selected from H, halogen, CN, CF₃, acyl, C(O)OR¹⁴, C(O)NR¹⁴R¹⁵, OR¹⁴, S(O)₂OR¹⁴, S(O)_pR¹⁴, SO₂NR¹⁴R¹⁵, NR¹⁴R¹⁵, NR¹⁴C(O)R¹⁵, NR¹⁴S(O)₂R¹⁵, substituted or unsubstituted alkyl, substituted or unsubstituted heteroalkyl, substituted or unsubstituted aryl, substituted or unsubstituted heteroaryl and substituted or unsubstituted heterocycloalkyl, wherein p is an integer selected from 0 to 2. R¹ and R², together with the atoms to which they are attached, are optionally joined to form a 3- to 7-membered ring. R¹⁴ and R¹⁵ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. R¹⁴ and R¹⁵, together with the atoms to which they are attached, are optionally joined to form a 5- to 7-membered ring.

In Formula (I), R⁶ is a member selected from OR⁸, O⁻X⁺, NR⁹R¹⁰, NR⁹NR⁹'R¹⁰, NR⁹OR¹⁰, NR⁹SO₂R¹¹, wherein X⁺ is a cation. R⁶ and R⁷, together with the atoms to which they are attached, are optionally joined to form a 5- to 7-membered ring. R⁸ is a member selected from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl and a single negative charge. R⁹, R⁹' and R¹⁰ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. R¹¹ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. At least two of R⁸, R⁹, R⁹', R¹⁰ and R¹¹, together with the atoms to which they are attached, are optionally joined to form a 5- to 7-membered ring.

In one example according to any of the above embodiments, in Formula (I), A is NR⁷ (e.g., NH). In another example according to any of the above embodiments, in Formula (I), R⁶ is OR⁸ or O⁻X⁺. For example, R⁸ is a member selected from H and a single negative charge. In another example according to any of the above embodiments, in Formula (I), R¹ and R² are members independently selected from H, F, methyl, ethyl, n-propyl, iso-propyl, n-butyl, iso-butyl, substituted or unsubstituted arylalkyl, substituted or unsubstituted heteroarylalkyl, substituted or unsubstituted cycloalkyl-substituted alkyl and substituted or unsubstituted heterocycloalkyl-substituted alkyl. In another example according to any of the above embodiments, in Formula (I), at least one of X, Q and Y is other than —CH₂—.

Compounds of Formula (I) include any enantiomer, diastereoisomer, racemic mixture, enantiomerically enriched mixture, and enantiomerically pure form of each compound.

In one example, the compound of Formula (I) has a structure according to Formula (VI):

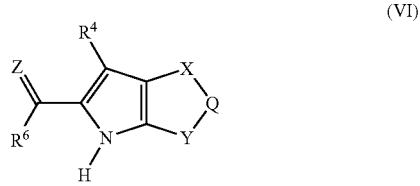

(VI)

wherein Z, $R^4$, $R^6$, X, Q and Y are defined as outlined herein above. All exemplary embodiments outlined herein above for Formula (VI), equally apply to the compounds of this paragraph and the methods of the invention.

The invention further provides a method of enhancing cognition in a mammalian subject (e.g., a human patient). The method includes administering to the subject an effective amount of a compound of the invention. The compound can be any compound described herein above. In one example, the compound is a compound according to Formula (I). In another example, the compound is a compound according to Formula (VI). Any embodiments described herein above for Formula (I) and Formula (VI) equally apply to the method of this paragraph.

The invention further provides a method of inhibiting D-amino acid oxidase (DAAO) activity, said method comprising contacting said DAAO with a compound of the invention, wherein the compound can be any compound described herein above. In one example, the compound is a compound according to Formula (I). In another example, the compound is a compound according to Formula (VI). Any embodiments described herein above for Formula (I) and Formula (VI) equally apply to the method of this paragraph.

The invention further provides a method of increasing D-serine level in the brain (e.g., cerebellum) of a mammal (e.g., a rodent or a human). The method includes administering to the mammal an effective amount of a compound of the invention, wherein the compound can be any compound described herein above. In one example, the compound is a compound according to Formula (I). In another example, the compound is a compound according to Formula (VI). Any embodiments described herein above for Formula (I) and Formula (VI) equally apply to the method of this paragraph.

DETAILED DESCRIPTION OF THE INVENTION

I. Definitions

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which can be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" with the difference that the heteroalkyl group, in order to qualify as an alkyl group, is linked to the remainder of the molecule through a carbon atom. Alkyl groups that are limited to hydrocarbon groups are termed "homoalkyl".

The term "alkenyl" by itself or as part of another substituent is used in its conventional sense, and refers to a radical derived from an alkene, as exemplified, but not limited, by substituted or unsubstituted vinyl and substituted or unsubstituted propenyl. Typically, an alkenyl group will have from 1 to 24 carbon atoms, with those groups having from 1 to 10 carbon atoms being preferred.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S, B and P and wherein the nitrogen and sulfur atoms can optionally be oxidized and the nitrogen heteroatom can optionally be quaternized. The heteroatom(s) can be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, and —CH═CH—N($CH_3$)—$CH_3$. Up to two heteroatoms can be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent can be attached to the remainder of the molecule directly or through a linker. An exemplary linker is alkylene. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (e.g., from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring can optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are independently selected from hydrogen or substituted or unsubstituted ($C_1$-$C_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems can include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

The symbol "R" is a general abbreviation that represents a substituent group. Exemplary substituent groups include substituted or unsubstituted alkyl, substituted or unsubstituted heteroalkyl, substituted or unsubstituted aryl, substituted or unsubstituted heteroaryl, and substituted or unsubstituted heterocycloalkyl groups.

As used herein, the term "aromatic ring" or "non-aromatic ring" is consistent with the definition commonly used in the art. For example, aromatic rings include phenyl and pyridyl. Non-aromatic rings include cyclohexanes.

The phrase "therapeutically effective amount" as used herein means that amount of a compound, material, or composition comprising a compound of the present invention which is effective for producing a desired therapeutic effect, at a reasonable benefit/risk ratio applicable to any medical treatment.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When a residue is defined as "O$^-$", then the formula is meant to optionally include an organic or inorganic cationic counterion. For example, the resulting salt form of the compound is pharmaceutically acceptable.

The neutral forms of the compounds are, for example, regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. For instance, prodrugs for carboxylic acid analogs of the invention include a variety of esters. In an exemplary embodiment, the pharmaceutical compositions of the invention include a carboxylic acid ester. In another exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention can exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

The compounds of the present invention can contain unnatural proportions of atomic isotopes at one or more of the atoms that constitute such compounds. For example, heavy atoms such as deuterium ($^2$H), and/or carbon-13 ($^{13}$C), e.g., to modify reaction kinetics; the compounds can be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

In the context of the present invention, compounds that are considered to possess activity as DAAO inhibitors are those displaying 50% inhibition of the enzymatic activity of DAAO ($IC_{50}$) at a concentration of not higher than about 100 µM. For example, the $IC_{50}$ is not higher than about 10 µM, not higher than about 1 µM or not higher than about 100 nM. In one example, the $IC_{50}$ is not higher than about 25 nM.

The term "neurological disorder" refers to any undesirable condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any undesirable condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Peripheral neuropathic pain includes without limitation diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis. Other types of pain that are meant to be included in the definition of neuropathic pain include pain from neuropathic cancer pain, HIV/AIDS induced pain, phantom limb pain, and complex regional pain syndrome. In a preferred embodiment, the compounds of the invention are of use for treating neuropathic pain.

Common clinical features of neuropathic pain include sensory loss, allodynia (non-noxious stimuli produce pain), hyperalgesia and hyperpathia (delayed perception, summation, and painful after sensation). Pain can be a combination of nociceptive and neuropathic types, for example, mechanical spinal pain and radiculopathy or myelopathy.

"Acute pain", is the normal, predicted physiological response to a noxious chemical, thermal or mechanical stimulus typically associated with invasive procedures, trauma and disease. It is generally time-limited, and can be viewed as an appropriate response to a stimulus that threatens and/or produces tissue injury. "Acute pain", as described above, refers to pain which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain can be disproportionate to the intensity of the noxious stimulus or underlying process. "Chronic pain", as described above, refers to pain associated with a chronic disorder, or pain that persists beyond resolution of an underlying disorder or healing of an injury, and that is often more intense than the underlying process would predict. It can be subject to frequent recurrence.

"Inflammatory pain" is pain in response to tissue injury and the resulting inflammatory process. Inflammatory pain is adaptive in that it elicits physiologic responses that promote healing. However, inflammation can also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain which is produced as a symptom or a result of inflammation or an immune system disorder.

"Visceral pain", as described above, refers to pain which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia", as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia", as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It can occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia, "Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "Diabetic Peripheral Neuropathic Pain" (DPNP, also called diabetic neuropathy, DN or diabetic peripheral neuropathy) refers to chronic pain caused by neuropathy associated with diabetes mellitus. The classic presentation of DPNP is pain or tingling in the feet that can be described not only as "burning" or "shooting" but also as severe aching pain. Less commonly, patients can describe the pain as itching, tearing, or like a toothache. The pain can be accompanied by allodynia and hyperalgesia and an absence of symptoms, such as numbness.

The term "Post-Herpetic Neuralgia", also called "Postherpetic Neuralgia" (PHN), is a painful condition affecting nerve fibers and skin. It is a complication of shingles, a second outbreak of the varicella zoster virus (VZV), which initially causes chickenpox.

The term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

The term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

The term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

The term "Trigeminal Neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

The term "Complex Regional Pain Syndrome (CRPS)," formerly known as Reflex Sympathetic Dystrophy (RSD), is a chronic pain condition. The key symptom of CRPS is continuous, intense pain out of proportion to the severity of the injury, which gets worse rather than better over time. CRPS is divided into type 1, which includes conditions caused by tissue injury other than peripheral nerve, and type 2, in which the syndrome is provoked by major nerve injury, and is sometimes called causalgia.

The term "Fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

The term "convulsion" refers to a CNS disorder and is used interchangeably with "seizure," although there are many types of seizure, some of which have subtle or mild symptoms instead of convulsions. Seizures of all types can be caused by disorganized and sudden electrical activity in the brain. Convulsions are a rapid and uncontrollable shaking. During convulsions, the muscles contract and relax repeatedly.

Compositions Including Stereoisomers

Certain compounds of the present invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term "chiral", "enantiomerically enriched" or "diastereomerically enriched" refers to a compound having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess", those with at least two stereocenters are referred to as being present in "diastereomeric excess".

The term "enantiomeric excess" is well known in the art and is defined as:

$$ee_a = \left(\frac{conc.\ of\ a - conc.\ of\ b}{conc.\ of\ a + conc.\ of\ b}\right) \times 100$$

The term "enantiomeric excess" is related to the older term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Hence, in one embodiment, the invention provides a composition including a first stereoisomer and at least one additional stereoisomer of a compound of the invention. The first stereoisomer can be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. In another embodiment, the compound of the invention is enantiomerically or diastereomerically pure (diastereomeric or enantiomeric excess is about 100%). Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

II. Introduction

The present invention relates to novel inhibitors of the enzyme D-amino acid oxidase. The compounds of the invention are useful for treating or preventing any disease and/or condition, wherein modulation of D-serine levels, and/or its oxidative products, is effective in ameliorating symptoms. Inhibition of the enzyme can lead to increases in D-serine levels and a reduction in the formation of toxic D-serine oxidation products. Thus, the invention provides methods for the treatment or prevention of neurological disorders and methods of enhancing learning, memory and/or cognition. For example, compounds of the invention can be used for treating or preventing loss of memory and/or cognition associated with neurodegenerative diseases (e.g., Alzheimer's disease) and for preventing loss of neuronal function characteristic of neurodegenerative diseases. Further, methods are provided for the treatment or prevention of pain, ataxia and convulsion.

III. Compositions

A. Fused Heterocycles

The heterocyclic inhibitors of the invention are characterized by a variety of core-moieties. In an exemplary embodiment, the core-moiety includes a 5-membered, aromatic heterocyclic ring (first ring), such as a pyrrole, a furan, a thiophene or an imidazole fused to a second ring, wherein the second ring is a non-aromatic ring. In Formula (I), below, the second ring is marked with "(a)". The second ring can optionally be fused to at least one additional ring (e.g., a cyclopropane ring). In one embodiment, second ring (a) is substituted or unsubstituted cyclopentene or substituted or unsubstituted cyclohexene. For the purpose of characterizing the second ring (a), a double bond is assumed to be located between the first and second ring. Two examples according to this embodiment are shown below:

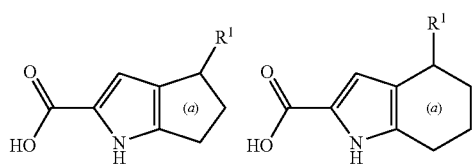

Other exemplary second rings (a) include substituted or unsubstituted cyclopentadienes, substituted or unsubstituted cyclohexadienes. In one embodiment, the second ring is substituted with a carbonyl group. Exemplary rings according to this embodiment include substituted or unsubstituted cyclopentenones, substituted or unsubstituted cyclopentadienones, substituted or unsubstituted cyclohexenones and substituted or unsubstituted cyclohexadienones.

In one embodiment, the compound of the invention has a structure according to Formula (I):

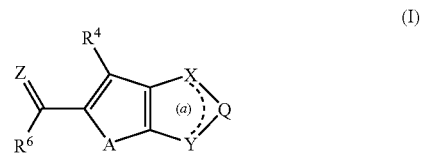

(I)

In one embodiment in Formula (I), Z is O. In another embodiment, Z is S. In yet another embodiment, A is $NR^7$. In a further embodiment, A is S. In another embodiment, A is O.

In Formula (I), X, Q and Y are members independently selected from O, S, $NR^3$, $CR^1$, $—(CR^1R^2)_q—$, C=O, C=S, C=$NR^3$ and C=$CR^{40}R^{41}$, wherein each q is an integer independently selected from 1 and 2. In one embodiment, at least one of X, Q and Y is a member selected from $CR^1$, $—(CR^1R^2)_q—$, C=O and C=S. In another embodiment, X, Q and Y are members independently selected from $CR^1$, $—(CR^1R^2)_q—$, C=O and C=S and C=$CR^{40}R^{41}$. In yet another example, at least one member selected from X and Y is $CH_2$, CHF or $CF_2$ and the other member is $CHR^1$, wherein $R^1$ is other than H. In a further example, at least one member selected from X and Y is $CH_2$ and the other member is $CHR^1$, wherein $R^1$ is other than H. In another example, Q is a member selected from $—(CH_2)_r—$, CHF, $CF_2$, CHCl, CHOH, CHMe, C=O and C=S, wherein r is an integer selected from 1 and 2. X and Q are optionally joined to form a 3- to 7-membered ring. Y and Q are optionally joined to form a 3- to 7-membered ring. X and Y, together with the atoms to which they are attached, are optionally joined to form a 3- to 7-membered ring (e.g., forming a bridged bicyclic substructure).

In Formula (I), the ring, which includes X, Q and Y [ring (a)] is a non-aromatic ring and can be a 5-, 6-, 7- or 8-membered ring. In one embodiment, ring (a) is a 5-membered ring. Exemplary 5-membered rings according to this embodiment include substituted or unsubstituted cyclopentene, substituted or unsubstituted cyclopentadienes, substituted or unsubstituted dihydrofuranes, substituted or unsubstituted dihydrothiophenes, substituted or unsubstituted dihydropyrroles, substituted or unsubstituted dihydroimidazoles and substituted or unsubstituted 3H-pyrazoles. When ring (a) is a 5-membered ring and includes a double bond between X and Q or between Y and Q, then ring (a) does preferably not include a heteroatom.

In another embodiment, ring (a) is a six-membered ring. Exemplary six-membered rings according to this embodiment, include substituted or unsubstituted cyclohexene, substituted or unsubstituted cyclohexadienes, substituted or unsubstituted dihydropyranes, substituted or unsubstituted tetrahydropyridines, substituted or unsubstituted dihydropyridines, substituted or unsubstituted dihydrothiopyranes, substituted or unsubstituted 1,2 thiazines, substituted or unsubstituted 1,3, thiazines, substituted or unsubstituted dihydropyrimidines and substituted or unsubstituted dihydropyrazines.

In Formula (I), each $R^3$ and each $R^7$ are members independently selected from H, $OR^{12}$, acyl, $NR^{12}R^{13}$, $SO_2R^{13}$, $SOR^{13}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{12}$ and $R^{13}$ are members independently selected from substituted or unsubstituted alkyl, substituted or unsubstituted heteroalkyl, substituted or unsubstituted aryl, substituted or unsubstituted heteroaryl and substituted or unsubstituted heterocycloalkyl.

In Formula (I), each $R^1$, each $R^2$, each $R^{40}$, each $R^{41}$ and $R^4$ are members independently selected from H, halogen (e.g., F, Cl, Br, I), CN, halogen-substituted alkyl (e.g., $CF_3$), acyl, $C(O)OR^{14}$, $C(O)NR^{14}R^{15}$, $OR^{14}$, $S(O)_2OR^{14}$, $S(O)_pR^{14}$, $SO_2NR^{14}R^{15}$, $NR^{14}R^{15}$, $NR^{14}C(O)R^{15}$, $NR^{14}S(O)_2R^{15}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein p is an integer selected from 0 to 2. $R^{14}$ and $R^{15}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{14}$ and $R^{15}$, together with the atoms to which they are attached, are optionally joined to form a 5- to 7-membered ring.

$R^1$ and $R^2$, together with the atoms to which they are attached, are optionally joined to form a 3- to 7-membered ring. In one example, $R^1$ and $R^2$ are members independently selected from substituted or unsubstituted alkyl (e.g., methyl, ethyl, propyl, butyl, pentyl or hexyl), substituted or unsubstituted arylalkyl (e.g., phenyl-alkyl), substituted or unsubstituted heteroarylalkyl (e.g., pyridinyl-alkyl), substituted or unsubstituted cycloalkyl-alkyl and substituted or unsubstituted heterocycloalkyl-alkyl. In one embodiment, at least one of $R^1$, $R^2$, $R^3$ and $R^4$ is other than H. In another embodiment, at least one of $R^1$ and $R^2$ is other than H. In an exemplary embodiment $CR^1R^2$ is $CF_2$.

In one example, $R^4$ represents a small substituent, such as H, halogen (e.g., F, Cl, Br, I), CN, $CF_3$, OH, OMe, OEt, methyl, ethyl and propyl. In another example, $R^4$ is H, F, Cl, CN or Me. In yet another example, $R^4$ is H or F.

In Formula (I), $R^6$ is a member selected from $OR^8$, $O^-X^+$, $NR^9R^{10}$, $NR^9NR^{9'}R^{10}$, $NR^9OR^{10}$, $NR^9SO_2R^{11}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $X^+$ is an organic or inorganic cation (e.g., $Na^+$, $NH_4^+$, $K^+$ or another pharmaceutically acceptable salt forms). In one example, $R^6$ is a member selected from $OR^8$, $O^-X^+$, $NR^9R^{10}$, $NR^9NR^{9'}R^{10}$, $NR^9OR^{10}$ and $NR^9SO_2R^{11}$. In another example, $R^6$ is a member selected from $OR^8$ and $O^-X^+$. $R^6$ and $R^7$, together with the atoms to which they are attached, are optionally joined to form a 5- to 7-membered ring. $R^6$ and $R^4$, together with the atoms to which they are attached, are optionally joined to form a 5- to 7-membered ring.

In Formula (I), $R^8$ is a member selected from H, a single negative charge, substituted or unsubstituted alkyl, substituted or unsubstituted heteroalkyl, substituted or unsubstituted aryl, substituted or unsubstituted heteroaryl and substituted or unsubstituted heterocycloalkyl. $R^9$, $R^{9'}$ and $R^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{11}$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. At least two of $R^8$, $R^9$, $R^{9'}$, $R^{10}$ and $R^{11}$, together with the atoms to which they are attached, are optionally joined to form a 5- to 7-membered ring.

In one embodiment, wherein $R^4$ is H or $CH_3$, A is $NR^7$, and Z is O, X, Q and Y are preferably not all $CH_2$. In another embodiment, wherein $R^4$ is H or $CH_3$, A is $NR^7$, Z is O and one member selected from X, Q and Y is $CH_2CH_2$, the other two members are preferably not both $CH_2$. For example, when $R^4$ is H, A is $NR^7$ and Z is O, ring (a) is preferably not unsubstituted cyclohexene or unsubstituted cyclopentene.

In one embodiment, the compound of the invention has a structure according to one of the following Formulae:

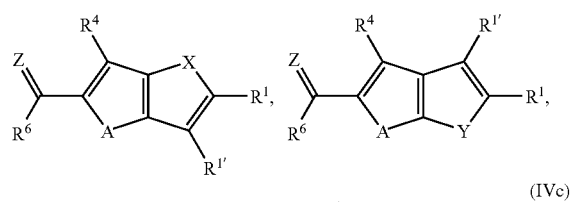

(IVc)

(Vc)

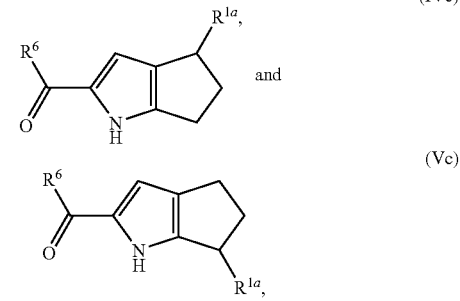

wherein X and Y are members selected from $-(CR^1R^2)_q-$, $C=CR^{40}R^{41}$, C=O, C=S and $C=NR^3$, wherein q is selected from 1 and 2; and wherein $R^{1a}$ is a member selected from H, alkyl, and

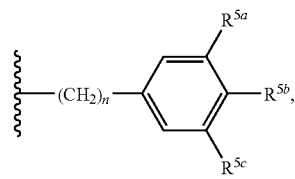

where n is an integer from 0 to 3; and $R^{5a}$, $R^{5b}$ and $R^{5c}$ are members independently selected from H, $C_1$ to $C_4$ alkyl, $C_1$ to $C_4$ alkyne, nitrile, Br, Cl, F, $OR^{18a}$, furan, tetrahydrofuran, and pyrrole; and where $R^6$ is a member selected from OH and $O^-X^+$, wherein $X^+$ is a cation. In various embodiments, n is an integer from 0 to 1 and two of $R^{5a}$, $R^{5b}$ and $R^{5c}$ are halogens selected independently from Cl and F.

In another embodiment, the compound of the invention has a structure according to one of the following Formulae:

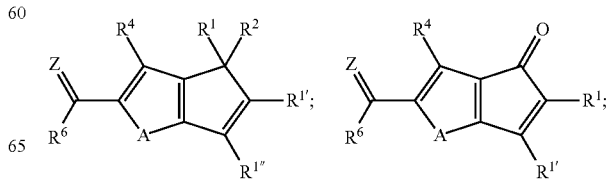

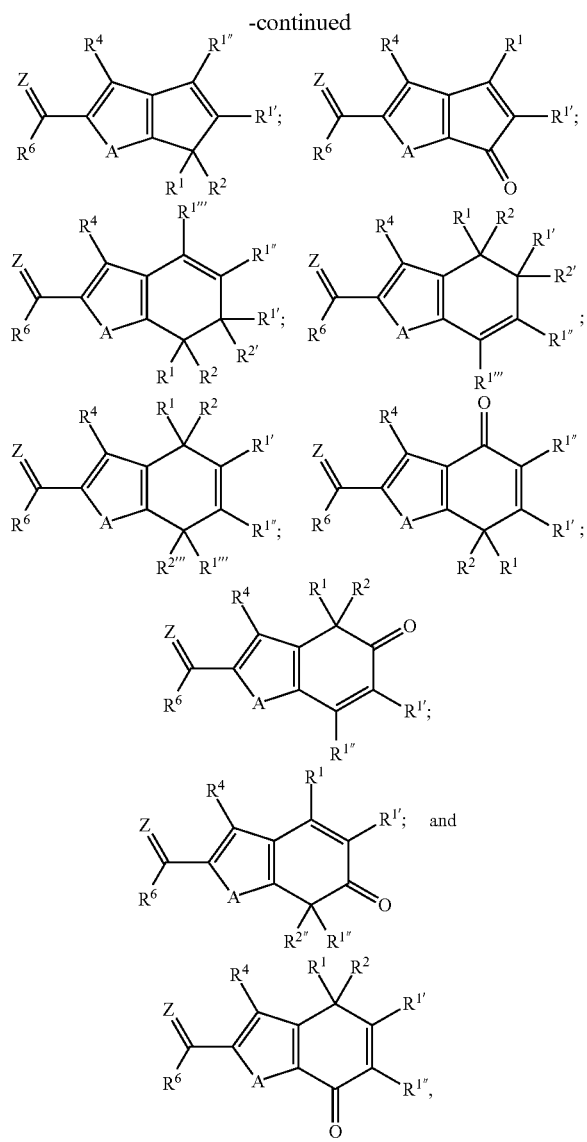

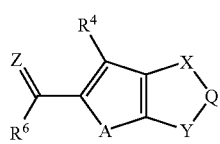

wherein Z, A, $R^6$, $R^4$, $R^1$ and $R^2$ are defined as for Formula (I), above. $R^{1'}$, $R^{1''}$, $R^{1'''}$ are defined as $R^1$. $R^{2'}$, $R^{2''}$, $R^{2'''}$ are defined as $R^2$. In one example, in the above structures, $R^4$ is H. In another example, in the above structures, A is NH. In yet another example, in the above structures A is O. In a further example, $R^6$ is $OR^8$, wherein $R^8$ is defined as herein above.

In yet another embodiment, the invention provides a compound having a structure according to Formula (II):

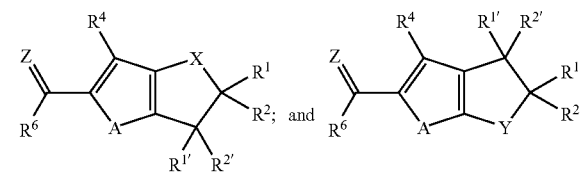

(II)

wherein Z, A, $R^4$ and $R^6$ are defined as for Formula (I), above. Exemplary embodiments listed for Formula (I) equally apply to compounds of Formula (II). In one example, in Formula (II), X, Q and Y are members independently selected from O, S, $NR^3$, $—(CR^1R^2)_q—$, $C=CR^{40}R^{41}$, $C=O$, $C=S$ and $C=NR^3$, wherein q, $R^1$, $R^2$, $R^3$, $R^{40}$ and $R^{41}$ are defined as above for Formula (I). In one example, X, Q and Y are members independently selected from $—(CR^1R^2)_q—$, $C=CR^{40}R^{41}$, $C=O$ and $C=S$. In one example, at least one of $R^1$, $R^2$, $R^3$ and $R^4$ in Formula (II) is other than H. In another example, at least one of $R^1$ and $R^2$ in Formula (II) is other than H.

In a further embodiment, the compound of the invention has a structure according to one of the following Formulae:

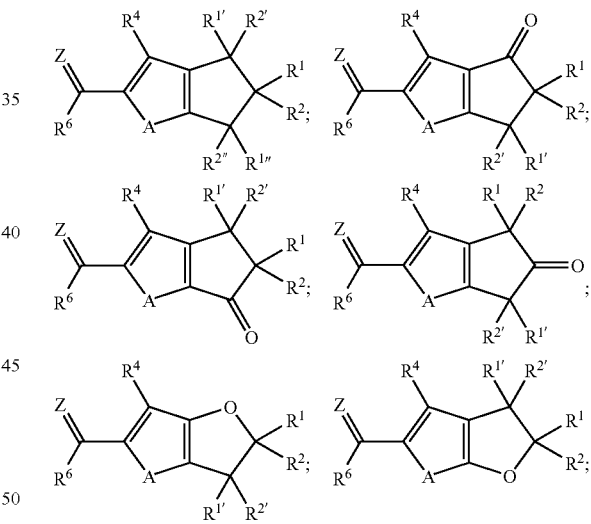

wherein Z, A, $R^4$ and $R^6$ are defined as for Formula (I), above, and X and Y are members independently selected from O, S, $NR^3$, $—(CR^1R^2)_q—$, $C=CR^{40}R^{41}$, $C=O$, $C=S$ and $C=NR^3$. In one example according to this embodiment, X, Q and Y are members independently selected from $—(CR^1R^2)_q—$, $C=CR^{40}R^{41}$, $C=O$, $C=S$ and $C=NR^3$.

In yet another embodiment, the compound of the invention has a structure according to one of the following Formulae:

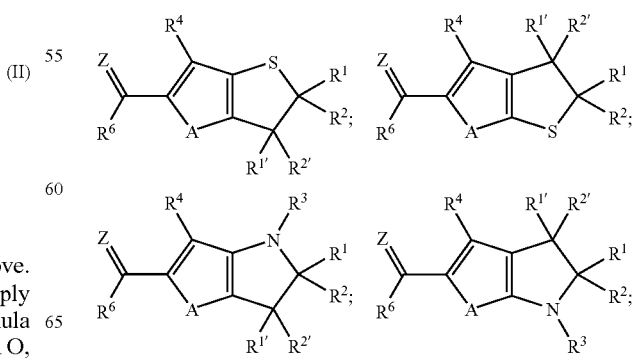

-continued

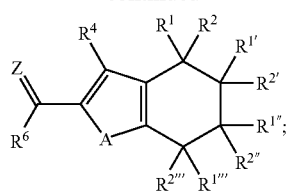

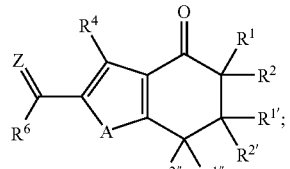

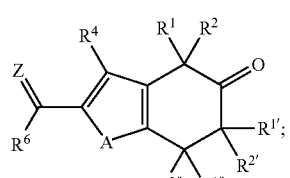

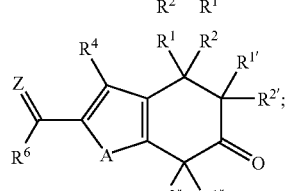

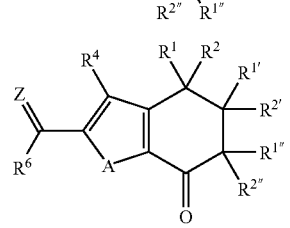

wherein Z, A, $R^6$, $R^4$, $R^1$ and $R^2$ are defined as for Formula (I), above. $R^{1'}$, $R^{1''}$, $R^{1'''}$ are defined as $R^1$. $R^{2'}$, $R^{2''}$, $R^{2'''}$ are defined as $R^2$. In one example, in the above structures, $R^4$ is H. In another example, in the above structures, A is NH. In yet another example, in the above structures A is O. In a further example, $R^6$ is $O^-X^+$ or $OR^8$, wherein $R^8$ and $X^+$ are defined as herein above. For example, $R^8$ is a member selected from H and a single negative charge.

In another embodiment, at least one of X, Q and Y includes F. In one example, at least one of X, Q and Y is CHF or $CF_2$. Exemplary compounds according to this example have a formula, which is a member selected from:

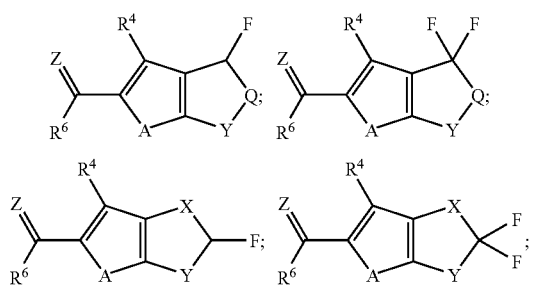

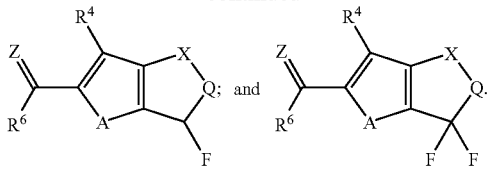

Other exemplary compounds according to this embodiment include:

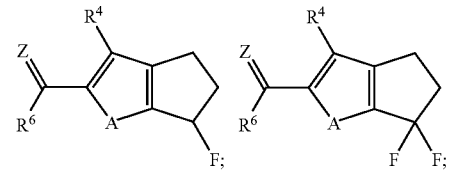

In another exemplary embodiment, the compound of the invention has a structure selected from:

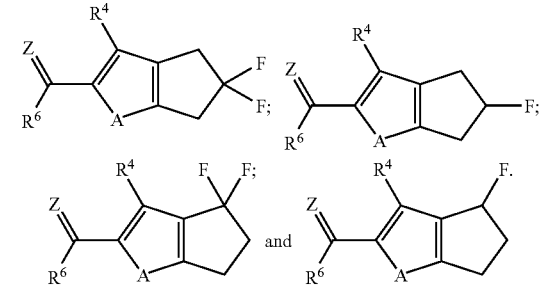

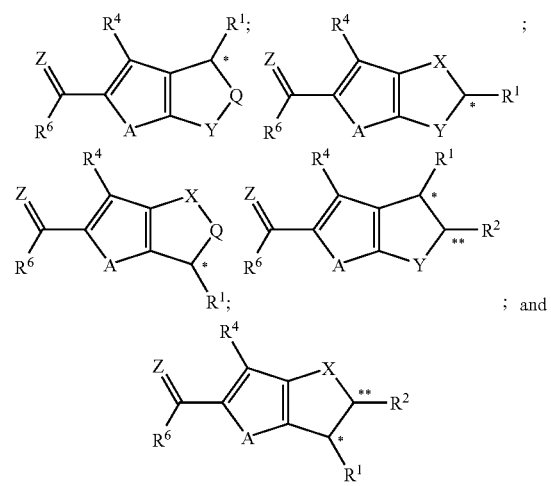

wherein Z, A, $R^4$, $R^6$, $R^1$ and $R^2$ are defined as for Formula (I). In the above structures, each stereocenter marked with an asterix "*" or "**" is independently either racemic or defined. In one example, the stereocenter marked with "*" has (R)-configuration. In another example, the stereocenter marked with "*" has (S)-configuration. $R^1$ and $R^2$, together with the atoms to which they are attached, are optionally joined to form a 3- to 7-membered ring.

In one embodiment $R^1$ and $R^2$ are joined to form a substituted or unsubstituted cyclopropane ring. Exemplary compounds according to this embodiment have a structure selected from the following formulae (VIIa), (VIIb), (VIIIa), and (VIIIb):

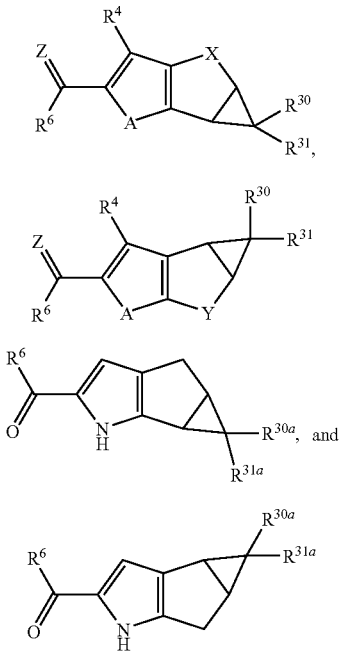

(VIIa)

(VIIb), (VIIIa)

(VIIIb)

wherein $R^{30}$ and $R^{31}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and wherein $R^{30a}$ and $R^{31a}$ are members independently selected from H, $C_1$ to $C_4$ alkyl, and

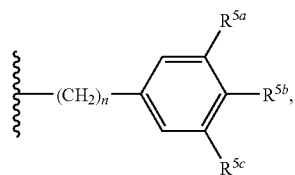

where n is an integer from 0 to 3; and $R^{5a}$, $R^{5b}$ and $R^{5c}$ are members independently selected from H, $C_1$ to $C_4$ alkyl, $C_1$ to $C_4$ alkyne, nitrile, Br, Cl, F, and $OR^{18a}$; and where $R^{18a}$ is a member selected from H and $C_1$ to $C_4$ alkyl; and where $R^6$ is a member selected from OH and $O^-X^+$, wherein $X^+$ is a cation. In various embodiments, n is an integer from 0 to 1 and two of $R^{5a}$, $R^{5b}$ and $R^{5c}$ are halogens selected independently from Cl and F.

Exemplary compounds include:

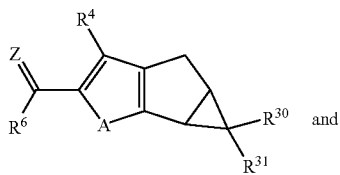
and

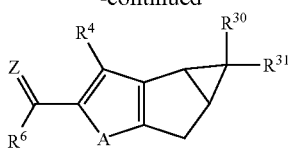

In one example, according to the above embodiments, at least one of $R^{30}$ and $R^{31}$ has the formula:

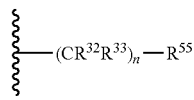

wherein n is an integer from 0 to 5. $R^{55}$ is a substituted or unsubstituted aromatic or non-aromatic ring. Exemplary embodiments described herein below for $R^{50}$ equally apply to $R^{55}$. In one example, $R^{55}$ is a member selected from substituted or unsubstituted aryl, substituted or unsubstituted heteroaryl, substituted or unsubstituted cycloalkyl and substituted or unsubstituted heterocycloalkyl. In one example, each $R^{32}$ and each $R^{33}$ is a member independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In another example, each $R^{32}$ and each $R^{33}$ is a member independently selected from H, substituted or unsubstituted alkyl and substituted or unsubstituted heteroalkyl. In one example, example, n is 1, 2 or 3. In another example, $(CR^{32}R^{33})_n$ is a member selected from unsubstituted methylene ($CH_2$), unsubstituted ethylene ($CH_2CH_2$) and unsubstituted n-propylene ($CH_2CH_2CH_2$). $R^{32}$ and $R^{33}$, together with the carbon atom to which they are attached, are optionally joined to form a 3- to 7-membered ring, which is optionally fused to $R^{55}$. In one example, the ring formed by $R^{32}$ and $R^{33}$ is a member selected from substituted or unsubstituted cycloalkyl and substituted or unsubstituted heterocycloalkyl.

In another example, according to the above embodiments, $R^{55}$ is an aromatic ring. In one example according to this embodiment, at least one of $R^{30}$ and $R^{31}$ has the formula:

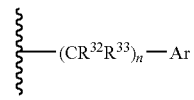

wherein Ar is a member selected from substituted or unsubstituted aryl and substituted or unsubstituted heteroaryl.

In yet another embodiment, the compound of the invention has the structure:

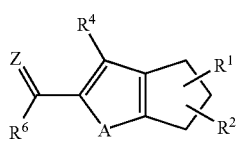

wherein Z, A, $R^4$, $R^6$, $R^1$ and $R^2$ are defined as herein above for Formula (I). In a preferred embodiment, at least one of $R^1$, $R^2$ and $R^4$ is other than H. In another preferred embodiment, at least one of $R^1$ and $R^2$ is other than H.

Exemplary compounds according to the above embodiment have a structure according to one of the following formulae:

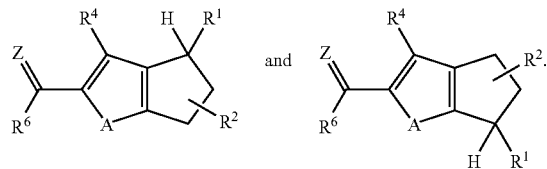

In one exemplary embodiment, the compound of the invention is chiral. Exemplary compounds according to this embodiment have a structure selected from:

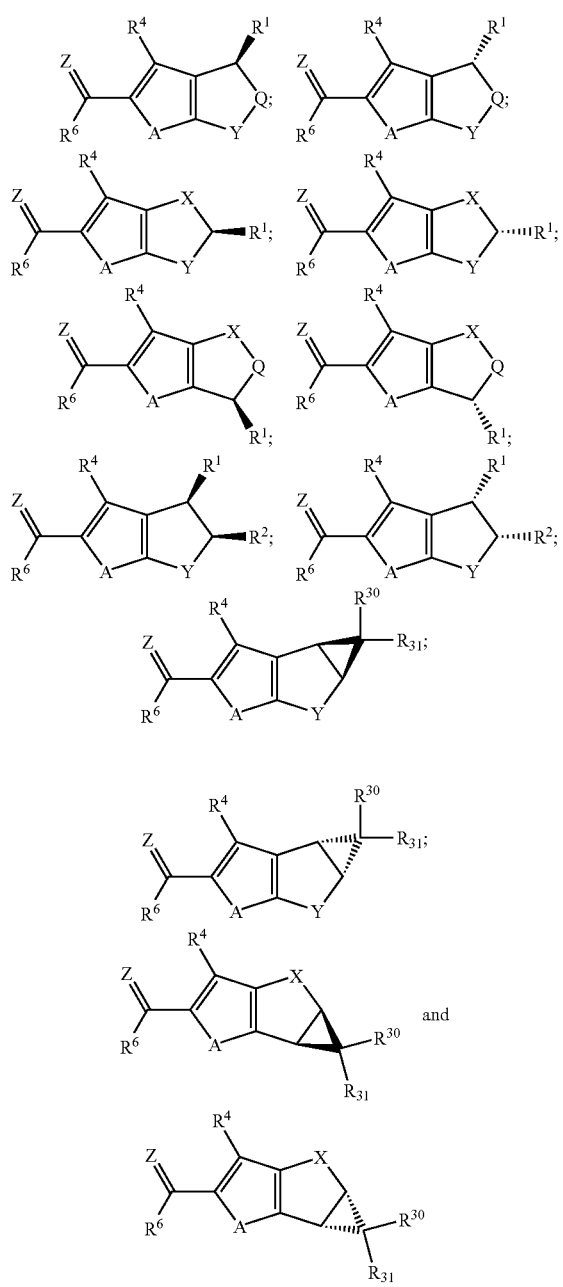

wherein Z, A, $R^4$, $R^6$, $R^1$ and $R^2$ are defined as herein above for Formula (I), with the proviso that $R^1$ is other than H. In the above structures, absolute stereochemistry is shown.

Exemplary compounds according to this embodiment include:

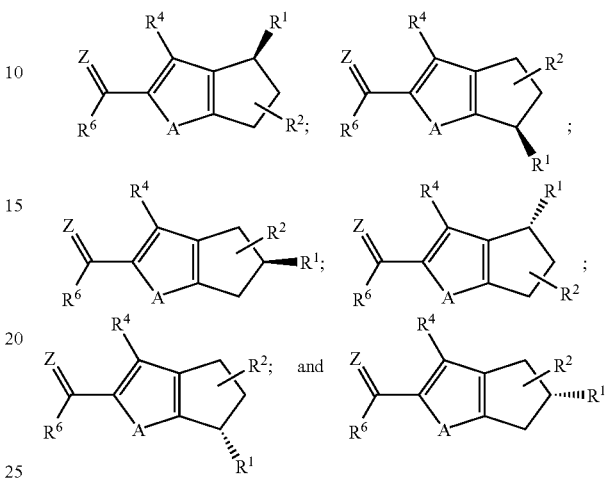

wherein absolute stereochemistry is shown. A person of skill in the art will understand that when $R^1$ and $R^2$ are the same and are both bound to the same carbon atom, the resulting compound is not chiral with respect to the shown stereocenter.

In another embodiment, the compound has a structure according to Formula (IVa), Formula (IVb), Formula (Va) or Formula (Vb):

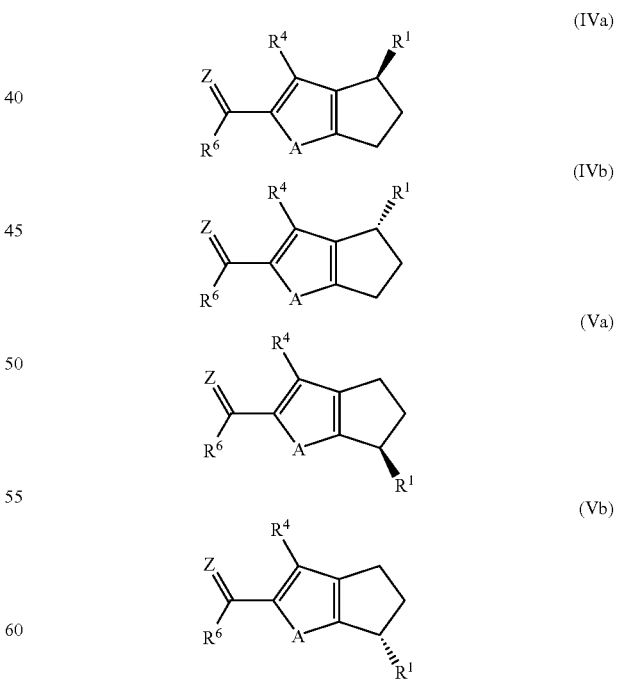

wherein absolute stereochemistry is shown. In the above structures, $R^1$ is defined as above with the proviso that $R^1$ is other than H. In one example, in Formula (IVa), Formula (IVb), Formula (Va) or Formula (Vb), $R^1$ is a member selected from $C_1$-$C_{10}$ substituted or unsubstituted alkyl. In another example, $R^1$ is a member selected from substituted or unsubstituted methyl, ethyl, n-propyl, iso-propyl, n-butyl and iso-butyl. In yet another example, $R^1$ is aryl-substituted or heteroaryl-substituted methyl, ethyl or propyl. In a particular example, $R^1$ is phenyl-substituted methyl, ethyl or propyl. In yet another example, in the above structures $R^4$ is H or F.

In yet another exemplary embodiment, the compound has a structure according to the following formulae:

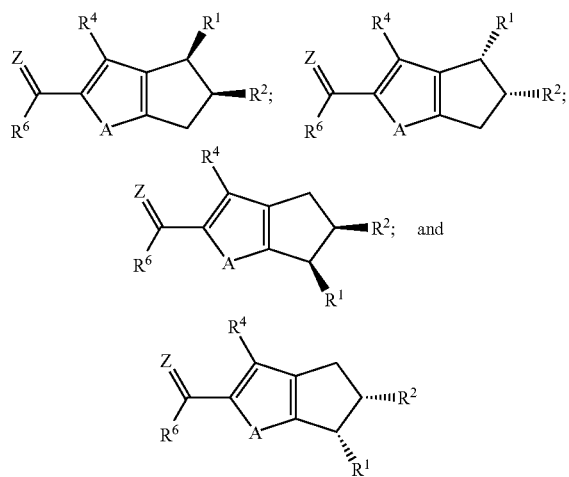

wherein absolute stereochemistry is shown. In the above structures, $R^1$ and $R^2$ are other than H. $R^1$ and $R^2$, together with the atoms to which they are attached, are optionally joined to form a 3- to 7-membered ring. In one example, $R^1$ and $R^2$ are joined to form a substituted or unsubstituted cyclopropane ring.

In one example according to any of the embodiments outlined herein above, at least one of $R^1$, $R^2$ and $R^3$ includes a ring or a fused ring system. In one embodiment, at least one of $R^1$, $R^2$ and $R^3$ has the formula:

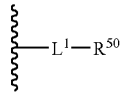

wherein $R^{50}$ is selected from a substituted or unsubstituted aromatic or non-aromatic ring. In one example, $R^{50}$ is a member selected from substituted or unsubstituted aryl, substituted or unsubstituted heteroaryl, substituted or unsubstituted cycloalkyl and substituted or unsubstituted heterocycloalkyl. Exemplary aromatic rings $R^{50}$ include substituted or unsubstituted phenyl, substituted or unsubstituted pyridines, substituted or unsubstituted pyrimidines, substituted or unsubstituted furanes, substituted or unsubstituted oxazoles, substituted or unsubstituted isoxazoles, substituted or unsubstituted thiazoles and substituted or unsubstituted isothiazoles. Exemplary non-aromatic rings $R^{50}$ include substituted or unsubstituted cyclohexanes, substituted or unsubstituted tetrahydro-2H-pyranes, substituted or unsubstituted morpholines, substituted or unsubstituted piperidines, substituted or unsubstituted N-alkyl-piperazines, substituted or unsubstituted cyclopentanes, substituted or unsubstituted pyrrolidines and substituted or unsubstituted oxazolidines.

$L^1$ is a linker moiety, which is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. In one example, $L^1$ is a member selected from substituted or unsubstituted alkyl and substituted or unsubstituted heteroalkyl. In another example, $L^1$ is a substituted or unsubstituted alkyl chain, wherein one or more carbon atoms are optionally replaced with a heteroatom or a functional group, forming e.g., ether, thioether, amines, amides, sulfonamides, sulfones carbonates, ureas or the like. In another example, $L^1$ is unsubstituted methylene, ethyl, n-propylene, n-butylene or n-propylene, optionally linked to the remainder of the molecule or the ring $R^{50}$ via a heteroatom or a functional group, e.g., via an ether, amine, carbonamide or sulfonamide group.

In another example according to any of the embodiments herein above, at least one of $R^1$, $R^2$ and $R^3$ has a formula, which is a member selected from:

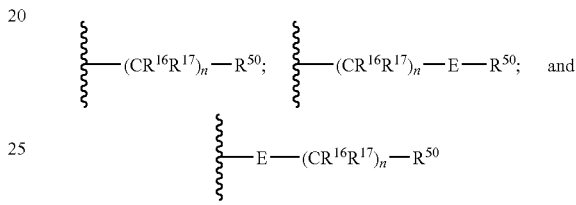

wherein n is an integer from 0 to 5. E is a heteroatom or a functional group, such as ether, thioether, carbonamide, sulfonamide, carbonate, urea and the like. In one example, E is a member selected from O, S, $NR^{43}$, $C(O)NR^{43}$, $NR^{43}C(O)$, $S(O)_2NR^{43}$ and $NR^{43}S(O)_2$, wherein $R^{43}$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl. Each $R^{16}$ and each $R^{17}$ is a member independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In one example, example, n is 1, 2 or 3. In a further example, $(CR^{16}R^{17})_n$ is a member selected from unsubstituted methylene ($CH_2$), unsubstituted ethylene ($CH_2CH_2$) and unsubstituted n-propylene ($CH_2CH_2CH_2$). In one example, $R^{16}$ and $R^{17}$ are both H. At least two of $R^{16}$ and $R^{17}$, together with the carbon atom to which they are attached, are optionally joined to form a 3- to 7-membered ring. In an exemplary embodiment, the ring is a member selected from substituted or unsubstituted cycloalkyl and substituted or unsubstituted heterocycloalkyl, and is optionally fused to $R^{50}$. In one example according to this embodiment, $R^{50}$ is selected from substituted or unsubstituted aryl and substituted or unsubstituted heteroaryl.

In yet another example according to the above embodiments, $R^{50}$ represents an aromatic ring or a fused ring system including an aromatic ring. In one embodiment, at least one of $R^1$, $R^2$ and $R^3$ has the formula:

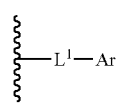

wherein Ar is a member selected from substituted or unsubstituted aryl, substituted or unsubstituted heteroaryl and a fused ring system, wherein the fused ring system includes at least one aromatic ring. $L^1$ is defined herein above. In one example according to any of the above embodiments, Q is $CHR^1$ or $CFR^1$, wherein $R^1$ represents a small substituent, such as H, F, Cl or methyl and one of X and Y is $CHR^2$ or $NR^3$, wherein a member selected from $R^2$ and $R^3$ includes the aromatic moiety.

In an exemplary embodiment, Ar is a phenyl ring and has the formula:

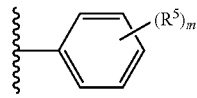

wherein m is an integer from 0 to 5. Each $R^5$ is a member independently selected from aryl group substituents. In an exemplary embodiment, each $R^5$ is a member independently selected from H, halogen, CN, halogen substituted alkyl (e.g., $CF_3$), hydroxy, alkoxy (e.g., methoxy and ethoxy), acyl (e.g., acetyl), $CO_2R^{18}$, $OC(O)R^{18}$, $NR^{18}R^{19}$, $C(O)NR^{18}R^{19}$, $NR^{18}C(O)R^{20}$, $NR^{18}SO_2R^{20}$, $S(O)_2R^{20}$, $S(O)R^{20}$, substituted or unsubstituted alkyl (e.g., methyl, ethyl, propyl or butyl), substituted or unsubstituted heteroalkyl, substituted or unsubstituted aryl, substituted or unsubstituted heteroaryl and substituted or unsubstituted heterocycloalkyl, wherein adjacent $R^5$ are optionally joined to form a ring, such as substituted or unsubstituted cycloalkyl, substituted or unsubstituted heterocycloalkyl, substituted or unsubstituted aryl and substituted or unsubstituted heteroaryl.

$R^{18}$ and $R^{19}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{20}$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. $R^{18}$ and a member selected from $R^{19}$ and $R^{20}$, together with the atoms to which they are attached, are optionally joined to form a 5- to 7-membered ring.

Exemplary compounds according to the above embodiments include:

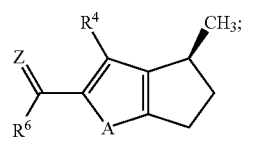
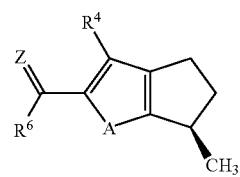

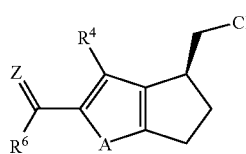
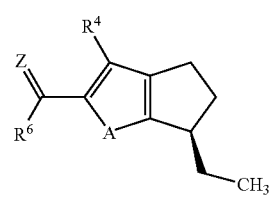

-continued

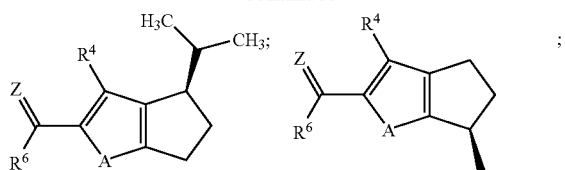

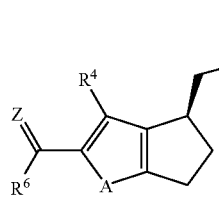

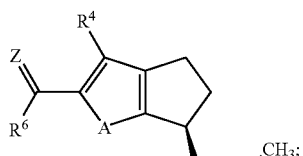

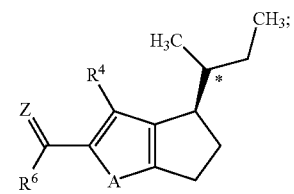

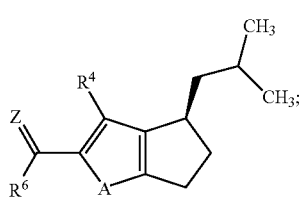

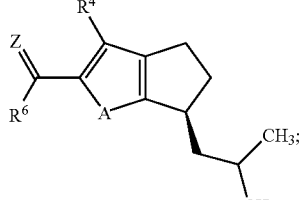

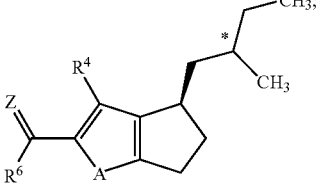

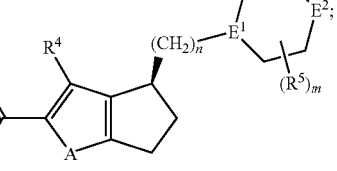

-continued

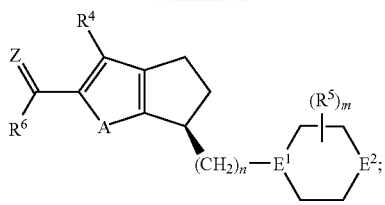

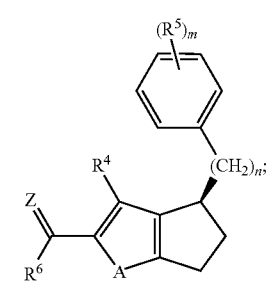

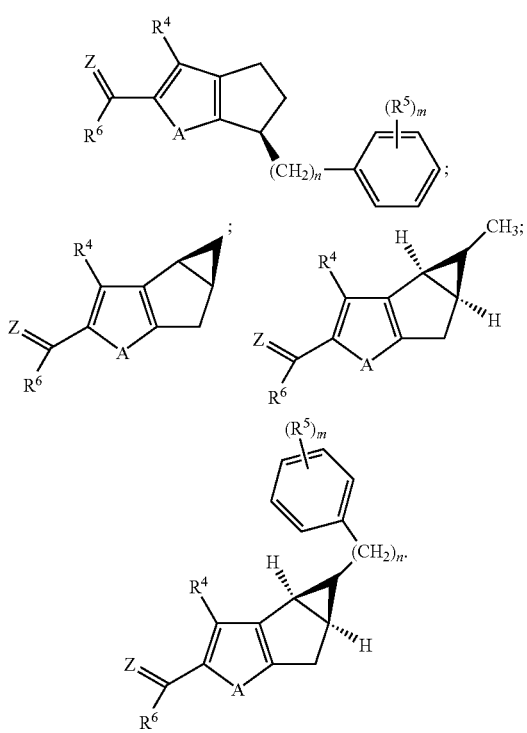

wherein m is an integer selected from 0 to 5 and n is an integer selected from 0 to 5. In one example, n is 1. In another example, n is 2. $E^1$ is selected from CH and N. $E^2$ is a member selected from $CH_2$, O and $NR^{51}$, wherein $R^{51}$ is a member selected from substituted or unsubstituted alkyl, e.g., methyl or ethyl. In one example, A is NH. In another example, A is S. In yet another example, A is O. In a further example, Z is O. In a particular example, Z is O, and A is NH or S and $R^6$ is $OR^8$ or $O^-X^+$.

In one example, according to any of the above embodiments, e.g., in Formulae (I) to (V), the compound of the invention is a pyrrole analog, in which A is $NR^7$. In one example the compound of the invention has a structure according to Formula (III):

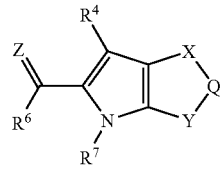

wherein Z, $R^4$, $R^6$ and $R^7$ are defined as for Formula (I), above. Exemplary embodiments outlined herein above for Formulae (I) and (II) equally apply to Formula (III). In one embodiment in Formula (III), $R^4$ is H. In another embodiment, Z is O. In yet another embodiment, $R^6$ is $OR^8$ or $O^-X^+$. In one example in Formula (III), X, Q and Y are members independently selected from O, S, $NR^3$, $CR^1R^2$, $C=CR^{40}R^{41}$, C=O, C=S and $C=NR^3$, wherein $R^1$, $R^2$, $R^3$, $R^{40}$ and $R^{41}$ are defined as for Formula (I), above. In one example, in Formula (III), X, Q and Y are members independently selected from $CR^1R^2$, $C=CR^{40}R^{41}$, C=O and C=S. In one example according to any of the above embodiments, $R^7$ is H. In another example according to any of the above embodiments, Z is O.

In one example according to any of the above embodiments, $R^7$ is H. Exemplary fused pyrroles have the structure:

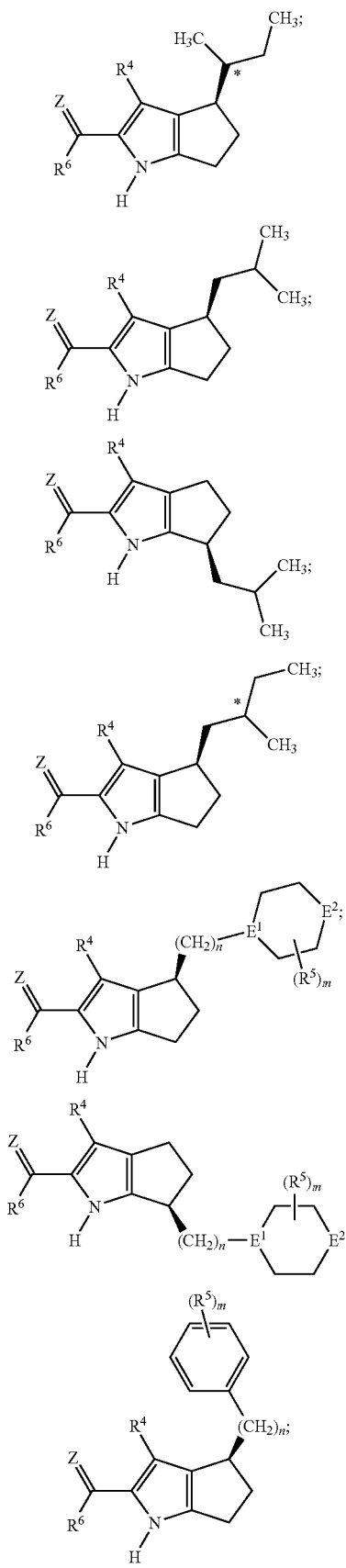

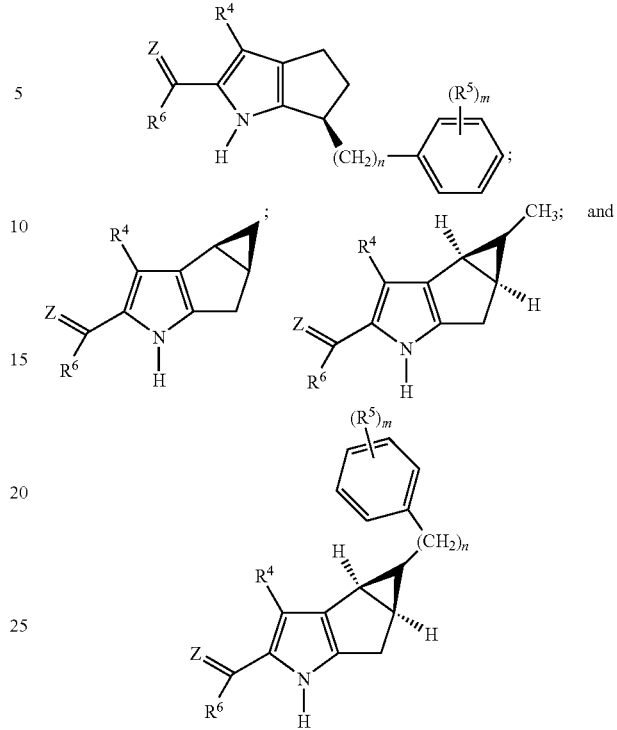

wherein absolute stereochemistry is shown. In the above structures, m and n are integers independently selected from 0 to 5. In one example, n is 1. In another example, n is 2. $R^5$ is defined as above. $E^1$ is selected from CH and N. $E^2$ is a member selected from $CH_2$, O and $NR^{51}$, wherein $R^{51}$ is a member selected from substituted or unsubstituted alkyl, e.g., methyl or ethyl. In a preferred embodiment in the above structures, Z is O.

Other exemplary compounds include:

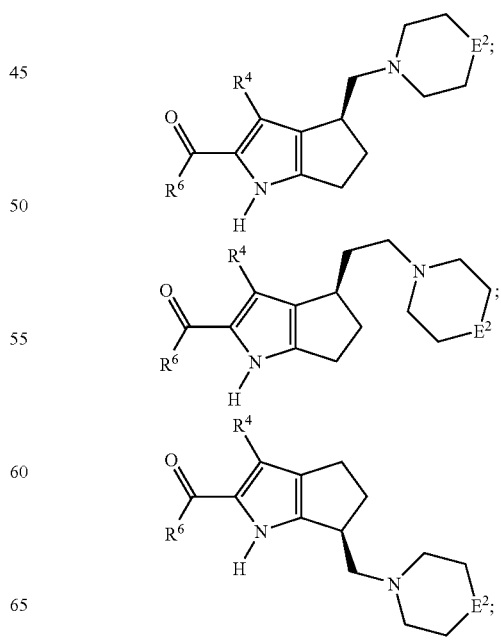

-continued

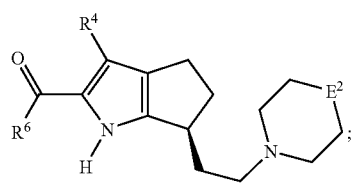

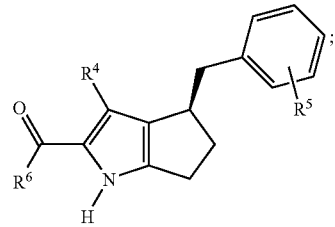

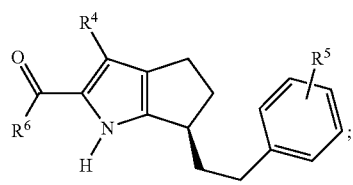

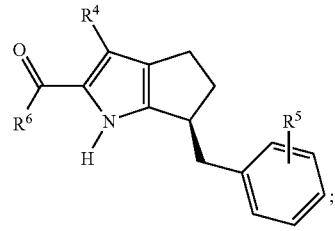

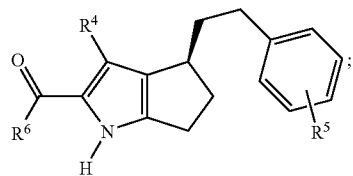

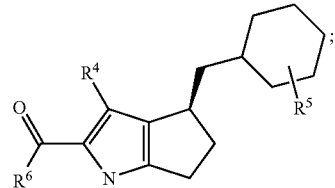

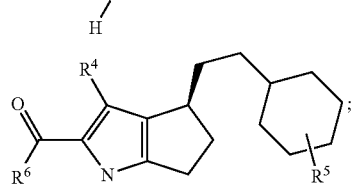

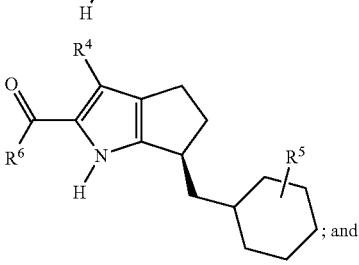

-continued

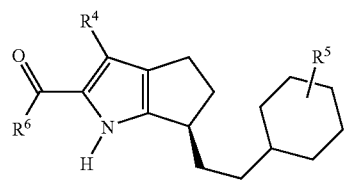

wherein absolute stereochemistry is shown. In one example, according to the above structures, $R^6$ is $OR^8$ or $O^-X^+$. In a preferred embodiment, $R^8$ is a member selected from H and a single negative charge. $X^+$ is a cation (salt counterion), such as $Na^+$, $K^+$ or another pharmaceutically acceptable organic or inorganic salt. In another example according to the above structures, $R^4$ is selected from H and F.

In one example according to any of the above embodiments, e.g., in Formulae (I) to (V), Z is O. In another example according to any of the above embodiments, e.g. in Formulae (I) to (VIII), $R^6$ is $OR^8$ or $O^-X^+$. In a preferred embodiment, $R^8$ is a member selected from H and a single negative charge. $X^+$ is a cation (salt counterion), for example, $Na^+$, $K^+$ or another pharmaceutically acceptable organic or inorganic cation. In yet another example, according to any of the above embodiments, $R^4$ is H or F.

In yet another example according to any of the above embodiments, Z is O and $R^6$ is $OR^8$ or $O^-X^+$, wherein $R^8$ is a member selected from H and a single negative charge.

Exemplary compounds according to this embodiment include:

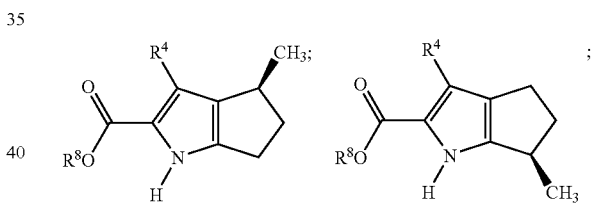

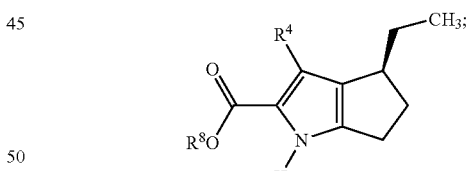

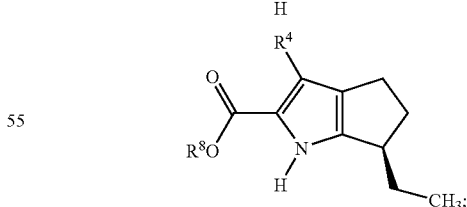

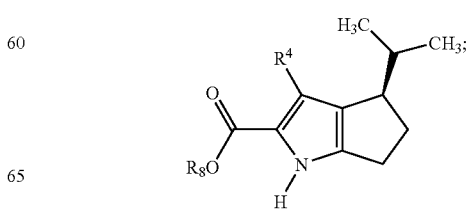

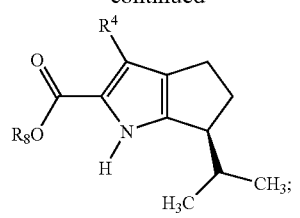
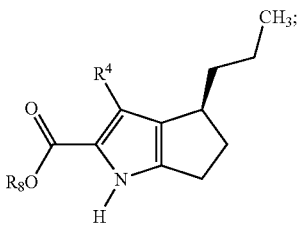
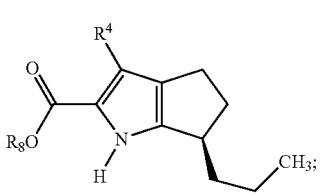
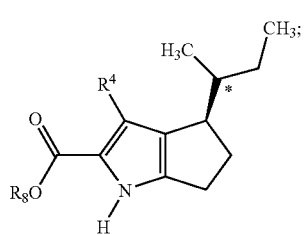
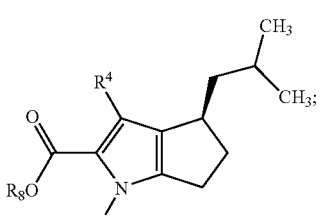
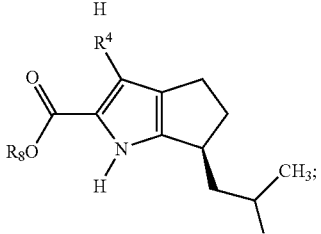
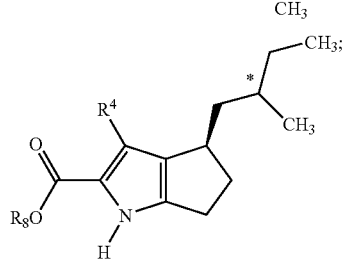
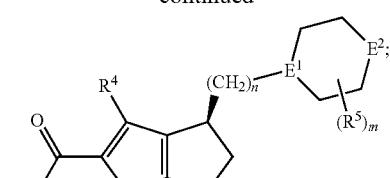
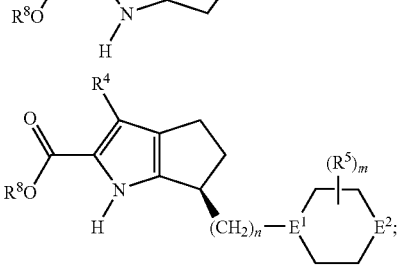
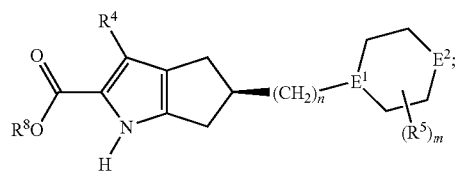
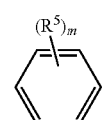
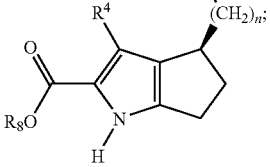
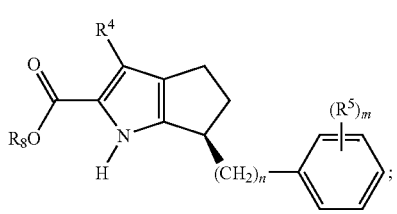
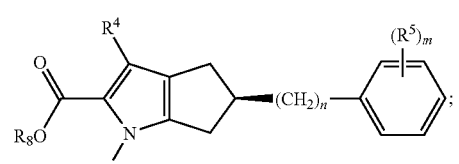
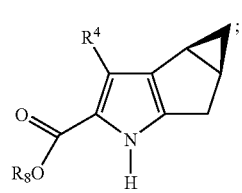

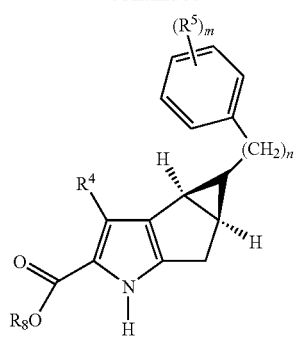
wherein absolute stereochemistry is shown. In one example, according to the above structures, R⁴ is H.
Other exemplary compounds of the invention include:
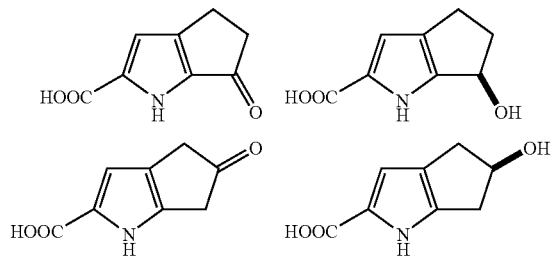
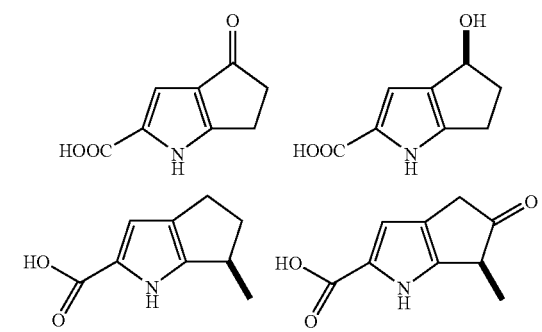
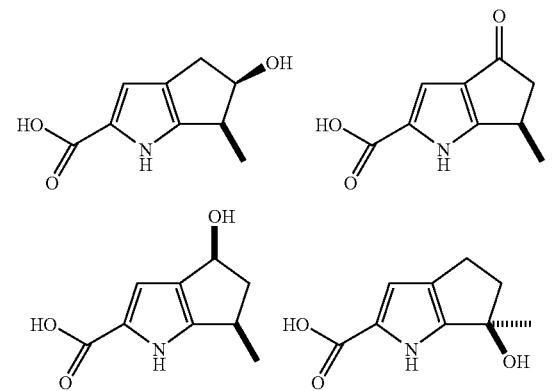
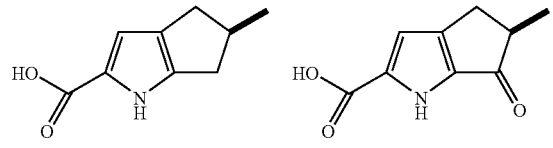
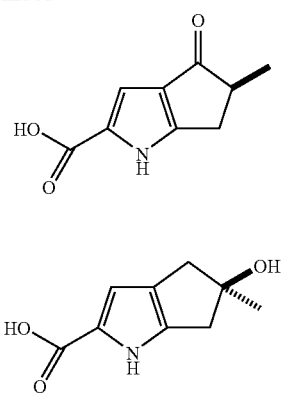

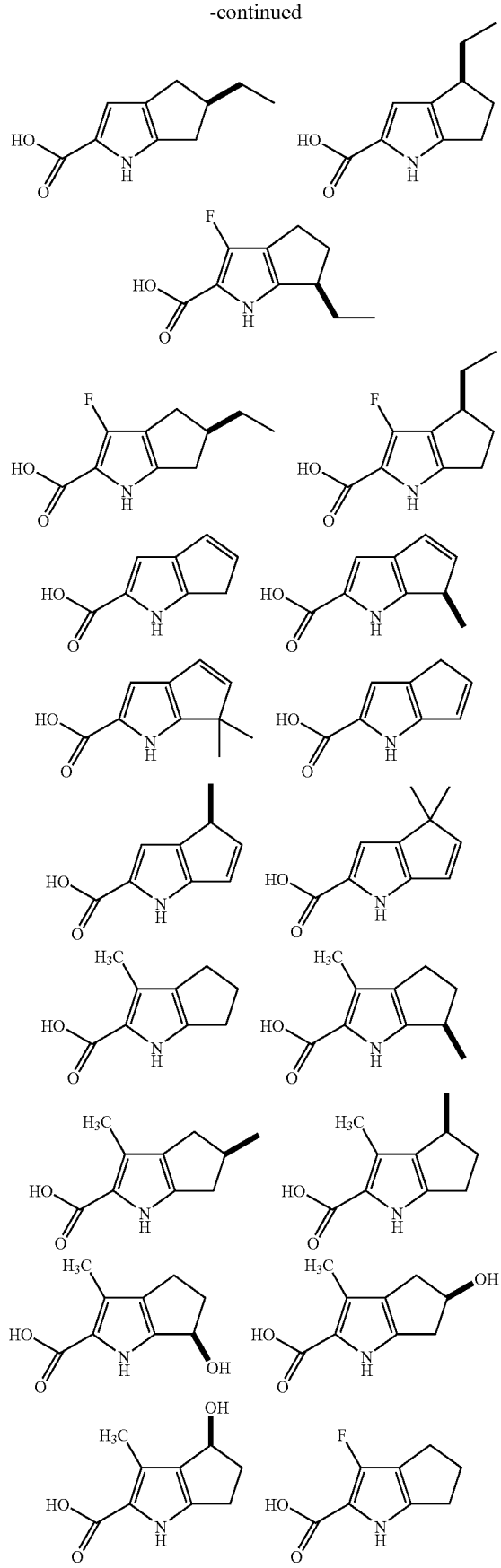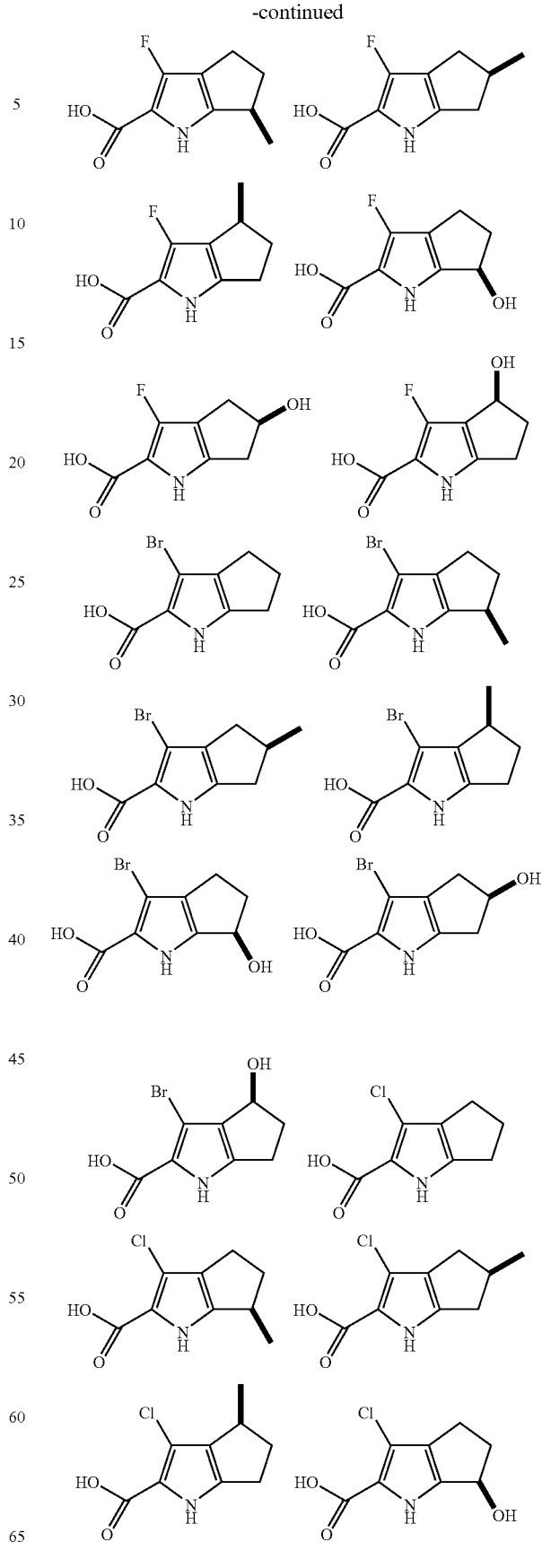

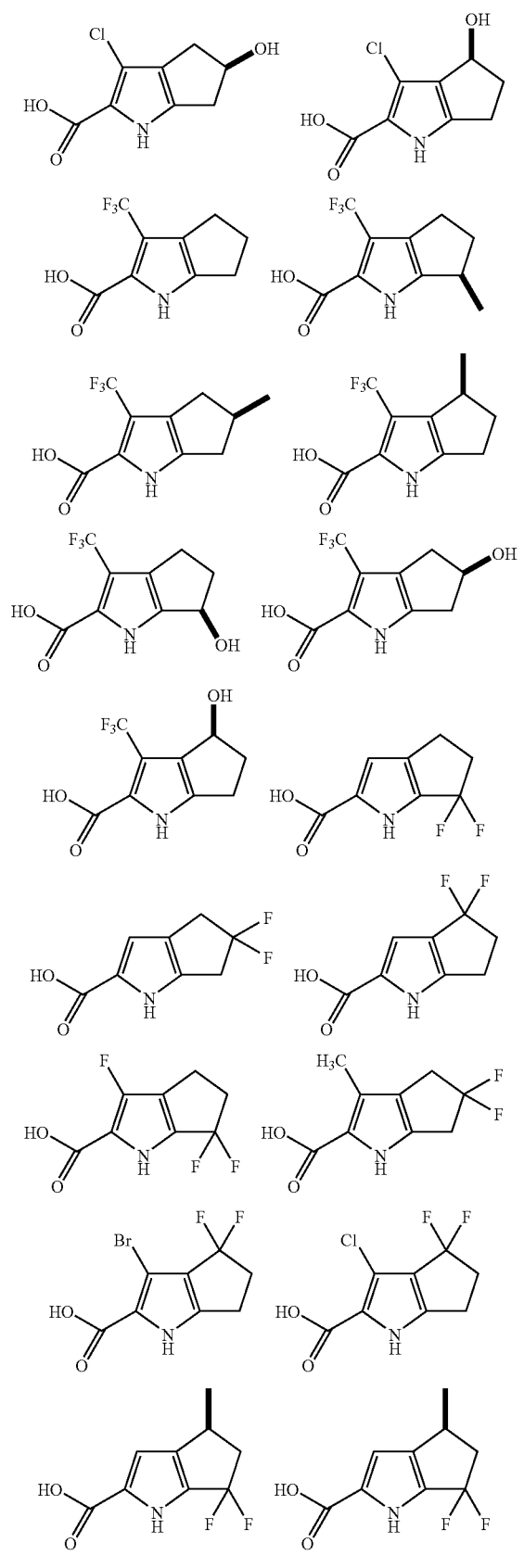
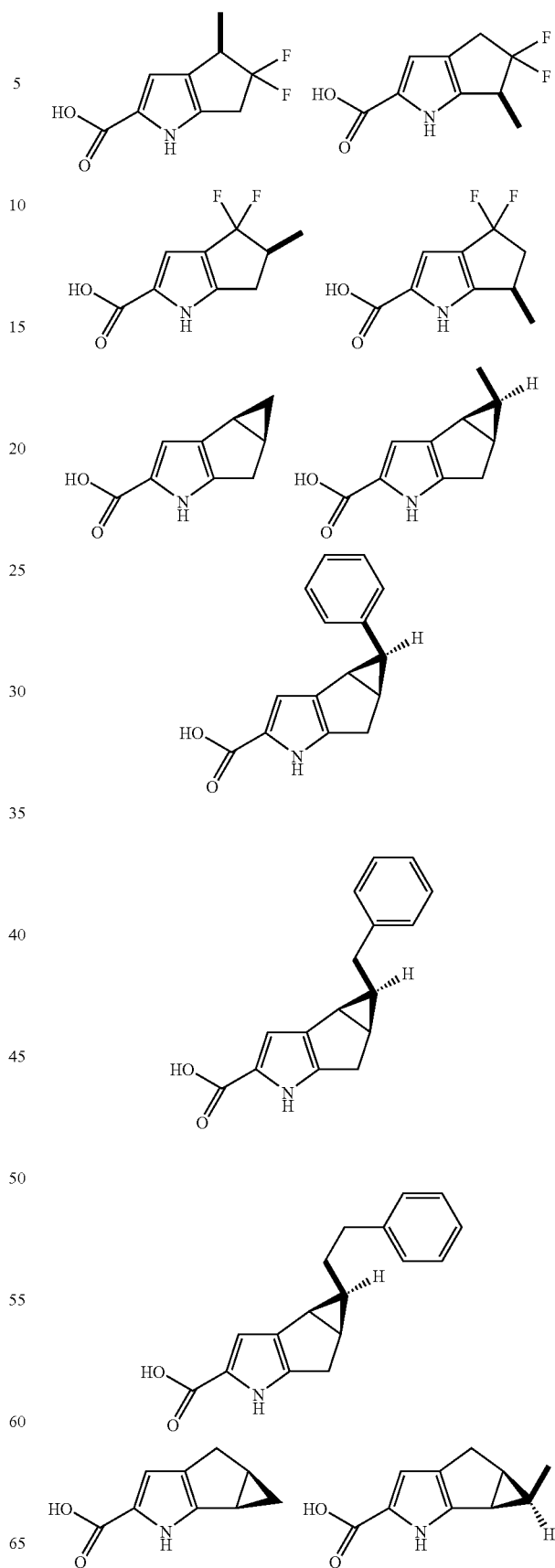

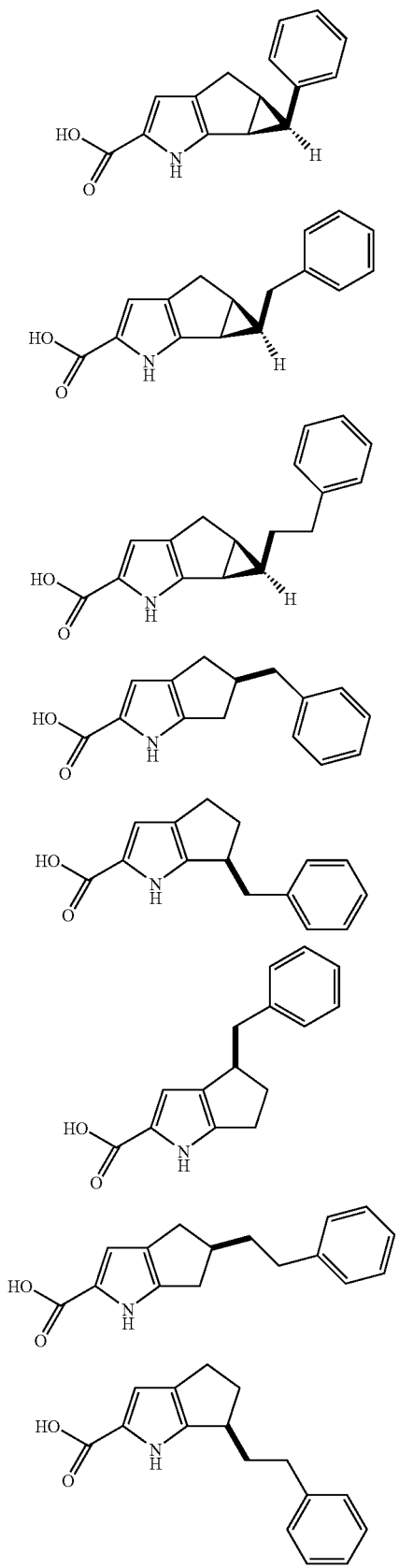
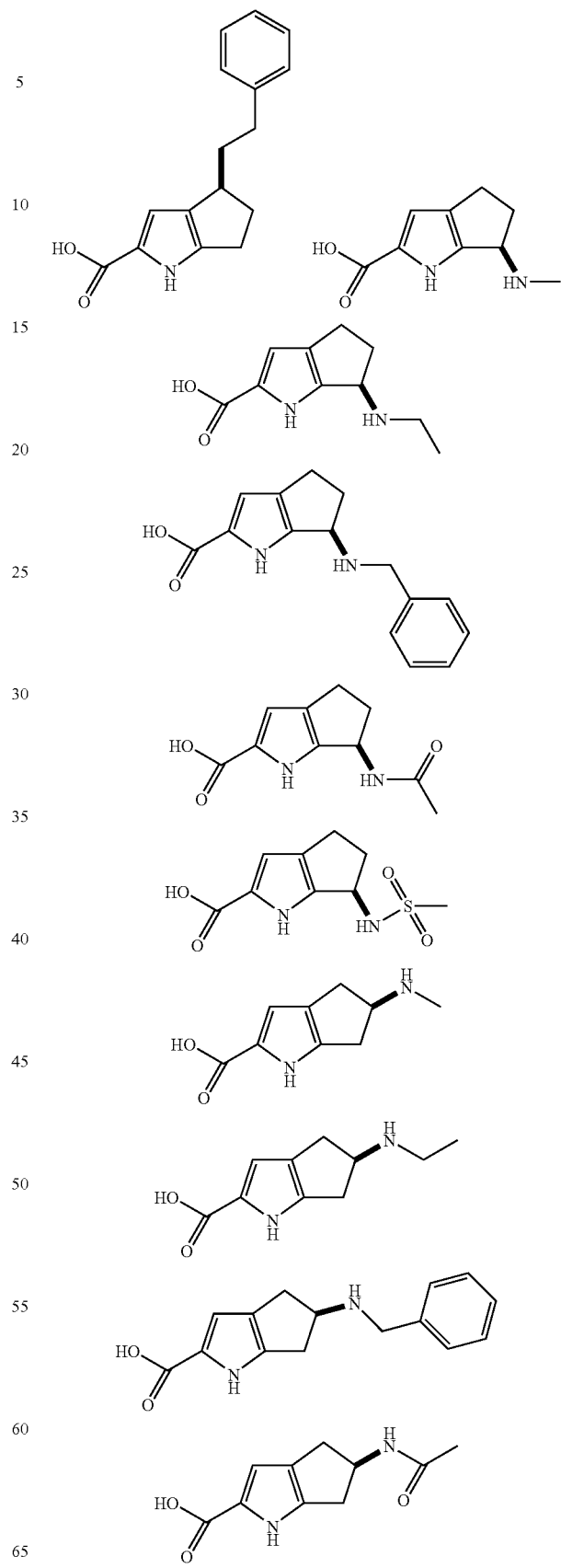

51
-continued
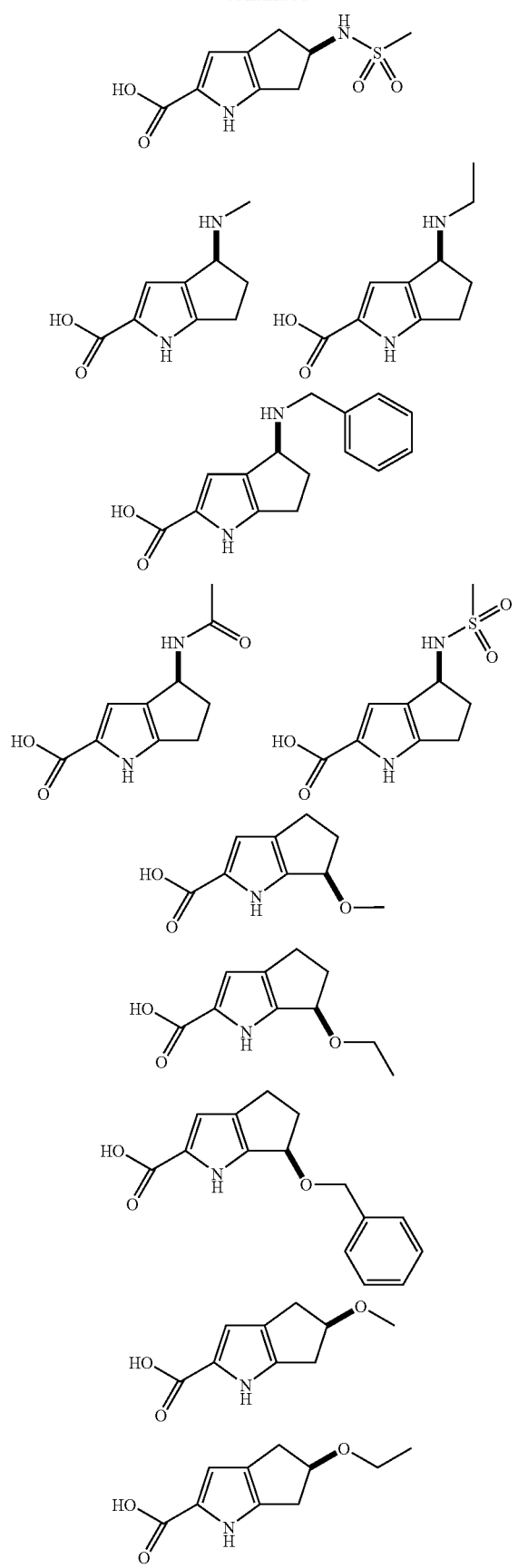
52
-continued
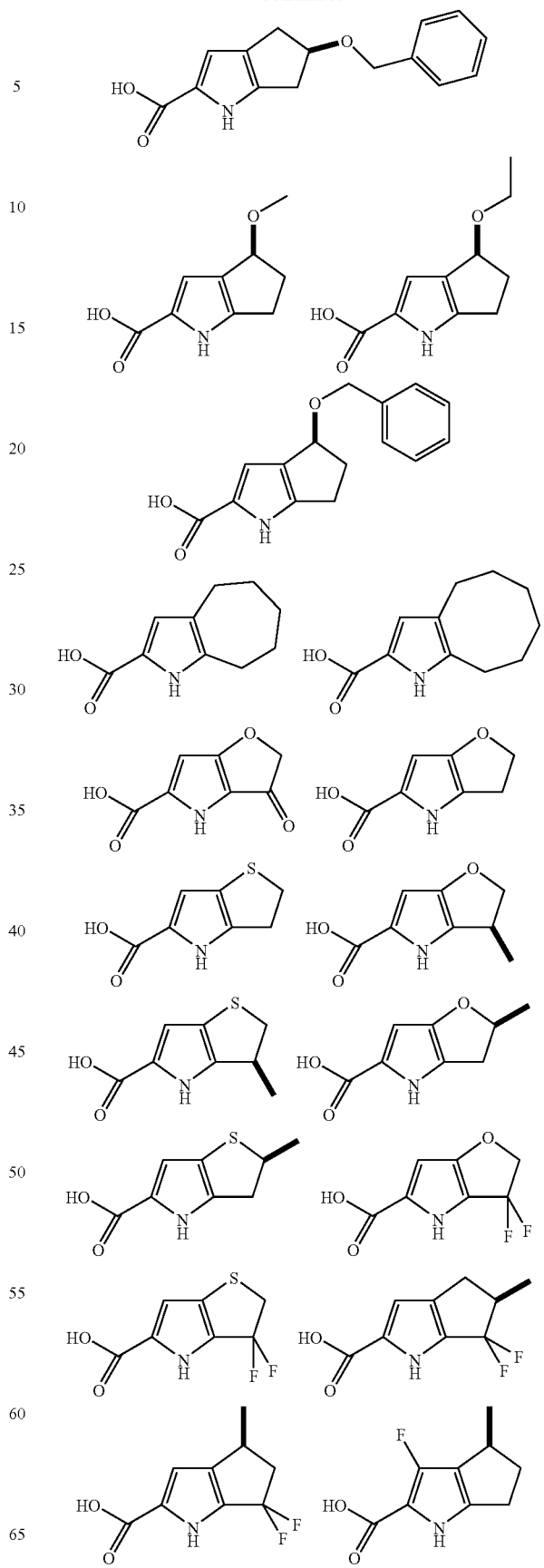

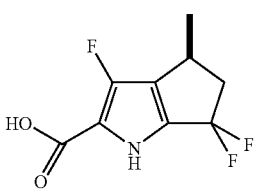

wherein relative stereochemistry is shown. A person of skill in the art will appreciate that the carboxylic acid group of the above compounds can optionally be deprotonated or the compounds can be present as a salt form, wherein the hydrogen of the carboxylic acid group is replaced with a cation (salt counterion).

In another exemplary embodiment, X and Y, together with the atoms to which they are attached, are optionally joined to form a 5- to 7-membered ring. In this case a bicyclic substructure is formed, which can optionally be further substituted. Exemplary compounds according to this embodiment include:

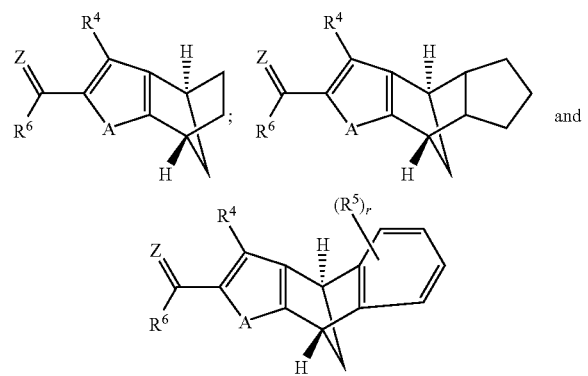

wherein r is a member selected from 0 to 4. Relative stereochemistry is shown.

In yet another exemplary embodiment, at least one of X, Y and Q is C=O or CHOH. Exemplary compounds include:

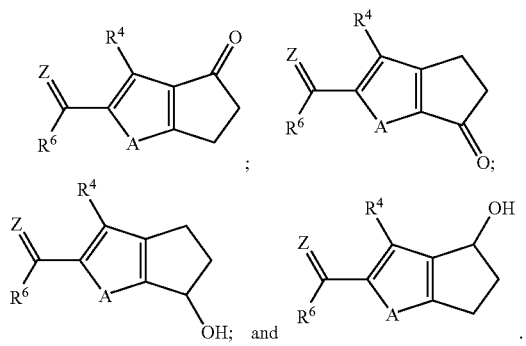

In another example, according to any of the above embodiments, e.g., in Formulae (I) to (VIII), the compound of the invention is a thiophene or furan analog, in which A is S or O. In one example the compound of the invention has a structure according to the formulae:

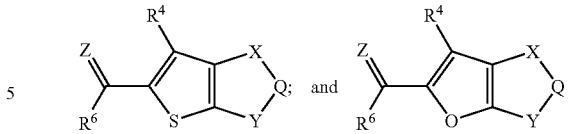

wherein Z, $R^6$ and $R^4$ are defined as for Formula (I), above. In one embodiment, $R^4$ is H. In another embodiment, Z is O. In yet another embodiment, $R^6$ is $OR^8$ or $O^-X^+$. X, Q and Y are members independently selected from O, S, $NR^3$, $CR^1R^2$, $C=CR^{40}R^{41}$, C=O, C=S and $C=NR^3$. In one example, in the above structures, at least one of X, Q and Y is other than —$CH_2$—. In another example, in the above structures Z, $R^6$ and $R^4$, X, Q and Y are defined as for Formula (VI). In yet another example, in the above structures Y is not C=O.

B. Synthesis

The compounds of the present invention, including compounds of Formula (I) to Formula (V), can be prepared by methods known in the art. One of ordinary skill in the art will know how to modify procedures to obtain the analogs of the present invention. Suitable procedures are described e.g., in *Helvetica Chimica Acta* 1995, 78: 109-121; *Journal of the Chemical Society, Perkin Transactions* 1: *Organic and Bio-Organic Chemistry* (1972-1999) 1989: 1369-1373; *Organic Preparations and Procedures International* 1997, 29: 471-473; *Journal of Medicinal Chemistry* 1998, 41: 808-820; *Chemische Berichte* 1975, 108: 2161-2170; *Bulletin de la Societe Chimique de France* 1974: 1147-1150; *Science of Synthesis* 2002, 9: 441-552; *Canadian Journal of Chemistry* 1971, 49: 3544-3564; *Tetrahedron Letters* 1999, 40: 6117-6120; *Journal of the American Chemical Society* 1968, 90: 6877-6879; *Journal of Organic Chemistry* 1987, 52: 5395-5400; *Journal of the Chemical Society, Perkin Transactions* 1: *Organic and Bio-Organic Chemistry* 1995: 1131-1136; *Tetrahedron Letters* 1993, 34: 6603-6606; *Tetrahedron Letters* 1968: 1317-1319; *Journal fuer Praktische Chemie* (Leipzig) 1972, 314: 353-364; *Journal of the Chemical Society, Perkin Transactions* 1: *Organic and Bio-Organic Chemistry* (1972-1999) 1974: 490-501; *Energy & Fuels* 1990, 4: 668-674; *Journal of Organic Chemistry* 1992, 57: 4809-4820; *Tetrahedron* 1993, 49: 4159-4172; *Energy & Fuels* 1993, 7: 172-178; *Journal of the Chemical Society, Perkin Transactions* 1: *Organic and Bio-Organic Chemistry* (1972-1999) 1984: 111-118; *Journal of the American Chemical Society* 1992, 114: 9859-9869; *Journal of Organic Chemistry* 1987, 52: 5364-5374; *Journal of Organic Chemistry* 1987, 52: 3986-3993; *Water Science and Technology* 1996, 33: 9-15; *Liebigs Annalen der Chemie* 1980: 564-589; *Journal of Heterocyclic Chemistry* 1993, 30: 477-482; *Khimiya Geterotsiklicheskikh Soedinenii* 1972: 342-344; *Journal of Organic Chemistry* 1983, 48: 4779-4781; *Ann.* 1935, 517: 152-169; *Tetrahedron Letters* 1985, 26: 1839-1842; *Angew Chem, Int Ed Engl* 1993, 32: 1051-1052 (See also *Angew Chem*, 1993, 1105(1057), 1116-1117); *Youji Huaxue* 1997, 17: 524-528; *Tetrahedron Letters* 2003, 44: 7253-7256; WO/9940913; WO/9948868; U.S. Pat. No. 4,587,258; WO/8600896; CN/94-107461 (1106386); and DE/84-3431541; each of which is incorporated herein by reference in its entirety. Pure enantiomers of chiral compounds can also be obtained by chiral separation methods known in the art, such as chiral HPLC. In addition, compounds can be prepared using the methods described herein below in Schemes 1 through 18 and Examples 1 through 5 or modified versions thereof.

Synthesis of Fused Analogs

In an exemplary embodiment, fused pyrrole analogs of the invention are prepared using procedures outlined in Schemes 1 through Scheme 18, below. Esters in these examples can be hydrolyzed using standard ester hydrolysis conditions such as those described in General Procedure 7.

In one example, compounds of the invention are prepared using the procedures outlined in *Org. Preparations and Procedures International,* 1997, 29: 471-473 and references cited therein. For example, compounds of the invention are synthesized according to a procedure outlined in Scheme 1, below.

Scheme 1: Synthesis of Core Scaffold

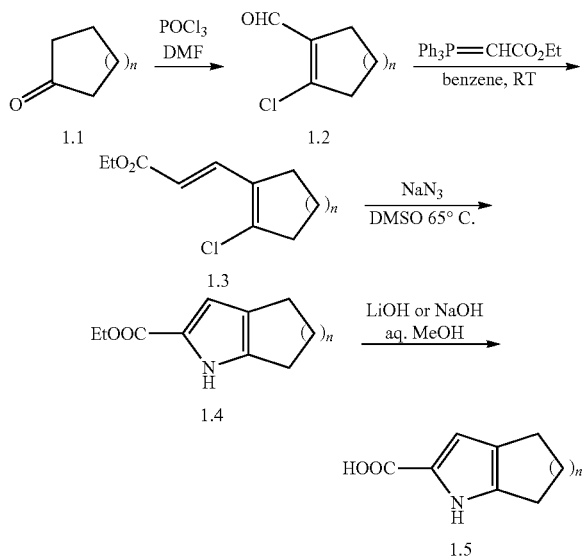

n = 1, 2, 3, 4,

In Scheme 1, chloroformylation of a cyclic ketone such as 1.1, with a reagent such as phosphoryl trichloride in DMF, provides a β-chlorovinyl aldehyde such as 1.2. Olefination of the resulting aldehyde with an olefination reagent such as (carbethoxymethylene)-triphenylphosphorane provides an acrylic acid ester such as 1.3. Cyclization of the acrylic acid ester 1.3 with sodium azide in DMSO provides the cyclized ester 1.4. Hydrolysis of the ester under standard conditions (e.g., aqueous, alcoholic lithium hydroxide or sodium hydroxide) provides the desired acid, such as 1.5.

In another example, compounds of the invention are prepared using the procedures outlined in *J.C.S. Perkins Trans.* 1, 1989, 8: 1369-1373; *J. Org. Chem.,* 1965, 30: 1126-1129; and WO 99/40913 and references cited within. For example, compounds of the invention are synthesized according to a procedure outlined in Scheme 2, below.

Scheme 2: Synthesis of Core Scaffold

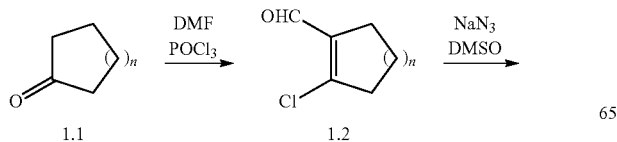

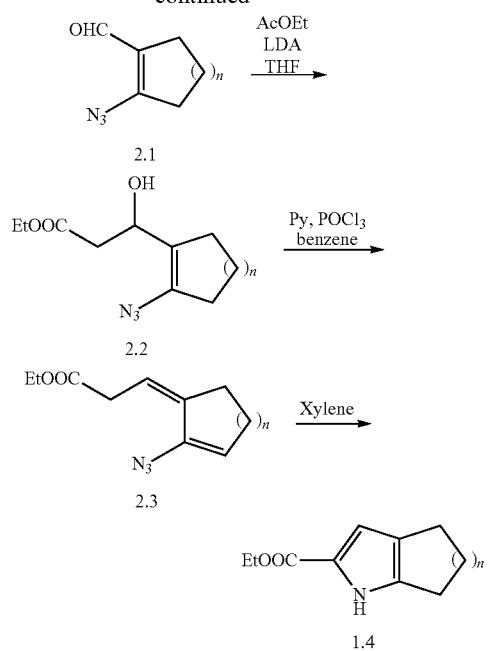

n = 1, 2, 3, 4,

In Scheme 2, chloroformylation of a cyclic ketone such as 1.1 with phosphoryl trichloride in DMF provides a β-chlorovinyl aldehyde, such as 1.2. Treatment of the β-chlorovinyl aldehyde with sodium azide in DMSO provides the corresponding 2-azido cycloalkene 1-carbaldehyde 2.1. Aldol condensation with ethyl acetate provides alcohol 2.2. Dehydration, with phosphoryl trichloride in pyridine provides 2.3, which undergoes thermal cyclization in xylene to provide analog 1.4, which can be hydrolized to the corresponding acid as described herein.

In another example, compounds of the invention are prepared using the procedures outlined in *Tetrahedron Lett.,* 1985, 26: 1839-1842; *Tetrahedron Lett.,* 1968, 11: 1317-1319; and U.S. Pat. No. 5,550,255 as well as references cited therein. For example, compounds of the invention are synthesized according to a procedure outlined in Scheme 3, below.

Scheme 3: Synthesis of Core Scaffold

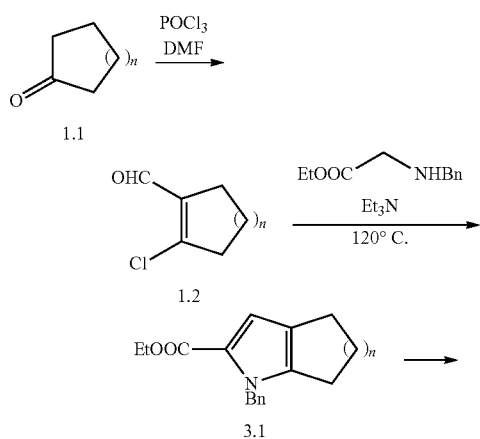

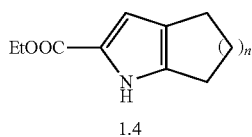

1.4

In Scheme 3, chloroformylation of a cyclic ketone such as 1.1 with phosphoryl trichloride in DMF provides a β-chlorovinyl aldehyde, such as 1.2. Condensation with a protected glycine ester, such as N-benzylglycine ethyl ester, followed by cyclization provides a protected pyrrole, such as 3.1. Subsequent deprotection of the pyrrole nitrogen provides analog 1.4, which can be hydrolized to the corresponding acid 1.5 as described herein.

In another example, compounds of the invention are prepared using the procedures outlined in WO 86/00896 to Gold, Neustadt, and Smith. For example, compounds of the invention are synthesized according to a procedure outlined in Scheme 4, below.

Scheme 4: Synthesis of Core Scaffold

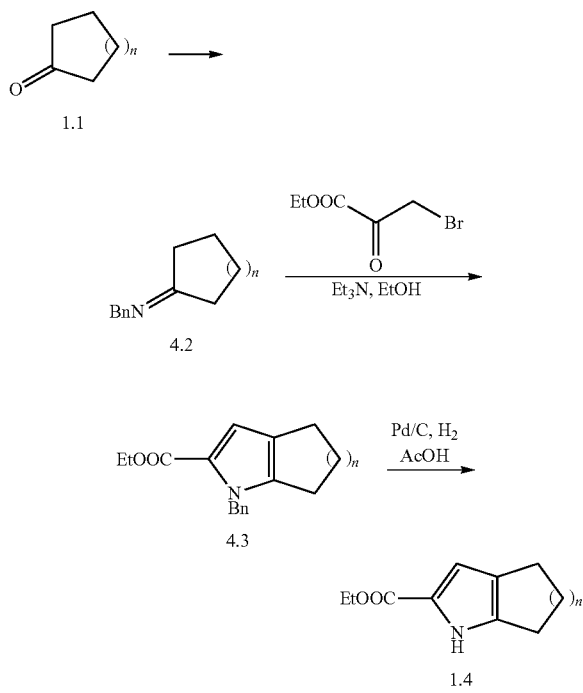

In Scheme 4, condensation of an alkyl amine (e.g., benzylamine) with a cyclic ketone (e.g., 1.1) provides the corresponding cycloalkylimine 4.2. Reaction with a halopyruvate ester (e.g., ethyl bromopyruvate) provides the cyclized product 4.3. The protecting group derived from the alkyl amine can be removed to provide the deprotected pyrrole (e.g., ester 1.4.). Suitable protecting groups for amines, such as aromatic amines, and corresponding methods for deprotection are know to those of skill in the art. For example, as shown in Scheme 4, N-benzyl pyrroles (e.g., 4.3.) can be deprotected using hydrogenation conditions. The ester group of compound 1.4. can be deprotected using hydrolysis conditions described herein.

Exemplary cyclic ketones in Schemes 1 to 4 include:

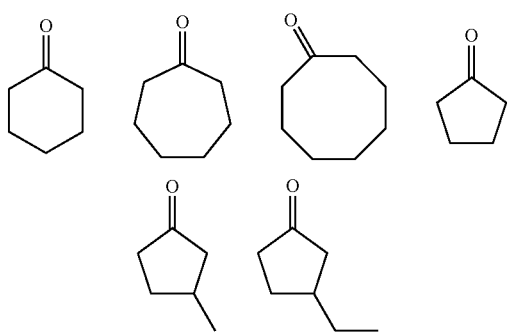

In another example, compounds of the invention are prepared using the procedures outlined in *J. Chem. Soc., Perkins Trans.* 1, 1984, 1: 111-118, and references cited therein. In one example, compounds of the invention are synthesized according to a procedure outlined in Scheme 5, below.

Scheme 5: Synthesis of Compounds including $R^4$

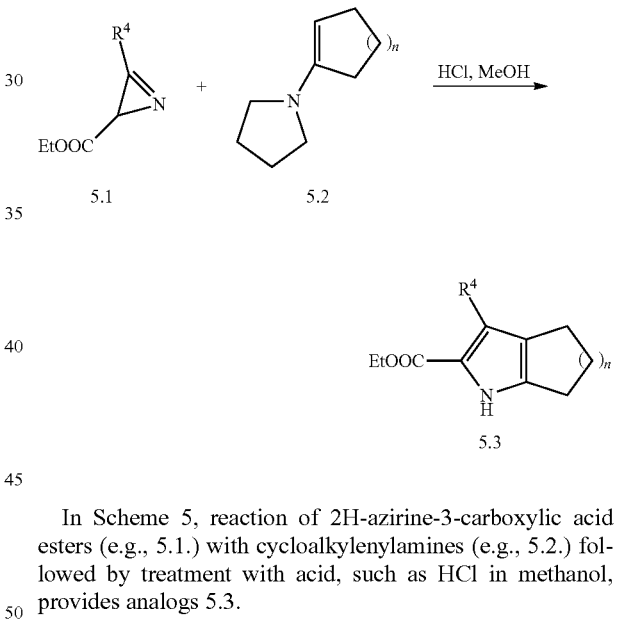

In Scheme 5, reaction of 2H-azirine-3-carboxylic acid esters (e.g., 5.1.) with cycloalkylenylamines (e.g., 5.2.) followed by treatment with acid, such as HCl in methanol, provides analogs 5.3.

In another example, compounds of the invention are prepared using the procedures outlined in *J. Heterocyclic Chem.* 1993, 30: 477-482; *Energy & Fuels* 1993, 7: 172-178; and *Synthesis* 2005: 1569-1571 and references cited therein. In one example, compounds of the invention are synthesized according to a procedure outlined in Scheme 6, below.

Scheme 6: Synthesis of Scaffold 6.4

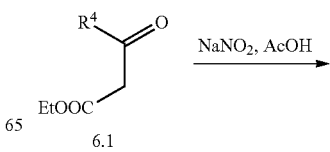

-continued

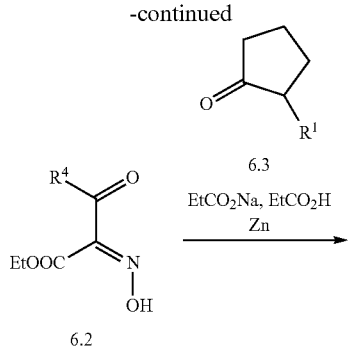

In Scheme 6, reaction of oxime 6.2 (e.g., derived from β-keto ester 6.1), with a cyclic ketone (e.g., 6.3), under Knorr pyrrole formation conditions, provides analog 6.4, which can be converted to the corresponding carboxylic acid analog according to procedures described herein.

Synthesis of Fused Keto Analogs

In an exemplary embodiment, keto-substituted analogs of the invention are prepared using a procedure outlined in Schemes 7, below.

Scheme 7: Synthesis of 4-oxo intermediate (7.5)

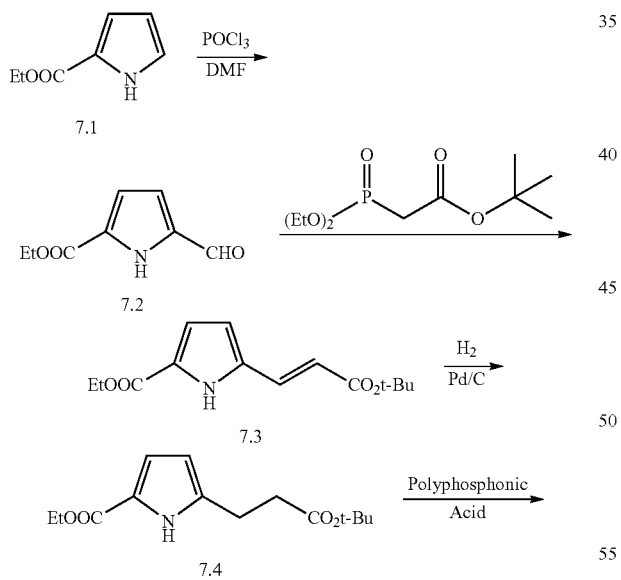

In Scheme 7, Villsmeier formylation of a 1H-pyrrole-2-carboxylic acid ester (e.g., with phosphoryl trichloride) provides aldehyde 7.2. Olefination (e.g., with tert-butyl diethylphosphonoacetate) provides α,β-unsaturated esters, such as 7.3. Hydrogenation to 7.4, followed by cyclization (e.g., using polyphosphoric acid) provides the ketone analog 7.5.

In an exemplary embodiment, 4-keto-substituted analogs of the invention are prepared using a procedure described in *J. Org. Chem.*, 1983, 48: 4779-4781; *Synthetic Commun.*, 2002, 32: 897-902; *J. Org. Chem.*, 1987, 52: 5395-5400 and references cited therein. In one example, analogs of the invention are prepared using procedures outlined in Schemes 8, 9 or 10, below.

Scheme 8: Synthesis of 4-Keto Analogs (8.2)

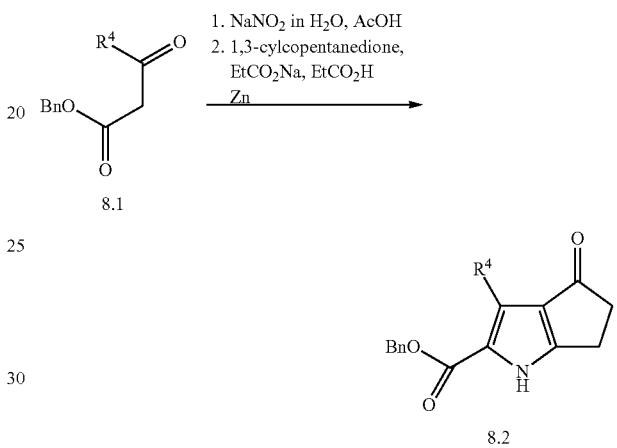

In a method similar to that described in Scheme 6, Scheme 8 describes the reaction of the oxime derived from β-keto ester 8.1 with 1,3-cyclopentanedione, under Knorr pyrrole formation conditions, to provide 4-keto analogs 8.2.

Scheme 9: Synthesis of 4-Keto Analogs (9.2)

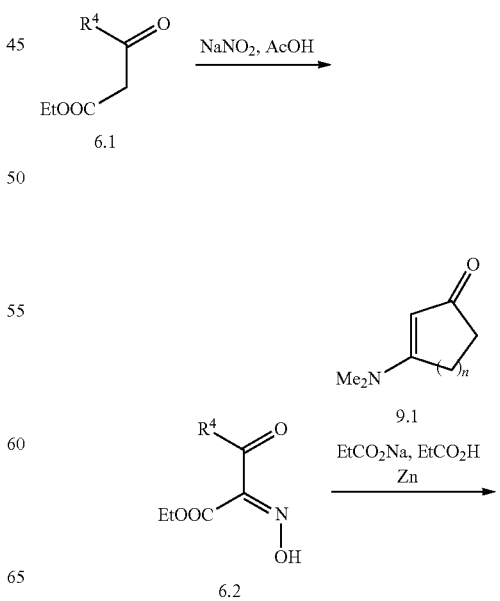

-continued

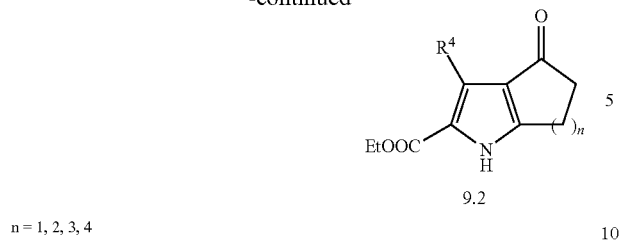

9.2 n = 1, 2, 3, 4

In Scheme 9, reaction of oxime 6.2, derived from β-keto ester 6.1, with the cyclic enamine ketone 9.1, under Knorr pyrrole formation conditions, provides 4-keto analogs 9.2.

Scheme 10: Synthesis of 4-Keto Analogs (10.4)

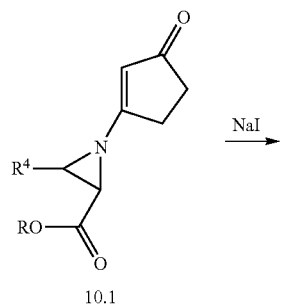

10.1

-continued

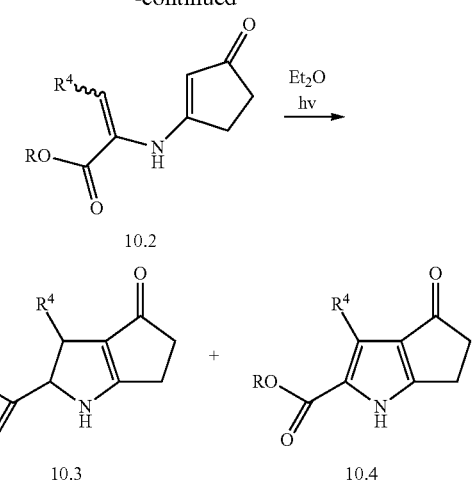

In Scheme 10, N-vinylaziridine 10.1 (e.g., synthesized according to *Can. J. Chem.* 1982, 60: 2830) is isomerized in the presence of sodium iodide to provide dieneamine 10.2. Photocyclization of dieneamine 10.2 provides a mixture of 10.3 and 4-keto analog 10.4.

5-Keto-analogs of the invention can be prepared using procedures outlined in *Tetrahedron* 2004, 60: 1505-1511. In one example, compounds of the invention are synthesized according to the procedure outlined in Scheme 11, below.

Scheme 11: Synthesis of a 5-Keto Analogs

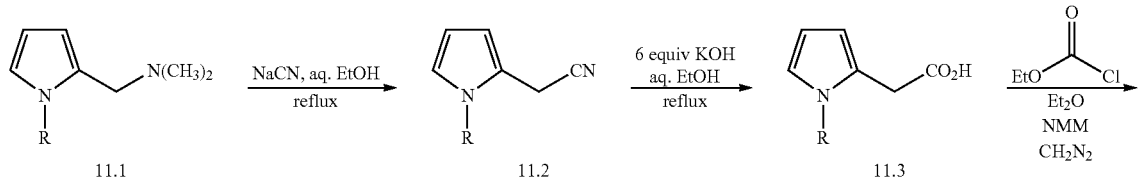

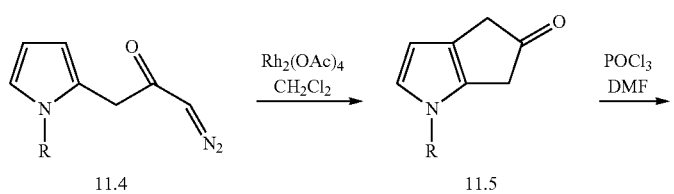

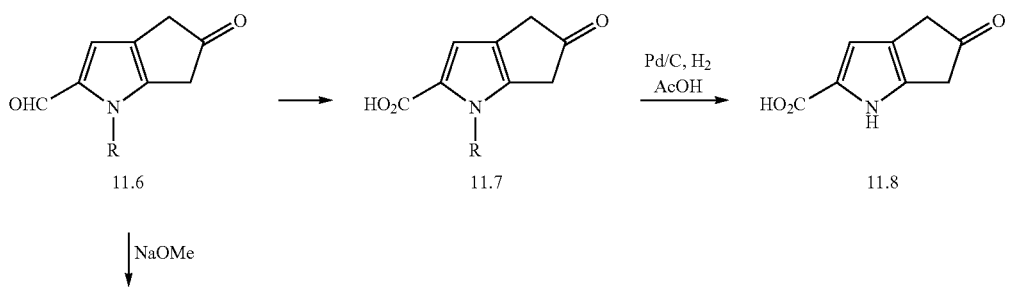

↓ NaOMe

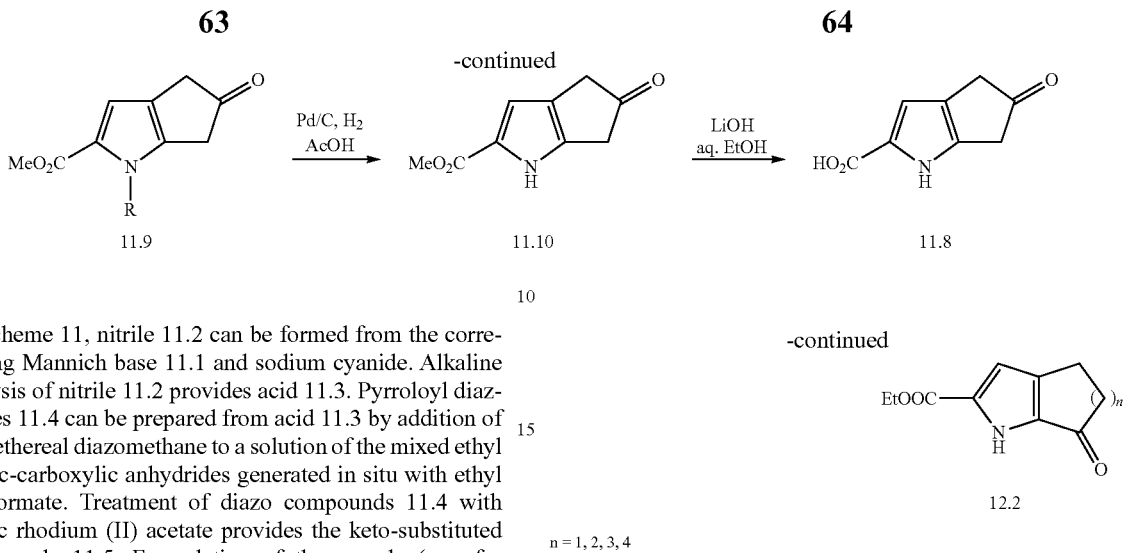

In Scheme 11, nitrile 11.2 can be formed from the corresponding Mannich base 11.1 and sodium cyanide. Alkaline hydrolysis of nitrile 11.2 provides acid 11.3. Pyrroloyl diazoketones 11.4 can be prepared from acid 11.3 by addition of excess ethereal diazomethane to a solution of the mixed ethyl carbonic-carboxylic anhydrides generated in situ with ethyl chloroformate. Treatment of diazo compounds 11.4 with catalytic rhodium (II) acetate provides the keto-substituted fused pyrrole 11.5. Formylation of the pyrrole (see, for example *Tetrahedron Lett* 2006, 47: 3693-3696, *Tetrahedron* 2004, 60: 1197-1204, and *Bioorg. Med. Chem. Lett.* 2004, 14: 187-190) provides the aldehyde 11.6. The aldehyde is converted to the desired acid or ester and the pyrrole nitrogen is deprotected using standard methods, such as those outlined in Scheme 11 to provide 11.8 or 11.10 (see also *J. Med. Chem.* 2004, 47:5167-5182; *Bull. Chem. Soc. Japan* 2002, 75: 2215-2220; *J. Org. Chem.*, 1999, 64: 478-487; *Revista de Chimi* 2001, 52: 206-209; *Organic Preparations and Procedures International* 1994, 26: 123-125; *J. Heterocyclic Chem.* 1986, 23: 769-773; *J. Heterocyclic Chem.*, 1985, 22: 259-263; *J. Organometallic Chem.* 1981, 212: 1-9; *J. Med. Chem.* 1980, 23: 462-465; *Tetrahedron Lett.* 2006, 47: 3521-3523; *Heterocycles* 2006, 68: 713-719; *Tetrahdefron Lett.* 2006, 47: 1071-1075; *J. Am. Chem. Soc.* 2006, 128: 6314-6315; *Heterocycles* 2005, 65: 2693-2703; *Org. Lett.* 2006, 8: 115-118; *Bioorg. Med. Chem. Lett.*, 2005, 15: 4540-4542. In Scheme 11, benzyl is used as a protecting group. A person of skill in the art will appreciate that other pyrrole protecting groups can also be used.

6-Keto-analogs of the invention can be prepared using procedures outlined in *European J. Org. Chem.* 2006, 2: 414-422, *Tetrahedron* 1993, 49: 4159-4172; *J. Am. Chem. Soc.* 1968, 90: 6877-6879; *J. Am. Chem. Soc.* 1954, 76: 5641-5646; *Ann* 1928, 462: 246; *Ann* 1928, 466: 171; *Ann* 1932, 492: 154 and references cited therein. In one example, compounds of the invention are synthesized according to the procedure outlined in Schemes 12 and 13, below.

In Scheme 12, oxidation of analog 1.5 with lead tetraacetate, followed by hydrolysis provides the 6-keto analog 12.2.

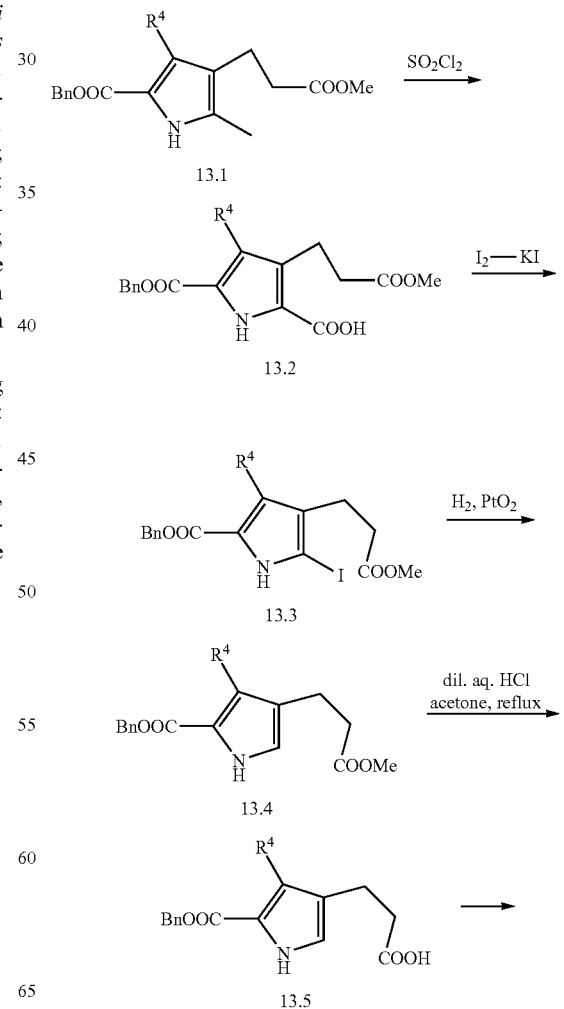

In Scheme 13, the α-methyl group of 13.1 is oxidized to the carboxylic acid of 13.2 (e.g., by treatment with sulfuryl chloride in acetic acid). Iodo-decarboxylation with $I_2$/KI provides 13.3. Hydrogenation removes the iodine and hydrolysis of the methyl ester provides acid 13.5. An alternative route to a related analog, 3(-5-(methoxycarbonyl)-1H-pyrrol-3-yl)propanoic acid, is described in the Examples section. Conversion of 13.5 to the acid chloride, followed by $SnCl_4$-catalyzed cyclization provides analog 13.8. 13.8 can also be synthesized from acid 13.5 using polyphosphoric acid, as described in the Examples section.

Other conditions for oxidation of core scaffolds such as 1.5, 5.4, and 6.4 to the desired keto-derivatives can also be found in the following references, as well as references cited therein: *Heterocycles* 1990, 30: 1131-1140; *J. Org. Chem.* 1990, 55: 3858-3866; and *Tetrahedron* 1985, 41: 3813-3823.

In Schemes 1-13, $R^1$ and $R^4$ are defined as herein above. In one example, $R^1$ and $R^4$ are members independently selected from H and substituted or unsubstituted alkyl. In another example, $R^1$ and $R^4$ in these Schemes are independently selected from substituted or unsubstituted methyl, ethyl, propyl and butyl. In yet another example, $R^1$ is methyl. In a further example, $R^4$ is methyl.

In addition, esters in these examples can be hydrolyzed using standard ester hydrolysis conditions such as lithium hydroxide or sodium hydroxide in aqueous ethanol or methanol. Exemplary hydrolysis conditions are described herein below, in General Procedure 7.

The above describe keto-substituted analogs of the invention can be used as intermediates in the synthesis of additional analogs through standard functional group manipulations such as protection, deprotection, alkylation, hydrolysis, hydrogenation, and the like. Methods for the conversion (e.g., alkylation) of keto groups are known to those skilled in the art. Exemplary methods are shown in Scheme 14, below. Exemplary keto-intermediates include 7.1, 8.2, 9.2, 10.4, 11.8, 12.2, and 13.8.

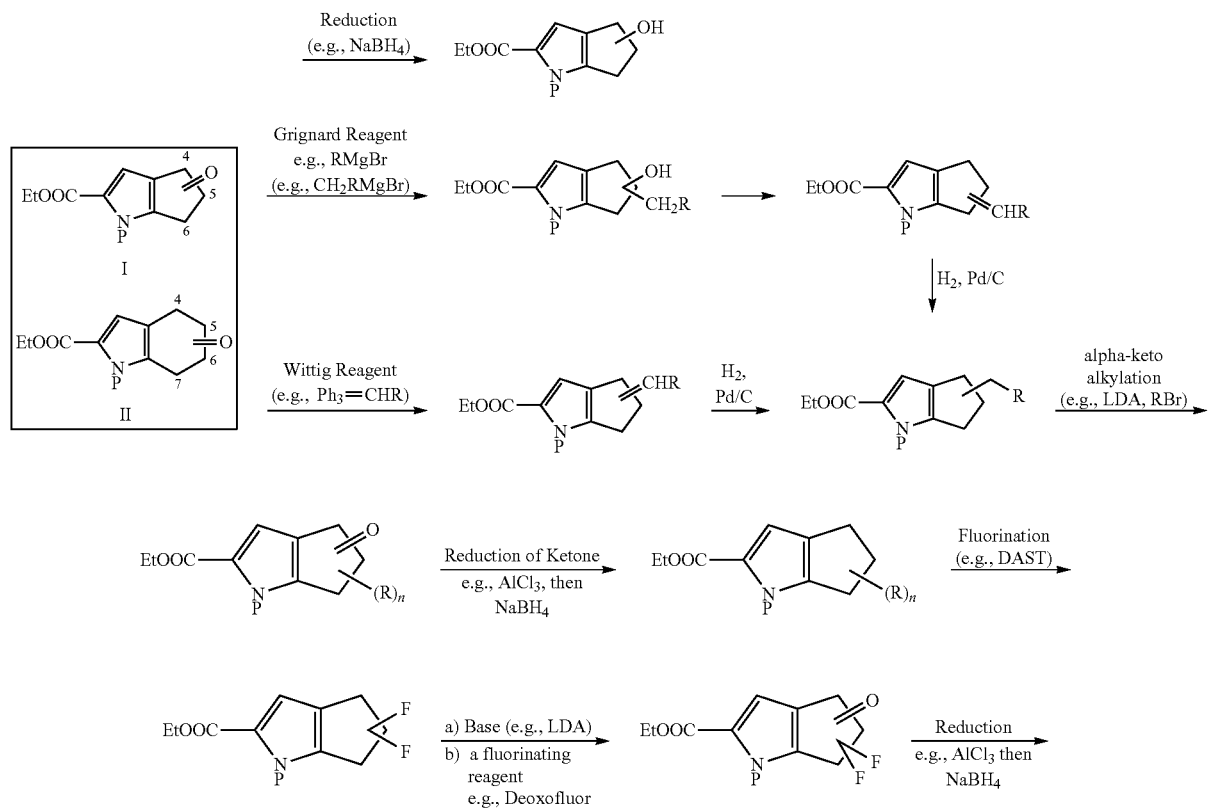

Scheme 14: Synthesis of Substituted Analogs from Keto Intermediates

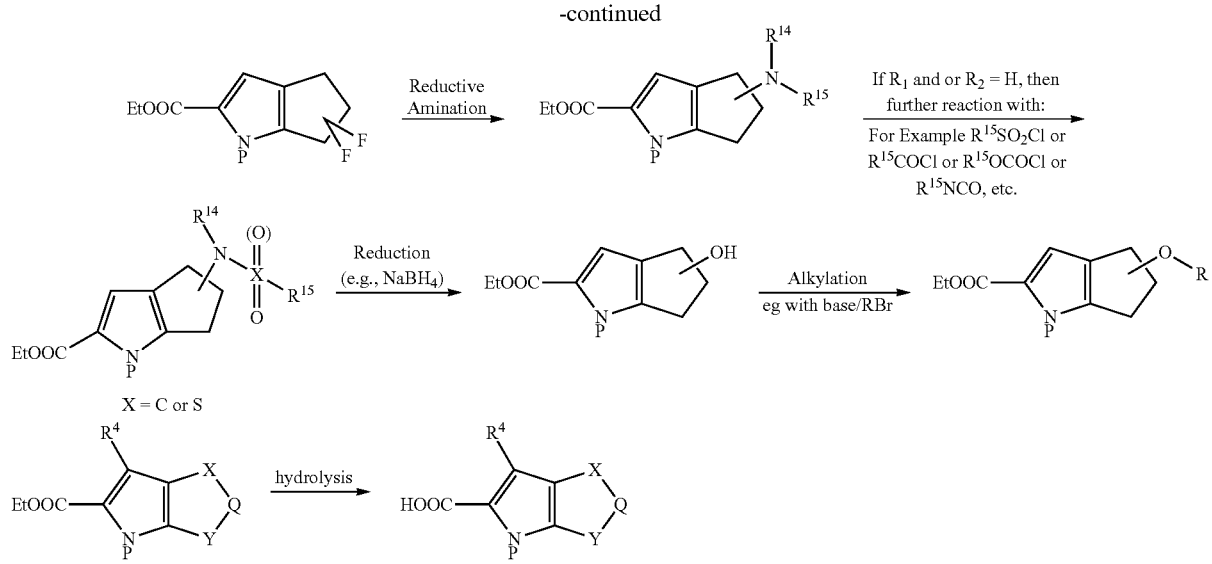

X = C or S

In Scheme 14, R represents H, substituted or unsubstituted alkyl, substituted or unsubstituted heteroalkyl, substituted or unsubstituted aryl, substituted or unsubstituted heteroaryl and substituted or unsubstituted heterocycloalkyl. In one example, R is selected from H, substituted or unsubstituted methyl, ethyl, propyl or butyl and substituted or unsubstituted phenyl. The keto group of compound I is found at position 4, 5 or 6 of the 5-membered ring. The keto group of compound II can be at positions 4, 5, 6 or 7 of the 6-membered ring. In Scheme 14, the group P is a member selected from H and a protecting group. Protecting groups useful for the protection of amines (e.g., aromatic amines) are known to those of skill in the art (see, for example, T W Greene and P G M Wuts, *Protective Groups in Organic Synthesis*, third edition 1999, John Wiley & Sons). In an exemplary embodiment, the protecting group is selected from Bn and SEM.

In Scheme 14, the ketone can be reduced to the corresponding alcohol, for example, using NaBH$_4$ (see, e.g., *Tetrahedron*, 1993, 49: 4159-4172). In another example, the ketone is alkylated using a Grignard reagent. The resulting alcohol can be converted to an alkene, which is optionally reduced to the corresponding alkyl analog (e.g., using palladium on charcoal). In yet another example, the ketone can be alkylated using a Wittig reagent to obtain an alkene, which is optionally reduced to the corresponding alkane. Grignard and Wittig reactions are well known to those of skill in the art. Alternatively, any hydrogen atom in the 5- or 6-membered ring can be replaced with a halogen atom. For example, difluorination can be accomplished using DAST or Deoxofluor. Alternatively, the carbonyl group can be replaced using DAST or Deoxofluor. In another example, reaction of the carbonyl group with a reducing agent in the presence of an amine (reductive amination) can produce a substituted or unsubstituted amine. This amine can be further functionalized with an acid chloride, sulfonyl chloride, isocyanate and the like to produce an amide, sulfonamide, urea or the like. In a further example, the carbonyl can be reduced to an alcohol with a reducing agent such as sodium borohydride and the resulting alcohol can be reacted with a suitable electrophile to produce an ether. Standard hydrolysis conditions, such as those disclosed herein (e.g., lithium hydroxide monohydrate), can be used to convert esters to carboxylic acids.

Fluorinated analogs of the invention can also be prepared using procedures outlined in *Tetrahedron* 2005, 61: 9338-9348; *Heterocycles* 1991, 32: 949-963; *Tetrahedron* 2003, 59: 5215-5223, and references cited therein. In one example, compounds of the invention are synthesized according to the procedures outlined in Schemes 15 and 16, below.

Scheme 15 Synthesis of Difluoro Analogs (15.8)

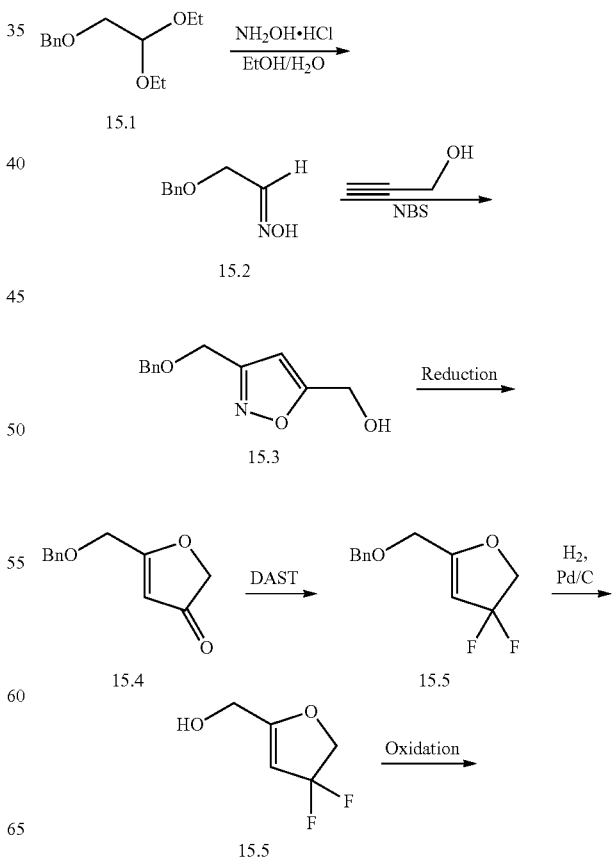

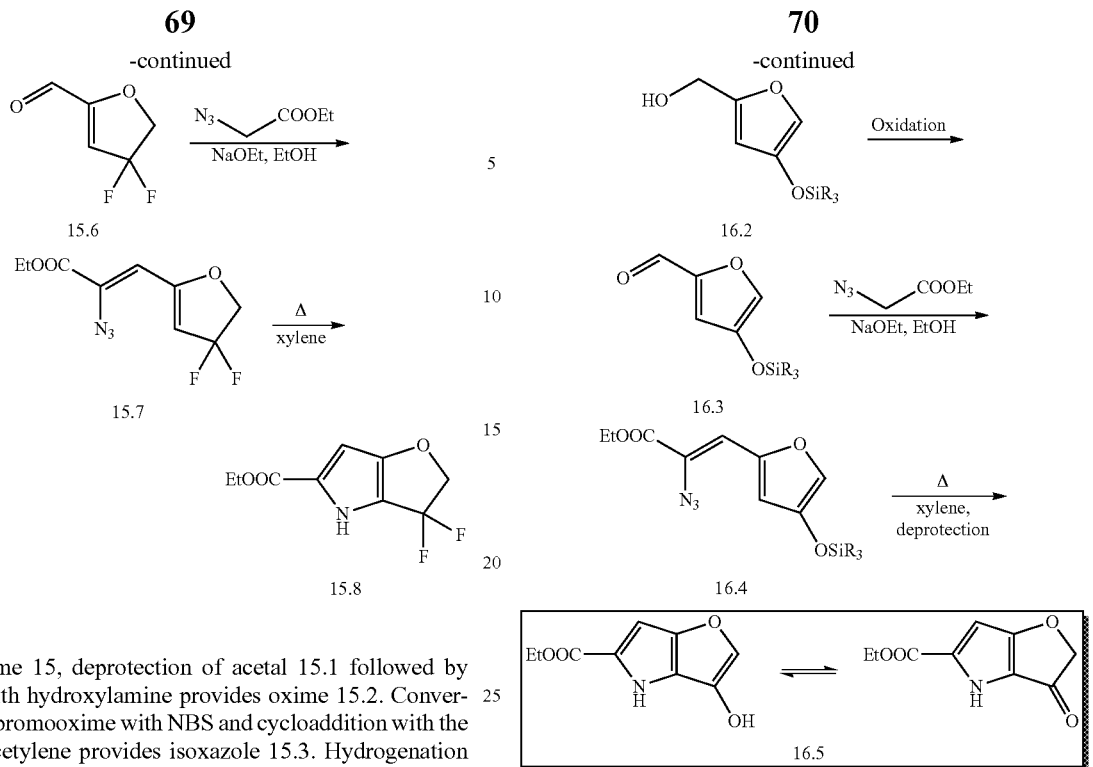

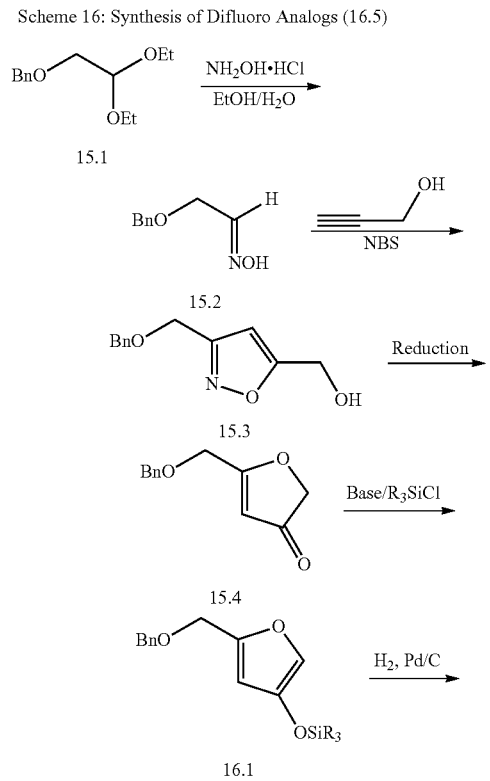

In Scheme 15, deprotection of acetal 15.1 followed by reaction with hydroxylamine provides oxime 15.2. Conversion to the bromooxime with NBS and cycloaddition with the required acetylene provides isoxazole 15.3. Hydrogenation of 15.3 and subsequent cyclization provides 3(2H)-furanone 15.4. Reaction with fluorinating agent DAST provides 15.5. Hydrogenation removes the benzyl protecting group to give 15.5, which is oxidized to aldehyde 15.6, condensed with ethyl 2-azidoacetate to provide 15.7, and cyclized in xylene to obtain analog 15.8. Those skilled in the art would know that other hydroxyl protecting groups can also be used.

In Scheme 16, 15.4 is converted to furan 16.1 by treatment with base and a silylating reagent. Removal of the protecting group provides alcohol 16.2, which is oxidized to aldehyde 16.3, condensed with ethyl 2-azidoacetate to provide 16.4, cyclized in xylene and deprotected to achieve analog 16.5. Those skilled in the art will appreciate that other hydroxyl protecting groups can be used.

Compounds of the invention including a bicyclic substructure can be synthesised according to described methods (see e.g., Estep, K. G. *Syn. Commun.* 1995, 25: 507-514; *Tetrahedron: Asymmetry* 1996, 7: 1269-1272.; *Chem. Berichte* 1978, 111: 1195-1209.; *Chem. Ber.* 1975, 108: 1756-1767.; *J. Chem. Res.* 1997: 102-103.; *J. Org. Chem.* 2000, 65: 2900-2906; *Heterocycles* 1989, 28: 1077; and references cited therein). In on example, such compounds are synthesized according to a procedure outlined in Scheme 17, below.

Scheme 17: Synthesis of Bridged Analogs (17.7)

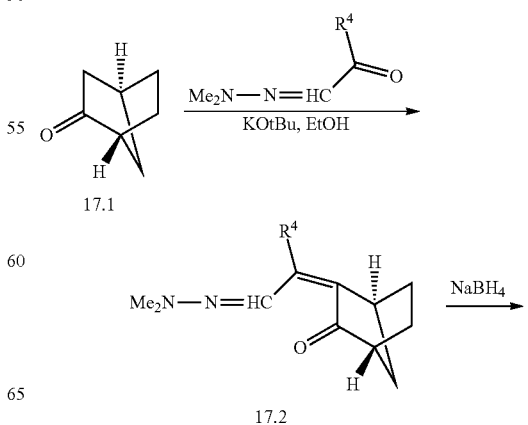

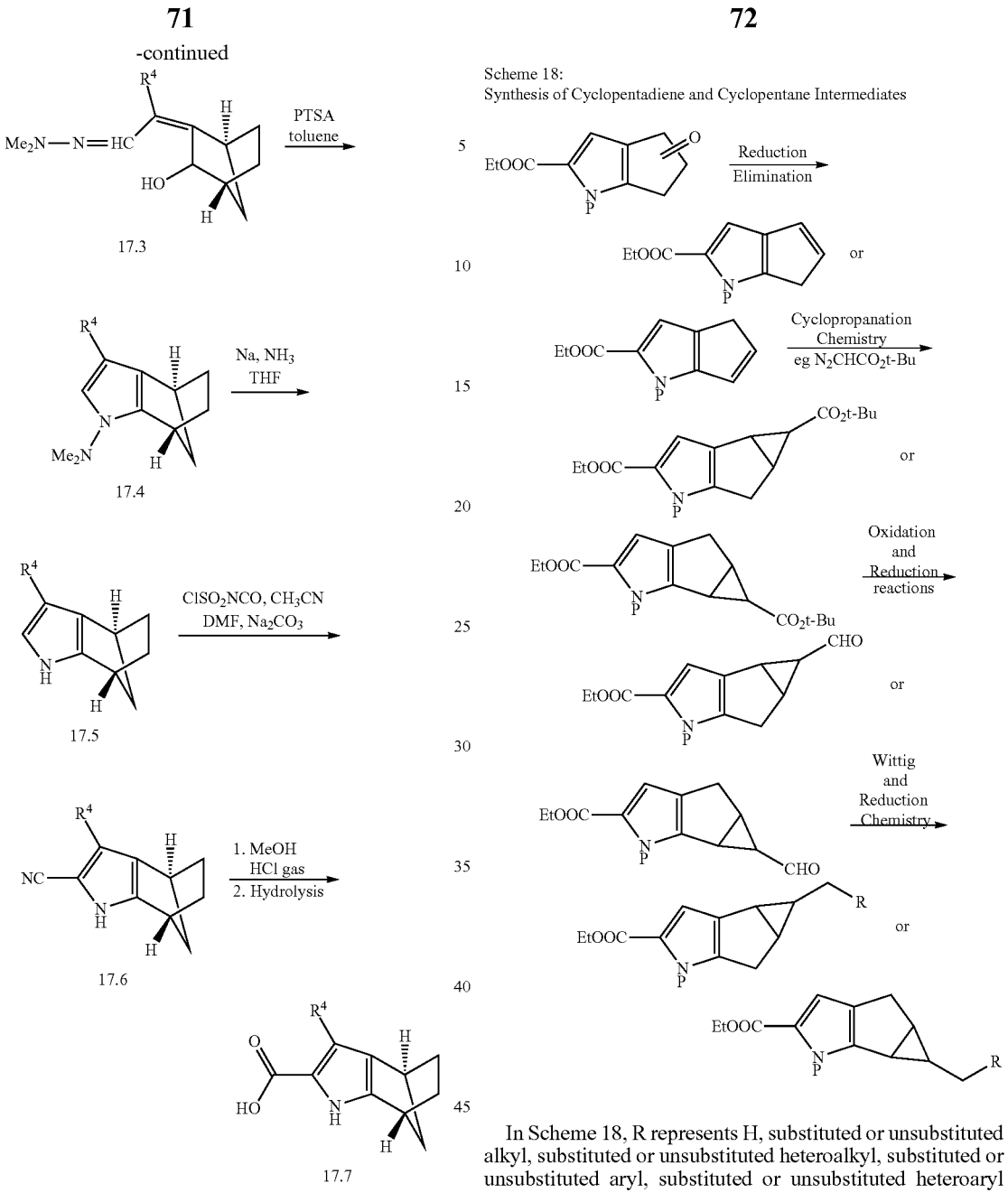

Scheme 18:
Synthesis of Cyclopentadiene and Cyclopentane Intermediates

In Scheme 17, Aldol condensation of ketone 17.1 with a keto hydrazone provides 17.2. Reduction of the ketone with sodium borohydride followed by PTSA-catalyzed cyclization provides pyrrole 17.4. Sodium-liquid ammonia reduction provides 17.5. Cyanation of the pyrrole with chlorosulfonyl isocyanate provides 17.6, which can be hydrolyzed to acid 17.7.

Compounds of the invention, including a cyclopentadiene-containing fused rings and fused 5- and 6-membered rings with additionally fused substituted or unsubstituted cyclopentane rings, can be synthesized according to described methods (see e.g., Helvetica Chemica Acta 2004, 87: 1767-1793, and references cited therein) and using other standard functional group manipulations well-known to those skilled in the art. In on example, such compounds are synthesized according to a procedure outlined in Scheme 18, below.

In Scheme 18, R represents H, substituted or unsubstituted alkyl, substituted or unsubstituted heteroalkyl, substituted or unsubstituted aryl, substituted or unsubstituted heteroaryl and substituted or unsubstituted heterocycloalkyl. The keto group is found at position 4, 5 or 6 of the 5-membered ring. In Scheme 18, the group P is a member selected from H and a protecting group. Protecting groups useful for the protection of amines (e.g., aromatic amines) are known to those of skill in the art (see, for example, T W Greene and P G M Wuts, *Protective Groups in Organic Synthesis*, third edition 1999, John Wiley & Sons). In an exemplary embodiment, the protecting group is selected from Bn and SEM. In Scheme 18, the ketone can be reduced to an alcohol with a reducing agent such as sodium borohydride. The resulting alcohol can then be eliminated to produce an olefin. This olefin is optionally reacted with a diazo compound (e.g., diazoacetate) to produce a cyclopropyl ester. The cyclopropyl ester can be converted to an alcohol by reduction and further to the corresponding aldehyde by oxidation. Functionalization of the aldehyde produces additional cyclopropyl analogs. For example, the aldehyde can be reacted with an appropriate Wittig reagent, and then reduced (e.g., hydrogen gas and a catalyst).

Hydroxy and alkoxy substituted analogs of the invention may be prepared using procedures outlined in *Liebigs Ann Chem* 1980, 4: 564-589, and references cited within. In one example, compounds of the invention are synthesized according to the procedure outlined in Scheme 19 below.

Scheme 19:
Synthesis of hydroxy (18.3) and alkoxy-substituted analogs (19.4)

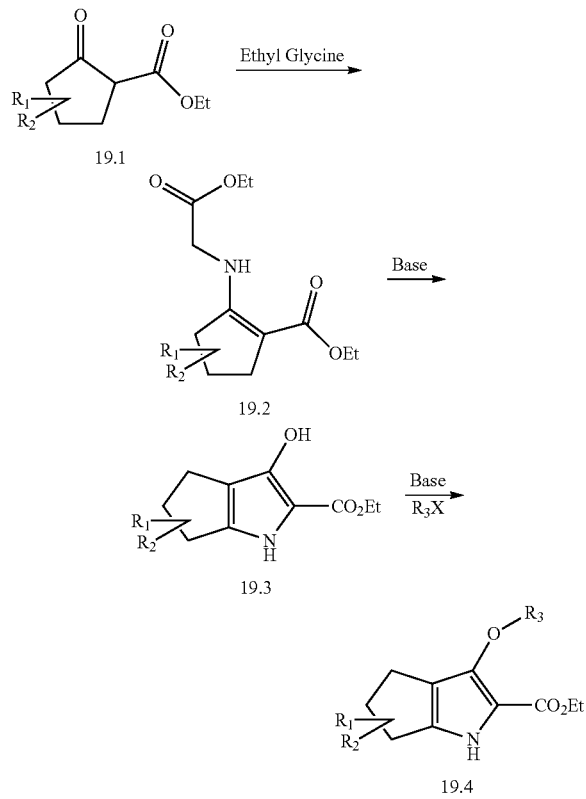

In Scheme 19, $R_1$, $R_2$ and $R_3$ represent H, substituted or unsubstituted alkyl, substituted or unsubstituted heteroalkyl, substituted or unsubstituted aryl, substituted or unsubstituted heteroaryl and substituted or unsubstituted heterocycloalkyl. In one example, R is selected from H, substituted or unsubstituted methyl, ethyl, propyl or butyl and substituted or unsubstituted phenyl. $R_1$ and $R_2$ can be found at position 4, 5 or 6 of the 5-membered ring. Additionally, $R_1$ and $R_2$ can both occupy position 4, 5 or 6 of the 5-membered ring.

In Scheme 18, the starting keto ester can be reacted with glycine ethyl ester to produce an enamine. This enamine can then be further treated with a base such as sodium ethoxide to form the pyrrole ring. The hydroxyl of this compound can be further elaborated to form ethers through reaction of a base such as sodium hydride and an electrophile such as methyl iodide.

The reagents and reaction conditions, such as those given in Schemes 1 to 18 are exemplary and can be replaced with other suitable reagents and conditions, known to those of skill in the art.

C. Pharmaceutical Compositions

While it is possible for compounds of the present invention to be administered as the raw chemical, it is preferable to present them as a pharmaceutical composition. According to a further aspect, the present invention provides a pharmaceutical comprising a compound of the invention, e.g., those of Formula (I) to Formula (Vb), or a pharmaceutically acceptable salt, solvate, hydrate or prodrug thereof, together with one or more pharmaceutical carrier and optionally one or more therapeutic ingredient. The carrier(s) must be "acceptable" in the sense of being compatible with the other ingredients of the formulation and not deleterious to the recipient thereof. The term "pharmaceutically acceptable carrier" includes vehicles and diluents.

The formulations include those suitable for oral, parenteral (including subcutaneous, intradermal, intramuscular, intravenous and intraarticular), rectal and topical (including dermal, buccal, sublingual and intraocular) administration, as well as those for administration by inhalation. The most suitable route can depend upon the condition and disorder of the recipient. The formulations can conveniently be presented in unit dosage form and can be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: *The Science and Practice of Pharmacy*, A. R. Gennaro, ed. (1995), the entire disclosure of which is incorporated herein by reference.

Pharmaceutical compositions containing compounds of the invention, e.g., those of Formula (I) to Formula (VIIIb), can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 7000 mg per day, preferably about 1 mg per day to about 100 mg per day, and more preferably, from about 10 mg per day to about 100 mg per day, and even more preferably from about 20 mg to about 100 mg, 20 mg to about 80 mg or 20 mg to about 60 mg. In some embodiments, the total daily dose can range from about 50 mg to about 500 mg per day, and preferably about 100 mg to about 500 mg per day. It is further recommended that children, patients over 65 years old, and those with impaired renal or hepatic function, initially receive low doses and that the dosage be titrated based on individual physiological responses and/or pharmacokinetics. It can be necessary to use dosages outside these ranges in some cases, as will be apparent to those in the art. Further, it is noted that the clinician or treating physician knows how and when to interrupt, adjust or terminate therapy in conjunction with an individual patient's response.

It should be understood that in addition to the ingredients particularly mentioned above, the formulations of this invention can include other agents conventional in the art having regard to the type of formulation in question, for example those suitable for oral administration can include flavoring agents.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

A tablet can be made by compression or molding, optionally using one or more accessory ingredients. Compressed tablets can be prepared by compressing in a suitable machine the active ingredient in a free-flowing form such as a powder or granules, optionally mixed with a binder, lubricant, inert diluent, lubricating, surface active or dispersing agent. Molded tablets can be made by molding in a suitable machine a mixture of the powdered compound moistened with an inert liquid diluent. The tablets can optionally be coated or scored and can be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: *The Science and Practice of Pharmacy*, pages 1660-1675 (1995), the disclosure of which is incorporated herein by reference.

Formulations for parenteral administration include aqueous and non-aqueous sterile injection solutions which can contain anti-oxidants, buffers, bacteriostats and solutes which render the formulation isotonic with the blood of the intended recipient. Formulations for parenteral administration also include aqueous and non-aqueous sterile suspensions, which can include suspending agents and thickening agents. The formulations can be presented in unit-dose of multi-dose containers, for example sealed ampoules and vials, and can be stored in a freeze-dried (lyophilized) condition requiring only the addition of a sterile liquid carrier, for example saline, phosphate-buffered saline (PBS) or the like, immediately prior to use. Extemporaneous injection solutions and suspensions can be prepared from sterile powders, granules and tablets of the kind previously described. Formulations for rectal administration can be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The pharmaceutically acceptable carrier can take a wide variety of forms, depending on the route desired for administration, for example, oral or parenteral (including intravenous). In preparing the composition for oral dosage form, any of the usual pharmaceutical media can be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents can be used in the case of oral solid preparations such as powders, capsules and caplets, with the solid oral preparation being preferred over the liquid preparations. Preferred solid oral preparations are tablets or capsules, because of their ease of administration. If desired, tablets can be coated by standard aqueous or nonaqueous techniques. Oral and parenteral sustained release dosage forms can also be used.

Exemplary formulations, are well known to those skilled in the art, and general methods for preparing them are found in pharmacy textbooks, for example, Remington, THE SCIENCE AND PRACTICE OF PHARMACY, 21st Ed., Lippincott.

IV. Methods

A. Methods of Treatment or Prevention

Subjects for treatment according to methods of the present invention include humans (patients) and other mammals. In one example, the subject is in need of therapy for the stated condition.

In a further aspect the invention provides a method for treating or preventing a disease or condition which is a member selected from a neurological disorder, pain, ataxia and convulsion. The method includes administering to a subject in need thereof a therapeutically effective amount of a compound of the invention (e.g., those of Formula (I) to Formula (VIIIb)) or a pharmaceutically acceptable salt, solvate, hydrate or prodrug thereof. For example, the compound useful in the above method is a member selected from compounds 1-37, disclosed herein.

The invention also provides the use of a compound of the invention in the manufacture of a medicament for the treatment of a disease or condition in a mammal (e.g., a human patient), wherein said disease or condition is a neurological disorder, pain, ataxia or convulsion.

The invention further provides the use of a compound of the invention in the manufacture of a medicament for the enhancement of cognition in a mammal (e.g., a human).

The invention further provides a compound of the invention for use in treating a neurological disorder in a mammal (e.g., human). Exemplary neurological disorders are provided herein.

The invention further provides a compound of the invention for use in treating pain (e.g., neuropathic pain), ataxia or convulsion in a mammal (e.g., a human).

The invention further provides a compound of the invention for use in enhancing cognition in a mammal (e.g., a human).

Compounds of the invention possess unique pharmacological characteristics with respect to inhibition of DAAO and influence the activity of the NMDA receptor in the brain, particularly by controlling the levels of D-serine. Therefore, these compounds are effective in treating conditions and disorders (especially CNS-related disorders), which are modulated by DAAO, D-serine and/or NMDA receptor activity. In one embodiment, compounds of the invention are associated with diminished side effects compared to administration of the current standards of treatment.

Accordingly, the present invention relates to methods for increasing the concentration of D-serine and/or decreasing the concentration of toxic products of D-serine oxidation by DAAO in a mammal. In one embodiment the invention provides a method for treating or preventing a disease or condition, such as those disclosed herein. In one example, the disease or condition is selected from a neurological disorder, pain, ataxia and convulsion. In another embodiment, the invention provides a method of enhancing the cognitive capabilities of a human subject.

In one embodiment, the invention provides a method of enhancing cognition in a mammalian subject (e.g., human). The method includes administering to the subject an effective amount of a compound of the invention (e.g., of Formula (I), Formula (II), Formula (III), Formula (IVa), Formula (IVb), Formula (IVc), Formula (Va), Formula (Vb), Formula (Vc), Formula (VI), Formula (VIIa), Formula (VIIb), Formula (VIIIa), or Formula (VIIIb)), or a pharmaceutically acceptable salt, solvate or prodrug thereof. For example, the compound useful in the above method is a member selected from compounds 1-37, disclosed herein. In one example, the subject has been diagnosed with a neurological disorder, such as a neurodegenerative disease disclosed herein (e.g., Alzheimer's disease), with brain injury or spinal cord injury. In another example, the subject benefits from enhanced cognitive capabilities with respect to increased quality of life, performance (e.g., test situations) or coping with stressful situations. For example, the subject is mentally disabled (e.g., due to brain injury). In another example, compounds of the invention are useful in relieving negative symptoms of stress, sleep deprivation (e.g., arising from emergency situations) and disruptions of the circadian rhythm (e.g., jet-lag, nightshifts, time adjustments, such as those to daylight savings time, and the like).

In an exemplary embodiment, the method of the invention includes administering to a mammalian subject (e.g., a human patient) in need thereof a therapeutically effective amount of a compound of the invention, for example a compound of Formula (I), Formula (II), Formula (III), Formula (IVa), Formula (IVb), Formula (IVc), Formula (Va), Formula (Vb), Formula (Vc), Formula (VI), Formula (VIIa), Formula (VIIb), Formula (VIIIa), or Formula (VIIIb), or a pharmaceutically acceptable salt, solvate, hydrate or prodrug thereof. Exemplary prodrugs are esters, for example those in which $R^6$ is $OR^8$. In this example, $R^8$ is selected from substituted or unsubstituted alkyl (e.g., methyl, ethyl, propyl, butyl), substituted or unsubstituted heteroalkyl, substituted or unsubstituted aryl and substituted or unsubstituted heteroaryl.

Compounds of the invention are typically more selective than known DAAO inhibitors, including indole-2-carboxylates, and demonstrate higher selectivity for DAAO inhibition relative to binding at the NMDA receptor's D-serine binding site. The compounds also exhibit an advantageous profile of activity including good bioavailability. Accordingly, they offer advantages over many art-known methods for treating disorders modulated by DAAO, D-serine or NMDA receptor activity. For example, unlike many conventional antipsychotic therapeutics, DAAO inhibitors can produce a desirable reduction in the cognitive symptoms of schizophrenia. Conventional antipsychotics often produce undesirable side effects, including tardive dyskinesia (irreversible involuntary movement disorder), extra pyramidal symptoms, and akathesia, and these can be reduced or eliminated by administering compounds of the invention.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s). Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

Compounds of the present invention can also be used in conjunction with therapy involving administration of D-serine or an analog thereof, such as a salt of D-serine, an ester of D-serine, alkylated D-serine, D-cycloserine or a precursor of D-serine Compounds of the present invention can also be used in conjunction with therapy for neuropathic pain. Agents for this purpose include tricyclic antidepressants, such as imipramine (Tofranil), amitriptyline (Elavil), and nortriptyline (Pamelor, Aventyl); selective serotonin reuptake inhibitors (SSRIs), such as citalopram (Celexa), escitalopram (Lexpro), fluoxetine (Prozac), paroxetine (Paxil) and sertraline (Zoloft); serotinin and norepinephrine reuptake inhibitors (SNRIs), such as Cymbalta (duloxetine); anticonvulsants, such as gabapentin (Neurontin) and pregabalin (Lyrica); opioids such as morphine, oxycodone (OxyContin, Percoset), and fentanyl; and carbamazepine, lidocaine and lamotrigine.

Compounds of the present invention can also be used in conjunction with cognition enhancing agents, e.g., MAO inhibitors, such as selegiline (Eldepryl); cholinesterase inhibitors, such as galantamine (Razadyne), rivastigmine (Exelon), donepezil (Aricept) and Memantine (NMDA antagonist).

Compounds of the present invention can also be used in conjunction with antipsychotics for schizophrenia, which include risperidone (Risperidal), Olanzapine (Zyprexa), Clozapine (Clozaril), Paliperidone (Invega), Quetiapine (Seroquel), Ziprasidone (Geodon), Aripiprazole (Abilify), Asenapine and Lloperidone.

The compounds of the invention can also be used in conjunction with therapy involving administration of antipsychotics (for treating schizophrenia and other psychotic conditions, such as risperidone, olanzapine, clozapine, paliperidone, quetiapine, ziprasidone, aripiprazole, asenapine, loperidone), psychostimulants (for treating attention deficit disorder, depression, or learning disorders), antidepressants, nootropics (for example, piracetam, oxiracetam or aniracetam), acetylcholinesterase inhibitors (for example, galantamine, rivastigmine, the physostigmine related compounds, tacrine or donepezil), GABA analogs (e.g., gabapentin) or GABA receptor modulators, Alzheimer's disease therapeutics (e.g., memantine hydrochloride, and selegiline) and/or analgesics (for treating of persistent or chronic pain, e.g. neuropathic pain). Such methods for conjoint therapies are included within the invention.

In another embodiment, the compounds of the invention can be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the subject compound may be employed in combination with sedatives, hypnotics, anxiolytics, antipsychotics, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chiordiazepoxide, clorethate, chiorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, metha~ualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, Iricetamide, triclofos, trifluoperazine, trimetozine, trimipramine, uldazepam, venlafaxine, zaleplon, ziprasidone, zola.zepam, zolpidem, and salts thereof, and combinations thereof, and the like, or the subject compound may be administered in conjunction with the use of physical methods such as with light therapy or electrical stimulation. In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MAO-B inhibitors, antioxidants, $A_{2a}$ adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form. In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compounds of the invention can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the invention can be employed in combination with a compound useful in the treatment of pain, for example carbamazepine, lidocaine, and lamotrigine, an NSAID such as ibuprofen, an antinociceptive agent such as an NR2B antagonist, a COX-2 inhibitor such as ARCOXIA, a Selective Serotonin Reuptake Inhibitor (SSRI) such as citalopram, escitalopram, fluoxetine, paroxetine, and sertraline, a Serotinin and Norepinephrine Reuptake Inhibitor (SNRI) such as Cymbalta, an anticonvulsants such as gabapentin (Neurontin) and pregabalin (Lyrica), an opioids such as morphine, oxycodone, and fentanyl, a tricyclic antidepressants such as imipramine, amitriptyline, and nortriptyline, or a sodium channel blocker.

The compounds of the invention can also be used in conjunction (coadministration) with one or more other therapeutic compound. For example, compounds of the invention can be used in conjunction with therapy involving administration of antipsychotics (e.g., for treating schizophrenia and other psychotic conditions), psychostimulants (e.g., for treating attention deficit disorder, depression, or learning disorders), antidepressants, nootropics (for example, piracetam, oxiracetam or aniracetam), acetylcholinesterase inhibitors (for example, physostigmine related compounds, tacrine or donepezil), GABA analogs (e.g., gabapentin or pregabalin) or GABA receptor modulators, Alzheimer's disease therapeutics (e.g., memantine hydrochloride) and/or analgesics (e.g., for treating persistant or chronic pain, e.g. neuropathic pain). Such methods for conjoint therapies are included within the invention.

In another example, the invention provides a method of inhibiting D-amino acid oxidase (DAAO) enzyme activity, said method comprising contacting said DAAO with a compound of the invention. In one embodiment, the DAAO is located within a cell (e.g., a mammalian cell). In one example according to this embodiment, the cell is located within a mammal. For example, the cell is located within the central (i.e., brain) or peripheral nervous system of a mammal. The invention also provides a composition comprising a compound of the invention and a mammalian cell. The invention further provides a composition comprising a compound of the invention and a DAAO enzyme.

Conditions and Disorders

In one embodiment, the compounds of the present invention are useful for the treatment of neurological disorders, pain (e.g., neuropathic pain), ataxia and convulsion. Neurological disorders include neurodegenerative diseases (e.g., Alzheimers disease) and neuropsychiatric disorders (e.g., schizophrenia).

Compounds of the invention are useful for the treatment of neurological disorders, pain (e.g., neuropathic pain), ataxia and convulsion, including the treatment of schizoaffective disorder, delusional disorder, brief psychotic disorder, shared psychotic disorder, psychotic disorder due to a general medical condition and substance-induced or drug-induced (phencyclidine, ketamine, and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome), including both the positive and negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline; anxiety disorders including acute stress disorder, agoraphobia, generalized anxiety disorder, obsessive-compulsive disorder, panic attack, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general condition, and substance-induced mood-disorders; learning disorders, pervasive development disorder including autistic disorder, attention disorders including attention-deficit hyperactivity disorder (ADHD) and conduct disorder; NMDA-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressively supranuclear palsy, multiple system atrophy, corticobasal degeneration, parkinsonism-ALS dementia complex and basal gangli calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor, and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal cyloclonus), tics (including simple tics, complex tics, and symptomatic tics), and dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomia and narcolepsy.

Neuropsychiatric Disorders

In one example, the compounds of the invention can be used treat neuropsychiatric disorders. Neuropsychiatric disorders include schizophrenia, autism, and attention deficit disorder. Clinicians recognize a distinction among such disorders, and there are many schemes for categorizing them. *The Diagnostic and Statistical Manual of Mental Disorders*, Revised, Fourth Ed., (DSM-IV-R), published by the American Psychiatric Association, provides a standard diagnostic system upon which persons of skill rely, and is incorporated herein by reference. According to the framework of the DSM-IV, the mental disorders of Axis I include: disorders diagnosed in childhood (such as Attention Deficit Disorder (ADD) and Attention Deficit-Hyperactivity Disorder (ADHD)) and disorders diagnosed in adulthood. The disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

ADD and ADHD are disorders that are most prevalent in children and are associated with increased motor activity and a decreased attention span. These disorders are commonly treated by administration of psychostimulants such as methylphenidate and dextroamphetamine sulfate.

The compounds (and their mixtures) of the present invention are also effective for treating disruptive behavior disorders, such as attention deficit disorder (ADD) and attention deficit disorder/hyperactivity (ADHD), which is in accordance with its accepted meaning in the art, as provided in the DSM-IV-TR™. These disorders are defined as affecting one's behavior resulting in inappropriate actions in learning and social situations. Although most commonly occurring during childhood, disruptive behavior disorders can also occur in adulthood.

Schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates. So-called negative symptoms of schizophrenia include affect blunting, anergia, alogia and social withdrawal, which can be measured using SANS (Andreasen, 1983, *Scales for the Assessment of Negative Symptoms* (SANS), Iowa City, Iowa). Positive symptoms of schizophrenia include delusion and hallucination, which can be measured using PANSS (Positive and Negative Syndrome Scale) (Kay et al., 1987, *Schizophrenia Bulletin* 13:261-276). Cognitive symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, *J. Nerv. Ment. Dis.* 182:631-638) or with cognitive tasks such as the Wisconsin Card Sorting Test. Conventional antipsychotic drugs, which act on the dopamine $D_2$ receptor, can be used to treat the positive symptoms of schizophrenia, such as delusion and hallucination. In general, conventional antipsychotic drugs and atypical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

Disorders treatable with the compounds of the present invention include, but are not limited to, depression, bipolar disorder, chronic fatigue disorder, seasonal affective disorder, agoraphobia, generalized anxiety disorder, phobic anxiety, obsessive compulsive disorder (OCD), panic disorder, acute stress disorder, social phobia, posttraumatic stress disorder, premenstrual syndrome, menopause, perimenopause and male menopause.

Compounds and compositions of the invention are also effective for treating substance-related disorders and addictive behaviors: Particular substance-related disorders and addictive behaviors are persisting dementia, persisting amnestic disorder, psychotic disorder or anxiety disorder induced by substance abuse; and tolerance of, dependence on or withdrawal from substances of abuse.

Compounds and compositions of the present invention are also effective for treating eating disorders. Eating disorders are defined as a disorder of one's appetite or eating habits or of inappropriate somatotype visualization. Eating disorders include, but are not limited to, anorexia nervosa; bulimia nervosa, obesity and cachexia.

In addition to their beneficial therapeutic effects, compounds of the present invention provide the additional benefit of avoiding one or more of the adverse effects associated with conventional mood disorder treatments. Such side effects include, for example, insomnia, breast pain, weight gain, extrapyramidal symptoms, elevated serum prolactin levels and sexual dysfunction (including decreased libido, ejaculatory dysfunction and anorgasmia).

Learning, Memory and Cognition

The compounds of the present invention have utility in treating or improving mammalian brain function, especially human cognition. For example, the compounds have utility improving brain function in human disease conditions such as Alzheimer's, schizophrenia, autism, dyslexia, obsessive-compulsive disorder, depression, anxiety, insomnia, sleep deprivation, and in brain injuries.

Generally, compounds of the invention can be used for improving or enhancing learning and memory in subjects with or without cognitive deficits. Patients, who can benefit from such treatment, include those exhibiting symptoms of dementia or learning and memory loss. Individuals with an amnesic disorder are impaired in their ability to learn new information or are unable to recall previously learned information or past events. The memory deficit is most apparent on tasks to require spontaneous recall and can also be evident when the examiner provides stimuli for the person to recall at a later time. The memory disturbance must be sufficiently severe to cause marked impairment in social or occupational functioning and must represent a significant decline from a previous level of functioning. The memory deficit can be age-related or the result of disease or other cause. Dementia is characterized by multiple clinically significant deficits in cognition that represent a significant change from a previous level of functioning, including memory impairment involving inability to learn new material or forgetting of previously learned material. Memory can be formally tested by measuring the ability to register, retain, recall and recognize information. A diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

Compounds of the invention are useful for preventing loss of neuronal function, which is characteristic of neurodegenerative diseases. Therapeutic treatment with a compound of the invention improves and/or enhances memory, learning and cognition. In one embodiment, the compounds of the invention can be used to treat a neurodegenerative disease such as Alzheimer's, Huntington's disease, Parkinson's disease and amyotrophic lateral sclerosis, as well as MLS (cerebellar ataxia), Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, and closed head injury.

Compounds of the invention are useful for treating or preventing loss of memory and/or cognition associated with a neurodegenerative disease. The compounds also ameliorate cognitive dysfunctions associated with aging and improve catatonic schizophrenia.

Alzheimer's disease is manifested as a form of dementia that typically involves mental deterioration, reflected in memory loss, confusion, and disorientation. In the context of the present invention, dementia is defined as a syndrome of progressive decline in multiple domains of cognitive function, eventually leading to an inability to maintain normal social and/or occupational performance. Early symptoms include memory lapses and mild but progressive deterioration of specific cognitive functions, such as language (aphasia), motor skills (apraxia) and perception (agnosia). The earliest manifestation of Alzheimer's disease is often memory impairment, which is required for a diagnosis of dementia in both the National Institute of Neurological and Communicative Disorders and Stroke-Alzheimer's Disease- and the Alzheimer's Disease and Related Disorders Association (NINCDS-ADRDA) criteria (McKhann et al., 1984, Neurology 34:939-944), which are specific for Alzheimer's disease, and the American Psychiatric Association's Diagnostic and Statistical Manual of Mental Disorders, Fourth Edition (DSM-IV) criteria, which are applicable for all forms of dementia. The cognitive function of a patient can also be assessed by the Alzheimer's disease Assessment Scale-cognitive subscale (ADAS-cog; Rosen et al., 1984, *Am. J. Psychiatry* 141:1356-1364). Alzheimer's disease is typically treated by acetylcholine esterase inhibitors such as tacrine hydrochloride or donepezil. Unfortunately, the few forms of treatment for memory loss and impaired learning available at present are not considered effective enough to make any significant difference to a patient, and there is currently a lack of a standard nootropic drug for use in such treatment.

Other conditions that are manifested as deficits in memory and learning include benign forgetfulness and closed head injury. Benign forgetfulness refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale. Closed head injury refers to a clinical condition after head injury or trauma. Such a condition, which is characterized by cognitive and memory impairment, can be diagnosed as "amnestic disorder due to a general medical condition" according to DSM-IV.

Compounds and compositions of the invention are also effective for treating cerebral function disorders. The term cerebral function disorder, as used herein, includes cerebral function disorders involving intellectual deficits, and can be exemplified by senile dementia, Alzheimer's type dementia, memory loss, amnesia/amnestic syndrome, epilepsy, disturbances of consciousness, coma, lowering of attention, speech disorders, Parkinson's disease and autism.

In a specific embodiment the present invention provides a method for improving mammalian (e.g., human) brain function related to associative learning, executive function, attention, rehearsal, retrieval, early consolidation, late consolidation, declarative memory, implicit memory, explicit memory, episodic memory, semantic memory, rote learning, informal learning, formal learning, multimedia learning, electronic learning, play, imprinting, social cognition including theory of mind, learning, empathy, cooperativity, altruism, language, non-verbal and verbal communicative skills, telepathy, and sensory integration of environmental cues including temperature, odor, sounds, touch, and taste. The skilled artisan will recognize that there are various methods of measuring improvements in brain function and are practices in behavioral and psychological testing that detect improvements in brain function.

Particular tests of associative learning where the compounds of the present invention have utility are classical or respondent conditioning including forward conditioning, simultaneous conditioning, backward conditioning, temporal conditioning, unpaired conditioning, CS-alone conditioning, discrimination reversal conditioning, interstimulus interval conditioning, latent inhibition conditioning, conditioned inhibition conditioning, blocking, aversion therapy, systematic desensitization, or any other form of conditioning known in the psychological and behavioral literature to those skilled in the art of measuring brain function.

Particular tests of brain function where the compounds of the present invention have utility are measurements of brain function include tests classified as operant conditioning including reinforcement, punishment, and extinction, operant variability, avoidance learning, verbal behavior, four term contingency, operant hoarding, or other tests of modified behaviors.

The compounds also have utility improving brain function in conditions that are not characterized as diseased impairments such as normal aging, low IQ, mental retardation, or any other mental capacity characterized by low brain function. The compounds also have utility in improving brain function during defined tasks performed by humans with normal mental status, such as during extended time periods, in which concentration, attention, problem-solving skills and/or learning is required. For example, compounds of the invention can be used by people operating machinery for extended time periods or people working in emergency or combat situations.

Pain

The compounds of the invention are useful to treat any kind of acute or chronic pain. In a preferred embodiment, the compounds of the invention are useful to treat chronic pain. In a particularly preferred embodiment, the compounds of the invention are useful to treat neuropathic pain. The term "pain" includes central neuropathic pain, involving damage to the brain or spinal cord, such as can occur following stroke, spinal cord injury, and as a result of multiple sclerosis. It also includes peripheral neuropathic pain, which includes diabetic neuropathy (DN or DPN), post-herpetic neuralgia (PHN), and trigeminal neuralgia (TGN). It also includes dysfunctions of the nervous system such as Complex Regional Pain Syndrome (CRPS), formerly known as Reflex Sympathetic Dystrophy (RSD), and causalgia, and neuropathic pain symptoms such as sensory loss, allodynia, hyperalgesia and hyperpathia. It further includes mixed nociceptive and neuropathic pain types, for example, mechanical spinal pain and radiculopathy or myelopathy, and the treatment of chronic pain conditions such as fibromyalgia, low back pain and neck pain due to spinal nerve root compression, and reflex sympathetic dystrophy.

In one embodiment, the compounds of the present invention are of use in the prevention or treatment of diseases and conditions in which pain and/or inflammation predominates, including chronic and acute pain conditions. In addition to those stated elsewhere, the compounds of the present invention are of use in the treatment and prevention of pain associated with the conditions which include rheumatoid arthritis; osteoarthritis; post-surgical pain; musculo-skeletal pain, particularly after trauma; spinal pain; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, for example, odontalgia, abdominal pain, gynaecological pain, for example, dysmenorrhoea, pain associated with cystitis and labor pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; itching conditions including pruritis, itch due to hemodialysis, and contact dermatitis; pain (as well as broncho-constriction and inflammation) due to exposure (e.g. via ingestion, inhalation, or eye contact) of mucous membranes to capsaicin and related irritants such as tear gas, hot peppers or pepper spray; chemotherapy-induced neuropathy and "non-painful" neuropathies; pain associated with carcinoma, often referred to as cancer pain; sciatica and ankylosing spondylitis; gout; scar pain; irritable bowel syndrome; bone and joint pain; repetitive motion pain; dental pain; inflammatory bowel disease; urinary incontinence including bladder detrusor hyper-reflexia and bladder hypersensitivity; respiratory diseases including chronic obstructive pulmonary disease (COPD), chronic bronchitis, cystic fibrosis and asthma; autoimmune diseases; and immunodeficiency disorders.

Other conditions and disorders include, but are not limited to, autism, childhood learning disorders, depressions, anxieties and sleep disorders. Compounds of the invention are also useful for the treatment of neurotoxic injury that follows cerebral stroke, thromboembolic stroke, hemorrhagic stroke, cerebral ischemia, cerebral vasospasm, hypoglycemia, amnesia, hypoxia (including e.g., sleep/breathing disorders, such as sleep apnea), anoxia, perinatal asphyxia and cardiac arrest.

The term "treating" when used in connection with the foregoing disorders means amelioration, prevention or relief from the symptoms and/or effects associated with these disorders and includes the prophylactic administration of a compound of the invention, a mixture thereof, a solvate (e.g., hydrate), prodrug (e.g., ethyl or methyl esters of the current carboxylic acid inhibitors) or a pharmaceutically acceptable salt of either, to substantially diminish the likelihood or seriousness of the condition.

B. Models of Disease

Several established animal models of learning and memory are available to examine beneficial, cognitive enhancing effects as well as potential side effects associated with administration of the compounds of the invention. Exemplary methods that can be employed to assess changes in cognition in non-human species are described in the following references, which are incorporated by reference into this application in their entirety: Sarter M, *Intern. J. Neuroscience* 1987, 32:765-774; *Methods and Findings in Experimental and Clinical Pharmacology* 1998, 20(3): 249-277; *Indian Journal of Pharmacology* 1997, 29(4): 208-221.

In one example, compounds of the invention are tested using the "Morris Water Maze" (see, e.g., Stewart and Morris, "*Behavioral Neuroscience. A Practical Approach*. Volume I", 1993, R. Saghal, Ed., 107-122; *Journal of Neuroscience Methods* 1984, 11(1): 47-60). The Morris water maze is one of the best-validated models of learning and memory, and it is sensitive to the cognitive enhancing effects of a variety of pharmacological agents. The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia. In addition, this animal paradigm accurately models the increasing degree of impairment with advancing age and the increased vulnerability of the memory trace to pre-test delay or interference which is characteristic of amnesiac patients.

In another example, compounds of the invention are tested using "Contextual Fear Conditioning" (see, e.g., Barad, M et al., *Proc Natl Acad Sci USA* 1998, 95(25): 15020-5 and Bourtchouladze, R et al., *Cell,* 1994, 79: 59-68). Contextual fear conditioning is a form of associative learning in which animals learn to fear a new environment (or an emotionally neutral conditioned stimulus) because of its temporal association with an aversive unconditioned stimulus (US), such as a foot shock. When exposed to the same context or conditioned stimulus at a later time, conditioned animals show a variety of conditioned fear responses, including freezing behavior. Because robust learning can be triggered with a single training trial, contextual fear conditioning has been used to study temporally distinct processes of short-term and long-term memory. Contextual fear conditioning is believed to be dependent on both the hippocampus and amygdala function.

In another example, compounds of the invention are tested using "Conditioned Fear Extinction" (see, e.g., Walker, D L et al., *J Neurosci.* 2002, 22(6): 2343-51 and Davis, M et al., *Biol. Psychiatry* 2006, 60: 369-375). Fear extinction is an example of learning and is a process exhibited in both human and animals, including rodents. Extinction of fear refers to the reduction in the measured level of fear to a cue previously paired with an aversive event when that cue is presented repeatedly in the absence of the aversive event. Extinction of fear is not the erasure of the original fear memory, but instead results from a new form of learning that acts to inhibit or suppress the original fear memory (Bouton, M D and Bolles, R C; *J. Exp. Psychol. Anim. Behav. Process.* 1979, 5: 368-378; Konorski, *J. Inegrative Activity of the Brain: An Interdisciplinary Approach,* 1967, Chicago: The University of Chicago Press; Pavlov, I. P. *Conditioned Reflexes.* 1927, Oxford, United Kingdom: Oxford University Press). The literature also suggests that glutamate acting at the NMDA receptor is critically involved in learning and memory (Bear, M. F. *Proc. Nat. Acad. Sci.* 1996, 93: 13453-13459; Castellano, C.; Cestari, V.; Ciamei, A. *Curr. Drug Targets* 2001, 2: 273-283; Morris, R. G.; Davis, S.; Butcher, S. P. *Philos. Trans. R Soc. Lond. B Biol. Sci.* 1990, 329: 187-204; Newcomer, J. W.; Krystal, J. H. *Hippocampus* 2001, 11: 529-542). There is also evidence that the NMDA receptor is involved with extinction of fear. For example, NMDA antagonists such as 2-amino-5-phosphopentanoic acid (APV) are known to block fear extinction (Davis, M. et al., *Biol. Psychiatry* 2006, 60: 369-375; Kehoe, E. J.; Macrae, M.; Hutchinson, C. L. *Psychobiol.* 1996, 24: 127-135; Lee, H.; Kim, J. J. *J. Neurosci.* 1998, 18: 8444-8454; Szapiro, G. et al., *Hippocampus* 2003, 13: 53-58). NMDA agonists (such as the partial agonsist D-cycloserine), are known to facilitate fear extinction (Davis, M et al., *Biol. Psychiatry* 2006, 60: 369-375; Ledgerwood, L.; Richardson, R.; Cranney, *J. Behav. Neurosci.* 2003, 117: 341-349; and Walker, D. L. et al., *J. Neurosci.* 2002, 22: 2343-2351). Additional experimental conditions for fear extinction tests can be found in the references incorporated herein by reference.

In human exposure therapy, a patient is repeatedly exposed for prolonged periods to a feared object or situation in the absence of aversive consequences. As a result, the patient is often able to face their feared cues or situations with less fear and avoidance (extinction retention) due to the learning that took place during exposure therapy (extinction training). It has been shown that agents, such as D-cycloserine, that improve extinction in animals also improve the effectiveness of exposure-based psychotherapy. Examples of exposure based cognitive-behavioral therapy (CBT) improved by agents that improve extinction include exposure to phobic objects as therapy for phobia disorders (see, e.g., Davis, M et al., *Biol. Psychiatry* 2006, 60: 369-375; Ressler, K. J. et al., *Archives Gen. Psychiatry* 2004, 61: 1136-1144), exposure to phobic situations as therapy for panic disorders (for social anxiety disorder, see e.g., Hoffmann, S. G. et al., *Arch. Gen. Psychiatry* 2006, 63: 298-304; Hofmann, S. G.; Pollack, M. H.; Otto, M. W. *CNS Drug Reviews* 2006, 12: 208-217), recollection of traumatic memories as therapy for post-traumatic stress disorder, exposure to cues associated with drug cravings as therapy for drug addiction, and exposure to cues associated with smoking as therapy for smoking cessation. Because of the cognitive, learning aspects associated with psychotherapy based treatment for disorders such as phobias, anxiety, post-traumatic stress disorder and addiction, compounds of the invention are useful as an adjunct with psychotherapy for the treatment of these conditions. For example, compounds of the invention are useful as an adjunct to shorten the number of therapy sessions required or to improve the therapeutic outcome of therapy.

In another example, compounds of the invention are tested using "Delayed Non-Match to Sample" (see e.g., Bontempi, B. et al., *Journal of Pharmacology and Experimental Therapeutics* 2001, 299(1): 297-306; Alvarez, P. et al., *Proc Natl Acad Sci USA* 1994, 7; 91(12), 5637-41); "Delayed Alternation" (also called delayed non-matching to position) (see, e.g., Roux, S. et al., *Pharmacol Biochem Behav.* 1994, 49(3): 83-88; Ohta, H. et al., *Jpn J Pharmacol.* 1991, 56(3): 303-9); "Social Discrimination Models" (see, e.g., Engelmann, M. et al., *Physiol Behav.* 1995, 58(2): 315-21); "Social Recognition Test" (also called delay-induced forgetting) (see e.g., Lemaire, M. et al., *Psychopharmacology (Berl).* 1994, 115(4):435-40).

In humans, improved learning and memory can be measured by such tests as the Wechsler Memory Scale and the Minimental test. A standard clinical test for determining if a patient has impaired learning and memory is the Minimental Test for Learning and Memory (see e.g., Folstein et al., *J. Psychiatric Res.* 1975, 12:185), especially for those suffering from head trauma, Korsakoff's disease or stroke. The test result serves as an index of short-term, working memory of the kind that deteriorates rapidly in the early stages of dementing or amnesiac disorders. Ten pairs of unrelated words (e.g., army-table) are read to the subject. Subjects are then asked to recall the second word when given the first word of each pair. The measure of memory impairment is a reduced number of paired-associate words recalled relative to a matched control group. Improvement in learning and memory constitutes either (a) a statistically significant difference between the performance of treated patients as compared to members of a placebo group; or (b) a statistically significant change in performance in the direction of normality on measures pertinent to the disease model.

Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task. Another potential application for therapeutic interventions against memory impairment is suggested by age-related deficits in performance which are effectively modeled by the longitudinal study of recent memory in aging mice.

The Wechsler Memory Scale is a widely used pencil-and-paper test of cognitive function and memory capacity. In the normal population, the standardized test yields a mean of 100 and a standard deviation of 15, so that a mild amnesia can be detected with a 10-15 point reduction in the score, a more severe amnesia with a 20-30 point reduction, and so forth. During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory within the context of the present invention occurs when there is a statistically significant difference in the direction of normality in the paired-associate test, for example, between the performance of therapeutic agent treated patients as compared to members of the placebo group or between subsequent tests given to the same patient.

In animals, many established models of schizophrenia are available to examine the beneficial effects of treatment; many of which are described in the following references, as well as references cited therein: Saibo *Kogaku* 2007, 26(1): 22-27; Cartmell, J. et al., *J. Pharm. Exp. Ther.* 1999, 291(1): 161-170; Rowley, M; Bristow, L. J.; Hutson, P. H. *J. Med. Chem.* 2001, 1544(4): 477-501; Geyer, M. A.; Ellenbroek, B; *Prog Neuropsychopharmacol Biol Psychiatry* 2003, 27(7): 1071-1079; Geyer, M. A. et al., *Psychopharmacology (Berl).* 2001, 156(2-3):117-54; Jentsch, J. D.; Roth, R. H. *Neuropsychopharmacology* 1999, 20(3):201-25. The tests include "Prepulse Inhibition" (see e.g., Dulawa, S. C.; Geyer, M. A. *Chin J Physiol.* 1996, 39(3):139-46); "PCP Stereotypy Test" (see e.g., Meltzer et al., (*"PCP (Phencyclidine): Historical and Current Perspectives"*, ed. E. F. Domino, NPP Books, Ann Arbor, 1981: 207-242); "Amphetamine Stereotypy Test" (see e.g., Simon and Chemat, *J. Pharmacol.* (Paris) 1972, 3: 235-238); "PCP Hyperactivity" (se e.g., Gleason, S. D.; Shannon, H. E. *Psychopharmacology (Berl).* 1997, 129(1): 79-84); and "MK-801 Hyperactivity" (see e.g., Corbett, R. et al., *Psychopharmacology (Berl).* 1995, 120(1):67-74), the disclosures of which are each incorporated herein by reference.

The prepulse inhibition test can be used to identify compounds that are effective in treating schizophrenia. The test is based upon the observations that animals or humans that are exposed to a loud sound will display a startle reflex and the observation that animals or humans exposed to a series of lower intensity sounds prior to the higher intensity test sound will no longer display as intense of a startle reflex. This is termed prepulse inhibition. Patients diagnosed with schizophrenia display defects in prepulse inhibition, that is, the lower intensity prepulses no longer inhibit the startle reflex to the intense test sound. Similar defects in prepulse inhibition can be induced in animals via drug treatments (scopolamine, ketamine, PCP or MK-801) or by rearing offspring in isolation. These defects in prepulse inhibition in animals can be partially reversed by drugs known to be efficacious in schizophrenia patients. It is felt that animal prepulse inhibition models have face value for predicting efficacy of compounds in treating schizophrenia patients.

In animals, many established models of pain are available to examine the beneficial effects of treatment; many of which are reviewed in *Methods in Pain Research*, CRC Press, 2001, Kruger, L. (Editor). Tests of acute pain include the tail flick (see e.g., d'Amour and Smith, *J. Pharmacol. Exp. Ther.* 1941, 72: 74-79), hot plate (see e.g., Eddy, N. B.; Leimbach, D. *J Pharmacol Exp Ther.* 1953, 107(3):385-93), and paw withdrawal tests. The phenylbenzoquinone writhing assay is a measure of peritoneovisceral or visceral pain. Persistent pain tests, which use an irritant or foreign chemical agent as the nociceptive stimulus, include the formalin test (see e.g., Wheeler-Aceto, H; Cowan, A *Psychopharmacology (Berl)*. 1991, 104(1):35-44), Freund's adjuvant (see e.g., Basile, A. S. et al., *Journal of Pharmacology and Experimental Therapeutics* 2007, 321(3): 1208-1225; Ackerman, N. R. et al; *Arthritis & Rheumatism* 1979, 22(12): 1365-74), capsaicin (see e.g., Barrett, A. C. et al., *Journal of Pharmacology and Experimental Therapeutics* 2003, 307(1): 237-245), and carrageenin models. These models have an initial, acute phase, followed by a second, inflammatory phase.

Neuropathic pain models are reviewed in Wang and Wang, *Advanced Drug Delivery Reviews* 2003, and include the "Spinal Nerve Ligation (SNL) model" (also called the "Chung Model") (see e.g., Kim, S. H.; Chung, J. M. *Pain* 1992, 50(3):355-63; Chaplan et al., *Journal of Neuroscience Methods* 1994, 53(1):55-63); "Chronic Constriction Injury (CCI) model" (also called the "Bennett Model") (see e.g., Bennett, G. J; Xie,Y. K *Pain* 1988, 33(1):87-107); "Progressive Tactile Hypersensitivity (PTH) model) (see e.g., Decosterd, I. *Pain* 2002, 100(1): 155-162; *Anesth. Analg.* 2004, 99: 457-463); "Spared Nerve Injury (SNI) model" (see e.g., Decosterd, I., *Pain* 2002, 100(1): 155-162; *Anesth. Analg.* 2004, 99: 457-463); "lumbar nerve ligation model" (see e.g., Ringkamp, M. et al., *Pain* 1999, 79(2-3): 143-153); and "streptozocin- or chemotherapy induced diabetic neuropathy" (see e.g., Courteix, C.; Eschalier, A.; Lavarenne, J. *Pain* 1993, 53(1): 81-88; Aubel, B. et al *Pain* 2004, 110(1-2): 22-32).

Opioids, such as morphine, display robust efficacy in models of acute pain, such as the tail flick and hot plate tests, as well as in both the initial, acute phase and the second, inflammatory phase of persistent pain tests, such as the formalin test. Opioids also display efficacy in neuropathic pain models, such as the Spinal Nerve Ligation (SNL) model. The general analgesic effects of opiate compounds such as morphine in neuropathic pain models, however, are suggested by the increase in paw withdrawal threshold (PWT) in both the injured and the contralateral (uninjured) paw. Compounds that are useful specifically for the treatment of persistent or chronic pain states (e.g., neuropathic pain), such as gabapentin, tend to display efficacy in models of persistent inflammatory and neuropathic pain, such as the formalin (second phase) and SNL models. Compounds of this type, however, tend to increase PWT in the SNL model in only the injured paw. In addition, these compounds fail to display efficacy in acute tests such as the tail flick test and the hot plate test, and also fail to display efficacy in the initial, acute phase of the formalin test. The lack of effect of compounds in the acute pain tests supports the notion that the antinociceptive action of these compounds is related to specific mechanisms associated with a central sensitized state following injury. As a result, compounds that are efficacious in neuropathic pain model(s), such as the SNL (Chung) model, and the second phase of the formalin test, but are not efficacious in acute pain models, such as hot plate and tail flick, or in the first phase of the formalin test suggest that these compounds are more likely to be effective in persistent and chronic, rather than acute, pain states (see Table 1). In addition, their ability to increase PWT in the SNL model should be specific for the ipsilateral (injured) paw. Relevant references follow, and are included by reference. Singh, L. et al, *Psychopharmacology* 1996, 127: 1-9. Field, M. J. et al., *Br. J. Pharmacol.* 1997, 121: 1513-1522. Iyengar, S. et al, *J. Pharmacology and Experimental Therapeutics* 2004, 311: 576-584. Shimoyama, N. et al *Neuroscience Letters* 1997, 222: 65-67. Laughlin, T. M. et al., *J. Pharmacology and Experimental therapeutics* 2002, 302: 1168-1175. Hunter, J. C. et al., *European J. Pharmacol.* 1997, 324: 153-160. Jones, C. K. et al., *J. Pharmacology and Experimental therapeutics* 2005, 312: 726-732. Malmberg, A. B.; Yaksh, T. L. *Anesthesiology* 1993, 79: 270-281. Bannon, A. W. et al., *Brain Res.* 1998, 801: 158-63.

In one embodiment, the compounds of the invention are useful for the treatment of persistent or chronic pain states (e.g., neuropathic pain). As described above, such compounds can be profiled in vivo by evaluating their efficacy in models of both acute and neuropathic pain. Preferred compounds demonstrate efficacy in neuropathic pain models, but not in acute pain models.

TABLE 1

Profile of morphine and gabapentin in a variety of animal models

| Animal Model | Morphine | Gabapentin |
|---|---|---|
| Acute Pain | | |
| Hot plate | + | − |
| Tail flick | + | − |
| Formalin (early phase) | + | − |
| Tissue Injury/Inflammatory Pain | | |
| Formalin (second phase) | + | + |
| Carrageenan | + | + |
| Nerve Injury/Neuropathic Pain | | |
| Spinal Nerve Ligation (SNL; Chung) | + | + |
| Chronic Constriction Injury (CCI; Bennet) | + | + |

There are various animal models with chronic brain dysfunctions thought to reflect the processes underlying human epilepsy and seizures/convulsions, such as those described in *Epilepsy Res.* 2002, 50(1-2):105-23. Such chronic models include the "kindling model of temporal lobe epilepsy" (TLE); "post-status models of TLE", in which epilepsy develops after a sustained status epilepticus; and genetic models of different types of epilepsy. Currently, the kindling model and post-status models, such as the pilocarpine or kainate models, are the most widely used models for studies on epileptogenic processes and on drug targets by which epilepsy can be prevented or modified. Furthermore, the seizures in these models can be used for testing of antiepileptic drug effects. A comparison of the pharmacology of chronic models with models of acute (reactive or provoked) seizures in previously healthy (non-epileptic) animals, such as the maximal electroshock seizure test, demonstrates that drug testing in chronic models of epilepsy yields data which are more predictive of clinical efficacy and adverse effects.

The following examples are provided to illustrate selected embodiments of the invention and are not to be construed as limiting its scope.

EXAMPLES

General Procedures

Compounds of the invention can be synthesized using the following general procedures.

General Procedure 1: Synthesis of Fused Pyrrole Esters

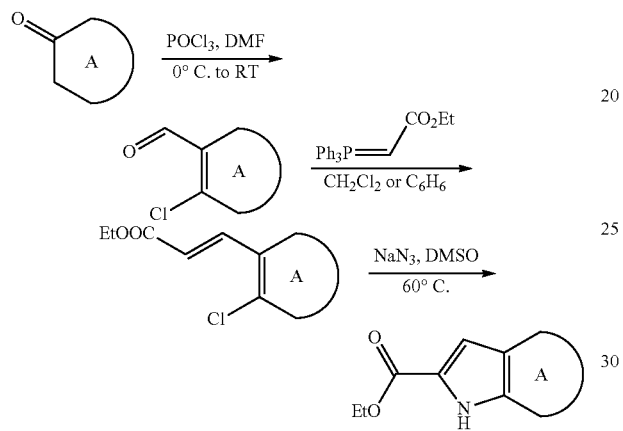

In the above Scheme, ring A represents any substituted or unsubstituted, non-aromatic ring. The ester is shown as ethyl, but other esters can be used, e.g., methyl, benzyl, etc.

1.1.A) Formylation of Ketones

To N,N'-dimethylformamide (DMF) (9.2 mL, 118.9 mmol) at 0° C. was slowly added phosphoryl trichloride (8.9 mL, 95.1 mmol) forming an orange solution that quickly solidified to an orange paste. The ketone (59.4 mmol) was added dropwise over ten minutes (min). The cooling bath was removed after 30 min. The flask was swirled until liquefaction began to occur. The flask was then reimmersed in an ice bath and allowed to gradually warm to room temperature (rt) overnight, forming a dark solution. The mixture was poured over ice and neutralized with solid $NaHCO_3$ until no further evolution of $CO_2$ was observed. The resulting mixture was extracted with ether (5×50 mL). The combined extracts were washed with water and brine, dried (e.g., $Na_2SO_4$), filtered and passed through a plug of silica before concentration to provide the β-chlorovinyl aldehyde (83%).

1.1.B) Olefination of Aldehydes

To a solution of the above β-chlorovinyl aldehyde (7.66 mmol) in $CH_2Cl_2$ (10 mL) under nitrogen was added ethoxycarbonylmethylene triphenylphosphorane (2.93 g, 8.42 mmol). The strongly exothermic reaction was refluxed for 6 h, and then stirred at rt for about 12 hours (h). The solvent was removed and the residue adsorbed onto silica and purified by flash chromatography (e.g., 0-30% ethyl acetate (EtOAc)/heptane) to give the ethyl 3-(2-chlorocycloalk-1-enyl)acrylate in 99% yield.

1.1.C) Cyclization

Sodium azide (0.73 g, 11.21 mmol) was added to a solution of the above ethyl 3-(2-chlorocycloalk-1-enyl)acrylate (7.48 mmol) in dimethylsulfoxide (DMSO) (11 mL) and the mixture was heated at 65° C. for about 12 h. After cooling, the mixture was diluted with water and extracted with EtOAc (5×50 mL). The combined organic extracts were washed with water (3×50 mL) and brine, dried (e.g., $Na_2SO_4$), filtered and concentrated. Purification by flash chromatography (e.g., 0-50% EtOAc/heptane) provided 418 mg (31%) of the fused pyrrole ester.

General Procedure 1.2: Synthesis of Fused Pyrrole Esters

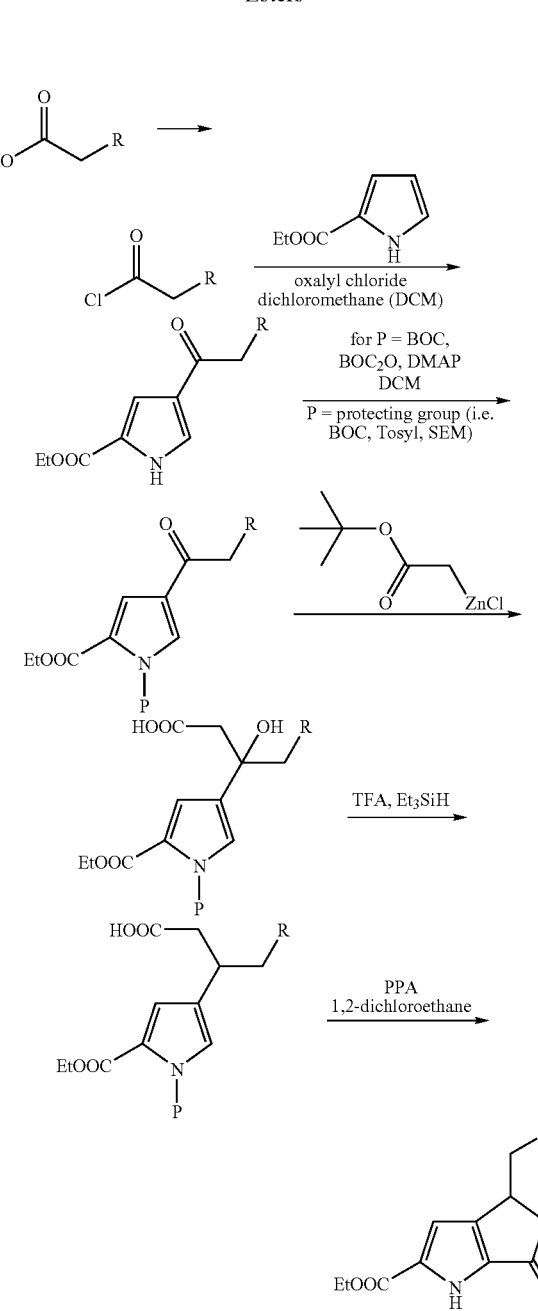

In the above Scheme, P represents a protecting group (i.e., tert-Butyloxycarbonyl (BOC), tosyl (Ts), 2-(trimethylsilyl)

ethoxymethyl (SEM)). For representative protection and deprotection or pyrroles, see *Tetrahedron*, 2006, 62, 11531-11563 and references cited within. The ester is shown as ethyl, but other esters can be used, e.g., methyl, benzyl, etc.

1.2.A) Acid Chloride Formation Followed by Acylation

References: *J. Med. Chem.* 2001; 44; 4468-4474; *Heterocycles* 1988; 27(8); 1855-1860.

To a 100-mL round bottom flask with magnetic stir bar under a nitrogen atmosphere at room temperature was added the starting acetic acid derivative (i.e. bromophenylacetic acid) (9.6 mmol, 1.2 equiv) and anhydrous dichloromethane (DCM) (15 mL). Oxalyl chloride solution (5.2 mL, 2M in DCM, 10 mmol, 1.3 equiv) was then added followed by 2 drops of DMF. Stirring was continued at room temperature for 1 hour. The solvent was then evaporated in vacuo and taken up in anhydrous dichloroethane (DCE) (10 mL).

In a separate vessel, the starting material (i.e. methylpyrrole-2-carboxylate) (8 mmol, 1 equiv) was dissolved in anhydrous DCE (10 mL) under a nitrogen atmosphere at room temperature. The vial was cooled to 0° C. and the anhydrous aluminum chloride (1.9 g, 14 mmol, 1.8 equiv) was added. Stirring was continued at 0° C. for 15 minutes before adding the acid chloride (i.e.; material from the oxalyl chloride step). Addition of the acid chloride in DCE was done drop-wise over approx. 10 minutes. The reaction vial was then brought to room temperature over 30 minutes before heating overnight at 65° C. The reaction was quenched by pouring the contents of the reaction vial into cold, concentrated aqueous NaHCO$_3$ solution (100 mL). The resulting aqueous mixture was extracted with EtOAc (3×50 mL). The combined extracts were washed with brine, dried (e.g., Na$_2$SO$_4$), filtered and concentrated. The resulting residue was purified by column chromatography (Isco CombiFlash) using a 0-50% gradient (EtOAc/Heptane) over 45 minutes to provide the desired product (i.e. methyl 4-(2-(4-bromophenyl)acetyl)-1H-pyrrole-2-carboxylate).

1.2.B) Pyrrole Protection

To a 40-mL scintillation vial with magnetic stir bar under a nitrogen atmosphere at room temperature was added the starting material (i.e. methyl-4-[2-(4-bromophenyl)-acetyl]-1H-pyrrole-2-carboxylate) (5.2 mmol, 1 equiv) and anhydrous DCM (75 mL). 4-Dimethylaminopyridine (DMAP) (0.064 g, 0.52 mmol, 0.1 equiv) was added and stirring was continued until the material was completely dissolved. In a separate vessel, di-tert-butyl dicarbonate (1.38 g, 6.3 mmol, 1.2 equiv) was dissolved in anhydrous DCM (25 mL) and added drop-wise to the main reaction vessel. Stirring was continued overnight at room temperature. The reaction mixture was quenched by addition to a 1:1 mixture of saturated ammonium chloride solution and water (100 mL). The layers were separated and the DCM layer set aside. The resulting aqueous layer was extracted with EtOAc (3×50 mL). The combined organic extracts were washed with saturated aqueous NaHCO$_3$ solution (50 mL), brine, dried (e.g., Na$_2$SO$_4$), filtered and concentrated. The resulting residue was purified by column chromatography (Isco CombiFlash) using a 0-30% gradient (EtOAc/Heptane) over 26 minutes to afford the desired product (i.e., 1-tert-butyl 2-methyl 4-(2-(4-bromophenyl)acetyl)-1H-pyrrole-1,2-dicarboxylate).

1.2.C) 2-tert-Butoxy-2-oxoethylzinc chloride addition

Reference: *Org. Lett.* 2002; 4(18); 3051-3054. To a 500-mL round bottom flask with magnetic stir bar under a nitrogen atmosphere at room temperature was added 2-tert-Butoxy-2-oxoethylzinc chloride (3.0 g, 28.2 mL, 0.5M in ether, 14 mmol, 3.5 equiv). The reaction flask was subsequently cooled to 0° C. In a separate vessel, the starting material (i.e., 1-tert-butyl 2-methyl 4-(2-(4-bromophenyl)acetyl)-1H-pyrrole-1,2-dicarboxylate) (4 mmol, 1 equiv) was dissolved in anhydrous THF (50 mL) and added drop-wise to the main reaction flask over 20 minutes. Stirring was continued for approximately 4 hours while allowing the flask to equilibrate to room temperature. The reaction was quenched by the addition of an approximately equal volume of dilute aqueous HCl solution (approx. 1N). The layers were separated and the organic layer set aside. The resulting aqueous mixture was extracted with EtOAc (3×50 mL). The combined organic extracts were washed with saturated aqueous NaHCO$_3$ solution (50 mL), brine, dried (e.g., Na$_2$SO$_4$), filtered and concentrated. The resulting residue was purified by column chromatography (Isco CombiFlash) to provide the desired product (i.e. 1-tert-butyl 2-methyl 4-(1-(4-bromophenyl)-4-tert-butoxy-2-hydroxy-4-oxobutan-2-yl)-1H-pyrrole-1,2-dicarboxylate).

1.2.D) Carbinol Reduction

To a 40-mL scintillation vial with magnetic stir bar under a nitrogen atmosphere at room temperature was added the starting material (i.e. 1-tert-butyl 2-methyl 4-(1-(4-bromophenyl)-4-tert-butoxy-2-hydroxy-4-oxobutan-2-yl)-1H-pyrrole-1,2-dicarboxylate) (3.7 mmol, 1 equiv) and trifluoroacetic acid (TFA) (8.25 mL, 0.45 M based on starting material). Triethylsilane (1.25 g, 1.72 mL, 2.9 equiv) was then added and stirring continued at room temperature overnight. The solvent was evaporated and the resulting residue taken up in EtOAc (30 mL). The resulting solution was dried (e.g., Na$_2$SO$_4$), filtered and concentrated. The resulting residue was purified by column chromatography (Isco CombiFlash) to provide the desired product (i.e., 4-(4-bromophenyl)-3-(5-(methoxycarbonyl)-1H-pyrrol-3-yl)butanoic acid). Note: If the protecting group (i.e. BOC) is not removed when subjected to the reaction conditions, it may be removed using standard deprotection conditions.

1.2.E) Cyclization

To a 250-mL round bottom flask with magnetic stir bar was added the polyphosphoric acid (PPA) (4 times the weight of the starting material, by mass). In a separate vessel, the starting material (i.e., 4-(4-bromophenyl)-3-(5-(methoxycarbonyl)-1H-pyrrol-3-yl)butanoic acid) (2.16 mmol, 1 equiv) was dissolved in anhydrous 1,2-dichloroethane (DCE) (50 mL) and then added to the main reaction vessel. The reaction flask was fitted with a Vigreux column and subsequently heated to 100° C. for 90 minutes. After cooling to room temperature, water was added (alternating with EtOAc) until the resulting black gelatinous mixture was solubilized. The resulting mixture was filtered through Celite®, the filter cake rinsed thoroughly with EtOAc (300 mL), and transferred to a separatory funnel. The layers were separated and the organic layer set aside. The aqueous layer was extracted with EtOAc (3×50 mL). The combined organic extracts were washed with saturated aqueous NaHCO$_3$ solution (50 mL), brine, dried (e.g., Na$_2$SO$_4$), filtered and concentrated. The resulting residue was purified by column chromatography to afford the desired product (i.e., methyl 4-(4-bromobenzyl)-6-oxo-1,4,5,6-tetrahydrocyclopenta[b]pyrrole-2-carboxylate).

General Procedure 2: Wittig Olefination of Keto-Substituted Fused Pyrrole Esters

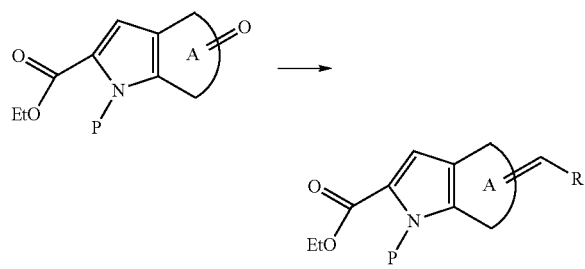

In the above Scheme, ring A represents any substituted or unsubstituted, non-aromatic ring. Exemplary rings for the starting material include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within. The ester is shown as ethyl, but other esters can be used, e.g., methyl, benzyl, etc.

NaH (145 mg, 3.63 mmol; 60% dispersed in oil), suspended in THF (10 mL) in a 40 mL scintillation vial was reacted with a Wittig reagent (i.e., (4-chlorobenzyl)-triphenylphosphonium chloride) (3.63 mmol) at rt for 2 h. The keto-substituted fused pyrrole ester (i.e., methyl 4-oxo-1,4,5,6-tetrahydrocyclopenta[b]pyrrole-2-carboxylate) (2.79 mmol) was added and the reaction mixture was heated at 65° C. for 48 h. The reaction was concentrated under vacuum and purified by flash chromatography to give the olefin-substituted fused pyrrole ester (i.e., 4-oxo-1,4,5,6-tetrahydrocyclopenta[b]pyrrole-2-carboxylic acid).

General Procedure 3: Grignard Addition to Keto-Substituted Fused Pyrrole Esters

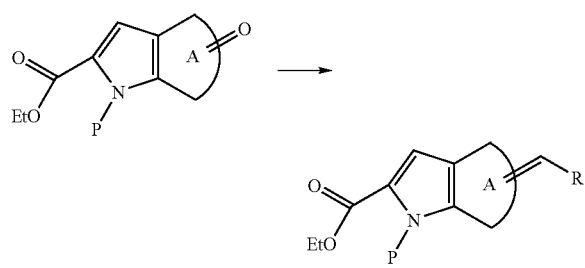

In the above Scheme, ring A represents any substituted or unsubstituted, non-aromatic ring. Exemplary rings for the starting material include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within. The ester is shown as ethyl, but other esters can be used, e.g., methyl, benzyl, etc.

To a solution of the Grignard reagent (i.e., isobutyl MgBr) (4 equiv) in THF (10 mL) at 0° C. was added the ketone (i.e. methyl 4-oxo-1,4,5,6-tetrahydrocyclopenta[b]pyrrole-2-carboxylate) (1.68 mmol) in THF (4 mL). The cooling bath was removed and the reaction mixture was heated to 67° C. for about 12 h. It was then quenched with a saturated solution of NH$_4$Cl and extracted with EtOAc (3×50 mL). The combined extracts were washed with brine, dried (e.g., Na$_2$SO$_4$), filtered and concentrated. In certain examples, the crude product was purified by flash chromatography (e.g., 0-40% EtOAc/heptane) to afford the olefin-substituted fused pyrrole ester (i.e., methyl 4-(2-methylpropylidene)-1,4,5,6-tetrahydrocyclopenta[b]pyrrole-2-carboxylate). In other examples, the crude reaction mixture was filtered through a silica gel plug and the dried product was used without further purification.

In examples with alkyl and aryl magnesium bromides, the products formed can often contain an endocyclic olefin, such as shown below.

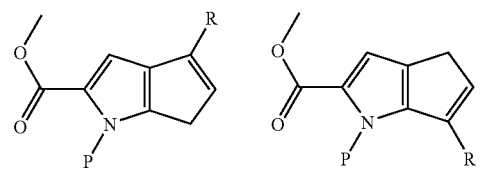

In examples with benzyl-substituted magnesium bromides, the products formed can often contain an exocyclic olefin, such as shown below.

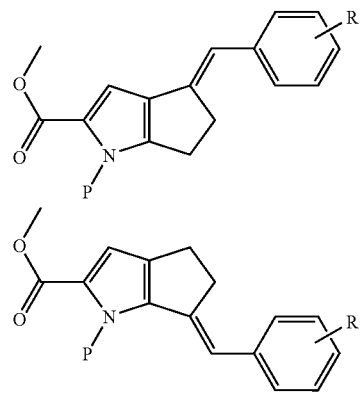

In some examples, the corresponding carbinol compound is formed, either alone or as a mixture with the olefin containing compound(s), such as shown below.

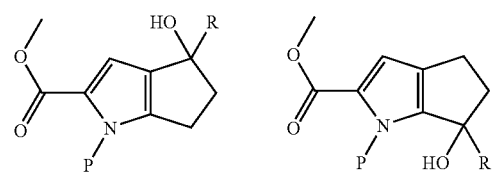

Both the olefin-containing compounds and carbinol-containing compounds may be taken, under the conditions in General Procedure 6, to the corresponding saturated compound, such as shown below.

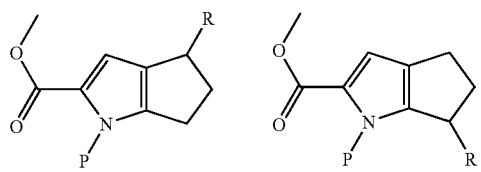

General Procedure 4: Alkylation of Ketones

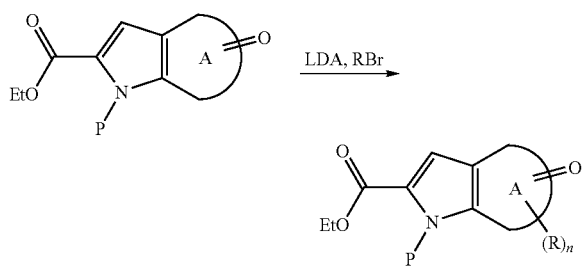

In the above Scheme, ring A represents any substituted or unsubstituted, non-aromatic ring. Exemplary rings include cyclopentenones and cyclohexenones. The R group is a substituent of ring A and is positioned at the alpha-position of the ketone. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within. When ring A is a 5-membered ring then n is selected from 1 and 2. When A is a 6-membered ring then n is selected from 1, 2 and 3. The ester is shown as ethyl, but other esters can be used, e.g., methyl, benzyl, etc.

To the ketone (i.e., 1-tert-butyl 2-methyl 4-oxo-5,6-dihydrocyclopenta[b]pyrrole-1,2(4H)-dicarboxylate) (1.9 mmol) in THF (20 mL) at −78° C. was added a freshly prepared 0.75 M lithium diisopropylamide (LDA) solution (3.3 mL, 2.47 mmol) and the mixture was stirred at −78° C. for 45 min. The alkyl halide (i.e., iodomethane) (1.9 mmol) was then added. The mixture was allowed to warm to rt and was stirred for about 18 h. The reaction was quenched with a saturated solution of NH₄Cl before extraction with EtOAc (e.g., 3×100 mL). The combined extracts were washed with brine and dried (e.g., over Na₂SO₄). The crude product was optionally purified by column chromatography.

General Procedure 5.1: Reduction of Ketones

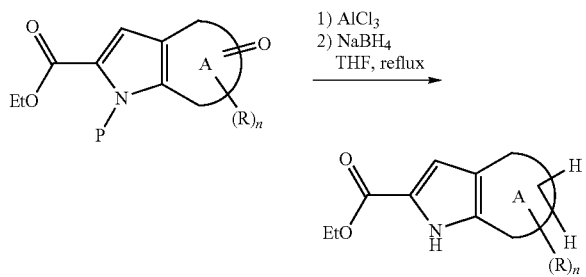

In the above Scheme, ring A represents any substituted or unsubstituted, non-aromatic ring. Exemplary rings include cyclopentenones and cyclohexenones. The R group is positioned adjacent to the newly formed methylene group. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) When BOC is used as the protecting group (P), a deprotected side product is typically obtained. The ester shown as ethyl, but other esters can be used, e.g., methyl, benzyl, etc.

To a solution of the above ketone (i.e., 1-tert-butyl 2-methyl 5-methyl-4-oxo-5,6-dihydrocyclopenta[b]pyrrole-1,2(4H)-dicarboxylate) (0.053 g, 0.181 mmol) in THF (5 mL) was added aluminum chloride (0.134 g, 1.0 mmol). The mixture was stirred for 15 min at rt before sodium borohydride (0.070 g, 1.85 mmol) was added. The mixture was heated to reflux for about 4 h. The reaction was allowed to cool to rt and was stirred for about 8 h to about 14 h. The reaction mixture was quenched with saturated aqueous NH₄Cl solution and was extracted with EtOAc (3×25 mL). The combined extracts were washed with brine and dried over Na₂SO₄. The crude product was purified by column chromatography (i.e., 0-30% EtOAc/heptane) to afford the desired product (i.e. methyl 5-methyl-1,4,5,6-tetrahydrocyclopenta[b]pyrrole-2-carboxylate).

General Procedure 5.2: Reduction of Ketones

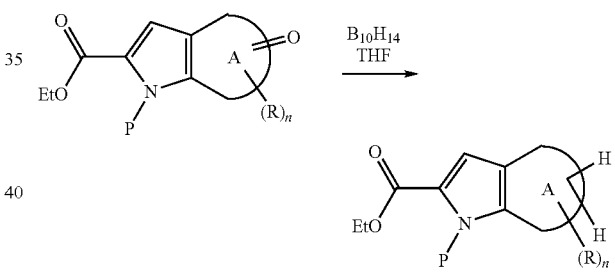

In the above Scheme, ring A represents any substituted or unsubstituted, non-aromatic ring. Exemplary rings include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) When BOC is used as the protecting group (P), a deprotected side product is typically obtained. The ester is shown as ethyl, but other esters can be used, e.g., methyl, benzyl, etc.

To a 40-mL scintillation vial with magnetic stir bar under a nitrogen atmosphere at room temperature was added the starting ketone (i.e. methyl 4-(4-bromobenzyl)-1,4,5,6-tetrahydrocyclopenta[b]pyrrole-2-carboxylate) (0.21 g, 0.6 mmol, 1 equiv) and anhydrous THF (25-30 mL). Decaborane (0.34 g, 3 mmol, 5 equiv) was then added, the vial flushed with nitrogen, and capped tightly before heating at 60° C. overnight. The reaction was quenched by pouring the contents of the reaction vial into an approximately equal volume of a 1:1 mixture of saturated aqueous ammonium chloride and water (approx. 30 mL). The resulting aqueous mixture was taken up in ethyl acetate (EtOAc (and extracted (3×50 mL). The combined extracts were washed with brine, dried (e.g., Na₂SO₄), filtered and concentrated. The resulting residue was purified by column chromatography (Isco CombiFlash) using a 0-30% gradient (EtOAc/Heptane) over 20 minutes to afford the desired product (i.e. 4-(4-bromobenzyl)-1,4,5,6-tetrahydrocyclopenta[b]pyrrole-2-carboxylic acid).

General Procedure 6: Hydrogenation of Olefin-Substituted Fused Pyrrole Esters

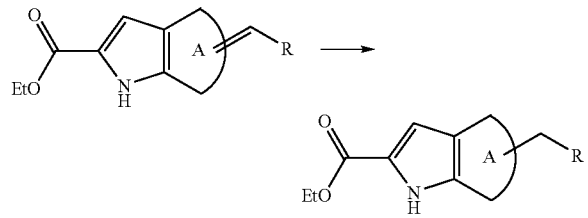

In the above Scheme, ring A represents any substituted or unsubstituted, non-aromatic ring. Exemplary rings include substituted cyclopentenes and cyclohexenes. The ester is shown as ethyl, but other esters can be used, e.g., methyl, benzyl, etc.

To a solution of the olefin-substituted fused pyrrole ester (i.e., 4-(4-chloro-benzylidene)-1,4,5,6-tetrahydro-cyclopenta[b]pyrrole-2-carboxylic acid methyl ester) (0.504 mmol) in EtOAc/MeOH (1:1, 5 mL) or ethanol was added 5-10% Pd/C or platinum (IV) oxide (PtO₂) under nitrogen. The system was evacuated and refilled with hydrogen three times before allowing the reaction to continue at rt. After the reaction was complete (typically 2.5 h to 3 h), the catalyst was filtered through Celite and the filtrate concentrated. The crude product can be purified by silica gel column chromatography.

When the olefin-containing substituent contains a halogen, (i.e., the substrate 4-(4-chloro-benzylidene)-1,4,5,6-tetrahydrocyclopenta[b]pyrrole-2-carboxylic acid methyl ester) a dehalogenation product (i.e. methyl 4-benzyl-1,4,5,6-tetrahydrocyclopenta[b]pyrrole-2-carboxylate), can also be formed. In those examples it can be necessary to purify the crude product using reverse phase chromatography to separate halogenated analogs from dehalogenated analogs. For example, purification by reverse-phase chromatography (i.e., (75:25 MeOH: water for 5 min)) provided the desired alkyl-substituted fused pyrrole ester (i.e. methyl 4-(4-chlorobenzyl)-1,4,5,6-tetrahydrocyclopenta[b]pyrrole-2-carboxylate).

General Procedure 7: Saponification of Ethyl and Methyl-Esters

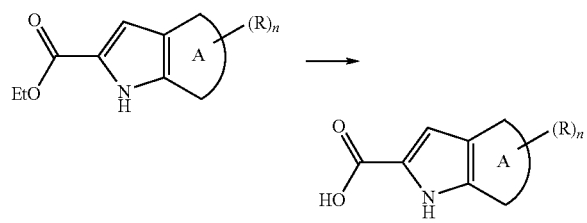

In the above Scheme, ring A represents any substituted or unsubstituted, non-aromatic ring. Exemplary rings include cyclopentenes and cyclohexenes. The ester is shown as ethyl, but other esters can be used, e.g., methyl, benzyl, etc.

To a solution or suspension of the ester (e.g., 0.33 g, 1.2 mmol) in MeOH or EtOH (e.g., 16.5 mL) was added an aqueous base, such as 10 M NaOH (e.g., 0.6 mL, 6 mmol), 5M KOH (e.g., 1.2 mL, 6 mmol) or 1 M LiOH (e.g., 6 mL). The solution was heated to a temperature between about 8° C. and refluxed for a time period between about 30 min and about 20 h (e.g., 5 h). The reaction mixture was cooled to rt and was then acidified. In one example, the mixture was poured into water (e.g., 200 mL) and the pH of the resulting mixture was adjusted to about pH 1-2 with HCl. In another example, excess solvent was removed in vacuo and the residue was dissolved in 5% citric acid (e.g., 15 mL). In yet another example, the solvent was removed in vacuo and the residue was dissolved in a saturated solution of NH₄Cl (e.g., 15 mL). The acidified solution was then extracted (e.g., 3×100 mL EtOAc) and the combined organic layers were washed (e.g., with brine), dried (e.g., over Na₂SO₄), filtered and concentrated in vacuo to give the carboxylic acid.

General Procedure 8: Separation of Enantiomers of Fused Pyrrole Carboxylic Acids

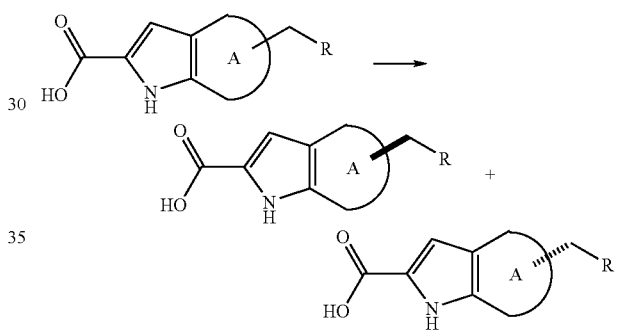

In the above Scheme, ring A represents any substituted or unsubstituted, non-aromatic ring. Exemplary rings include cyclopentenes and cyclohexenes.

Enantiomers of racemic fused pyrrole carboxylic acids were separated using chiral chromatography. An exemplary method uses an isocratic SFC method (40 to 50% methanol in CO₂ with 0.05% diethylamine) on a Chiralpak AD-H column (Chiral Technologies) in a 3.0×25 cm format with a mobile phase flow rate ranging from 70 to 72 g/minute. Alternatively, enantiomers can be separated by chiral chromatography or other art-recognized methods at the ester stage.

General Procedure 9.1: Aryl Halide Coupling

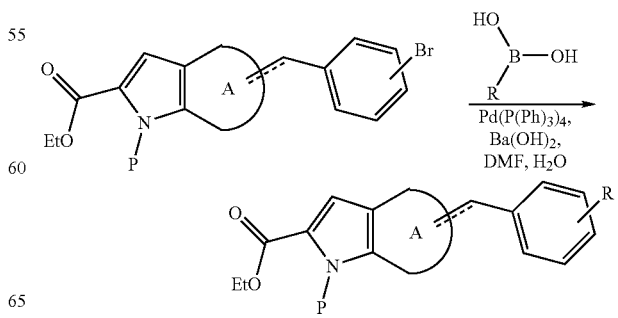

In the above Scheme, ring A represents any substituted or unsubstituted, non-aromatic ring. Exemplary rings include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) The ester is shown as ethyl, but other esters can be used, e.g., methyl, benzyl, etc.

The starting aryl halide (i.e., (E)-methyl 4-(3-bromobenzylidene)-1-tosyl-1,4,5,6-tetrahydrocyclopenta[b]pyrrole-2-carboxylate) (0.824 mmol) was dissolved in DMF (8 mL) and H$_2$O (2 mL) was added, forming a suspension. Barium hydroxide (0.213 g, 1.24 mmol) was then added, and the suspension was isolated and back-flushed four times with N$_2$. The boronic acid (i.e. furan-2-boronic acid) (1.23 mmol) was added, and the suspension was isolated and back-flushed with N$_2$ an additional four times and finally sparged with N$_2$ for about 5-10 min. Then tetrakis(triphenylphosphine)palladium (0) (0.143 g, 0.21 mmol) was added, and the reaction was placed in a preheated (80° C.) heating block and stirred for 1 hour. The reaction was diluted with H$_2$O (20 mL) and ethyl acetate (20 mL) and filtered through Celite. The organic layer was collected, washed once with H$_2$O, once with brine, and dried over Na$_2$SO$_4$. Purification by column chromatography afforded the desired coupled product (i.e., (E)-methyl 4-(3-(furan-2-yl)benzylidene)-1-tosyl-1,4,5,6-tetrahydrocyclopenta[b]pyrrole-2-carboxylate). De-protected product (i.e., (E)-methyl 4-(3-(furan-2-yl)benzylidene)-1,4,5,6-tetrahydrocyclopenta[b]pyrrole-2-carboxylate) may also be formed.

General Procedure 9.2: Aryl Halide Coupling

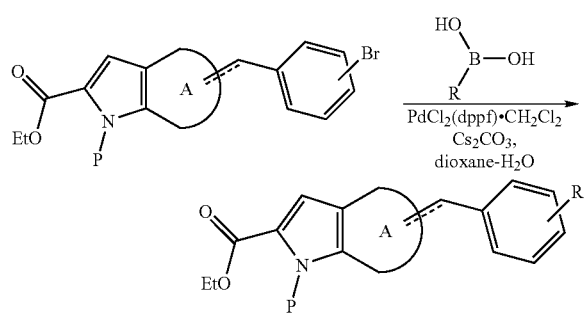

In the above Scheme, ring A represents any substituted or unsubstituted, non-aromatic ring. Exemplary rings include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) The ester is shown as ethyl, but other esters can be used, e.g., methyl, benzyl, etc.

The starting aryl halide (i.e., (E)-methyl 4-(3-bromobenzylidene)-1-tosyl-1,4,5,6-tetrahydrocyclopenta[b]pyrrole-2-carboxylate) (0.57 mmol), the boronic acid (i.e., methboronic acid) (2.28 mmol), PdCl$_2$(dppf).CH$_2$Cl$_2$ (0.03 mmol) and Cs$_2$CO$_3$ (2.85 mmol) were placed under nitrogen atmosphere, and then argon degassed dioxane-water (3:1, 40 mL) was added. The mixture was heated to 60° C. until the reaction was complete (~5 h). The mixture was cooled, diluted with EtOAc (~150 mL) and filtered through a pad of Celite. Water (100 mL) was added, the phases were split and aqueous phase was extracted with EtOAc, (100 mL) (×3), dried (Na$_2$SO$_4$) and the solvent was evaporated under reduced pressure. The product (i.e., (E)-methyl 4-(3-methylbenzylidene)-1-tosyl-1,4,5,6-tetrahydrocyclopenta[b]pyrrole-2-carboxylate) was purified by chromatography. De-protected product (i.e., (E)-methyl 4-(3-(furan-2-yl)benzylidene)-1,4,5,6-tetrahydrocyclopenta[b]pyrrole-2-carboxylate) may also be formed.

General Procedure 9.3: Aryl Halide Coupling

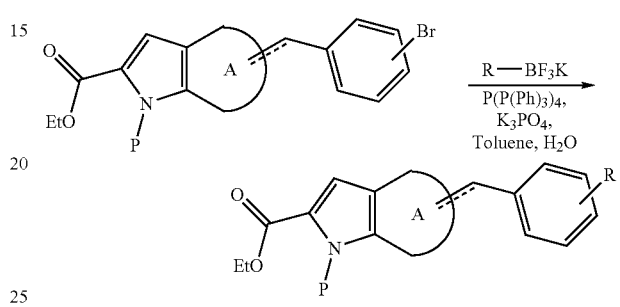

In the above Scheme, ring A represents any substituted or unsubstituted, non-aromatic ring. Exemplary rings include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) The ester is shown as ethyl, but other esters can be used, e.g., methyl, benzyl, etc.

The starting aryl halide (i.e., (E)-methyl 4-(3-bromobenzylidene)-1-tosyl-1,4,5,6-tetrahydrocyclopenta[b]pyrrole-2-carboxylate) (0.41 mmol) was dissolved in toluene:H$_2$O (~3:1, 4 mL). Potassium phosphate tribasic (1.23 mmol) and the trifluoroborate compound (i.e., potassium cyclopropyltrifluoroborate) (0.61 mmol) were added, and the solution was isolated and back-flushed four times with N$_2$. Tetrakis(triphenylphosphine)palladium(0) (0.04 mmol) was added, and the reaction placed in a preheated (100° C.) heating block and stirred until the reaction was complete (~18 h). The reaction was diluted with H$_2$O (20 mL) and extracted three times with ethyl acetate (20 mL). The organic layer was dried over Na$_2$SO$_4$. Purification by column chromatography afforded the desired compound (i.e., (E)-methyl 4-(3-cyclopropylbenzylidene)-1-tosyl-1,4,5,6-tetrahydrocyclopenta[b]pyrrole-2-carboxylate). De-protected product (i.e., (E)-methyl 4-(3-cyclopropylbenzylidene)-1,4,5,6-tetrahydrocyclopenta[b]pyrrole-2-carboxylate) may also be formed.

General Procedure 9.4: Aryl Halide Coupling

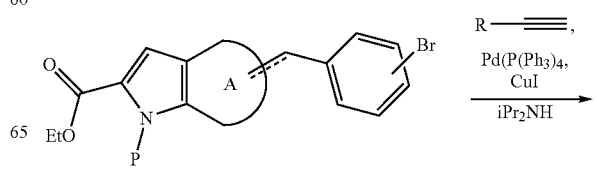

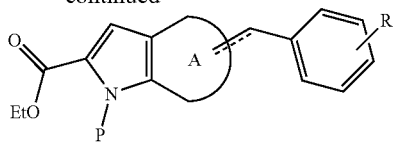

In the above Scheme, ring A represents any substituted or unsubstituted, non-aromatic ring. Exemplary rings include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) The ester is shown as ethyl, but other esters can be used, e.g., methyl, benzyl, etc.

The starting aryl halide (i.e., 1-tert-butyl 2-methyl 4-(3-bromobenzyl)-5,6-dihydrocyclopenta[b]pyrrole-1,2(4H)-dicarboxylate) (0.23 mmol) was dissolved in anhydrous diisopropylamine (2 mL), and copper(I) iodide (0.053 mmol) was added. The mixture was isolated and back-flushed four times with N$_2$. Tetrakis(triphenylphosphine)palladium(0) (0.053 mmol) and the alkyne (i.e., ethynyltrimethylsilane) (0.46 mmol) was added, and the reaction placed in a preheated (100° C.) heating block and stirred until the reaction was complete (~4 h). The reaction was cooled to ambient temperature and the solvent was taken off under reduced pressure. The desired product (i.e., 1-tert-butyl 2-methyl 4-(3-((trimethylsilyl)ethynyl)benzyl)-5,6-dihydrocyclopenta[b]pyrrole-1,2(4H)-dicarboxylate) was purified by column chromatography.

BOC-protected starting material (i.e., 1-tert-butyl 2-methyl 4-(3-bromobenzyl)-5,6-dihydrocyclopenta[b]pyrrole-1,2(4H)-dicarboxylate) may be synthesized from the starting pyrrole (i.e., methyl 4-(3-bromobenzyl)-1,4,5,6-tetrahydrocyclopenta[b]pyrrole-2-carboxylate) using standard conditions. For example, the pyrrole (i.e., methyl 4-(3-bromobenzyl)-1,4,5,6-tetrahydrocyclopenta[b]pyrrole-2-carboxylate) (2.88 mmol) was dissolved in anhydrous CH$_2$Cl$_2$ (30 mL) and 4-dimethylaminopyridine (0.85 mmol) was added. BOC anhydride (5.77 mmol) in anhydrous CH$_2$Cl$_2$ (10 mL) was added over 10 min, and the reaction stirred until completion (~18 h). The reaction was quenched with brine and extracted twice with CH$_2$Cl$_2$. The organic layer was dried over Na$_2$SO$_4$, concentrated and the desired product (i.e., 1-tert-butyl 2-methyl 4-(3-bromobenzyl)-5,6-dihydrocyclopenta[b]pyrrole-1,2(4H)-dicarboxylate) was purified by column chromatography.

General Procedure 9.5: Aryl Halide Coupling

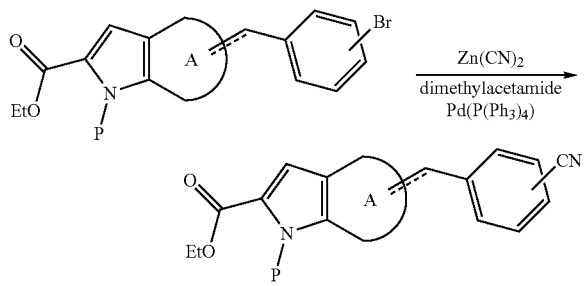

In the above Scheme, ring A represents any substituted or unsubstituted, non-aromatic ring. Exemplary rings include cyclopentenones and cyclohexenones. In the above Scheme, P represents hydrogen or a protecting group (i.e., tert-Butyloxycarbonyl (BOC), tosyl (Ts), 2-(trimethylsilyl)ethoxymethyl (SEM)). For representative protection and deprotection or pyrroles, see *Tetrahedron*, 2006, 62, 11531-11563 and references cited within.) The ester is shown as ethyl, but other esters can be used, e.g., methyl, benzyl, etc.

The starting aryl halide (i.e., methyl 4-(3-bromobenzyl)-1,4,5,6-tetrahydrocyclopenta[b]pyrrole-2-carboxylate) (0.577 mmol) was combined with zinc cyanide (0.639 mmol) and dissolved in dimethyl acetamide (4 mL). Then the solution was evacuated and back-flushed with N$_2$ four times and sparged with N$_2$ for an additional 5-10 min. Tetrakis(triphenylphosphine)palladium(0) (0.156 mmol) was added and the reaction placed in a preheated (85° C.) heating block and stirred for 1 hour. The reaction was then cooled to room temperature and diluted with aqueous H$_2$O (40 mL) and extracted three times with ethyl acetate. The organic layer was washed once with brine, then dried over Na$_2$SO$_4$. Purification by column chromatography afforded the desired product (i.e., methyl 4-(3-cyanobenzyl)-1,4,5,6-tetrahydrocyclopenta[b]pyrrole-2-carboxylate).

General Procedure 10.1: Pyrrole Deprotection

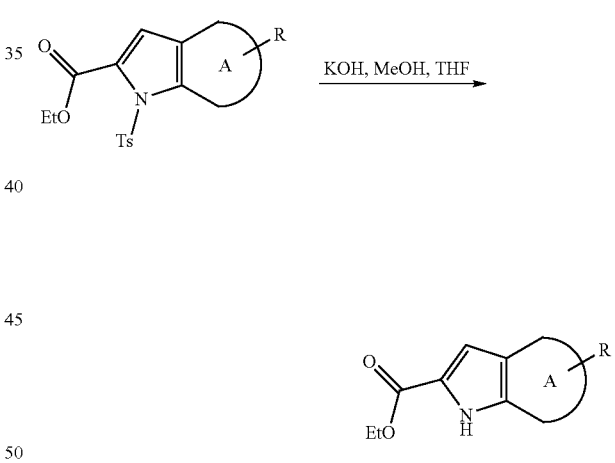

In the above Scheme, ring A represents any substituted or unsubstituted, non-aromatic ring. Exemplary rings include cyclopentenones and cyclohexenones. The ester is shown as ethyl, but other esters can be used, e.g., methyl, benzyl, etc.

Reference: *J. Org. Chem.* 1984; 49; 203-205. The starting tosyl protected pyrrole (i.e., (E)-methyl 4-(3-(furan-2-yl)benzylidene)-1-tosyl-1,4,5,6-tetrahydrocyclopenta[b]pyrrole-2-carboxylate) (0.36 mmol) was dissolved in THF (6 mL) and methanol (6 mL). Potassium hydroxide (0.101 g, 1.80 mmol) was added and the reaction was stirred at room temperature for approximately 6 hours. The reaction was diluted with H$_2$O (20 mL) and the pH adjusted to approximately 3 with 1 N HCl. The product was extracted three times with ethyl acetate, dried over Na$_2$SO$_4$, and purified by column chromatography to afford the desired deprotected product (i.e., (E)- methyl 4-(3-(furan-2-yl)benzylidene)-1,4,5,6-tetrahydrocyclopenta[b]pyrrole-2-carboxylate).

General Procedure 10.2: Pyrrole Deprotection

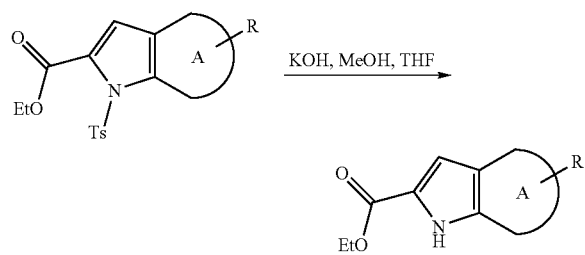

In the above Scheme, ring A represents any substituted or unsubstituted, non-aromatic ring. Exemplary rings include cyclopentenones and cyclohexenones. The ester is shown as ethyl, but other esters can be used, e.g., methyl, benzyl, etc.

The starting tosyl protected pyrrole (i.e., methyl 4-(4-chlorobenzylamino)-1-tosyl-1,4,5,6-tetrahydrocyclopenta[b]pyrrole-2-carboxylate) (0.351 mmol) was dissolved MeOH (20 mL) in ethyl acetate (25 mL) then potassium carbonate (0.194 g, 1.4 mmol) was added and the reaction heated to 60° C. for 18 h. The filtrate was concentrated and purified by column chromatography, affording the desired deprotected product (i.e., methyl 4-(4-chlorobenzylamino)-1,4,5,6-tetrahydrocyclopenta[b]pyrrole-2-carboxylate).

General Procedure 10.3: Pyrrole Deprotection

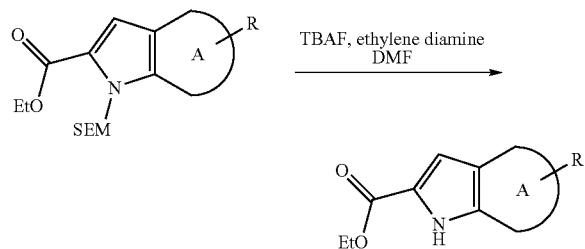

In the above Scheme, ring A represents any substituted or unsubstituted, non-aromatic ring. Exemplary rings include cyclopentenones and cyclohexenones. The ester is shown as ethyl, but other esters can be used, e.g., methyl, benzyl, etc.

To a 20-mL scintillation vial with magnetic stir bar was added the SEM-protected starting material (i.e., ethyl 6-methyl-1-((2-(trimethylsilyl)ethoxy)methyl)-1,4-dihydrocyclopenta[b]pyrrole-2-carboxylate) (0.2244 g, 0.7 mmol, 1 equiv) and DMF (4 mL). A solution of tetrabutylammonium fluoride (TBAF) (2.3 mL, 1M in THF, 2.3 mmol, 3 equiv) was added followed by ethylene diamine (0.31 mL, 0.4 mL per mmol of starting material). The reaction vial was then capped tightly and heated at approximately 45° C. for 24 hours.

The reaction was then quenched by the addition of approx. 15 mL of water, and the resulting aqueous mixture was extracted with EtOAc (3×50 mL). The combined extracts were washed with dilute aqueous HCl solution (10 mL), dilute aqueous NaHCO₃ solution (10 mL), dried (e.g., Na₂SO₄), filtered and concentrated. The resulting residue was purified by column chromatography (Isco CombiFlash) using a 0-50% gradient (EtOAc/Heptane) over 20 minutes to provide the desired deprotected product (i.e., ethyl 6-methyl-1,4-dihydrocyclopenta[b]pyrrole-2-carboxylate).

General Procedure 11: Cyclopentanone Synthesis

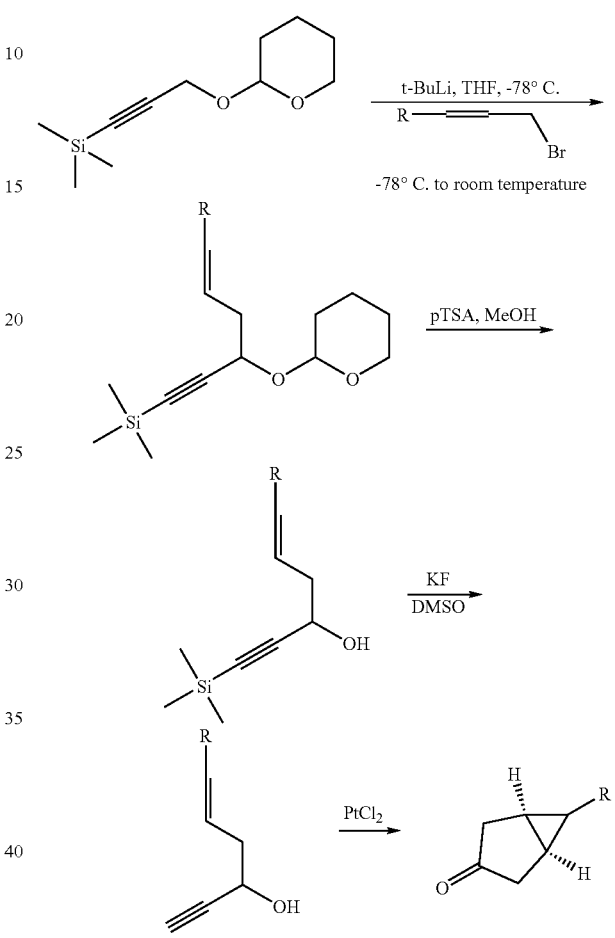

Reference: *J. Am. Chem. Soc.*, 2004, 126, 8656.

11.A) Alkylation

A heat dried 250 mL three next round bottom flask was equipped with stir bar, thermometer, septum and nitrogen inlet. This flask was then charged with trimethyl-[3-(tetrahydro-pyran-2-yloxy)-prop-1-ynyl]-silane, (30 mmol) and dry THF, (40 mL). The mixture was cooled using a dry ice/acetone bath and t-BuLi, (1.7 M in pentane, 19 mL, 33 mmol) was added dropwise, keeping the internal temperature below −60° C. The mixture was held in the dry ice bath for 1 h and then the alk-2-en-1-ol (i.e., cinnamyl bromide, where R=Ph), (5.3 mL, 36 mmol) dissolved in 5 mL of THF was added keeping the internal below −50° C. The mixture was held for approximately 1 h in the dry ice bath, and then allowed to warm to room temperature. The reaction mixture was added to saturated NH₄Cl, (250 mL), extracted with Et₂O (150 mL) (×3), washed with brine, (150 mL), dried (Na₂SO₄) and the solvent was evaporated under reduced pressure to give the desired trimethyl(6-alk-3-(tetrahydro-2H-pyran-2-yloxy)hex-5-en-1-ynyl)silane (i.e., trimethyl-[(E)-(6-phenyl-3-(tetrahydro-2H-pyran-2-yloxy)hex-5-en-1-ynyl)silane, where R=Ph). The material was used in the next step without characterization or purification.

11.B) Tetrahydropyran Removal

The trimethyl(6-alk-3-(tetrahydro-2H-pyran-2-yloxy) hex-5-en-1-ynyl)silane (i.e., trimethyl-[(E)-6-phenyl-3-(tetrahydro-pyran-2-yloxy)-hex-5-en-1-ynyl]-silane), (~30 mmol crude weight) was dissolved in MeOH, (30 mL) and p-toluene sulfonic acid (p-TSA) (114 mg, 0.6 mmol) was added. The reaction mixture was stirred at room temperature for 3 h, or until judged complete. The solvent was evaporated under reduced pressure and the material was purified by chromatography to afford the desired 6-alk-1-(trimethylsilyl)hex-5-en-1-yn-3-ol (i.e., 6-phenyl-1-(trimethylsilyl)hex-5-en-1-yn-3-ol).

11.C) Trimethylsilyl Removal

In a 100 mL round bottom flask, the 6-alk-1-(trimethylsilyl)hex-5-en-1-yn-3-ol (i.e., (E)-6-phenyl-1-trimethylsilanyl-hex-5-en-1-yn-3-ol) (I 1.5 mmol) was dissolved in DMSO, (24 mL) and water, (1 mL) and KF, (46.0 mmol) was added at ambient temperature. The reaction was stirred until the reaction was complete (approximately 1 h). The reaction was quenched with saturated NH$_4$Cl, (300 mL) extracted with Et$_2$O (100 mL) (×3), washed with brine, (300 mL) dried (Na$_2$SO$_4$) and the solvent was evaporated under reduced pressure. Purification by chromatography afforded the desired 6-alk-hex-5-en-1-yn-3-ol (i.e., 6-phenylhex-5-en-1-yn-3-ol).

11.D) Cyclization

In a 500 mL round bottom flask, the 6-alk-hex-5-en-1-yn-3-ol (i.e., (E)-6-phenyl-hex-5-en-1-yn-3-ol) (4.0 mmol) was dissolved in dry toluene (160 mL), and the solution was degassed with nitrogen by evacuating and flushing three times. Then PtCl$_2$, (53 mg, 0.2 mmol) catalyst was added, the suspension was further degassed, the flask fitted with a Vigreux column and the mixture was heated at 80° C. When the reaction was judged complete (approximately 1 hour), the mixture was filtered through a pad of Celite and the solvent was evaporated under reduced pressure. The material was purified by chromatography to afford the desired 6-alk-bicyclo[3.1.0]hexan-3-one (i.e., 6-phenylbicyclo[3.1.0]hexan-3-one).

Note: For steps 11A through 11D, the stereochemistry of trans starting olefins is retained through syntheses. For example, (E)-(3-bromoprop-1-enyl)benzene, where R=Ph, results in the synthesis of the trans product (racemic) below.

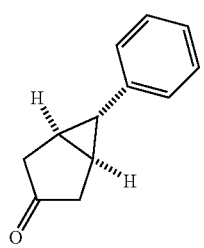

Also, the stereochemistry of cis starting olefins is retained as the major product throughout the synthesis. For example, (Z)-hept-5-en-1-yn-3-ol, where R=Me, results in the synthesis of the cis product (racemic) below as the major product.

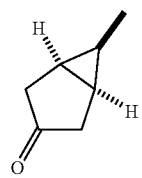

Some isomerization to the trans product from cis starting materials is sometimes observed in the cyclization step.

11.E) Synthesis of trimethyl(3-(tetrahydro-2H-pyran-2-yloxy)prop-1-ynyl)silane

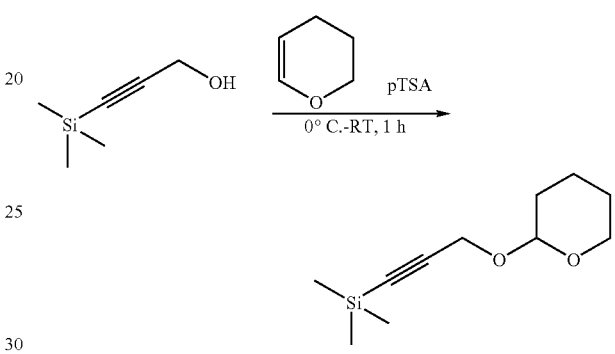

A 50 mL round bottom flask was charged with dihydropyran, (3.5 mL, 39 mmol) and pTSA, (7 mg, 0.039 mmol) was added. When the pTSA had dissolved, the solution was cooled to 0° C. in an ice bath and 3-(trimethylsilyl)propargyl alcohol, (5.7 mL, 39 mmol) was added dropwise. It was allowed then allowed to warm slowly to room temperature and held for 1 h. The mixture was added to saturated NaHCO$_3$, (250 mL) extracted with Et$_2$O, (150 mL) (×3), washed with brine, (150 mL), dried (Na$_2$SO$_4$) and the solvent was evaporated under reduced pressure. The material was purified by chromatography eluting with heptane-EtOAc, gradient 0 to 10% EtOAc. 8.5 g. $^1$H NMR (400 MHz, CHLOROFORM-d) δ ppm 0.19 (s, 9H) 0.77-0.94 (m, 1H) 1.49-1.59 (m, 1H) 1.57-1.70 (m, 2H) 1.69-1.93 (m, 2H) 3.35-3.63 (m, 1H) 3.78-3.91 (m, 1H) 4.19-4.35 (m, 2H) 4.82 (t, J=3.34 Hz, 1H).

11.F) Hydrogenation of Alkyne to Cis-Olefin

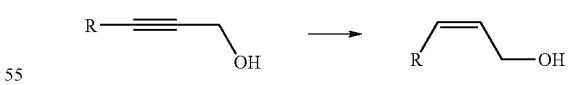

5% Palladium on calcium carbonate poisoned with lead (Lindlar's catalyst) (470 mg) was placed in a dry 1 L round-bottomed flask. The flask was evacuated and flushed with nitrogen. A degassed MeOH (225 mL) was added, followed by the starting alcohol (i.e., but-2-yn-1-ol) (141.2 mmol) and quinoline (1.65 mL, 1.5 mmol). The mixture was further degassed with nitrogen and flushed with hydrogen. The reaction mixture was then stirred under hydrogen atmosphere using a balloon. After the reaction is complete (by $^1$H NMR, approximately 4 h), the reaction mixture was vacuumed and then purged with nitrogen. The mixture was then filtered through a pad of Celite under a blanket of nitrogen. The solvent was evaporated under reduced pressure to give yellow oil. The oil was dissolved in Et₂O (400 mL), washed with 0.2M HCl (100 mL) and saturated NaHCO₃ (100 mL), dried over Na₂SO₄ and concentrated to give the desired product.

11.G) Conversion of Alcohol to Bromide

To a solution of the alcohol (i.e., (Z)-but-2-en-1-ol) (570.8 mmol) in Et₂O (60 mL) at −10° C. was added PBr₃ (3.3 mL, 35.0 mmol). The mixture was allowed to warm slowly to 0° C. over 45 minutes. When the reaction was judged complete (by TLC), the reaction was quenched with water (50 mL). After separation of layers, the aqueous layer was extracted with Et₂O (100 mL×3). The combined Et₂O was washed with saturated NaHCO₃ (100 mL), brine (100 mL), dried over Na₂SO₄ and concentrated. The crude was passed through a pad of silica gel eluting with Et₂O to give the desired product (i.e., (Z)-1-bromobut-2-ene).

Example 1

Synthesis of Pyrrole Analogs with Unsubstituted Fused Cyclopentanes 1.1. Synthesis of Ethyl 1,4,5,6-tetrahydrocyclopenta[b]pyrrole-2-carboxylate

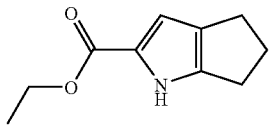

The title compound was synthesized from cyclopentanone according to General Procedures 1.1.A, 1.1.B and 1.1.C. In the last step 1.5 g (7.48 mmol) of (E)-ethyl 3-(2-chlorocyclopent-1-enyl)acrylate was cyclized. The crude product was purified by flash chromatography (0-50% EtOAc/heptane) to provide 418 mg (31%, final step) of ethyl 1,4,5,6-tetrahydrocyclopenta[b]pyrrole-2-carboxylate. ¹H NMR (400 MHz, CHLOROFORM-d) δ ppm 1.34 (t, J=7.13 Hz, 3H), 2.38-2.48 (m, 2H), 2.59-2.65 (m, 2H), 2.69-2.75 (m, 2H), 4.30 (q, J=7.13 Hz, 2H), 6.67 (d, J=1.37 Hz, 1H), 8.78 (br s, 1H); LCMS-MS (ESI+) 179.9 (M+H).

1.2. Synthesis of 1,4,5,6-tetrahydro-cyclopenta[b]pyrrole-2-carboxylic acid (1)

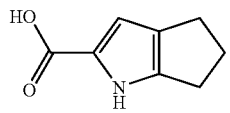

The title compound was synthesized from the above ethyl-1,4,5,6-tetrahydrocyclopenta[b]pyrrole-2-carboxylate (100 mg, 0.56 mmol) using lithium hydroxide monohydrate (94 mg, 2.23 mmol) as the base according to General Procedure 7. The crude product was purified by flash chromatography (0-100% EtOAc/heptane) to give 61 mg (73%) of 1,4,5,6-tetrahydro-cyclopenta[b]pyrrole-2-carboxylic acid (1). ¹H NMR (400 MHz, METHANOL-d) δ ppm 2.35-2.44 (m, 2H), 2.54-2.61 (m, 2H), 2.64-2.72 (m, 2H), 6.59 (s, 1H); LCMS-MS (ESI+) 151.9 (M+H); HPLC (UV=100%), (ELSD=100%).

Example 2

Synthesis of Pyrrole Analogs with 4-Substituted Fused Cyclopentanes 2.1.) Synthesis of Methyl 4-oxo-1,4,5,6-tetrahydro-cyclopenta[b]pyrrole-2-carboxylate

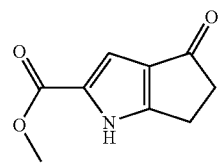

2.1.a) Synthesis of 5-formyl-1H-pyrrole-2-carboxylic acid methyl ester

To 1,2-dichloroethane (40 mL) was added DMF (13.6 mL, 176 mmol). The mixture was cooled to 0° C. and phosphorus oxychloride (16.4 mL, 176 mmol) was added dropwise over 5 min. The resulting solution was stirred for 15 min. To the solution at 0° C. was added dropwise methyl 1H-pyrrole-2-carboxylate (20 g, 160 mmol) in dichloroethane (80 mL) (about 1 h). The cooling bath was removed, and the reaction mixture was heated to reflux for about 1 h and was then cooled to rt. EtOAc (250 mL) in ice water (400 mL) was added and the organic layer was separated. The aqueous layer was neutralized with NaHCO₃ solution, and then extracted with EtOAc (4×100 mL). The organic layer and the combined organic extracts were washed with dilute NaHCO₃ solution, brine, dried (Na₂SO₄) and filtered. Silica gel was added, the solvent removed and the silica gel-imbedded material was purified by flash chromatography (0-50% EtOAc/Heptane) to afford a major product, methyl 5-formyl-1H-pyrrole-2-carboxylate (16.3 g) and a minor product, methyl 4-formyl-1H-pyrrole-2-carboxylate (6.94 g). Combined yield: 23.3 g (95%).

Methyl 5-formyl-1H-pyrrole-2-carboxylate: ¹H NMR (400 MHz, CHLOROFORM-d) δ ppm: 3.93 (s, 3H), 6.95 (d, J=2.39 Hz, 2H), 9.68 (s, 1H), 9.82 (br s, 1H); LCMS-MS (ESI+) 153.9 (M+H).

Methyl 4-formyl-1H-pyrrole-2-carboxylate: ¹H NMR (400 MHz, CHLOROFORM-d) δ ppm: 3.91 (s, 3H), 7.32 (dd, J=2.29, 1.61 Hz, 1H), 7.57 (dd, J=3.32, 1.51 Hz, 1H), 9.55 (br s, 1H), 9.86 (s, 1H); LCMS-MS (ESI+) 153.8 (M+H).

2.1.b) Synthesis of (Z)-methyl 5-(3-tert-butoxy-3-oxoprop-1-enyl)-1H-pyrrole-2-carboxylate and (E)-methyl 5-(3-tert-butoxy-3-oxoprop-1-enyl)-1H-pyrrole-2-carboxylate To a suspension of NaH (5.74 g, 143.5 mmol; 60% in oil) in THF (200 mL) at 0° C. was added (tert-butoxycarbonylmethyl)triphenylphosphonium bromide (66 g, 143.5 mmol) as a solid in three portions. Cooling was removed and the mixture was stirred at rt for 30 min. It was then cooled to 0° C. and methyl 5-formyl-1H-pyrrole-2-carboxylate (16.9 g, 110.4 mmol) in THF (60 mL) was added dropwise over 40 min. The reaction mixture was allowed to warm to rt and was stirred overnight. Silica was added and the solvent was removed. The crude product was purified by flash chromatography (0-20% EtOAc/Heptane) to afford two isomeric compounds:

(Z)-methyl 5-(3-tert-butoxy-3-oxoprop-1-enyl)-1H-pyrrole-2-carboxylate (6.9 g, 25.1%) as a white solid; $^1$H NMR (400 MHz, CHLOROFORM-d) δ ppm 1.55 (s, 9H), 3.91 (s, 3H), 5.67 (d, J=12.64 Hz, 1H), 6.43 (dd, J=3.83, 2.32 Hz, 1H), 6.67 (d, J=12.64 Hz, 1H), 6.88 (dd, J=3.81, 2.44 Hz, 1H), 12.80 (br s, 1H); LCMS-MS (ESI+) 195.7 (M-56).

(E)-methyl 5-(3-tert-butoxy-3-oxoprop-1-enyl)-1H-pyrrole-2-carboxylate (20.3 g, 72.9%) as a white solid; $^1$H NMR (400 MHz, CHLOROFORM-d) δ ppm 1.53 (s, 9H), 3.90 (s, 3H), 6.19 (d, J=16.01 Hz, 1H), 6.51 (dd, J=3.86, 2.68 Hz, 1H), 6.90 (dd, J=3.88, 2.37 Hz, 1H), 7.41 (d, J=16.01 Hz, 1H), 9.42 (br s, 1H); LCMS-MS (ESI+) 195.8 (M-56).

2.1.c) Synthesis of methyl 5-(3-tert-butoxy-3-oxopropyl)-1H-pyrrole-2-carboxylate To a solution of (z)-methyl 5-(3-tert-butoxy-3-oxoprop-1-enyl)-1H-pyrrole-2-carboxylate or (E)-methyl 5-(3-tert-butoxy-3-oxoprop-1-enyl)-1H-pyrrole-2-carboxylate (13.6 g, 54.1 mmol, 2 equal batches) in EtOAc (200 mL) under nitrogen was added 10% Pd/C. The flask was flushed with hydrogen three times before allowing the reaction to stir under hydrogen for about 18 h. The catalyst was filtered off using Celite and the filtrate was concentrated to give 27.4 g methyl 5-(3-tert-butoxy-3-oxopropyl)-1H-pyrrole-2-carboxylate as a white solid (100%) for each stereoisomer. $^1$H NMR (400 MHz, CHLOROFORM-d) δ ppm 1.46 (s, 9H), 2.54-2.59 (m, 2H), 2.90 (t, J=6.83 Hz, 2H), 3.83 (s, 3H), 5.97 (dd, J=3.49, 2.86 Hz, 1H), 6.81 (dd, J=3.61, 2.59 Hz, 1H), 9.30 (br s, 1H); LCMS-MS (ESI+) 197.86 (M-isobutylene).

2.1.d) Synthesis of 3-(5-(methoxycarbonyl)-1H-pyrrol-2-yl)propanoic acid

Methyl 5-(3-tert-butoxy-3-oxopropyl)-1H-pyrrole-2-carboxylate (14.8 g, 58.4 mmol) was treated with 4 N HCl (100 mL) at rt for about 12 h. The solvent was removed and the white solid product was dried to give 12.8 g (94%) of 3-(5-(methoxycarbonyl)-1H-pyrrol-2-yl)propanoic acid. $^1$H NMR (400 MHz, CHLOROFORM-d) δ ppm 2.73 (t, J=6.81 Hz, 2H), 2.98 (t, J=6.79 Hz, 2H), 3.83 (s, 3H), 6.01 (dd, J=3.59, 2.61 Hz, 1H), 6.83 (dd, J=3.61, 2.63 Hz, 1H), 9.70 (br s, 1H); LCMS-MS (ESI+) 198.2 (M+H).

2.1.e) Synthesis of methyl 4-oxo-1,4,5,6-tetrahydrocyclopenta[b]pyrrole-2-carboxylate A suspension of polyphosphoric acid (115%, 109 g) and powdered 3-(5-(methoxycarbonyl)-1H-pyrrol-2-yl)propanoic acid (12.1 g, 51.8 mmol) in 1,2-dichloroethane (40 mL) was heated for 1 h at 100° C. with occasional mixing with a large spatula. Water (100 mL) was added and the mixture was carefully poured into a large Erlenmeyer flask containing solid sodium bicarbonate and ice. The reaction was neutralized (pH 7) and then extracted with EtOAc (5×150 mL). The combined organic extracts were washed with water, NaHCO$_3$, brine, dried (Na$_2$SO$_4$), filtered and concentrated. The crude product was purified by flash chromatography (0-80% EtOAc/Heptane) to afford 8.0 g of methyl 4-oxo-1,4,5,6-tetrahydrocyclopenta[b]pyrrole-2-carboxylate (86%). $^1$H NMR (400 MHz, CHLOROFORM-d) δ ppm 2.93-2.98 (m, 2H), 2.99-3.04 (m, 2H), 3.90 (s, 3H), 6.98 (d, J=1.71 Hz, 1H), 9.42 (br s, 1H); LCMS-MS (ESI+) 180.0 (M+H).

2.2. Synthesis of methyl 3-tert-butyl-4-oxo-1,4,5,6-tetrahydrocyclopenta[b]pyrrole-2-carboxylate and methyl 4-oxo-1,4,5,6-tetrahydrocyclopenta[b]pyrrole-2-carboxylate

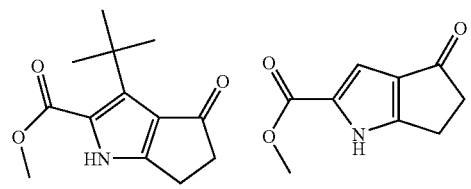

Methyl 5-(3-tert-butoxy-3-oxopropyl)-1H-pyrrole-2-carboxylate (5.1 g, 20.1 mmol) in 5 mL of 1,2-dichloroethane (DCE) was added to polyphosphoric acid (115% assay, 8.5 g) in DCE (15 mL), and the reaction was heated to 100° C. for 2 h. It was then cooled, water (50 mL) was added, and the mixture was extracted with ethyl acetate (4×50 mL). The combined organic extracts were washed with water, dilute NaHCO$_3$ and brine, dried (Na$_2$SO$_4$), filtered and concentrated. Purification by flash chromatography (0-70% EtOAc/heptane) afforded methyl 3-tert-butyl-4-oxo-1,4,5,6-tetrahydrocyclopenta[b]pyrrole-2-carboxylate (1.1 g, 30%). $^1$H NMR (400 MHz, CDCl$_3$) δ ppm 1.50 (s, 3H), 2.86-2.90 (m, 2H), 2.91-2.96 (m, 2H), 3.88 (s, 3H), 9.10 (br s, 1H); LCMS-MS (ESI+) 235.8 (M+H), and methyl 4-oxo-1,4,5,6-tetrahydrocyclopenta[b]pyrrole-2-carboxylate (2.0 g, 42%). $^1$H NMR (400 MHz, CHLOROFORM-d) δ ppm 2.93-2.98 (m, 2H), 2.99-3.04 (m, 2H), 3.90 (s, 3H), 6.98 (d, J=1.71 Hz, 1H), 9.42 (br s, 1H); LCMS-MS (ESI+) 180.0 (M+H). 2.3.

2.3. Synthesis of methyl 4-methyl-1,4,5,6-tetrahydrocyclopenta[b]pyrrole-2-carboxylate

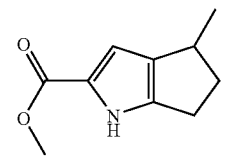

The title compound was synthesized from methyl 4-oxo-1,4,5,6-tetrahydrocyclopenta[b]pyrrole-2-carboxylate (400 mg, 2.23 mmol) and methyl-MgBr (6.38 mL, 8.93 mmol; 1.4 M in toluene/THF: 75:25) according to General Procedure 3 to give methyl 4-methylene-1,4,5,6-tetrahydrocyclopenta[b]pyrrole-2-carboxylate, followed by General Procedure 6 and was purified by column chromatography (0-40% EtOAc/heptane) to afford 19 mg of methyl 4-methyl-1,4,5,6-tetrahydrocyclopenta[b]pyrrole-2-carboxylate as a white solid (5% over two steps). $^1$H NMR (400 MHz, METHANOL-d$_4$) δ ppm 1.17 (d, J=6.78 Hz, 3H), 1.85-1.96 (m, 1H), 2.56-2.76 (m, 3H), 2.95-3.05 (m, 1H), 3.77 (s, 3H), 6.58 (s, 1H); LCMS-MS (ESI+) 180.0 (M+H).

2.4. Synthesis of methyl 4-propyl-1,4,5,6-tetrahydro-cyclopenta[b]pyrrole-2-carboxylate

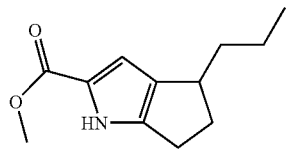

The title compound was synthesized from methyl 4-oxo-1,4,5,6-tetrahydrocyclopenta[b]pyrrole-2-carboxylate (300 mg, 1.67 mmol) and allyl-MgBr (3.35 mL, 6.70 mmol; 2.0 M in THF) according to General Procedure 3 to give (E)-methyl 4-allylidene-1,4,5,6-tetrahydrocyclopenta[b]pyrrole-2-carboxylate, followed by General Procedure 6. The crude product was purified by column chromatography (0-40% EtOAc/heptane) to give 99 mg of methyl 4-propyl-1,4,5,6-tetrahydrocyclopenta[b]pyrrole-2-carboxylate as a white solid (29% over two steps). $^1$H NMR (400 MHz, METHANOL-$d_4$) δ ppm 0.95 (t, J=7.03 Hz, 3H), 1.37-1.55 (m, 4H), 1.91-2.03 (m, 1H), 2.53-2.76 (m, 3H), 2.86-2.95 (m, 1H), 3.78 (s, 3H), 6.60 (s, 1H); LCMS-MS (ESI+) 208.0 (M+H).

2.5. Synthesis of methyl 4-isopropyl-1,4,5,6-tetrahydrocyclopenta[b]pyrrole-2-carboxylate

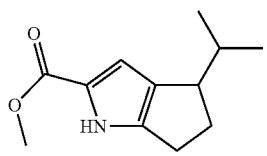

2.5.a) Synthesis of ethyl 4-(propan-2-ylidene)-1,4,5,6-tetrahydrocyclopenta[b]pyrrole-2-carboxylate The title compound was synthesized from methyl 4-oxo-1,4,5,6-tetrahydrocyclopenta[b]pyrrole-2-carboxylate (442 mg, 2.47 mmol) and isopropyl magnesium bromide (1M, 9.87 mL, 9.87 mmol, 4 equiv) according to General Procedure 3. Purification by flash chromatography (0-40% EtOAc/heptane) provided 131 mg of a yellow solid (26%). $^1$H NMR (400 MHz, CHLOROFORM-d) δ ppm 1.75 (s, 3H) 1.92 (s, 3H) 2.80-2.87 (m, 2H) 2.96-3.03 (m, 2H) 3.85 (s, 3H) 6.86 (d, J=1.76 Hz, 1H) 9.16 (br. s., 1H).

2.5.b) Synthesis of methyl 4-isopropyl-1,4,5,6-tetrahydrocyclopenta[b]pyrrole-2-carboxylate The title compound was synthesized from methyl 4-(propan-2-ylidene)-1,4,5,6-tetrahydrocyclopenta[b]pyrrole-2-carboxylate according to General Procedure 6. Purification by column chromatography (0-100% EtOAc/heptane) gave 91 mg of methyl 4-isopropyl-1,4,5,6-tetrahydrocyclopenta[b]pyrrole-2-carboxylate as a white solid (66%). $^1$H NMR (400 MHz, METHANOL-$d_4$) δ ppm 0.93 (d, J=1.37 Hz, 3H) 0.94 (d, J=1.37 Hz, 3H) 1.61-1.72 (m, 1H) 2.04-2.14 (m, J=12.76, 8.91, 5.66, 5.66 Hz, 1H) 2.45-2.55 (m, 1H) 2.56-2.80 (m, 3H) 3.78 (s, 3H) 6.63 (s, 1H); LCMS-MS (ESI+) 208.0 (M+H).

2.6. Synthesis of methyl 4-isobutyl-1,4,5,6-tetrahydrocyclopenta[b]pyrrole-2-carboxylate

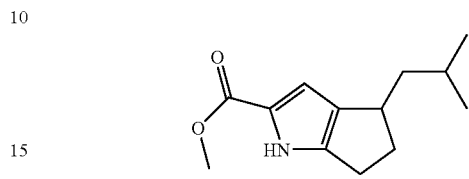

The title compound was synthesized from methyl 4-oxo-1,4,5,6-tetrahydrocyclopenta[b]pyrrole-2-carboxylate (300 mg, 1.68 mmol) and isobutyl-MgBr (4 equiv.) according to General Procedure 3 to give (E)-methyl 4-(2-methylpropylidene)-1,4,5,6-tetrahydrocyclopenta[b]pyrrole-2-carboxylate, followed by General Procedure 6. Purification by column chromatography (0-40% EtOAc/heptane) gave 99 mg of methyl 4-isobutyl-1,4,5,6-tetrahydrocyclopenta[b]pyrrole-2-carboxylate as a white solid (29% over two steps). $^1$H NMR (400 MHz, METHANOL-$d_4$) δ ppm 0.94 (d, J=6.54 Hz, 3H), 0.98 (d, J=6.59 Hz, 3H), 1.22-1.32 (m, 1H), 1.39-1.47 (m, 1H), 1.71-1.83 (m, 1H), 1.89-2.00 (m, 1H), 2.51-2.76 (m, 3H), 2.95-3.04 (m, 1H), 3.78 (s, 3H), 6.59 (s, 1H); LCMS-MS (ESI+) 224.0 (M+H).

2.7. Synthesis of methyl 4-(cyclohexylmethyl)-1,4,5,6-tetrahydrocyclopenta[b]pyrrole-2-carboxylate

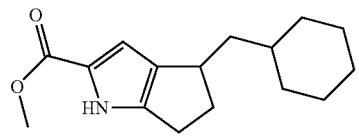

A solution of cyclohexylmethyl-MgBr (41.56 mL, 10.39 mmol, 0.25 M in THF, 4 eqv.) was added to a stirred solution of 4-oxo-1,4,5,6-tetrahydro-cyclopenta[b]pyrrole-2-carboxylic acid methyl ester (465 mg, 2.59 mmol) in THF (15 mL) at 0° C. under nitrogen. The cold bath was removed and the resulting solution was heated to 67° C. for about 12 h. The reaction was then cooled to rt and quenched with a saturated solution of NH$_4$Cl before extraction with EtOAc (3×50 mL). The combined extracts were washed with brine, dried (Na$_2$SO$_4$), filtered through a plug of silica gel and concentrated. The crude product was subjected to hydrogenation with 10% Pd—C and hydrogen at rt for 4 h in methanol. The catalyst was removed by filtration over Celite and the filtrate concentrated onto silica gel. Purification by column chromatography (0-100% EtOAc/heptane) gave a white solid (90 mg, 13%). $^1$H-NMR (400 MHz, CHLOROFORM-d) δ ppm 0.85-1.00 (m, 2H) 1.11-1.36 (m, 5H) 1.38-1.51 (m, 2H) 1.64-1.78 (m, 3H) 1.81-1.91 (m, 1H) 1.92-2.03 (m, 1H) 2.53-2.80 (m, 3H) 3.00-3.12 (m, 1H) 3.83 (s, 3H) 6.67 (d, J=1.46 Hz, 1H) 8.89 (br. s., 1H). LCMS-MS (ESI+) 262.0 (M+H).

2.8. Synthesis of methyl 4-(4-fluorobenzyl)-1,4,5,6-tetrahydrocyclopenta[b]pyrrole-2-carboxylate

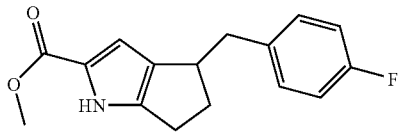

2.8.a) Synthesis of (E/Z)-methyl 4-(4-fluorobenzylidene)-1,4,5,6-tetrahydrocyclopenta[b]pyrrole-2-carboxylate The title compound was synthesized from methyl 4-oxo-1,4,5,6-tetrahydrocyclopenta[b]pyrrole-2-carboxylate (0.4 g, 2.2 mmol) and 4-fluorobenzyl triphenylphosphonium chloride salt (1.09 g, 2.7 mmol) according to General Procedure 2. The crude product was purified by flash chromatography (0-50% EtOAc/heptane) to afford 31.1 mg of (E/Z)-methyl 4-(4-fluorobenzylidene)-1,4,5,6-tetrahydrocyclopenta[b]pyrrole-2-carboxylate in 5% yield. $^1$H NMR (400 MHz, CHLOROFORM-d) δ ppm 8.93 (br. s., 1H), 7.43-7.50 (m, 2H), 7.04-7.09 (m, 2H), 6.89 (d, J=1.61 Hz, 1H), 6.47 (t, J=2.03 Hz, 1H), 3.36 (td, J=5.79, 2.55 Hz, 2H), 2.93-2.99 (m, 2H); $^{19}$F NMR (376 MHz, CDCl$_3$) δ ppm −116.03 (s, 1F).

2.8.b) Synthesis of methyl 4-(4-fluorobenzyl)-1,4,5,6-tetrahydrocyclopenta[b]pyrrole-2-carboxylate Methyl 4-(4-fluorobenzyl)-1,4,5,6-tetrahydrocyclopenta[b]pyrrole-2-carboxylate was synthesized from (E/Z)-methyl 4-(4-fluorobenzylidene)-1,4,5,6-tetrahydrocyclopenta[b]pyrrole-2-carboxylate according to General Procedure 6.

2.9. Syntheses of methyl 4-benzyl-1,4,5,6-tetrahydrocyclopenta[b]pyrrole-2-carboxylate and methyl 4-(4-chlorobenzyl)-1,4,5,6-tetrahydrocyclopenta[b]pyrrole-2-carboxylate

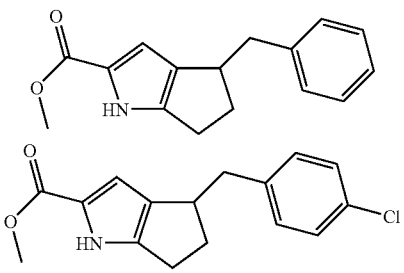

2.9.a) Synthesis of ethyl 4-(4-chlorobenzylidene)-1,4,5,6-tetrahydrocyclopenta[b]pyrrole-2-carboxylate The title compound was synthesized from methyl 4-oxo-1,4,5,6-tetrahydrocyclopenta[b]pyrrole-2-carboxylate (500 mg, 2.79 mmol) and (4-chlorobenzyl)-triphenylphosphonium chloride (1.54 g, 3.63 mmol) according to General Procedure 2. The crude product was purified by flash chromatography (0-20% EtOAc/Heptane) to give 152 mg of methyl 4-(4-chlorobenzylidene)-1,4,5,6-tetrahydrocyclopenta[b]pyrrole-2-carboxylate (20%). $^1$H NMR (400 MHz, CHLOROFORM-d) δ ppm 2.97 (m, 2H), 3.37 (m, 2H), 3.87 (s, 3H), 6.46 (t, J=2.30 Hz, 1H), 6.89 (d, J=1.71 Hz, 1H), 7.29 (m, 4H), 8.93 (br s, 1H).

2.9.b) Synthesis of methyl 4-benzyl-1,4,5,6-tetrahydrocyclopenta[b]pyrrole-2-carboxylate and methyl 4-(4-chlorobenzyl)-1,4,5,6-tetrahydrocyclopenta[b]pyrrole-2-carboxylate The title compounds were synthesized from methyl 4-(4-chlorobenzylidene)-1,4,5,6-tetrahydrocyclo penta[b]pyrrole-2-carboxylate according to General Procedure 6. Purification by reverse-phase chromatography (75:25 MeOH:water) provided the 4-chloro product (peak 2) in addition to a dehalogenated benzyl adduct (peak 1) in a 4:1 ratio:

Methyl 4-(4-chlorobenzyl)-1,4,5,6-tetrahydrocyclopenta[b]pyrrole-2-carboxylate: (85 mg, 58.2%) as a yellow solid; $^1$H NMR (400 MHz, CHLOROFORM-d) δ ppm 2.10 (m, 1H), 2.58 (m, 1H), 2.66 (m, 2H), 2.77 (dd, J=7.10, 1.95 Hz, 2H), 3.28 (m, 1H), 3.81 (s, 3H), 6.37 (d, J=1.56 Hz, 1H), 7.12 (m, 2H), 7.25-7.29 (m, 2H), 8.69 (br s, 1H); LCMS-MS (ESI+) 312.0 (M+Na).

Methyl 4-benzyl-1,4,5,6-tetrahydrocyclopenta[b]pyrrole-2-carboxylate: (28 mg, 21.8%) as a yellow solid; $^1$H NMR (400 MHz, CHLOROFORM-d) δ ppm 2.07-2.17 (m, 1H), 2.52-2.63 (m, 1H), 2.63-2.70 (m, 2H), 2.81 (dd, J=7.38, 2.46 Hz, 2H), 3.27-3.36 (m, 1H), 3.80 (s, 3H), 6.39 (d, J=1.66 Hz, 1H), 7.18-7.25 (m, 3H), 7.28-7.33 (m, 2H), 8.75 (br s, 1H); LCMS-MS (ESI+) 278.2 (M+Na).

2.10. Synthesis of methyl 4-phenethyl-1,4,5,6-tetrahydrocyclopenta[b]pyrrole-2-carboxylate

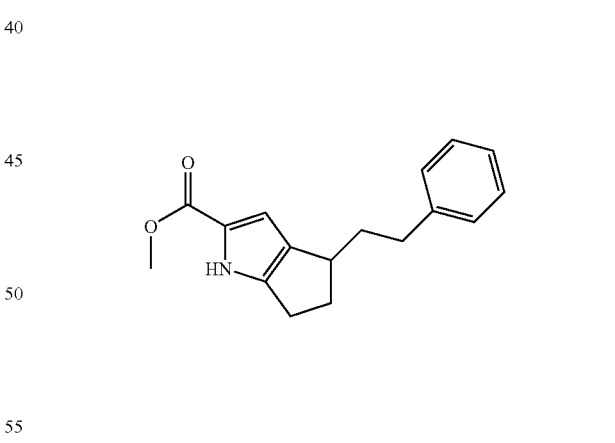

The title compound was synthesized from methyl 4-oxo-1,4,5,6-tetrahydrocyclopenta[b]pyrrole-2-carboxylate (400 mg, 2.23 mmol) and phenethyl-MgBr (17.9 mL, 8.93 mmol; 0.5 M in THF) according to General Procedure 3 to give (E)-methyl 4-(2-phenylethylidene)-1,4,5,6-tetrahydrocyclopenta[b]pyrrole-2-carboxylate, followed by General Procedure 6. The crude product was purified by column chromatography (0-25% EtOAc/heptane) to give 366 mg of methyl 4-phenethyl-1,4,5,6-tetrahydrocyclopenta-[b]pyrrole-2-carboxylate as a white solid (61% over two steps). $^1$H NMR (400 MHz, METHANOL-d$_4$) δ ppm 1.68-1.87 (m, 2H), 1.98-2.09

(m, 1H), 2.55-2.79 (m, 5H), 2.88-2.98 (m, 1H), 3.79 (s, 3H), 6.68 (s, 1H), 7.10-7.32 (m, 5H); LCMS-MS (ESI+) 292.0 (M+Na).

2.11. Synthesis of 4-oxo-1,4,5,6-tetrahydrocyclopenta[b]pyrrole-2-carboxylic acid (2)

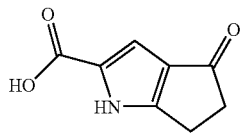

The title compound was synthesized from methyl 4-oxo-1,4,5,6-tetrahydrocyclopenta[b]pyrrole-2-carboxylate (11 mg, 0.06 mmol) and lithium hydroxide monohydrate (10 mg, 0.25 mmol) according to General Procedure 7 (6.8 mg, 67%). $^1$H NMR (400 MHz, METHANOL-$d_4$) δ ppm 2.89-2.93 (m, 2H), 2.98-3.02 (m, 2H), 6.89 (s, 1H); LCMS-MS (ESI+) 163.7 (M−H); HPLC (UV=100%).

2.12. Synthesis of 3-tert-butyl-4-oxo-1,4,5,6-tetrahydrocyclopenta[b]pyrrole-2-carboxylic acid (3)

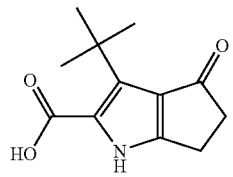

The title compound was synthesized from methyl 3-tert-butyl-4-oxo-1,4,5,6-tetrahydrocyclopenta[b]pyrrole-2-carboxylate (33 mg, 0.14 mmol) and lithium hydroxide monohydrate (30 mg, 0.71 mmol) according to General Procedure 7. Purification by reverse phase semi-preparative HPLC provided a pure fraction (11.6 mg, 37%) of 3-tert-butyl-4-oxo-1,4,5,6-tetrahydrocyclopenta[b]pyrrole-2-carboxylic acid (3). $^1$H NMR (400 MHz, METHANOL-$d_4$) δ ppm 1.46 (s, 9H), 2.82-2.90 (m, 4H); LCMS-MS (ESI+) 221.7 (M−H); HPLC (UV=95.8%).

2.13. Synthesis of 4-methyl-1,4,5,6-tetrahydrocyclopenta[b]pyrrole-2-carboxylic acid (4)

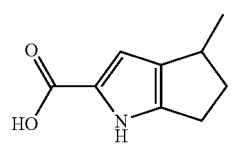

The title compound was synthesized from methyl 4-methyl-1,4,5,6-tetrahydrocyclopenta[b]pyrrole-2-carboxylate and lithium hydroxide monohydrate (17 mg, 0.40 mmol) according to General Procedure 7. The crude product was dried onto Silica gel and was purified by flash chromatography (0-80% EtOAc/Heptane) to give 8.6 mg of 4-methyl-1,4,5,6-tetrahydrocyclopenta[b]pyrrole-2-carboxylic acid (4) as a light yellow solid (52%). $^1$H NMR (400 MHz, METHANOL-$d_4$) δ ppm 1.17 (d, J=6.78 Hz, 3H), 1.85-1.96 (m, 1H), 2.56-2.77 (m, 3H), 2.95-3.06 (m, 1H), 6.59 (s, 1H); LCMS-MS (ESI+) 166.0 (M+H); HPLC (UV=100%).

The enantiomers of 4-methyl-1,4,5,6-tetrahydrocyclopenta[b]pyrrole-2-carboxylic acid were separated according to General Procedure 8 with 20% methanol in $CO_2$ with 0.2% diethylamine to give 4-methyl-1,4,5,6-tetrahydrocyclopenta[b]pyrrole-2-carboxylic acid (4), (peak 2, retention time=9.7 min; 96% ee) and 4-methyl-1,4,5,6-tetrahydrocyclopenta[b]pyrrole-2-carboxylic acid (6) (peak 1, retention time=8.1 min; 100% ee).

2.14. Synthesis of 4-propyl-1,4,5,6-tetrahydrocyclopenta[b]pyrrole-2-carboxylic acid (7)

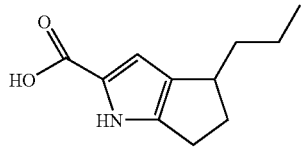

The title compound was synthesized from methyl 4-propyl-1,4,5,6-tetrahydrocyclopenta[b]pyrrole-2-carboxylate (95 mg, 0.46 mmol) and lithium hydroxide monohydrate (77 mg, 1.83 mmol) according to General Procedure 7. The crude product was dried onto Silica gel and was purified by flash chromatography (0-80% EtOAc/Heptane) to give 70 mg of 4-propyl-1,4,5,6-tetrahydrocyclopenta[b]pyrrole-2-carboxylic acid (7) as a light yellow solid (79%). $^1$H NMR (400 MHz, METHANOL-$d_4$) δ ppm 0.96 (t, J=7.03 Hz, 3H), 1.36-1.56 (m, 4H), 1.92-2.03 (m, 1H), 2.52-2.76 (m, 3H), 2.87-2.96 (m, 1H), 6.61 (s, 1H); LCMS-MS (ESI−) 192.2 (M−H); HPLC (UV=100%).

The enantiomers of 4-propyl-1,4,5,6-tetrahydrocyclopenta[b]pyrrole-2-carboxylic acid were separated according to General Procedure 8 using 40% methanol in $CO_2$ with 0.05% diethylamine to give 4-propyl-1,4,5,6-tetrahydrocyclopenta[b]pyrrole-2-carboxylic acid (9) (peak 1, retention time=3.5 min; 100% ee) and 4-propyl-1,4,5,6-tetrahydrocyclopenta[b]pyrrole-2-carboxylic acid (8) (peak 2, retention time=6.3 min; 100% ee).

2.15. Synthesis of 4-isopropyl-1,4,5,6-tetrahydrocyclopenta[b]pyrrole-2-carboxylic acid (10)

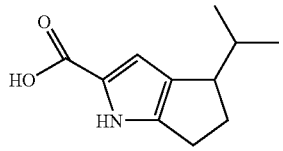

The title compound was synthesized from methyl 4-isopropyl-1,4,5,6-tetrahydrocyclopenta[b]pyrrole-2-carboxylate (0.09 g, 0.43 mmol) and lithium hydroxide monohydrate (185 mg, 4.3 mmol) according to General Procedure 7. The crude product was dried onto Silica gel and was purified by chromatography (0 to 100% EtOAc/heptane) to give 4-isopropyl-1,4,5,6-tetrahydrocyclopenta[b]pyrrole-2-carboxylic acid (10) as brown solid (0.018 g, 21%). $^1$H NMR (400 MHz, METHANOL-$d_4$) δ ppm 0.93 (d, J=2.68 Hz, 3H) 0.95 (d, J=2.68 Hz, 3H) 1.67 (dq, J=13.37, 6.67 Hz, 1H) 2.04-2.14 (m, J=12.81, 8.91, 5.71, 5.71 Hz, 1H) 2.44-2.55 (m, 1H) 2.56-2.80 (m, 3H) 6.63 (s, 1H). LCMS m/e 194 (M+H). 92.0% pure by HPLC.

2.16. Synthesis of 4-isobutyl-1,4,5,6-tetrahydrocyclopenta[b]pyrrole-2-carboxylic acid (11)

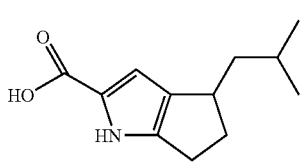

The title compound was synthesized from methyl 4-isobutyl-1,4,5,6-tetrahydrocyclopenta[b]pyrrole-2-carboxylate (37 mg, 0.17 mmol) and lithium hydroxide monohydrate (28 mg, 0.67 mmol) according to General Procedure 7. The crude product was dried onto Silica gel and was purified by flash chromatography (0-80% EtOAc/Heptane) to give 4-isobutyl-1,4,5,6-tetrahydrocyclopenta[b]pyrrole-2-carboxylic acid (11) as a light yellow solid (22 mg, 63%). $^1$H NMR (400 MHz, METHANOL-$d_4$) δ ppm 0.94 (d, J=6.62 Hz, 3H), 0.98 (d, J=6.59 Hz, 3H), 1.23-1.32 (m, 1H), 1.40-1.48 (m, 1H), 1.73-1.84 (m, 1H), 1.89-2.01 (m, 1H), 2.53-2.76 (m, 3H), 2.95-3.05 (m, 1H), 6.59 (s, 1H); LCMS-MS (ESI−) 206.2 (M−H); HPLC (UV=100%).

2.17. Synthesis of 4-(cyclohexylmethyl)-1,4,5,6-tetrahydrocyclopenta[b]pyrrole-2-carboxylic acid (12)

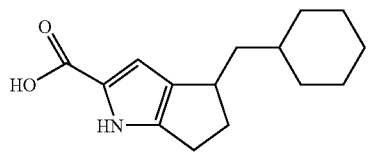

The title compound was synthesized from methyl 4-(cyclohexylmethyl)-1,4,5,6-tetrahydrocyclopenta[b]pyrrole-2-carboxylate and lithium hydroxide monohydrate according to General Procedure 7. The crude product was dried onto silica gel and purified by chromatography (0 to 100% EtOAc/heptane) to give 4-(cyclohexylmethyl)-1,4,5,6-tetrahydrocyclopenta[b]pyrrole-2-carboxylate as a brown solid (0.018 g, 21%). $^1$H NMR (400 MHz, METHANOL-$d_4$) δ ppm 0.87-1.02 (m, 2H) 1.14-1.36 (m, 5H) 1.36-1.54 (m, 2H) 1.63-1.80 (m, 3H) 1.83-2.00 (m, 2H) 2.50-2.77 (m, 3H) 2.97-3.09 (m, 1H) 6.59 (s, 1H). LCMS m/e 248 (M+H). 97.5% pure by HPLC.

2.18. Synthesis of (E)-4-(4-fluorobenzylidene)-1,4,5,6-tetrahydrocyclopenta[b]pyrrole-2-carboxylic acid (13)

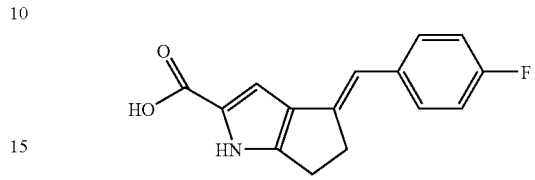

The title compound was synthesized from (E/Z)-methyl 4-(4-fluorobenzylidene)-1,4,5,6-tetrahydrocyclopenta[b]pyrrole-2-carboxylate (2.4 mg, 0.0088 mmol) and sodium hydroxide according to General Procedure 7. The crude product was purified by preparative HPLC (40%-100% methanol/water with 0.1% formic acid and 1% acetonitrile) to afford a 1:1 mixture of (E)- and (Z)-4-(4-fluorobenzylidene)-1,4,5,6-tetrahydrocyclopenta[b]pyrrole-2-carboxylic acid (13) (0.9 mg, 39%). 98.5% (HPLC, UV). LCMS m/e 258 (M+H); 256 (M−H). $^1$H NMR (400 MHz, methanol-$d_4$) δ ppm 8.50 (br. s., 1H), 7.33-7.43 (m, 2H), 6.98-7.07 (m, 2H), 6.78 (s, 1H), 6.42 (t, J=2.22 Hz, 1H), 3.15-3.20 (m, 1H), 2.89-2.96 (m, 2H), 2.80-2.86 (m, 1H). $^{19}$F NMR (376 MHz, METHANOL-$d_4$) δ ppm −156.24 (s, 1F).

The title compound can be converted to 4-(4-fluorobenzyl)-1,4,5,6-tetrahydrocyclopenta[b]pyrrole-2-carboxylic acid using General Procedure 6.

2.19. Synthesis of 4-(4-chlorobenzyl)-1,4,5,6-tetrahydrocyclopenta[b]pyrrole-2-carboxylic acid (14)

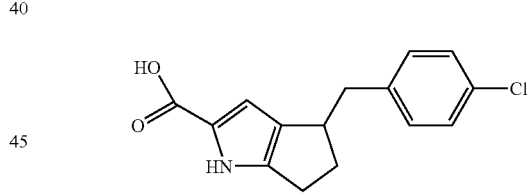

The title compound was synthesized from methyl 4-(4-chlorobenzyl)-1,4,5,6-tetrahydrocyclopenta[b]pyrrole-2-carboxylate (85 mg, 0.293 mmol) and lithium hydroxide monohydrate (67 mg, 1.58 mmol) according to General Procedure 7. The crude product was purified by flash chromatography (0-80% EtOAc/Heptane) to give 4-(4-chlorobenzyl)-1,4,5,6-tetrahydrocyclopenta[b]pyrrole-2-carboxylic acid (14) as a light red solid (60 mg, 69%). $^1$H NMR (400 MHz, METHANOL-$d_4$) δ ppm 2.04-2.14 (m, 1H), 2.42-2.59 (m, 1H), 2.59-2.65 (m, 2H), 2.72 (dd, J=13.37, 7.91, 1H), 2.78 (dd, J=13.37, 6.83, 1H), 3.21-3.29 (m, 1H), 6.29 (s, 1H), 7.14-7.19 (m, 2H), 7.24-7.28 (m, 2H); LCMS-MS (ESI+) 274.2 (M−H); HPLC (UV=100%).

The enantiomers of 4-(4-chlorobenzyl)-1,4,5,6-tetrahydrocyclopenta[b]pyrrole-2-carboxylic acid were separated according to General Procedure 8 using 50% methanol in $CO_2$ with 0.05% diethylamine to give 4-(4-chlorobenzyl)-1,4,5,6-tetrahydrocyclopenta[b]pyrrole-2-carboxylic acid (16) (retention time=4.5 min; 100% ee) and 4-(4-chlorobenzyl)-

1,4,5,6-tetrahydrocyclopenta[b]pyrrole-2-carboxylic acid (15) (retention time=6.9 min; 98.5% ee).

2.20. Synthesis of 4-benzyl-1,4,5,6-tetrahydrocyclopenta[b]pyrrole-2-carboxylic acid (17)

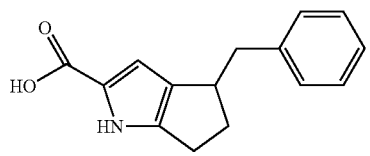

The title compound was synthesized from methyl 4-benzyl-1,4,5,6-tetrahydrocyclopenta[b]pyrrole-2-carboxylate (25 mg, 0.098 mmol) and lithium hydroxide monohydrate (25 mg, 0.39 mmol) according to General Procedure 7. The crude product was dried onto Silica gel and was purified by flash chromatography (0-80% EtOAc/Heptane) to give 4-benzyl-1,4,5,6-tetrahydrocyclopenta[b]pyrrole-2-carboxylic acid (17) as a light red solid (19 mg, 81%). $^1$H NMR (400 MHz, METHANOL-$d_4$) δ ppm 2.05-2.14 (m, 1H), 2.48-2.58 (m, 1H), 2.59-2.66 (m, 2H), 2.74 (dd, J=13.32, 7.81, 1H), 2.79 (dd, J=13.32, 6.98, 1H), 3.22-3.30 (m, 1H), 6.29 (s, 1H), 7.15-7.21 (m, 3H), 7.24-7.29 (m, 2H); LCMS-MS (ESI+) 240.2 (M−H); HPLC (UV=100%).

2.21. Synthesis of 4-phenethyl-1,4,5,6-tetrahydrocyclopenta[b]pyrrole-2-carboxylic acid (18)

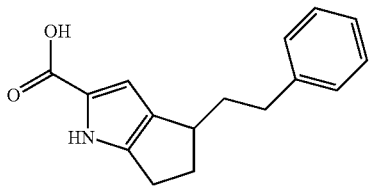

The title compound was synthesized from methyl 4-phenethyl-1,4,5,6-tetrahydrocyclopenta[b]pyrrole-2-carboxylate and lithium hydroxide monohydrate (81 mg, 1.93 mmol) according to General Procedure 7. Silica gel was added, the solvent stripped off and the silica gel-imbedded material was purified by flash chromatography (0-80% EtOAc/Heptane) to give 4-phenethyl-1,4,5,6-tetrahydrocyclopenta[b]pyrrole-2-carboxylic acid (18) as a light yellow solid (103.6 mg, 84%). $^1$H NMR (400 MHz, METHANOL-$d_4$) δ ppm 1.68-1.87 (m, 2H), 1.98-2.09 (m, 1H), 2.55-2.80 (m, 5H), 2.88-2.97 (m, 1H), 6.68 (s, 1H), 7.11-7.16 (m, 1H), 7.17-7.29 (m, 4H); LCMS-MS (ESI+) 256.0 (M+H); HPLC (UV=100%), (ELSD=100%).

The enantiomers of 4-phenethyl-1,4,5,6-tetrahydrocyclopenta[b]pyrrole-2-carboxylic acid were separated according to General Procedure 8 with 20% of a mixture of 50:50 methanol/isopropanol in CO$_2$ with 0.2% diethylamine to give 4-phenethyl-1,4,5,6-tetrahydrocyclopenta[b]pyrrole-2-carboxylic acid (19) (peak 1, retention time=12.8 min; 100% ee) and 4-phenethyl-1,4,5,6-tetrahydrocyclopenta[b]pyrrole-2-carboxylic acid (20) (peak 2, retention time=13.8 min; 95% ee).

2.22. Synthesis of methyl 4-(4-isopropylbenzyl)-1,4,5,6-tetrahydrocyclopenta[b]pyrrole-2-carboxylate

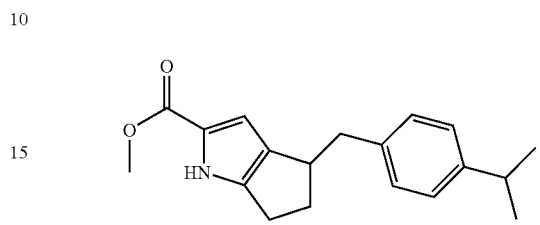

The title compound was synthesized from methyl 4-oxo-1,4,5,6-tetrahydrocyclopenta[b]pyrrole-2-carboxylate in two steps. First, methyl 4-oxo-1,4,5,6-tetrahydrocyclopenta[b]pyrrole-2-carboxylate (0.3 g, 1.7 mmol, 1 equiv) was reacted with 4-4-isopropylbenzyl-MgCl (26.8 mL, 0.25M in THF, 6.7 mmol, 4 equiv) according to General Procedure 3. The resulting olefin was then converted to the title compound according to General Procedure 6. Purification by preparative HPLC (Chromeleon purification system, 0.1% formic acid/1% acetonitrile mixture in water with methanol, 50 mm Dynamax HPLC C-18 column, 28 mL/min; 80-100% methanol) gave methyl 4-(4-isopropylbenzyl)-1,4,5,6-tetrahydrocyclopenta[b]pyrrole-2-carboxylate (17.7 mg). $^1$H NMR (400 MHz, CHLOROFORM-d) δ ppm 8.69 (br. s., 1H), 7.10-7.20 (m, 4H), 6.44 (d, J=1.42 Hz, 1H), 3.81 (s, 3H), 3.23-3.35 (m, 1H), 2.50-2.97 (m, 6H), 2.05-2.19 (m, 1H), 1.27 (d, J=6.91 Hz, 6H).

2.23. Synthesis of 4-(4-isopropylbenzyl)-1,4,5,6-tetrahydrocyclopenta[b]pyrrole-2-carboxylic acid (33)

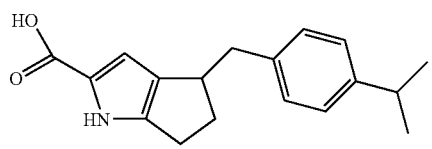

The title compound was synthesized from methyl 4-(4-isopropylbenzyl)-1,4,5,6-tetrahydrocyclopenta[b]pyrrole-2-carboxylate and lithium hydroxide monohydrate according to General Procedure 7. Silica gel was added, the solvent stripped off and the silica gel-imbedded material was purified by flash chromatography (0-80% EtOAc/Heptane) to give 4-(4-isopropylbenzyl)-1,4,5,6-tetrahydrocyclopenta[b]pyrrole-2-carboxylic acid (33) as a light yellow solid.

2.24. Synthesis of methyl 4-(4-methoxyphenethyl)-1,4,5,6-tetrahydrocyclopenta[b]pyrrole-2-carboxylate

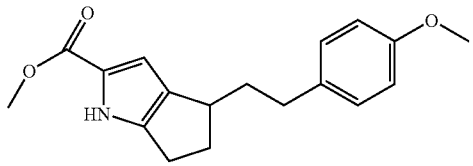

The title compound was synthesized from methyl 4-oxo-1,4,5,6-tetrahydrocyclopenta[b]pyrrole-2-carboxylate in two steps. First, methyl 4-oxo-1,4,5,6-tetrahydrocyclopenta[b]pyrrole-2-carboxylate (300 mg, 1.67 mmol) was reacted with 4-methoxyphenethyl-MgCl (13.4 mL, 6.70 mmol; 0.5 M in THF) according to General Procedure 3. The resulting olefin was then converted to the title compound according to General Procedure 6. The crude product was purified by column chromatography (0-40% EtOAc/heptane) to give methyl 4-(4-methoxyphenethyl)-1,4,5,6-tetrahydrocyclopenta[b]pyrrole-2-carboxylate (240 mg, 48% over two steps). $^1$H NMR (400 MHz, METHANOL-$d_4$) δ ppm 1.64-1.87 (m, 2H), 1.96-2.07 (m, 1H), 2.51-2.77 (m, 5H), 2.87-2.96 (m, 1H), 3.75 (s, 3H), 3.78 (s, 3H), 6.66 (s, 1H), 6.78-6.83 (m, 2H) 7.06-7.12 (m, 2H); LCMS-MS (ESI+) 322.2 (M+Na).

2.25. Synthesis of 4-(4-methoxyphenethyl)-1,4,5,6-tetrahydrocyclopenta[b]pyrrole-2-carboxylic acid (34)

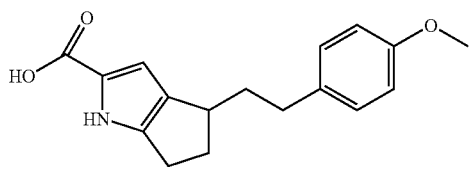

The title compound was synthesized from methyl 4-(4-methoxyphenethyl)-1,4,5,6-tetrahydrocyclopenta[b]pyrrole-2-carboxylate (235 mg, 0.78 mmol) and lithium hydroxide monohydrate (132 mg, 3.14 mmol) according to General Procedure 7. Silica gel was added, the solvent stripped off and the silica gel-imbedded material was purified by flash chromatography (0-80% EtOAc/Heptane) to give 4-(4-methoxyphenethyl)-1,4,5,6-tetrahydrocyclopenta[b]pyrrole-2-carboxylic acid (34) as a light yellow solid (142 mg, 63%). $^1$H NMR (400 MHz, METHANOL-$d_4$) δ ppm 1.64-1.84 (m, 2H), 1.96-2.08 (m, 1H), 2.53-2.78 (m, 5H), 2.85-2.97 (m, 1H), 3.75 (s, 3H), 6.67 (s, 1H), 6.77-6.86 (m, 2H), 7.06-7.16 (m, 2H); LCMS-MS (ESI+) 286.1 (M+H); HPLC (UV=100%), (ELSD=100%).

2.26. Synthesis of methyl 4-(2-methyl-2-phenylpropyl)-1,4,5,6-tetrahydro-cyclopenta[b]pyrrole-2-carboxylate

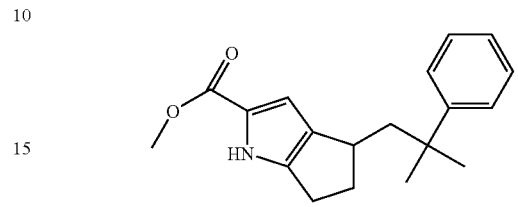

The title compound was synthesized from methyl 4-oxo-1,4,5,6-tetrahydrocyclopenta[b]pyrrole-2-carboxylate in two steps. First, methyl 4-oxo-1,4,5,6-tetrahydrocyclopenta[b]pyrrole-2-carboxylate (420 mg, 2.34 mmol) was reacted with (2-methyl-2-phenylpropyl)-MgCl (19 mL, 9.38 mmol, 0.5 M in THF, 4 equiv) according to General Procedure 3. The resulting olefin was then converted to the title compound according to General Procedure 6. Purification by column chromatography (Isco CombiFlash), eluting with a gradient of 0-100% EtOAc/heptane, gave methyl 4-(2-methyl-2-phenylpropyl)-1,4,5,6-tetrahydrocyclopenta[b]pyrrole-2-carboxylate as a white solid (50 mg, 7.2%). $^1$H NMR (400 MHz, CHLOROFORM-d) δ ppm 1.40 (s, 3H) 1.42 (s, 3H) 1.73-1.85 (m, 2H) 2.15 (dd, J=14.11, 4.00 Hz, 1H) 2.29 (dt, J=9.27, 7.76 Hz, 1H) 2.47-2.65 (m, 2H) 2.73-2.82 (m, 1H) 3.81 (s, 3H) 6.47 (d, J=1.07 Hz, 0H) 7.22-7.27 (m, 1H) 7.31-7.36 (m, 2H) 7.39-7.44 (m, 2H) 8.77 (br. s, 1H). LCMS-MS (ESI+) 298.0 (M+H).

2.27. Synthesis of 4-(2-methyl-2-phenylpropyl)-1,4,5,6-tetrahydrocyclopenta[b]pyrrole-2-carboxylic acid (35)

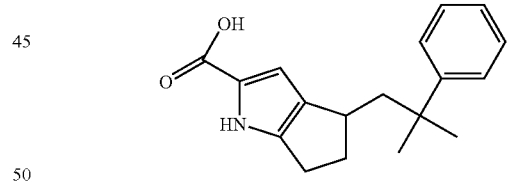

The title compound was synthesized from methyl 4-(2-methyl-2-phenylpropyl)-1,4,5,6-tetrahydrocyclopenta[b]pyrrole-2-carboxylate (0.10 g, 0.33 mmol) and lithium hydroxide monohydrate (142 mg, 3.3 mmol) according to General Procedure 7. Silica gel was added, the solvent stripped off and the silica gel-imbedded material was purified by flash chromatography (0-100% EtOAc/Heptane) to give 4-(2-methyl-2-phenylpropyl)-1,4,5,6-tetrahydrocyclopenta[b]pyrrole-2-carboxylic acid (35) as a reddish brown solid (2.4 mg).
$^1$H NMR (400 MHz, METHANOL-$d_4$) δ ppm 1.38 (s, 3H) 1.41 (s, 3H) 1.69-1.83 (m, 2H) 2.13 (dd, J=14.06, 3.86 Hz, 1H) 2.20-2.30 (m, 1H) 2.42-2.62 (m, 2H) 2.66-2.77 (m, 1H) 6.40 (s, 1H) 7.13-7.19 (m, 1H) 7.30 (t, J=7.79 Hz, 2H) 7.39-7.45 (m, 2H) 8.48 (s, 1H). LCMS m/e 284 (M+H). 97.9% pure by HPLC.

2.28. Synthesis of methyl 4-(3-phenylpropyl)-1,4,5,6-tetrahydrocyclopenta[b]pyrrole-2-carboxylate The title compound was synthesized from methyl 4-oxo-1,4,5,6-tetrahydrocyclopenta[b]pyrrole-2-carboxylate in two steps. First, methyl 4-oxo-1,4,5,6-tetrahydrocyclopenta[b]pyrrole-2-carboxylate (300 mg, 1.67 mmol) was reacted with 3-phenyl-1-propyl-MgBr (13.4 mL, 6.70 mmol; 0.5 M in THF) according to General Procedure 3. The resulting olefin was then converted to the title compound according to General Procedure 6. The crude product was purified by column chromatography (0-40% EtOAc/heptane) to afford methyl 4-(3-phenylpropyl)-1,4,5,6-tetrahydrocyclopenta[b]pyrrole-2-carboxylate (212 mg, 45% over two steps). $^1$H NMR (400 MHz, METHANOL-$d_4$) δ ppm 1.41-1.58 (m, 2H), 1.63-1.83 (m, 2H), 1.90-2.00 (m, 1H), 2.52-2.74 (m, 5H), 2.87-2.96 (m, 1H), 3.77 (s, 3H), 6.60 (s, 1H), 7.11-7.20 (m, 3H) 7.22-7.27 (m, 2H); LCMS-MS (ESI+) 306.2 (M+Na).

2.29. Synthesis of 4-(3-phenylpropyl)-1,4,5,6-tetrahydrocyclopenta[b]pyrrole-2-carboxylic acid (36)

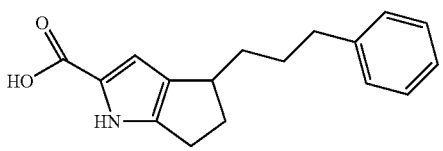

The title compound was synthesized from methyl 4-(3-phenylpropyl)-1,4,5,6-tetrahydrocyclopenta[b]pyrrole-2-carboxylate (210 mg, 0.74 mmol) and lithium hydroxide monohydrate (124 mg, 2.96 mmol) according to General Procedure 7. Silica gel was added, the solvent stripped off and the silica gel-imbedded material was purified by flash chromatography (0-80% EtOAc/Heptane) to give 4-(3-phenylpropyl)-1,4,5,6-tetrahydrocyclopenta[b]pyrrole-2-carboxylic acid (36) as a light brown solid (113.8 mg, 57%). $^1$H NMR (400 MHz, METHANOL-$d_4$) δ ppm 1.42-1.59 (m, 2H), 1.64-1.84 (m, 2H), 1.90-2.01 (m, 1H), 2.52-2.75 (m, 5H), 2.88-2.97 (m, 1H), 6.61 (s, 1H), 7.10-7.20 (m, 3H), 7.21-7.28 (m, 2H); LCMS-MS (ESI+) 270.1 (M+H); HPLC (UV=100%), (ELSD=100%).

2.30. Synthesis of methyl 4-p-tolyl-1,4,5,6-tetrahydrocyclopenta[b]pyrrole-2-carboxylate

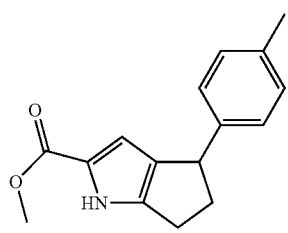

The title compound was synthesized from methyl 4-oxo-1,4,5,6-tetrahydrocyclopenta[b]pyrrole-2-carboxylate in two steps. First, methyl 4-oxo-1,4,5,6-tetrahydrocyclopenta[b]pyrrole-2-carboxylate (0.3 g, 1.7 mmol) was reacted with p-tolyl-MgBr (6.7 mL, 1 M in THF, 6.7 mmol) according to General Procedure 3. The resulting olefin was then converted to the title compound according to General Procedure 6. The desired methyl 4-p-tolyl-1,4,5,6-tetrahydrocyclopenta[b]pyrrole-2-carboxylate was used in the next step without further purification (0.289 g). $^1$H NMR (400 MHz, CHLOROFORM-d) δ ppm 9.06 (br. s., 1H), 7.11 (s, 4H), 6.65 (d, J=1.59 Hz, 1H), 4.20 (t, J=7.27 Hz, 1H), 3.83 (s, 3H), 2.72-2.98 (m, 3H), 2.34 (s, 3H), 2.23-2.32 (m, 1H).

2.31. Synthesis of 4-p-tolyl-1,4,5,6-tetrahydrocyclopenta[b]pyrrole-2-carboxylic acid (37)

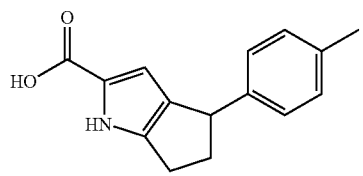

The title compound was synthesized from methyl 4-p-tolyl-1,4,5,6-tetrahydrocyclopenta[b]pyrrole-2-carboxylate (0.2888 g, 1.2 mmol, 1 equiv) and sodium hydroxide (2.94 mL, 10 M, 25 equiv) according to General Procedure 7. The resulting product was purified by preparative HPLC (water with 0.1% formic acid and 1% acetonitrile/methanol; 50 mm Dynamax HPLC C-18 column; 28 mL/min; 60% to 100% methanol) to give 4-p-tolyl-1,4,5,6-tetrahydrocyclopenta[b]pyrrole-2-carboxylic acid (37) (76.9 mg, 28%) $^1$H NMR (400 MHz, METHANOL-$d_4$) δ ppm 7.02-7.10 (m, 4H), 6.50 (s, 1H), 4.13 (t, J=7.20 Hz, 1H), 2.68-2.94 (m, 3H), 2.29 (s, 3H), 2.14-2.25 (m, 1H); LCMS m/e 240 (M−H).

2.32. Synthesis of methyl 4-(2,2,2-trifluoroethyl)-1,4,5,6-tetrahydrocyclopenta[b]pyrrole-2-carboxylate

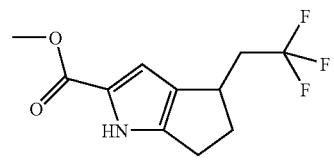

The title compound was synthesized from methyl 1H-pyrrole-2-carboxylate (2.0 g, 16 mmol, 1 equiv) and 3,3,3-trifluoropropionyl chloride (2.92 g, 19.8 mmol, 1.25 equiv) according to General Procedures 1.2 and 5.2. The resulting product was purified by column chromatography (Isco CombiFlash) using a 0-30% gradient (EtOAc/Heptane) over 20 minutes. Approximate retention time of isolated material: 14.5-16.5 minutes. 0.1016 g. $^{19}$F NMR (376 MHz, CHLOROFORM-d) δ ppm −65.00 (t, J=9.57 Hz, 3F). $^1$H NMR (400 MHz, CHLOROFORM-d) δ ppm 2.07-2.29 (m, J=11.13, 3.73, 3.73, 3.73, 3.73 Hz, 2H) 2.41 (qd, J=11.17, 8.29 Hz, 1H) 2.67-2.84 (m, 3H) 3.30 (quin, J=6.77 Hz, 1H) 3.84 (s, 3H) 6.70 (s, 1H) 8.87 (br. s, 1H).

2.33. Synthesis of methyl 4-(4-fluorobenzyl)-1-tosyl-1,4,5,6-tetrahydrocyclopenta[b]pyrrole-2-carboxylate

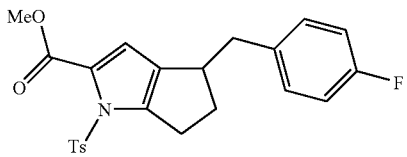

The title compound was synthesized from tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (0.60 g, 1.8 mmol) and 4-fluorobenzylmagnesium chloride (0.25M in THF, 52 mL, 13 mmol) according to General Procedure 3 to give exo olefin-containing methyl 4-(4-fluorobenzylidene)-1-tosyl-1,4,5,6-tetrahydrocyclopenta[b]pyrrole-2-carboxylate (as a mixture of cis/trans isomers), then hydrogenation according to General Procedure 6. In this example, Degussa type, 5% palladium on carbon (~0.200 g, 0.2 mmol) was used, and the reaction placed under a hydrogen atmosphere in a Parr shaker (~40 PSI) for 2 hours. Purification by column chromatography (Isco CombiFlash) eluting with a gradient of 0-50% EtOAc/heptane affording the title compound as white crystals: 0.070 g (14% yield). $^1$H NMR (400 MHz, CHLOROFORM-d) δ ppm 2.05-2.15 (m, 1H), 2.44 (s, 3H), 2.55-2.65 (m, 1H), 2.70-2.85 (m, 2H), 3.08 (t, 1H), 3.20-3.35 (m, 1H), 3.71 (s, 3H), 6.49 (s, 1H), 6.95-7.00 (m, 2H), 7.10-7.15 (m, 1H), 7.30-7.35 (d, J=8.4 Hz, 2H), 7.87 (d, J=8.4 Hz, 1H).

2.34. Synthesis of methyl 4-(3,4-difluorobenzyl)-1,4,5,6-tetrahydrocyclopenta[b]pyrrole-2-carboxylate

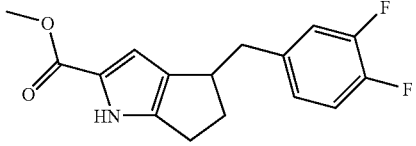

The title compound was synthesized from methyl 4-oxo-1,4,5,6-tetrahydrocyclopenta[b]pyrrole-2-carboxylate in two steps. First, methyl 4-oxo-1,4,5,6-tetrahydrocyclopenta[b]pyrrole-2-carboxylate (0.60 g, 3.35 mmol) was reacted with 3,4-difluorobenzylmagnesium bromide (0.25 M in diethyl ether, 33.5 mL, 8.4 mmol) according to General Procedure 3. The resulting olefin was then converted to the title compound by hydrogenation according to General Procedure 6 (5% Pd on carbon). The crude product was purified by column chromatography (Isco CombiFlash) eluting with a gradient of 0-40% EtOAc/heptane to afford the title compound: 0.100 g. $^1$H NMR (400 MHz, CHLOROFORM-d) δ ppm 1.98-2.18 (m, 1 H) 2.48-2.64 (m, 1H) 2.64-2.83 (m, 4H) 3.27 (quin, J=7.00 Hz, 1H) 3.81 (s, 3H) 6.29-6.41 (m, 1H) 6.89 (ddd, J=6.19, 4.14, 2.03 Hz, 1H) 6.94-7.14 (m, 2H) 9.01 (br. s, 1H).

2.35. Synthesis of methyl 4-(2,4-difluorobenzyl)-1,4,5,6-tetrahydrocyclopenta[b]pyrrole-2-carboxylate

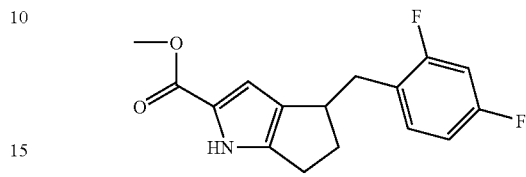

The title compound was synthesized in two steps. First, methyl 4-oxo-1,4,5,6-tetrahydrocyclopenta[b]pyrrole-2-carboxylate (0.50 g, 2.8 mmol) was reacted with 2,4-difluorobenzylmagnesium chloride (0.25 M in diethyl ether, 28 mL, 7 mmol) according to General Procedure 3. The resulting exo-olefin ((E)-methyl 4-(2,4-difluorobenzylidene)-1,4,5,6-tetrahydrocyclopenta[b]pyrrole-2-carboxylate) was then converted to the title compound by hydrogenation according to General Procedure 6 (with 5% Pd/C). The crude product was purified by column chromatography (Isco CombiFlash) eluting with a gradient of 0-20% EtOAc/heptane to afford the title compound: 0.062 g. $^1$H NMR (400 MHz, CHLOROFORM-d) δ ppm 2.05-2.15 (m, 1H), 2.55-2.65 (m, 1H), 2.65-2.75 (m, 2H), 2.79 (d, J=7.4, 2H), 3.25-3.35 (m, 1H), 3.81 (s, 3H), 6.38 (d, J=1.4 Hz, 1H), 6.78-6.90 (m, 2H), 7.10-7.15 (m, 1H).

2.36. Synthesis of methyl 4-(3-chloro-4-fluorobenzyl)-1,4,5,6-tetrahydrocyclopenta[b]pyrrole-2-carboxylate

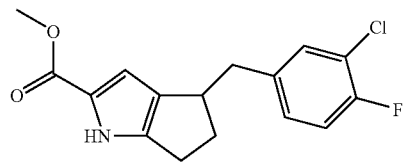

The title compound was synthesized in two steps. First, methyl 4-oxo-1,4,5,6-tetrahydrocyclopenta[b]pyrrole-2-carboxylate (0.50 g, 2.8 mmol) was reacted with 3-chloro-4-fluorobenzylmagnesium chloride (0.25 M in diethyl ether, 28 mL, 7 mmol) according to General Procedure 3. The resulting exo-olefin ((E)-methyl 4-(3-chloro-4-fluorobenzylidene)-1,4,5,6-tetrahydrocyclopenta[b]pyrrole-2-carboxylate) was then converted to the title compound by hydrogenation according to General Procedure 6 (with Pt$_2$O). The crude product was purified by column chromatography (Isco CombiFlash) eluting with a gradient of 0-50% EtOAc/heptane to afford the title compound. 0.034 g. $^1$H NMR (400 MHz, CHLOROFORM-d) δ ppm 2.00-2.16 (m, 1H) 2.50-2.64 (m, 1H) 2.64-2.71 (m, 2H) 2.75 (d, J=7.37 Hz, 2H) 3.16-3.38 (m, 1H) 3.82 (s, 3H) 6.37 (d, J=1.66 Hz, 1H) 6.97-7.11 (m, 2H) 7.23 (dd, J=7.13, 2.00 Hz, 1H) 8.85 (br. s, 1H)).

2.37. Synthesis of methyl 4-(4-fluoro-2-methylbenzyl)-1,4,5,6-tetrahydrocyclopenta[b]pyrrole-2-carboxylate

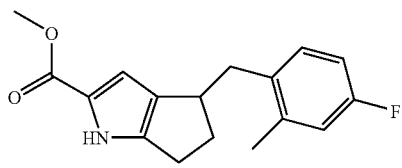

The title compound was synthesized in two steps. First, methyl 4-oxo-1,4,5,6-tetrahydrocyclopenta[b]pyrrole-2-carboxylate was reacted with (4-fluoro-2-methylbenzyl)magnesium bromide) according to General Procedure 3. The resulting product was then converted to the title compound by hydrogenation according to General Procedure 6.

2.38. Synthesis of methyl 4-(3-fluorobenzyl)-1,4,5,6-tetrahydrocyclopenta[b]pyrrole-2-carboxylate

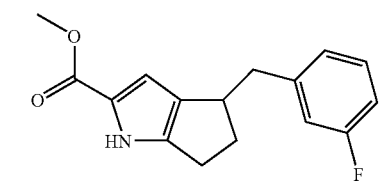

The title compound was synthesized in two steps. First, methyl 4-oxo-1,4,5,6-tetrahydrocyclopenta[b]pyrrole-2-carboxylate (0.50 g, 2.79 mmol) was reacted with 3-fluorobenzylmagnesium chloride (0.25 M in diethyl ether, 52 mL, 13 mmol) according to General Procedure 3. The resulting exo-olefin ((E)-methyl 4-(3-fluorobenzylidene)-1,4,5,6-tetrahydrocyclopenta[b]pyrrole-2-carboxylate) was then converted to the title compound by hydrogenation according to General Procedure 6. In this example, Degussa type, 5% palladium on carbon (0.100 g, 0.1 mmol) was used, and the reaction placed under a hydrogen atmosphere in a Parr shaker (40 PSI) for 2 hours. Purification by column chromatography (Isco Combi-Flash) eluting with a gradient of 0-40% EtOAc/heptane afforded the title compound. 0.075 g. $^1$H NMR (400 MHz, CHLOROFORM-d) δ ppm 2.03-2.11 (m, 1H), 2.47-2.56 (m, 1H), 2.59-2.73 (m, 2H), 2.78 (d, J=7.4 Hz, 2H), 3.24-3.32 (m, 1H), 3.81 (s, 3H), 6.39 (d, J=1.7 Hz, 1H), 6.90-7.00 (m, 3H), 7.20-7.35 (m, 1H), 8.94 (br s, 1H).

2.39. Synthesis of methyl 4-(3-chloro-5-fluorobenzyl)-1,4,5,6-tetrahydrocyclopenta[b]pyrrole-2-carboxylate

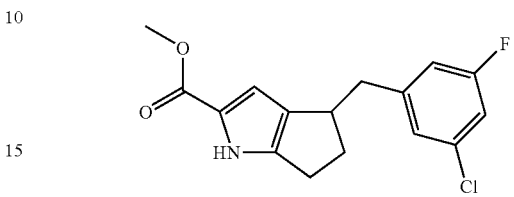

The title compound was synthesized in two steps. First, methyl 4-oxo-1,4,5,6-tetrahydrocyclopenta[b]pyrrole-2-carboxylate (0.40 g, 2.23 mmol) was reacted with 3-chloro-5-fluorobenzylmagnesium chloride ((0.25 M in diethyl ether, 23.0 mL, 5.6 mmol) according to General Procedure 3. The resulting exo-olefin ((E)-methyl 4-(3-chloro-5-fluorobenzylidene)-1,4,5,6-tetrahydrocyclopenta[b]pyrrole-2-carboxylate) was then converted to the title compound by hydrogenation according to General Procedure 6 (with PtO$_2$). The crude product was purified by column chromatography (Isco CombiFlash) eluting with a gradient of 0-100% EtOAc/heptane to afford the title compound. 0.045 g The material was taken on to hydrolysis in impure form.

2.40. Synthesis of methyl 4-(3-chlorobenzyl)-1,4,5,6-tetrahydrocyclopenta[b]pyrrole-2-carboxylate

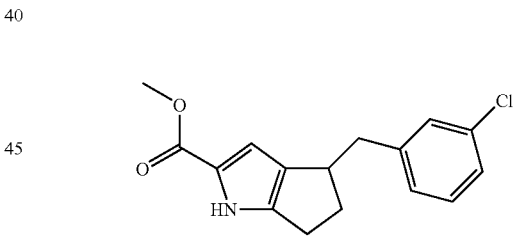

The title compound was synthesized in two steps. First, methyl 4-oxo-1,4,5,6-tetrahydrocyclopenta[b]pyrrole-2-carboxylate (447 mg, 2.5 mmol) was reacted with 3-chlorobenzylmagnesium chloride (0.25 M in hexanes, 25 mL, 6.3 mmol) according to General Procedure 3. The resulting products were then converted to the title compound by hydrogenation according to General Procedure 6 (with Pt$_2$O). The crude product was purified by column chromatography eluting with heptane-EtOAc, gradient 0 to 40% EtOAc to afford the title compound. 262 mg. $^1$H NMR (400 MHz, CHLOROFORM-d) δ ppm 2.04-2.15 (m, J=12.57, 8.03, 6.17, 6.17 Hz, 1H) 2.52-2.64 (m, 1H) 2.64-2.72 (m, 2H) 2.74-2.83 (m, 2H)

3.81 (s, 3H) 6.39 (d, J=1.37 Hz, 1H) 7.07 (d, J=8.25 Hz, 1H) 7.21 (d, J=1.81 Hz, 2H) 7.22-7.26 (m, 1H) 7.28-7.32 (m, 1H) 8.75 (br. s, 1H).

2.41. Synthesis of methyl 4-(3,4-dichlorobenzyl)-1,4,5,6-tetrahydrocyclopenta[b]pyrrole-2-carboxylate

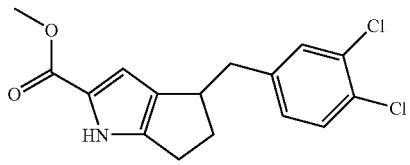

The title compound was synthesized in two steps. First, methyl 4-oxo-1,4,5,6-tetrahydrocyclopenta[b]pyrrole-2-carboxylate (0.50 g, 2.8 mmol) was reacted with 3,4-dichlorobenzylmagnesium chloride (0.25 M in diethyl ether, 28.0 mL, 7.0 mmol) according to General Procedure 3. The resulting exo-olefin ((E)-methyl 4-(3,4-dichlorobenzylidene)-1,4,5,6-tetrahydrocyclopenta[b]pyrrole-2-carboxylate) was then converted to the title compound by hydrogenation according to General Procedure 6 (with 5% $Pt_2O$). The crude product was purified by column chromatography (Isco CombiFlash) eluting with a gradient of 0-50% EtOAc/heptane to afford the title compound. 0.064 g.

2.42. Synthesis of methyl 4-(4-bromobenzyl)-1,4,5,6-tetrahydrocyclopenta[b]pyrrole-2-carboxylate

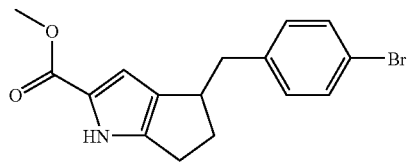

The title compound was synthesized in six steps. First, methyl 1H-pyrrole-2-carboxylate (1.0 g, 8 mmol, 1 equiv) in DCE (15 mL) was reacted with 4-bromophenylacetic acid (2.06 g, 9.6 mmol, 1.2 equiv) according to General Procedure 1.2.A to afford methyl 4-(2-(4-bromophenyl)acetyl)-1H-pyrrole-2-carboxylate, which was then BOC-protected according to General Procedure 1.2.B to provide 1-tert-butyl 2-methyl 4-(2-(4-bromophenyl)acetyl)-1H-pyrrole-1,2-dicarboxylate, which was next reacted with 2-tert-butoxy-2-oxoethylzinc chloride (3.0 g, 28.2 mL, 0.5M in ether, 14 mmol, 3.5 equiv) according to General Procedure 1.2.C to afford 1-tert-butyl 2-methyl 4-(1-(4-bromophenyl)-4-tert-butoxy-2-hydroxy-4-oxobutan-2-yl)-1H-pyrrole-1,2-dicarboxylate, which was reacted with trifluoroacetic acid (8.25 mL, 0.45 M) and triethylsilane (1.25 g, 1.72 mL, 2.9 equiv) according to General Procedure 1.2.D to provide 4-(4-bromophenyl)-3-(5-(methoxycarbonyl)-1H-pyrrol-3-yl)butanoic acid. This product was then cyclized by reaction with PPA (3.16 g) according to General Procedure 1.2.E to achieve methyl 4-(4-bromobenzyl)-6-oxo-1,4,5,6-tetrahydrocyclopenta[b]pyrrole-2-carboxylate. Reduction with decaborane (0.34 g, 3 mmol, 5 equiv) according to Procedure 5b afforded the title compound, which was purified by purified by column chromatography (Isco CombiFlash) using a 0-30% gradient (EtOAc/Heptane). 0.0998 g. $^1$H NMR (400 MHz, CHLORO-FORM-d) δ ppm 2.03-2.16 (m, 1H) 2.58 (dt, J=12.39, 6.88 Hz, 1H) 2.66 (t, J=6.99 Hz, 2H) 2.76 (d, J=7.39 Hz, 2H) 3.28 (dq, J=7.18, 6.92 Hz, 1H) 3.81 (s, 3H) 6.38 (d, J=1.48 Hz, 1H) 7.07 (d, J=8.31 Hz, 2H) 7.42 (q, J=4.17 Hz, 2H) 8.82 (br. s, 1H).

2.43. Synthesis of methyl 4-(3-bromobenzyl)-1,4,5,6-tetrahydrocyclopenta[b]pyrrole-2-carboxylate

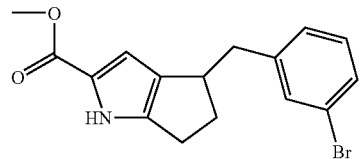

The title compound was synthesized in two steps. Methyl 4-oxo-1,4,5,6-tetrahydrocyclopenta[b]pyrrole-2-carboxylate (1.50 g, 8.37 mmol) was reacted with 3-bromobenzylmagnesium bromide (84 mL, 21 mmol) according to General Procedure 3 to give (E)-methyl 4-(3-bromobenzylidene)-1,4,5,6-tetrahydrocyclopenta[b]pyrrole-2-carboxylate, followed by hydrogenation according to General Procedure 6, and was purified by column chromatography (Isco CombiFlash) eluting with a gradient of 0-30% EtOAc/heptane to afford the title compound: 1.034 g. $^1$H NMR (400 MHz, ACETONE-$d_6$) δ ppm 2.03-2.11 (m, 1H), 2.47-2.56 (m, 1H), 2.59-2.73 (m, 2H), 2.78 (d, 7.47 Hz, 2H), 3.24-3.32 (m, 1H), 3.72 (s, 3H), 6.32 (d, 1.76 Hz, 1H), 7.20-7.28 (m, 3H), 7.37-7.40 (m, 1H), 7.43 (br s, 1H).

2.44. Synthesis of methyl 4-(3-methoxybenzyl)-1,4,5,6-tetrahydrocyclopenta[b]pyrrole-2-carboxylate

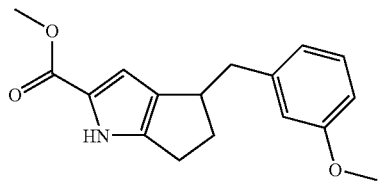

The title compound was synthesized in two steps. First, methyl 4-oxo-1,4,5,6-tetrahydrocyclopenta[b]pyrrole-2-carboxylate (447 mg, 2.5 mmol) was reacted with 3-methoxybenzylmagnesium bromide (0.25 M in hexanes, (25 mL, 6.3 mmol) according to General Procedure 3. The resulting exo-olefin ((E)-methyl 4-(3-methoxybenzylidene)-1,4,5,6-tetrahydrocyclopenta[b]pyrrole-2-carboxylate) was then converted to the title compound by hydrogenation according to General Procedure 6 (with 5% Pd/C). The crude product was purified by chromatography, eluting with heptane-EtOAc, gradient 0 to 40% EtOAc to afford the title compound. 155 mg. $^1$H NMR (400 MHz, CHLOROFORM-d) δ ppm 2.04-2.21 (m, 1H) 2.50-2.63 (m, 1H) 2.62-2.71 (m, 2H) 2.72-2.86

(m, 2H) 3.23-3.36 (m, 1H) 3.81 (s, 6H) 6.44 (d, J=1.56 Hz, 1H) 6.72-6.85 (m, 3H) 7.22 (t, J=7.78 Hz, 1H) 8.76 (br. s, 1H).

2.45. Synthesis of methyl 4-(3,4-dimethoxybenzyl)-1,4,5,6-tetrahydrocyclopenta[b]pyrrole-2-carboxylate

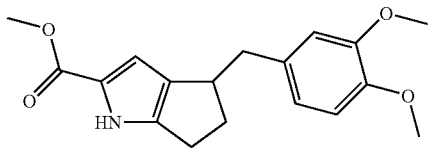

The title compound was synthesized in two steps. First, methyl 4-oxo-1,4,5,6-tetrahydrocyclopenta[b]pyrrole-2-carboxylate (0.50 g, 2.8 mmol) was reacted with 3,4-dimethoxybenzylmagnesium chloride (0.25 M in THF, 28.0 mL, 7.0 mmol) according to General Procedure 3. The resulting exo-olefin ((E)-methyl 4-(3,4-dimethoxybenzylidene)-1,4,5,6-tetrahydrocyclopenta[b]pyrrole-2-carboxylate) was then converted to the title compound by hydrogenation according to General Procedure 6 (with 5% Pd/C). The crude product was purified by column chromatography (Isco CombiFlash) eluting with a gradient of 0-50% EtOAc/heptane to afford the title compound: 0.050 g. $^1$H NMR (400 MHz, CHLOROFORM-d) δ ppm 2.06-2.18 (m, 1H) 2.50-2.68 (m, 3H) 2.68-2.81 (m, 2H) 3.20-3.35 (m, 1H) 3.74-3.94 (m, 9H) 6.36-6.46 (m, 1H) 6.69 (d, J=1.76 Hz, 1H) 6.74 (dd, J=8.10, 1.56 Hz, 1H) 6.82 (d, J=8.10 Hz, 1H) 8.80 (br. s, 1H).

2.46. Synthesis of methyl 4-(3-methylbenzyl)-1,4,5,6-tetrahydrocyclopenta[b]pyrrole-2-carboxylate

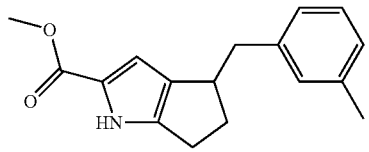

The title compound was synthesized in 4 steps. First, tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (1.50 g, 8.37 mmol) was reacted with 3-bromobenzylmagnesium bromide (15 mL, 3.75 mmol) according to General Procedure 3 to give exo olefin-containing compound (E)-methyl 4-(3-bromobenzylidene)-1-tosyl-1,4,5,6-tetrahydrocyclopenta[b]pyrrole-2-carboxylate, followed by coupling with methylboronic acid (136 mg, 2.28 mmol) according to General Procedure 9.2 to give (E)-methyl 4-(3-methylbenzylidene)-1-tosyl-1,4,5,6-tetrahydrocyclopenta[b]pyrrole-2-carboxylate, then tosyl deprotection according to General Procedure 10.1 to give (E)-methyl 4-(3-methylbenzylidene)-1,4,5,6-tetrahydrocyclopenta[b]pyrrole-2-carboxylate. Hydrogenation of (E)-methyl 4-(3-methylbenzylidene)-1,4,5,6-tetrahydrocyclopenta[b]pyrrole-2-carboxylate according to General Procedure 6 (with 5% Pd/C), then purification by chromatography, eluting with heptane-EtOAc, gradient 0 to 25% EtOAc to afford the title compound. 85 mg. $^1$H NMR (400 MHz, CHLOROFORM-d) δ ppm 2.02-2.20 (m, 1H) 2.35 (s, 3H) 2.49-2.64 (m, 1H) 2.64-2.86 (m, 4H) 3.24-3.36 (m, 1H) 3.81 (s, 3H) 6.42 (d, J=1.56 Hz, 1H) 6.95-7.09 (m, 3H) 7.20 (t, J=7.86 Hz, 1H) 8.73 (br. s, 1H).

2.47. Synthesis of methyl 4-(3,4-dimethylbenzyl)-1,4,5,6-tetrahydrocyclopenta[b]pyrrole-2-carboxylate

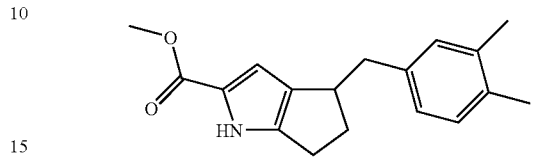

The title compound was synthesized in two steps. First, methyl 4-oxo-1,4,5,6-tetrahydrocyclopenta[b]pyrrole-2-carboxylate (0.50 g, 2.8 mmol) was reacted with 3,4-dimethylbenzylmagnesium chloride (0.25 M in THF, 28.0 mL, 7.0 mmol) according to General Procedure 3. The resulting exo-olefin ((E)-methyl 4-(3,4-dimethylbenzylidene)-1,4,5,6-tetrahydrocyclopenta[b]pyrrole-2-carboxylate) was then converted to the title compound by hydrogenation according to General Procedure 6 (with 5% Pd/C). The crude product was purified by column chromatography (Isco CombiFlash) eluting with a gradient of 0-50% EtOAc/heptane to afford the title compound. 0.050 g. $^1$H NMR (400 MHz, CHLOROFORM-d) δ ppm 2.02-2.19 (m, 1H) 2.19-2.35 (m, 6H) 2.44-2.62 (m, 1H) 2.62-2.87 (m, 4H) 3.19-3.38 (m, 1H) 3.82 (s, 3H) 6.46 (d, J=1.56 Hz, 1H) 6.95 (d, J=7.52 Hz, 1H) 7.00 (s, 1H) 7.07 (d, J=7.42 Hz, 1H) 8.93 (br. s, 1H).

2.48. Synthesis of methyl 4-(3,5-dimethylbenzyl)-1,4,5,6-tetrahydrocyclopenta[b]pyrrole-2-carboxylate

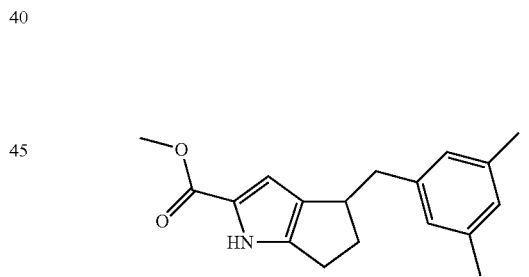

The title compound was synthesized in two steps. First, methyl 4-oxo-1,4,5,6-tetrahydrocyclopenta[b]pyrrole-2-carboxylate (0.5 g, 2.79 mmol) was reacted with 3,5-dimethylbenzylmagnesium bromide (28 mL, 6.97 mmol, 0.25 M in THF, 2.5 equiv) according to General Procedure 3 to give (E)-methyl 4-(3,5-dimethylbenzylidene)-1,4,5,6-tetrahydrocyclopenta[b]pyrrole-2-carboxylate, followed by hydrogenation according to General Procedure 6. The title compound was purified by column chromatography (Isco CombiFlash) eluting with a gradient of 0-100% EtOAc/heptane. $^1$H NMR (400 MHz, CHLOROFORM-d) δ ppm 2.07-2.18 (m, 1H) 2.33 (s, 6H) 2.50-2.77 (m, 4H) 2.77-2.84 (m, 1H) 3.30 (quin, J=7.08 Hz, 1H) 3.83 (s, 3H) 6.46 (d, J=1.46 Hz, 1H) 6.85 (s, 2H) 6.88 (s, 1H) 9.00 (br. s, 1H).

2.49. Synthesis of methyl 4-(3-cyclopropylbenzyl)-1,4,5,6-tetrahydrocyclopenta[b]pyrrole-2-carboxylate

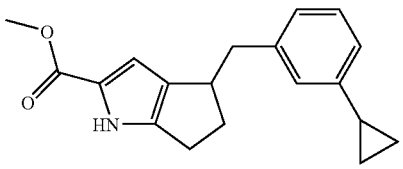

The title compound was synthesized in three steps. First, tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (1.50 g, 8.37 mmol) was reacted with 3-bromobenzylmagnesium bromide (15 mL, 3.75 mmol) according to General Procedure 3 to give exo olefin-containing compound (E)-methyl 4-(3-bromobenzylidene)-1-tosyl-1,4,5,6-tetrahydrocyclopenta[b]pyrrole-2-carboxylate, followed by coupling with potassium cyclopropyltrifluoroborate (0.090 g, 0.61 mmol) according to General Procedure 9.3 to give (E)-methyl 4-(3-cyclopropylbenzylidene)-1-tosyl-1,4,5,6-tetrahydrocyclopenta[b]pyrrole-2-carboxylate and tosyl deprotected (E)-methyl 4-(3-cyclopropylbenzylidene)-1,4,5,6-tetrahydrocyclopenta[b]pyrrole-2-carboxylate, which could be separated by chromatography. Tosyl deprotected (E)-methyl 4-(3-cyclopropylbenzylidene)-1,4,5,6-tetrahydrocyclopenta[b]pyrrole-2-carboxylate was hydrogenated to afford crude title compound, which was used in the next step without purification.

2.50. Synthesis of methyl 4-(3-ethynylbenzyl)-1,4,5,6-tetrahydrocyclopenta[b]pyrrole-2-carboxylate

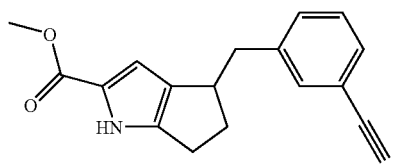

The title compound was synthesized in two steps. First, BOC protected methyl 4-(3-bromobenzyl)-1,4,5,6-tetrahydrocyclopenta[b]pyrrole-2-carboxylate (1-tert-butyl 2-methyl 4-(3-bromobenzyl)-5,6-dihydrocyclopenta[b]pyrrole-1,2(4H)-dicarboxylate) (0.101 g, 0.23 mmol) was coupled with ethynyltrimethylsilane (0.065 mL, 0.46 mmol) according to General Procedure 9.4 to give 1-tert-butyl 2-methyl 4-(3-((trimethylsilyl)ethynyl)benzyl)-5,6-dihydrocyclopenta[b]pyrrole-1,2(4H)-dicarboxylate. The trimethylsilyl group and BOC group were then removed. 1-tert-butyl 2-methyl 4-(3-((trimethylsilyl)ethynyl)benzyl)-5,6-dihydrocyclopenta[b]pyrrole-1,2(4H)-dicarboxylate (0.061 g, 0.135 mmol) was dissolved in anhydrous THF (2 mL), and tetrabutylammoniumfluoride (0.68 mL of 1 M solution in THF, 0.68 mmol) was added, and the reaction was stirred at ambient temperature for 5 min. The reaction was heated to 60° C. and stirred for 3 h, after which 2 drops of trifluoroacetic acid was added. The reaction was stirred at 60° C. for 18 h; then allowed to cool to ambient temperature. Aqueous ammonium chloride was added and the product extracted two times with ethyl acetate. The organic layer was dried over $Na_2SO_4$, concentrated and purified by column chromatography (Isco CombiFlash) eluting with a gradient of 0-20% EtOAc/heptane to afford both the title compound (methyl 4-(3-ethynylbenzyl)-1,4,5,6-tetrahydrocyclopenta[b]pyrrole-2-carboxylate) as well as N-BOC product (1-tert-butyl 2-methyl 4-(3-ethynylbenzyl)-5,6-dihydrocyclopenta[b]pyrrole-1,2(4H)-dicarboxylate). (0.014 g and 0.016 g, respectively). $^1$H NMR (400 MHz, ACETONE-$d_6$) δ ppm 2.06-2.14 (m, 1H) 2.47-2.58 (m, 1H) 2.58-2.74 (m, 2H) 2.80 (d, J=7.42 Hz, 2H) 3.25-3.33 (m, 1H) 3.60 (s, 1H) 3.71 (s, 3H) 6.27-6.30 (m, 1H) 7.23-7.39 (m, 4H) 10.48 (br. s, 1H).

2.51. Synthesis of methyl 4-(3-cyanobenzyl)-1,4,5,6-tetrahydrocyclopenta[b]pyrrole-2-carboxylate

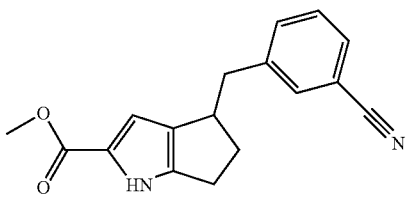

The title compound was synthesized from methyl 4-(3-bromobenzyl)-1,4,5,6-tetrahydrocyclopenta[b]pyrrole-2-carboxylate (0.193 g, 0.577 mmol) and zinc cyanide (0.075 g, 0.639 mmol) according to General Procedure 9.4. Purification by column chromatography (Isco CombiFlash) eluting with a gradient of 0-40% EtOAc/heptane afforded the title compound. 0.107 g. $^1$H NMR (400 MHz, ACETONE-$d_6$) δ ppm 2.06-2.13 (m, 1H), 2.49-2.60 (m, 1H), 2.62-2.67 (m, 2H), 2.87 (d, J=7.47 Hz, 2H), 3.29-3.36 (m, 1H), 3.71 (s, 3H), 6.26 (d, J=1.46 Hz, 1H), 7.49-7.53 (m, 1H), 7.55-7.58 (m, 1H), 7.61-7.63 (m, 2H), 10.50 (br s, 1H).

2.52. Synthesis of methyl 4-(3-acetylbenzyl)-1,4,5,6-tetrahydrocyclopenta[b]pyrrole-2-carboxylate

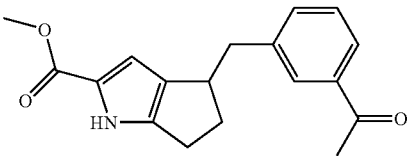

The title compound was synthesized from 1-tert-butyl 2-methyl 4-(3-ethynylbenzyl)-5,6-dihydrocyclopenta[b]pyrrole-1,2(4H)-dicarboxylate (see Example 2.51). 1-tert-Butyl 2-methyl 4-(3-ethynylbenzyl)-5,6-dihydrocyclopenta[b]pyrrole-1,2(4H)-dicarboxylate (0.016 g, 0.042 mmol) was dissolved in trifluoroacetic acid (1 mL) and stirred for 2 h. The reaction was then quenched with bicarbonate solution and extracted three times with ethyl acetate. The organic layer was dried over $Na_2SO_4$, concentrated and purified by column chromatography (Isco CombiFlash) eluting with a gradient of 0-25% EtOAc/heptane to afford the title compound. 0.006 g. $^1$H NMR (400 MHz, ACETONE-$d_6$) δ ppm 2.07-2.16 (m, 1H) 2.49-2.55 (m, 1H) 2.57 (s, 3H) 2.61-2.68 (m, 2H) 2.88 (d, J=7.40 Hz, 2H) 3.29-3.37 (m, 1H) 3.70 (s, 3H) 6.28 (d, J=1.59 Hz, 1H) 7.41-7.50 (m, 2H) 7.82-7.87 (m, 2H) 10.48 (br. s, 1H).

2.53. Synthesis of methyl 4-(naphthalen-2-ylmethyl)-1,4,5,6-tetrahydrocyclopenta[b]pyrrole-2-carboxylate

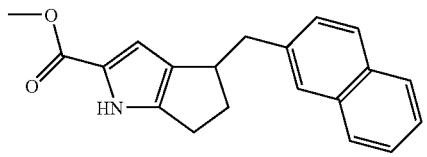

The title compound was synthesized in two steps. First, methyl 4-oxo-1,4,5,6-tetrahydrocyclopenta[b]pyrrole-2-carboxylate (1.00 g, 5.58 mmol) was reacted with 2-naphthalenylmagnesium bromide (55 mL, 21 mmol) according to General Procedure 3. In this example, the 2-naphthalenylmagnesium bromide was first placed in a separate flask and the $Et_2O$ was blown off with $N_2$. The residue was then dissolved in 50 mL THF, and added to the 4-oxo solution over 20 min via cannulae. The resulting exo-olefin ((E)-methyl 4-(naphthalen-2-ylmethylene)-1,4,5,6-tetrahydrocyclopenta[b]pyrrole-2-carboxylate) was converted to the title compound by hydrogenation according to General Procedure 6 (with 10% Pd/C). The crude product was used in the next step without further purification. $^1$H NMR (400 MHz, ACETONE-$d_6$) δ ppm 2.16 (ddt, J=12.27, 8.77, 6.00, 6.00 Hz, 1H) 2.51-2.62 (m, 1H) 2.62-2.78 (m, 2H) 2.97 (d, J=7.61 Hz, 2H) 3.37-3.46 (m, 1H) 3.67-3.69 (m, 3 H) 6.27 (d, J=1.71 Hz, 1H) 7.40-7.52 (m, 3H) 7.73 (s, 1H) 7.81-7.91 (m, 3H) 10.47 (br. s, 1H).

2.54. Synthesis of methyl 4-(biphenyl-4-ylmethyl)-1,4,5,6-tetrahydrocyclopenta[b]pyrrole-2-carboxylate

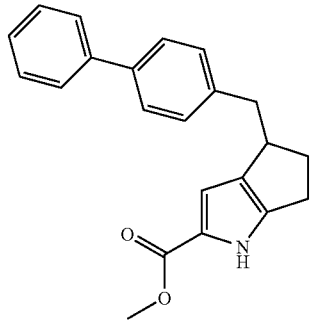

The title compound was synthesized in two steps. First, methyl 4-oxo-1,4,5,6-tetrahydrocyclopenta[b]pyrrole-2-carboxylate (200 mg, 1.12 mmol) was reacted with (biphenyl-4-ylmethyl)magnesium bromide (0.25 M in diethyl ether, 17.9 mL, 4.46 mmol) according to General Procedure 3. The resulting crude product was converted to the title compound by hydrogenation according to General Procedure 6 (with 10% Pd/C). The crude product was purified by column chromatography (Isco CombiFlash) eluting with a gradient of 0-40% EtOAc/heptane to afford the title compound, 122 mg. $^1$H NMR (400 MHz, METHANOL-$d_4$) δ ppm 2.08-2.19 (m, 1H), 2.51-2.72 (m, 3H), 2.75-2.87 (m, 2H), 3.26-3.35 (m, 1H), 3.76 (s, 3H), 6.34 (s, 1H), 7.24-7.28 (m, 2H), 7.28-7.33 (m, 1H), 7.38-7.44 (m, 2H), 7.51-7.56 (m, 2H), 7.59-7.63 (m, 2H); LCMS-MS (ESI+) 354.0 (M+Na).

2.55. Synthesis of methyl 4-(biphenyl-3-ylmethyl)-1,4,5,6-tetrahydrocyclopenta[b]pyrrole-2-carboxylate

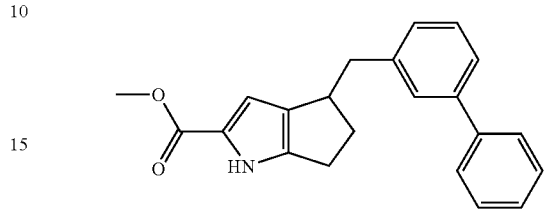

The title compound was synthesized in four steps. First tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (1.50 g, 8.37 mmol) was reacted with 3-bromobenzylmagnesium bromide (15 mL, 3.75 mmol) according to General Procedure 3 to give exo olefin-containing compound (E)-methyl 4-(3-bromobenzylidene)-1-tosyl-1,4,5,6-tetrahydrocyclopenta[b]pyrrole-2-carboxylate, followed by coupling with phenylboronic acid (0.305 g, 2.50 mmol) according to General Procedure 9.2 to give (E)-methyl 4-(biphenyl-3-ylmethylene)-1-tosyl-1,4,5,6-tetrahydrocyclopenta[b]pyrrole-2-carboxylate, then tosyl deprotection according to General Procedure 10.1 to give (E)-methyl 4-(biphenyl-3-ylmethylene)-1,4,5,6-tetrahydrocyclopenta[b]pyrrole-2-carboxylate. Hydrogenation of (E)-methyl 4-(biphenyl-3-ylmethylene)-1,4,5,6-tetrahydrocyclopenta[b]pyrrole-2-carboxylate according to General Procedure 6 (with 5% Pd/C), then purification by column chromatography (Isco CombiFlash) eluting with a gradient of 0-20% EtOAc/heptane afforded the title compound: 0.041 g. $^1$H NMR (400 MHz, ACETONE-$d_6$) δ ppm 2.09-2.19 (m, 1H) 2.50-2.60 (m, 1H) 2.60-2.68 (m, 2H) 2.86 (d, J=1.85 Hz, 1H) 2.88 (s, 1H) 3.31-3.39 (m, 1H) 3.71-3.72 (m, 3H) 6.36 (d, J=1.90 Hz, 1H) 7.21-7.25 (m, 1H) 7.26-7.30 (m, 1H) 7.31-7.51 (m, 5H) 7.61-7.67 (m, 2H) 10.49 (br.s, 1H).

2.56. Synthesis of methyl 4-(3-(pyridin-3-yl)benzyl)-1,4,5,6-tetrahydrocyclopenta[b]pyrrole-2-carboxylate

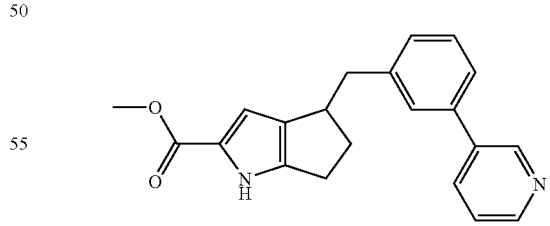

The title compound was synthesized in 4 steps. First, tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (1.50 g, 8.37 mmol) was reacted with 3-bromobenzylmagnesium bromide (15 mL, 3.75 mmol) according to General Procedure 3 to give exo olefin-containing compound (E)-methyl 4-(3-bromobenzylidene)-1-tosyl-1,4,5,6-tetrahydrocyclopenta[b]pyrrole-2- carboxylate, followed by coupling with pyridin-3-ylboronic acid (0.152 g, 1.24 mmol) according to General Procedure 9.2 to give (E)-methyl 4-(3-(pyridin-3-yl)benzylidene)-1-tosyl-1,4,5,6-tetrahydrocyclopenta[b]pyrrole-2-carboxylate, then tosyl deprotection according to General Procedure 10.1 to give (E)-methyl 4-(3-(pyridin-3-yl)benzylidene)-1,4,5,6-tetrahydrocyclopenta[b]pyrrole-2-carboxylate. Hydrogenation of (E)-methyl 4-(3-(pyridin-3-yl)benzylidene)-1,4,5,6-tetrahydrocyclopenta[b]pyrrole-2-carboxylate according to General Procedure 6 (with 5% Pd/C) gave the crude title compound, which was used in the next step without further purification. 0.051 g. $^1$H NMR (400 MHz, METHANOL-$d_4$) δ ppm 2.07-2.16 (m, 1H) 2.35 (s, 1H) 2.50-2.63 (m, 3H) 2.75-2.92 (m, 2H) 3.26-3.29 (m, 1H) 3.74 (s, 3H) 6.30 (s, 1H) 7.26 (d, J=7.57 Hz, 1H) 7.38-7.41 (m, 1H) 7.46-7.51 (m, 1H) 7.53 (dd, J=7.91, 4.93 Hz, 1H) 7.71 (d, J=8.20 Hz, 1H) 8.09 (dt, J=8.00, 1.73 Hz, 1H) 8.51 (dd, J=4.91, 1.20 Hz, 1H) 8.78 (d, J=1.76 Hz, 1H); LCMS-MS (ESI+) 333.2 (M+H).

2.57. Synthesis of methyl 4-((4'-(trifluoromethyl) biphenyl-3-yl)methyl)-1,4,5,6-tetrahydrocyclopenta [b]pyrrole-2-carboxylate

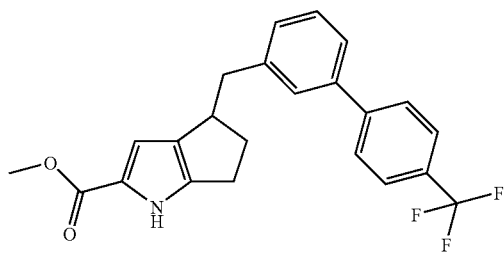

The title compound was synthesized in four steps. First, tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (1.50 g, 8.37 mmol) was reacted with 3-bromobenzylmagnesium bromide (15 mL, 3.75 mmol) according to General Procedure 3 to give exo olefin-containing compound (E)-methyl 4-(3-bromobenzylidene)-1-tosyl-1,4,5,6-tetrahydrocyclopenta[b]pyrrole-2-carboxylate, followed by coupling with 4-(trifluoromethyl) phenylboronic acid (0.178 g, 0.94 mmol) according to General Procedure 9.1 to give (E)-methyl 1-tosyl-4-((4'-(trifluoromethyl)biphenyl-3-yl)methylene)-1,4,5,6-tetrahydrocyclopenta[b]pyrrole-2-carboxylate, then tosyl deprotection according to General Procedure 10.1 to give (E)-methyl 4-((4'-(trifluoromethyl)biphenyl-3-yl)methylene)-1,4,5,6-tetrahydrocyclopenta[b]pyrrole-2-carboxylate. Hydrogenation of (E)-methyl 4-((4'-(trifluoromethyl)biphenyl-3-yl)methylene)-1,4,5,6-tetrahydrocyclopenta[b]pyrrole-2-carboxylate according to General Procedure 6 (with 5% Pd/C), then purification provided the title compound, which was used without purification in the next step. 0.047 g. $^{19}$F NMR (376 MHz, ACETONE-$d_6$) δ ppm −63.27 (s, 3F); LCMS-MS (ESI−) 398.0 (M−H).

2.58. Synthesis of methyl 4-((4'-hydroxybiphenyl-3-yl)methyl)-1,4,5,6-tetrahydrocyclopenta[b]pyrrole-2-carboxylate

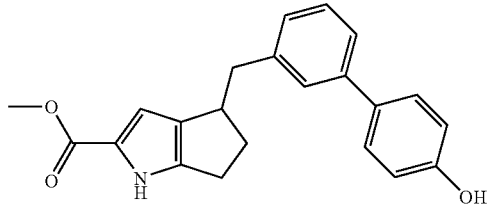

The title compound was synthesized in three steps. First, (E)-methyl 4-(3-bromobenzylidene)-1-tosyl-1,4,5,6-tetrahydrocyclopenta[b]pyrrole-2-carboxylate (0.301 g, 0.62 mmol) was coupled with 4-hydroxyphenylboronic acid (0.129 g, 0.94 mmol) according to General Procedure 9.1 to give (E)-methyl 4-((4'-hydroxybiphenyl-3-yl)methylene)-1-tosyl-1,4,5,6-tetrahydrocyclopenta[b]pyrrole-2-carboxylate, then tosyl deprotection according to General Procedure 10.1 to give (E)-methyl 4-((4'-hydroxybiphenyl-3-yl)methylene)-1,4,5,6-tetrahydrocyclopenta[b]pyrrole-2-carboxylate. Hydrogenation of (E)-methyl 4-((4'-hydroxybiphenyl-3-yl)methylene)-1,4,5,6-tetrahydrocyclopenta[b]pyrrole-2-carboxylate according to General Procedure 6 (with 5% Pd/C), provided the title compound, which was used without purification in the next step. $^1$H NMR (400 MHz, ACETONE-$d_6$) δ ppm 2.08-2.18 (m, 1H), 2.49-2.60 (m, 1H), 2.60-2.68 (m, 2H), 2.84 (d, J=7.27 Hz, 2H), 3.33 (d, J=6.93 Hz, 1H), 3.70-3.73 (m, 3H), 6.37 (d, J=1.81 Hz, 1H), 6.89-6.95 (m, 2H), 7.15 (d, J=7.66 Hz, 1H), 7.30-7.36 (m, 1H), 7.40-7.45 (m, 2H), 7.46-7.51 (m, 2H), 10.47 (br. s, 1H). LCMS ESI− 346.2 (M−H).

2.59. Synthesis of methyl 4-((4'-(hydroxymethyl) biphenyl-3-yl)methyl)-1,4,5,6-tetrahydrocyclopenta [b]pyrrole-2-carboxylate

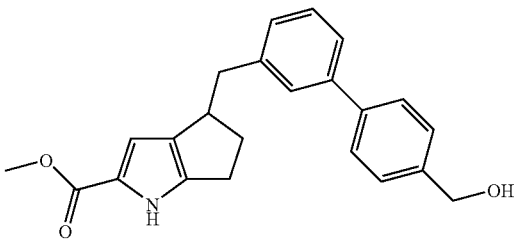

The title compound was synthesized in three steps. First, (E)-methyl 4-(3-bromobenzylidene)-1-tosyl-1,4,5,6-tetrahydrocyclopenta[b]pyrrole-2-carboxylate (0.301 g, 0.62 mmol) was coupled with 4-(hydroxymethyl)phenylboronic acid (0.141 g, 0.93 mmol) according to General Procedure 9.1 to give (E)-methyl 4-((4'-(hydroxymethyl)biphenyl-3-yl)methylene)-1-tosyl-1,4,5,6-tetrahydrocyclopenta[b]pyrrole-2-carboxylate, then tosyl deprotection according to General Procedure 10.1 to give (E)-methyl 4-((4'-(hydroxymethyl) biphenyl-3-yl)methylene)-1,4,5,6-tetrahydrocyclopenta[b]pyrrole-2-carboxylate. Hydrogenation of (E)-methyl 4-((4'-

(hydroxymethyl)biphenyl-3-yl)methylene)-1,4,5,6-tetrahydrocyclopenta[b]pyrrole-2-carboxylate according to General Procedure 6 (with 5% Pd/C), provided the title compound, which was used without purification in the next step. ¹H NMR (400 MHz, ACETONE-d₆) δ ppm 2.10-2.20 (m, 1H), 2.51-2.60 (m, 1H), 2.61-2.68 (m, 2H), 2.87 (dd, J=7.25, 2.03 Hz, 2H), 3.35 (quin, J=6.88 Hz, 1H), 3.71 (s, 3H), 4.20 (br. s, 1H), 4.67 (s, 2H), 6.35-6.37 (m, 1H), 7.23 (d, J=7.76 Hz, 1H), 7.35-7.40 (m, 1H), 7.42-7.46 (m, 2H), 7.47-7.51 (m, 2H) 7.59-7.63 (m, 2H), 10.48 (br. s, 1H); LCMS-MS (ESI+) 384.0 (M+Na).

2.60. Synthesis of methyl 4-(3-(furan-2-yl)benzyl)-1,4,5,6-tetrahydrocyclopenta[b]pyrrole-2-carboxylate

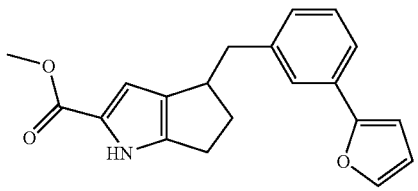

The title compound was synthesized in four steps. First, tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (1.50 g, 8.37 mmol) was reacted with 3-bromobenzylmagnesium bromide (15 mL, 3.75 mmol) according to General Procedure 3 to give exo olefin-containing compound (E)-methyl 4-(3-bromobenzylidene)-1-tosyl-1,4,5,6-tetrahydrocyclopenta[b]pyrrole-2-carboxylate, followed by coupling with furan-2-boronic acid (0.138 g, 1.23 mmol) according to General Procedure 9.1 to give (E)-methyl 4-(3-(furan-2-yl)benzylidene)-1-tosyl-1,4,5,6-tetrahydrocyclopenta[b]pyrrole-2-carboxylate, then tosyl deprotection according to General Procedure 10.1 to give (E)-methyl 4-(3-(furan-2-yl)benzylidene)-1,4,5,6-tetrahydrocyclopenta[b]pyrrole-2-carboxylate. Hydrogenation of (E)-methyl 4-(3-(furan-2-yl)benzylidene)-1,4,5,6-tetrahydrocyclopenta[b]pyrrole-2-carboxylate according to General Procedure 6, then purification by column (Isco CombiFlash) eluting with a gradient of 0-25% EtOAc/heptane afforded the title compound: 0.024 g.

2.61. Synthesis of methyl 4-(3-(tetrahydrofuran-3-yl)benzyl)-1,4,5,6-tetrahydrocyclopenta[b]pyrrole-2-carboxylate

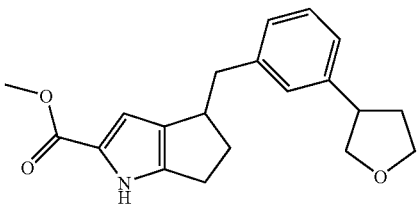

(E)-Methyl 4-(3-(furan-2-yl)benzylidene)-1,4,5,6-tetrahydrocyclopenta[b]pyrrole-2-carboxylate (0.066 g, 0.207 mmol) was dissolved in ethyl acetate (5 mL). Then palladium on carbon (5%) was added and the reaction placed under a hydrogen atmosphere using a balloon, stirred at room temperature for 5 h, then filtered through celite. The filtrate was concentrated and purified by column chromatography (Isco CombiFlash) eluting with a gradient of 0-25% EtOAc/heptane affording the title compound. 0.028 g.

2.62. Synthesis of methyl 4-(3-(1H-pyrrol-2-yl)benzyl)-1,4,5,6-tetrahydrocyclopenta[b]pyrrole-2-carboxylate

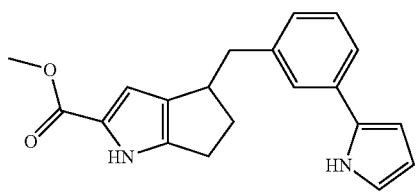

The title compound was synthesized in three steps. First, (E)-methyl 4-(3-bromobenzylidene)-1-tosyl-1,4,5,6-tetrahydrocyclopenta[b]pyrrole-2-carboxylate (0.400 g, 0.82 mmol) was coupled with 4-1-(tert-butoxycarbonyl)-1H-pyrrol-2-ylboronic acid (0.247 g, 1.17 mmol) according to General Procedure 9.1 to give (E)-methyl 4-(3-(1-(tert-butoxycarbonyl)-1H-pyrrol-2-yl)benzylidene)-1-tosyl-1,4,5,6-tetrahydrocyclopenta[b]pyrrole-2-carboxylate, then tosyl and BOC deprotection according to General Procedure 10.1 to give (E)-methyl 4-(3-(1H-pyrrol-2-yl)benzylidene)-1,4,5,6-tetrahydrocyclopenta[b]pyrrole-2-carboxylate. Hydrogenation of (E)-methyl 4-(3-(1H-pyrrol-2-yl)benzylidene)-1,4,5,6-tetrahydrocyclopenta[b]pyrrole-2-carboxylate according to General Procedure 6 (with 5% Pd/C), followed by purification by column chromatography (Isco CombiFlash) eluting with a gradient of 0-30% EtOAc/heptane affording the title compound as a slightly yellow solid: 0.054 g.

2.63. Synthesis of methyl 4-(3-fluorophenyl)-1,4,5,6-tetrahydrocyclopenta[b]pyrrole-2-carboxylate

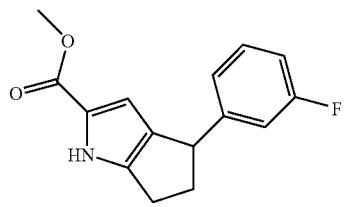

The title compound was synthesized in two steps. First, methyl 4-oxo-1,4,5,6-tetrahydrocyclopenta[b]pyrrole-2-carboxylate (0.5 g, 2.79 mmol) was reacted with (3-fluorophenyl)magnesium bromide (14 mL, 6.97 mmol, 0.5 M in THF, 2.5 equiv) according to General Procedure 3. The resulting endo-olefin (methyl 4-(3-fluorophenyl)-1,6-dihydrocyclopenta[b]pyrrole-2-carboxylate) was converted to the title compound by hydrogenation according to General Procedure 6 (with 5% Pd/C). The crude product was purified by column chromatography (Isco CombiFlash) eluting with a gradient of 0-100% EtOAc/heptane to afford the title compound: 150 mg. ¹H NMR (400 MHz, CHLOROFORM-d) δ ppm 2.24-2.35 (m, 1H), 2.73-3.01 (m, 3H), 3.84 (s, 3H) 4.22 (t, J=7.13 Hz, 1H), 6.65 (d, J=1.46 Hz, 1H), 6.86-6.93 (m, 2H) 7.00 (d, J=7.66 Hz, 1H), 7.19-7.30 (m, 1H) 9.07-9.28 (m, 1H).

2.64. Synthesis of methyl 4-(3,4-difluorophenyl)-1,4,5,6-tetrahydrocyclopenta[b]pyrrole-2-carboxylate

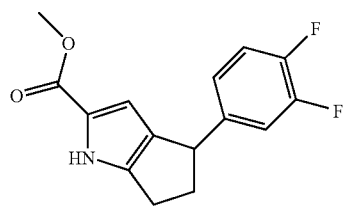

The title compound was synthesized in two steps. First, methyl 4-oxo-1,4,5,6-tetrahydrocyclopenta[b]pyrrole-2-carboxylate (0.5 g, 2.79 mmol) was reacted with 3,4-difluorophenylmagnesium bromide (14 mL, 7.0 mmol, 0.5 M in THF) according to General Procedure 3 to give methyl 4-(3,4-difluorophenyl)-1,6-dihydrocyclopenta[b]pyrrole-2-carboxylate, followed by hydrogenation according to General Procedure 6 (with 5% Pd/C), and was purified by column chromatography (Isco CombiFlash) eluting with a gradient of 0-30% EtOAc/heptane affording the title compound. 0.333 g. $^1$H NMR (400 MHz, ACETONE-$d_6$) δ ppm 2.16-2.27 (m, 1H), 2.70-2.98 (m, 3H), 3.75 (s, 3H), 4.22 (t, J=7.22 Hz, 1H), 6.53 (d, J=1.85 Hz, 1H), 7.02-7.07 (m, 1H), 7.11 (ddd, J=11.96, 7.86, 2.15 Hz, 1H), 7.21 (dt, J=10.68, 8.43 Hz, 1H), 10.68 (br. s, 1H).

2.65. Synthesis of methyl 4-(3,5-difluorophenyl)-1,4,5,6-tetrahydrocyclopenta[b]pyrrole-2-carboxylate

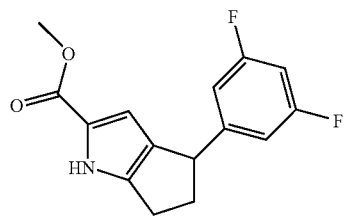

The title compound was synthesized in two steps. First, methyl 4-oxo-1,4,5,6-tetrahydrocyclopenta[b]pyrrole-2-carboxylate (0.5 g, 2.79 mmol) was reacted with 3,5-difluorophenylmagnesium bromide (14 mL, 6.97 mmol, 0.5 M in THF, 2.5 equiv) according to General Procedure 3 to give methyl 4-(3,5-difluorophenyl)-1,6-dihydrocyclopenta[b]pyrrole-2-carboxylate, followed by hydrogenation according to General Procedure 6 (with 5% Pd/C), and was purified by column chromatography (Isco CombiFlash) eluting with a gradient of 0-100% EtOAc/heptane afforded the title compound: 85 mg. $^1$H NMR (400 MHz, CHLOROFORM-d) δ ppm 2.27 (ddt, 1H), 2.73-3.00 (m, 3H), 3.84 (s, 3H), 4.17-4.23 (m, 1H), 6.60-6.67 (m, 2H), 6.69-6.75 (m, 2H), 9.01 (br. s, 1H) and $^{19}$F NMR (376 MHz, CHLOROFORM-d) δ ppm −110.76 (t, J=8.00 Hz).

2.66. Synthesis of methyl 4-(4-chlorophenyl)-1,4,5,6-tetrahydrocyclopenta[b]pyrrole-2-carboxylate

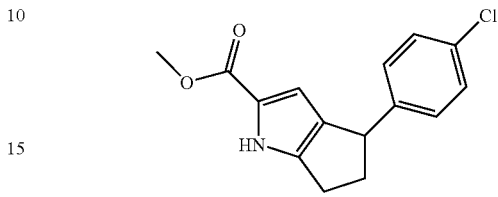

The title compound was synthesized in two steps. First, methyl 4-oxo-1,4,5,6-tetrahydrocyclopenta[b]pyrrole-2-carboxylate (0.3 g, 1.7 mmol) was reacted with (4-chlorophenyl)magnesium bromide (6.7 mL, IM in diethyl ether, 6.7 mmol, 4 equiv) according to General Procedure 3. The resulting endo-olefin (methyl 4-(4-chlorophenyl)-1,6-dihydrocyclopenta[b]pyrrole-2-carboxylate) was converted to the title compound by hydrogenation according to General Procedure 6 (with 5% Pd/C). The crude product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 60% methanol and increasing to 100% over 7 minutes) afforded the title compound. 49.2 mg. $^1$H NMR (400 MHz, CHLOROFORM-d) δ ppm 8.84 (br. s, 1H), 7.23-7.27 (m, 2H), 7.10-7.16 (m, 2H), 6.62 (d, J=1.61 Hz, 1H), 4.20 (t, J=7.22 Hz, 1H), 3.83 (s, 3H), 2.72-2.99 (m, 3H), 2.20-2.31 (m, J=12.81, 8.65, 6.47, 6.47 Hz, 1H).

2.67. Synthesis of methyl 4-(3-chlorophenyl)-1,4,5,6-tetrahydrocyclopenta[b]pyrrole-2-carboxylate

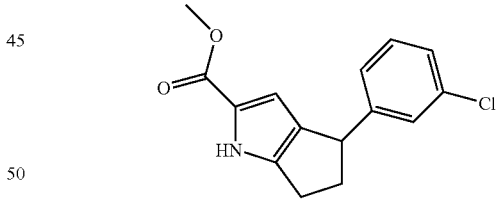

The title compound was synthesized in two steps. First, methyl 4-oxo-1,4,5,6-tetrahydrocyclopenta[b]pyrrole-2-carboxylate (0.504 g, 2.81 mmol) and 3-chlorophenylmagnesium bromide (0.5 M in THF, 14 mL, 7.0 mmol) were reacted according to General Procedure 3 to give a mixture of the endocyclic olefin-containing compound methyl 4-(3-chlorophenyl)-1,4,5,6-tetrahydrocyclopenta[b]pyrrole-2-carboxylate and the carbinol compound methyl 4-(3-chlorophenyl)-4-hydroxy-1,4,5,6-tetrahydrocyclopenta[b]pyrrole-2-carboxylate. The mixture was hydrogenated according to General Procedure 6 (with Pt$_2$O), and was purified by column chromatography (Isco CombiFlash) eluting with a gradient of 0-30% EtOAc/heptane to afford the title compound. 0.179 g. $^1$H NMR (400 MHz, ACETONE-$d_6$) δ ppm 2.17-2.28 (m, 1H), 2.71-2.99 (m, 3H), 3.74-3.76 (m, 3H), 4.19-4.25 (m, 1H), 6.53 (d, J=1.85 Hz, 1H), 7.15-7.20 (m, 1H), 7.21-7.23 (m, 2H), 7.27-7.32 (m, 1H), 10.68 (br. s, 1H).

2.68. Synthesis of methyl 4-(3-bromophenyl)-1,4,5,6-tetrahydrocyclopenta[b]pyrrole-2-carboxylate

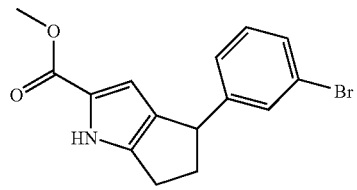

The title compound was synthesized in two steps. First, methyl 4-oxo-1,4,5,6-tetrahydrocyclopenta[b]pyrrole-2-carboxylate (0.502 g, 2.80 mmol) and (3-bromophenyl)magnesium bromide (synthesized in situ) were reacted according to General Procedure 3 to give the endo olefin-containing compound methyl 4-(3-bromophenyl)-1,6-dihydrocyclopenta[b]pyrrole-2-carboxylate. (Note: (3-Bromophenyl)magnesium bromide was synthesized as follows: Activated magnesium (0.306 g, 12.6 mmol) was placed in a flask and anhydrous THF (50 mL) was added. 1,3-dibromobenzene (1.6 mL, 13.2 mmol) and a catalytic amount of $I_2$ was added. The solution was stirred gently at ambient temperature for 30 min. Additional anhydrous THF (25 mL) was added and the solution refluxed for 3 h, and then allowed to cool to ambient temperature). Methyl 4-(3-bromophenyl)-1,6-dihydrocyclopenta[b]pyrrole-2-carboxylate was hydrogenated according to General Procedure 6 (with $Pt_2O$), and was purified by column chromatography (Isco CombiFlash) eluting with a gradient of 0-30% EtOAc/heptane affording a 1:1 mixture of the title compound and dehalogenated product as a slightly yellow solid: 0.315 g (67% yield). LCMS (ESI−) 318.0 (M−H).

2.69. Synthesis of methyl 4-(3,5-dimethylphenyl)-1,4,5,6-tetrahydrocyclopenta[b]pyrrole-2-carboxylate

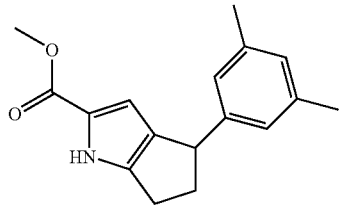

The title compound was synthesized in two steps. First, methyl 4-oxo-1,4,5,6-tetrahydrocyclopenta[b]pyrrole-2-carboxylate (0.5 g, 2.79 mmol) and 3,5-dimethylphenylmagnesium bromide (14 mL, 6.97 mmol, 0.5 M in THF, 2.5 equiv) were reacted according to General Procedure 3 to give the endo olefin-containing compound methyl 4-(3,5-dimethylphenyl)-1,6-dihydrocyclopenta[b]pyrrole-2-carboxylate, which was then hydrogenated according to General Procedure 6 (with 5% Pd/C), and was purified by column chromatography (Isco CombiFlash) eluting with a gradient of 0-100% EtOAc/heptane to afford the title compound. $^1$H NMR (400 MHz, CHLOROFORM-d) δ ppm 2.20-2.36 (m, 7H), 2.71-2.98 (m, 3H), 3.83-3.86 (m, 3H), 4.17 (t, J=7.35 Hz, 1H), 6.49 (s, 1H), 6.67 (d, J=1.42 Hz, 1H), 6.82-6.88 (m, 2H), 9.02 (br. s, 1H).

2.70. Synthesis of methyl 4-(3-cyanophenyl)-1,4,5,6-tetrahydrocyclopenta[b]pyrrole-2-carboxylate

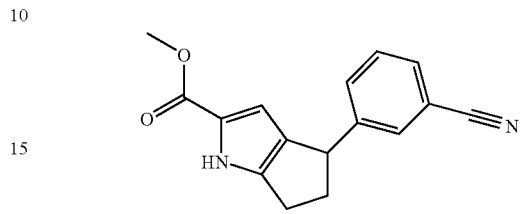

Methyl 4-(3-bromophenyl)-1,4,5,6-tetrahydrocyclopenta[b]pyrrole-2-carboxylate (0.103 g, 0.32 mmol) was combined with zinc cyanide (0.046 g, 0.39 mmol) and dissolved in dimethyl acetamide (3 mL). Then the solution was evacuated and back-flushed with $N_2$ four times and sparged with $N_2$ for an additional 5-10 min. Tetrakis(triphenylphosphine)palladium(0) (0.091 g, 0.08 mmol) was added and the reaction placed in a preheated (85° C.) heating block and stirred for 2 hour. The reaction was then cooled to room temperature and diluted with aqueous $H_2O$ (40 mL) and extracted three times with ethyl acetate. The organic layer was washed once with brine, then dried over $Na_2SO_4$. Purification by column chromatography (Isco CombiFlash) eluting with a gradient of 0-40% EtOAc/heptane afforded the title compound. 0.021 g. LCMS-MS (ESI+) 289.2 (M+Na).

2.71. Synthesis of methyl 4-(biphenyl-4-yl)-1,4,5,6-tetrahydrocyclopenta[b]pyrrole-2-carboxylate

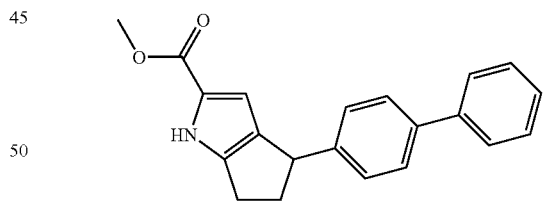

The title compound was synthesized in two steps. First, methyl 4-oxo-1,4,5,6-tetrahydrocyclopenta[b]pyrrole-2-carboxylate (300 mg, 1.67 mmol) and biphenyl-4-ylmagnesium bromide (13.4 mL, 6.70 mmol; 0.5 M in THF) were reacted according to General Procedure 3 to give the endo olefin-containing compound methyl 4-(biphenyl-4-yl)-1,6-dihydrocyclopenta[b]pyrrole-2-carboxylate, which was then hydrogenated according to General Procedure 6 (with 10% Pd/C), and was purified column chromatography (Isco CombiFlash) eluting with a gradient of 0-40% EtOAc/heptane to afford the title compound. 430 mg. $^1$H NMR (400 MHz, ACETONE-$d_6$) δ ppm 2.23-2.33 (m, 1H), 2.74-2.84 (m, 1H), 2.85-3.01 (m, 2H), 3.75 (s, 3H), 4.26 (t, J=7.20 Hz, 1H), 6.55 (d, J=1.76 Hz, 1H), 7.29-7.36 (m, 3H), 7.41-7.47 (m, 2H), 7.55-7.60 (m, 2H), 7.62-7.66 (m, 2H), 10.66 (s, 1H); LCMS-MS (ESI+) 340.2 (M+Na).

2.72. Synthesis of methyl 4-(4-benzylphenyl)-1,4,5,6-tetrahydrocyclopenta[b]pyrrole-2-carboxylate

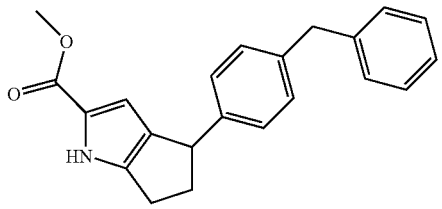

The title compound was synthesized in two steps. First, methyl 4-oxo-1,4,5,6-tetrahydrocyclopenta[b]pyrrole-2-carboxylate (0.64 g, 3.6 mmol) and (4-benzylphenyl)magnesium bromide were reacted according to General Procedure 3 to give methyl 4-(4-benzylphenyl)-1,6-dihydrocyclopenta[b]pyrrole-2-carboxylate. (4-Benzylphenyl)magnesium bromide was synthesized from 1-benzyl-4-bromobenzene. (In an inert Ar atmosphere, to a suspension of Mg (0.44 g, 18.2 mmol) turnings in 50 mL of THF was added very slowly (dropwise) 1-benzyl-4-bromobenzene, then catalytic amount of iodine was added. The reaction mixture was stirred for 30 min at room temperature, then 25 mL of THF was added and the mixture was stirred for 3 hours at 75-80° C. (gentle reflux of THF).) The methyl 4-(4-benzylphenyl)-1,6-dihydrocyclopenta[b]pyrrole-2-carboxylate was hydrogenated according to General Procedure 6 with 5% Pd/C and a hydrogen balloon, and was purified by column chromatography (Isco CombiFlash) eluting with a gradient of 0-100% EtOAc/heptane to afford the title compound. $^1$H NMR (400 MHz, CHLOROFORM-d) δ ppm 2.23-2.35 (m, 1H), 2.71-2.97 (m, 3H), 3.82 (s, 3H), 3.96 (s, 2H), 4.20 (t, J=7.32 Hz, 1H), 6.63 (d, J=1.76 Hz, 1H), 7.09-7.15 (m, 5H), 7.16-7.23 (m, 2H), 7.28-7.32 (m, 2H), 8.84 (br. s, 1H).

2.73. Synthesis of methyl 4-(4-chlorobenzylamino)-1,4,5,6-tetrahydrocyclopenta[b]pyrrole-2-carboxylate

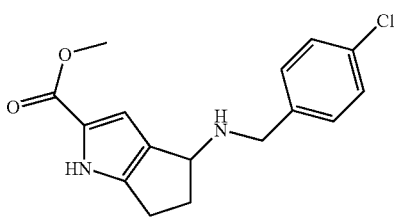

The title compound was synthesized in two steps. First, (4-chlorophenyl)methanamine (0.602 g, 4.25 mmol) was added to tosyl protected methyl 4-oxo-1,4,5,6-tetrahydrocyclopenta[b]pyrrole-2-carboxylate (methyl 4-oxo-1-tosyl-1,4,5,6-tetrahydrocyclopenta[b]pyrrole-2-carboxylate) (0.285 g, 0.85 mmol) in 1,2-dichloroethane (10 mL). The resulting mixture was then stirred 15 min at room temperature, then sodium triacetoxyborohydride (0.901 g, 4.25 mmol) was added and stirring continued for 5 days. The reaction was quenched with aqueous NH$_4$Cl, and the product extracted two times with ethyl acetate. The organic layer was dried over Na$_2$SO$_4$, concentrated and purified by column chromatography (Isco CombiFlash) eluting with a gradient of 0-100% EtOAc/heptane to provide methyl 4-(4-chlorobenzylamino)-1-tosyl-1,4,5,6-tetrahydrocyclopenta[b]pyrrole-2-carboxylate. The tosyl group was removed according to General Procedure 10.1, and the resulting title compound was purified by column chromatography (Isco CombiFlash) eluting with a gradient of 10-100% EtOAc/heptane to afford the title compound. 0.023 g.

2.74. Synthesis of 4-(2,2,2-trifluoroethyl)-1,4,5,6-tetrahydrocyclopenta[b]pyrrole-2-carboxylic acid (38)

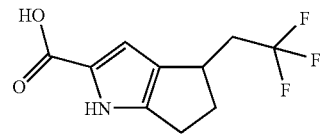

The title compound was synthesized from methyl 4-(2,2,2-trifluoroethyl)-1,4,5,6-tetrahydrocyclopenta[b]pyrrole-2-carboxylate (0.2888 g, 1.2 mmol, 1 equiv) and lithium hydroxide (1.1 mL, 2 M aqueous, 5.3 equiv) according to General Procedure 7. The resulting product was purified by preparative HPLC (using the Chromeleon purification system (0.1% formic acid/1% acetonitrile mixture in water (aqueous phase) and methanol (no modifier added—organic phase) using a 50 mm Dynamax HPLC C-18 column at 28 mL/min (initial gradient of 50% methanol and increasing to 100% over 7 minutes)) to afford the title compound. 60.2 mg, (63%), with purity by HPLC of 98.9% (UV). LCMS m/e 232 (M–H). $^{19}$F NMR (376 MHz, METHANOL-d$_4$) δ ppm –66.50 (t, J=9.94 Hz, 3F). $^1$H NMR (400 MHz, METHANOL-d$_4$) δ ppm 2.05-2.17 (m, 1H), 2.19-2.33 (m, 1H), 2.44 (ddd, J=14.88, 11.45, 6.56 Hz, 1H), 2.59-2.83 (m, 3H), 3.23 (quin, J=6.79 Hz, 1H), 6.65 (s, 1H).

2.75. Synthesis of 4-(4-fluorobenzyl)-1,4,5,6-tetrahydrocyclopenta[b]pyrrole-2-carboxylic acid (39)

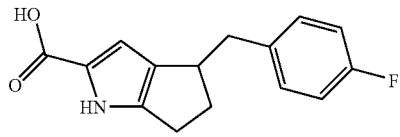

The title compound was synthesized from methyl 4-(4-fluorobenzyl)-1-tosyl-1,4,5,6-tetrahydrocyclopenta[b]pyrrole-2-carboxylate in two steps. First, the starting material's methyl ester was hydrolyzed according to General Procedure 7. In this case, 0.070 g (0.274 mmol) of starting ester and potassium hydroxide (10 M, 0.16 mL, 1.6 mmol) were used. The deprotected methyl ester (4-(4-fluorobenzyl)-1-tosyl-1,4,5,6-tetrahydrocyclopenta[b]pyrrole-2-carboxylic acid) (0.035 g, 0.13 mmol) was then dissolved in THF (3 mL) and MeOH (3 mL), and LiOH (0.055 g, 1.3 mmol) in H$_2$O (3 mL) was added and the reaction stirred at 70° C. for 6 h. The reaction was diluted in 25 mL H$_2$O and acidified to pH 2-3 with 1 N HCl, then extracted with 2×50 mL EtOAc. The organic layer was dried over $Na_2SO_4$, concentrated and purified by column chromatography (Isco CombiFlash) eluting with a gradient of 0-100% EtOAc/heptane to afford the title compound. 16 mg. $^{19}F$ NMR δ ppm −102.42 (m, J=5.4) LCMS-MS (ESI−) 258.0 (M−H); HPLC (UV=98.52%), (ELSD=100%).

The enantiomers of 4-(4-fluorobenzyl)-1,4,5,6-tetrahydrocyclopenta[b]pyrrole-2-carboxylic acid were separated according to General Procedure 8 with a mixture of 25%[50:50 methanol/isopropanol with 0.1% diethylamine] in $CO_2$ to give 4-(4-fluorobenzyl)-1,4,5,6-tetrahydrocyclopenta[b]pyrrole-2-carboxylic acid (40), (peak 1, retention time=3.0 min; 100% ee) and 4-(4-fluorobenzyl)-1,4,5,6-tetrahydrocyclopenta[b]pyrrole-2-carboxylic acid (41) (peak 2, retention time=3.6 min; 94.5% ee).

2.76. Synthesis of 4-(3,4-difluorobenzyl)-1,4,5,6-tetrahydrocyclopenta[b]pyrrole-2-carboxylic acid (42)

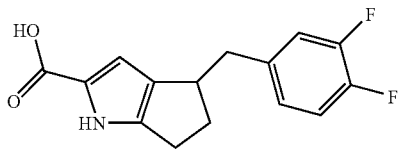

The title compound was synthesized from methyl 4-(3,4-difluorobenzyl)-1,4,5,6-tetrahydrocyclopenta[b]pyrrole-2-carboxylate (0.10 g, 0.34 mmol) and lithium hydroxide (0.143 g, 3.4 mmol), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane to afford the title compound. 46 mg. $^1H$ NMR (400 MHz, METHANOL-$d_4$) δ ppm 1.99-2.16 (m, 1H), 2.45-2.68 (m, 3H), 2.68-2.86 (m, 2H), 3.17-3.29 (m, 1H), 6.30 (s, 1H), 6.97 (ddd, J=6.36, 4.19, 2.05 Hz, 1H), 7.02-7.21 (m, 2H). $^{19}F$ NMR δ ppm −141.99 (m), −145.62 (m); LCMS-MS (ESI−) 276.0 (M−H); HPLC (UV=98.41%), (ELSD=100%).

The enantiomers of 4-(3,4-difluorobenzyl)-1,4,5,6-tetrahydrocyclopenta[b]pyrrole-2-carboxylic acid were separated according to General Procedure 8 with a mixture of 45% methanol in $CO_2$ to give 4-(3,4-difluorobenzyl)-1,4,5,6-tetrahydrocyclopenta[b]pyrrole-2-carboxylic acid (43), (peak 1, retention time=1.7 min; 100% ee) and 4-(3,4-difluorobenzyl)-1,4,5,6-tetrahydrocyclopenta[b]pyrrole-2-carboxylic acid (44) (peak 2, retention time=2.3 min; 99.1% ee).

2.77. Synthesis of 4-(2,4-difluorobenzyl)-1,4,5,6-tetrahydrocyclopenta[b]pyrrole-2-carboxylic acid (45)

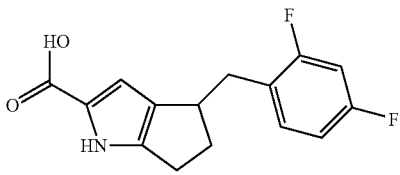

The title compound was synthesized from methyl 4-(2,4-difluorobenzyl)-1,4,5,6-tetrahydrocyclopenta[b]pyrrole-2-carboxylate (0.062 g, 0.213 mmol) and lithium hydroxide (0.045 g, 1.07 mmol), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane to afford the title compound. 41 mg. $^1H$ NMR (400 MHz, METHANOL-$d_4$) δ ppm 2.12 (m, 1H), 2.56 (m, 1H), 2.65 (m, 2H), 2.78 (d, J=7.37 Hz, 2H), 3.20-3.30 (m, 1H), 6.29 (s, 1H), 6.81-6.95 (m, 2H), 7.22 (m, 1H); $^{19}F$ NMR δ ppm −116.13 (m), −116.30 (m); LCMS-MS (ESI−) 276.0 (M−H); HPLC (UV=99.0%), (ELSD=100%).

The enantiomers of 4-(2,4-difluorobenzyl)-1,4,5,6-tetrahydrocyclopenta[b]pyrrole-2-carboxylic acid were separated according to General Procedure 8 with a mixture of 40% methanol in $CO_2$ to give 4-(2,4-difluorobenzyl)-1,4,5,6-tetrahydrocyclopenta[b]pyrrole-2-carboxylic acid (46), (peak 1, retention time=1.9 min; 100% ee) and 4-(2,4-difluorobenzyl)-1,4,5,6-tetrahydrocyclopenta[b]pyrrole-2-carboxylic acid (47) (peak 2, retention time=3.3 min; 100% ee).

2.78. Synthesis of 4-(3-chloro-4-fluorobenzyl)-1,4,5,6-tetrahydrocyclopenta[b]pyrrole-2-carboxylic acid (48)

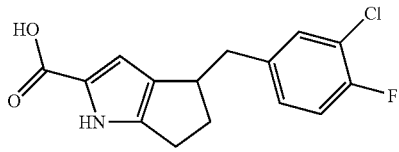

The title compound was synthesized from methyl 4-(3-chloro-4-fluorobenzyl)-1,4,5,6-tetrahydrocyclopenta[b]pyrrole-2-carboxylate (0.034 g, 0.11 mmol) and lithium hydroxide (0.023 g, 0.55 mmol), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane to afford the title compound. 17 mg. $^1H$ NMR (400 MHz, METHANOL-$d_4$) δ ppm 1.97-2.16 (m, 1H) 2.44-2.67 (m, 3H) 2.67-2.85 (m, 2H) 3.19-3.29 (m, 1H) 6.31 (s, 1H) 7.10-7.15 (m, 2H) 7.28 (d, J=7.52 Hz, 1H) $^{19}F$ NMR δ ppm −122.88 (q, J=7.1 Hz); LCMS-MS (ESI−) 292.0 (M−H); HPLC (UV=98.1%), (ELSD=100%).

The enantiomers of 4-(3-chloro-4-fluorobenzyl)-1,4,5,6-tetrahydrocyclopenta[b]pyrrole-2-carboxylic acid were separated according to General Procedure 8 with a mixture of 40% methanol in $CO_2$ to give 4-(3-chloro-4-fluorobenzyl)-1,4,5,6-tetrahydrocyclopenta[b]pyrrole-2-carboxylic acid (49), (peak 1, retention time=2.2 min; 100% ee) and 4-(3- chloro-4-fluorobenzyl)-1,4,5,6-tetrahydrocyclopenta[b]pyrrole-2-carboxylic acid (50) (peak 2, retention time=3.3 min; 100% ee).

2.79. Synthesis of 4-(4-fluoro-2-methylbenzyl)-1,4,5,6-tetrahydrocyclopenta[b]pyrrole-2-carboxylic acid (51)

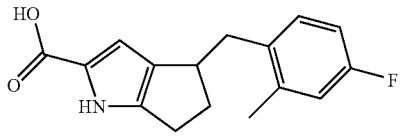

The title compound was synthesized from methyl 4-(4-fluoro-2-methylbenzyl)-1,4,5,6-tetrahydrocyclopenta[b]pyrrole-2-carboxylate and lithium hydroxide (0.92 mL, 44.2 mg, 1.85 mmol, 5.6 equiv) according to General Procedure 7. Methanol (5 mL) was used to solubilize the starting material. The resulting product was purified by silica-gel chromatography, eluting with a gradient of 0-40% EtOAc/heptane to afford to title compound. 44.9 mg. $^1$H NMR (400 MHz, ACETONITRILE-$d_3$) δ ppm 2.02-2.13 (m, J=12.81, 8.71, 5.64, 5.64 Hz, 1H) 2.26 (s, 3H) 2.46-2.58 (m, 1H) 2.59-2.70 (m, 1H) 2.70-2.81 (m, 3H) 3.23 (dd, J=7.47, 5.42 Hz, 1H) 6.21 (d, J=1.85 Hz, 1H) 6.87 (td, J=8.61, 2.78 Hz, 2H) 7.16 (dd, J=8.35, 6.20 Hz, 1H) 9.62 (br. s, 1H); $^{19}$F NMR (400 MHz, ACETONITRILE-$d_3$) δ ppm −120.19 (s, 1F); LCMS-MS (ESI−) 272.31 (M−1).

The enantiomers of 4-(4-fluoro-2-methylbenzyl)-1,4,5,6-tetrahydrocyclopenta[b]pyrrole-2-carboxylic acid were separated according to General Procedure 8 with a mixture of 50% methanol in $CO_2$ to give 4-(4-fluoro-2-methylbenzyl)-1,4,5,6-tetrahydrocyclopenta[b]pyrrole-2-carboxylic acid (52), (peak 1, retention time=5.1 min; 98.1% ee) and 4-(4-fluoro-2-methylbenzyl)-1,4,5,6-tetrahydrocyclopenta[b]pyrrole-2-carboxylic acid (53) (peak 2, retention time=6.0 min; 99.5% ee).

2.80. Synthesis of 4-(3-fluorobenzyl)-1,4,5,6-tetrahydrocyclopenta[b]pyrrole-2-carboxylic acid (54)

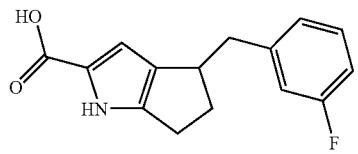

The title compound was synthesized from methyl 4-(3-fluorobenzyl)-1,4,5,6-tetrahydrocyclopenta[b]pyrrole-2-carboxylate (0.075 g, 0.274 mmol) and lithium hydroxide (0.053 g, 1.37 mmol in 3 mL water), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane to afford the title compound: 30 mg, 42% yield. $^1$H NMR (400 MHz, METHANOL-d) δ ppm 2.05-2.15 (m, 1H), 2.50-2.60 (m, 1H), 2.60-2.65 (m, 2H), 2.75-2.85 (m, 2H), 3.21-3.28 (m, 1H), 6.30 (s, 1H), 6.85-6.95 (m, 2H), 7.00-7.05 (d, 1H), 7.25-7.35 (q, 1H); $^{19}$F NMR δ ppm (m, −116.7); LCMS-MS (ESI−) 258.0 (M−H); HPLC (UV=100%), (ELSD=100%).

2.81. Synthesis of 4-(3-chloro-5-fluorobenzyl)-1,4,5,6-tetrahydrocyclopenta[b]pyrrole-2-carboxylic acid (55)

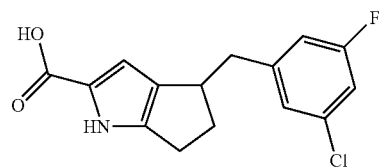

The title compound was synthesized from methyl 4-(3-chloro-5-fluorobenzyl)-1,4,5,6-tetrahydrocyclopenta[b]pyrrole-2-carboxylate (0.045 g, 0.15 mmol) and lithium hydroxide (0.063 g, 1.5 mmol in 2 mL water), according to General Procedure 7. A 1:1 mixture of methanol (MeOH) and THF (2 mL) was used. The resulting product was purified by column chromatography (Isco CombiFlash) eluting with a gradient of 0-100% EtOAc/heptane followed by reverse phase chromatography from MeOH and water (0.1% formic acid) to afford the title compound: 3.7 mg, 8.4% yield. $^1$H NMR (400 MHz, METHANOL-$d_4$) δ ppm 2.03-2.16 (m, 1H) 2.46-2.60 (m, 1H) 2.60-2.73 (m, 2H) 2.79 (dd, J=7.35, 2.03 Hz, 2H) 3.26 (m, 1H) 6.32 (s, 1H) 6.91 (dd, J=9.57, 1.51 Hz, 1H) 7.02 (dt, J=8.63, 2.13 Hz, 1H) 7.06 (s, 1H); $^{19}$F NMR δ ppm −114.32 (t, J=0.8 Hz); LCMS-MS (ESI−) 292.0 (M−H); HPLC (UV=100%), (ELSD=100%).

2.82. Synthesis of 4-(3-chlorobenzyl)-1,4,5,6-tetrahydrocyclopenta[b]pyrrole-2-carboxylic acid (56)

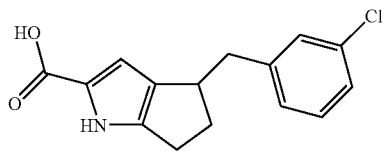

The title compound was synthesized from methyl 4-(3-chlorobenzyl)-1,4,5,6-tetrahydrocyclopenta[b]pyrrole-2-carboxylate (261 mg, 0.90 mmol) and lithium hydroxide (188 mg, 4.50 mmol in 3 mL $H_2O$), according to General Procedure 7. A 1:1 mixture of methanol (MeOH) and THF (6 mL) was used. The resulting product was purified by chromatography, eluting with heptane-EtOAc, gradient 0 to 50% EtOAc to afford the title compound. 147 mg. $^1$H NMR (400 MHz, CHLOROFORM-d) δ ppm 2.06-2.17 (m, 1H) 2.53-2.64 (m, 1H) 2.64-2.73 (m, 2H) 2.73-2.85 (m, 2H) 3.26-3.36 (m, 1H)

6.52 (d, J=1.32 Hz, 1H) 7.08 (dt, 1H) 7.19-7.26 (m, 3H) 8.87 (br. s, 1H). LCMS m/e 276 (M+H). Purity>98% (HPLC).

2.83. Synthesis of 4-(3,4-dichlorobenzyl)-1,4,5,6-tetrahydrocyclopenta[b]pyrrole-2-carboxylic acid (57)

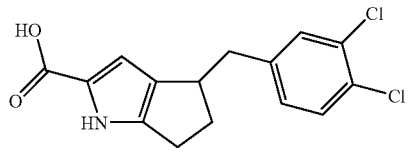

The title compound was synthesized from methyl 4-(3,4-dichlorobenzyl)-1,4,5,6-tetrahydrocyclopenta[b]pyrrole-2-carboxylate (0.064 g, 0.2 mmol) and lithium hydroxide (0.084 g, 2.0 mmol in 3 mL water), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane to afford a light brown solid: 14 mg, 23% yield. $^1$H NMR (400 MHz, METHANOL-$d_4$) δ ppm 2.00-2.15 (m, 1H), 2.46-2.67 (m, 3H), 2.69-2.84 (m, 2H), 3.19-3.29 (m, 1H), 6.31 (s, 1H), 7.11 (dd, J=8.20, 2.00 Hz, 1H), 7.34 (d, J=1.95 Hz, 1H), 7.37-7.45 (m, 1H); HPLC (UV=96.1%), (ELSD=100%).

The enantiomers of 4-(3,4-dichlorobenzyl)-1,4,5,6-tetrahydrocyclopenta[b]pyrrole-2-carboxylic acid were separated according to General Procedure 8 with a mixture of 45% methanol in $CO_2$ to give 4-(3,4-dichlorobenzyl)-1,4,5,6-tetrahydrocyclopenta[b]pyrrole-2-carboxylic acid (58), (peak 1, retention time=2.9 min; 100% ee) and 4-(3,4-dichlorobenzyl)-1,4,5,6-tetrahydrocyclopenta[b]pyrrole-2-carboxylic acid (59) (peak 2, retention time=4.7 min; 100% ee).

2.84. Synthesis of 4-(4-bromobenzyl)-1,4,5,6-tetrahydrocyclopenta[b]pyrrole-2-carboxylic acid (60)

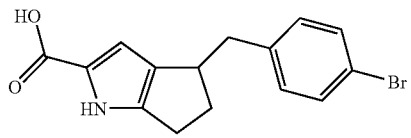

The title compound was synthesized from methyl 4-(4-bromobenzyl)-1,4,5,6-tetrahydrocyclopenta[b]pyrrole-2-carboxylate (0.0998 g, 0.3 mmol, 1 equiv) and lithium hydroxide (0.8 mL, 2 M aqueous, 1.6 mmol, 5.3 equiv), according to General Procedure 7. A 1:1 mixture of methanol (MeOH) and THF (5 mL) was used. The resulting product was purified via preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 70% methanol and increasing to 100% over 7 minutes) afforded the title compound. 67.2 mg, with purity by HPLC of 100% (UV). LCMS m/e 318 (M−H). $^1$H NMR (400 MHz, METHANOL-$d_4$) δ ppm 2.02-2.16 (m, 1H), 2.49-2.67 (m, 3H), 2.74 (dd, J=9.77, 7.37 Hz, 2H), 3.19-3.29 (m, 1H), 6.29 (s, 1H), 7.11 (d, J=8.35 Hz, 2H), 7.41 (q, J=4.25 Hz, 2H).

The enantiomers of 4-(4-bromobenzyl)-1,4,5,6-tetrahydrocyclopenta[b]pyrrole-2-carboxylic acid were separated according to General Procedure 8 with a mixture of 65% methanol in $CO_2$ to give 4-(4-bromobenzyl)-1,4,5,6-tetrahydrocyclopenta[b]pyrrole-2-carboxylic acid (61), (peak 1, retention time=1.8 min; 100% ee) and 4-(4-bromobenzyl)-1,4,5,6-tetrahydrocyclopenta[b]pyrrole-2-carboxylic acid (62) (peak 2, retention time=2.7 min; 100% ee).

2.85. Synthesis of 4-(3-bromobenzyl)-1,4,5,6-tetrahydrocyclopenta[b]pyrrole-2-carboxylic acid (63)

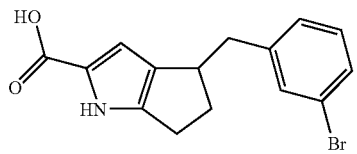

The title compound was synthesized from methyl 4-(3-bromobenzyl)-1,4,5,6-tetrahydrocyclopenta[b]pyrrole-2-carboxylate (0.099 g, 0.30 mmol, 1 equiv) and lithium hydroxide (0.124 g, 2.96 mmol), according to General Procedure 7. A 1:1 mixture of methanol (MeOH) and THF (2 mL) was used. The resulting product was purified by reverse phase HPLC, eluting with a gradient of 40-100% MeOH: water (with 0.1% formic acid) to the title compound: 37 mg, 39% yield. $^1$H NMR (400 MHz, METHANOL-$d_4$) δ ppm 2.03-2.11 (m, 1H), 2.48-2.57 (m, 1H), 2.60-2.64 (m, 2H), 2.75 (dd, J1=7.32 Hz, J2=3.71 Hz, 2H), 3.21-3.28 (m, 1H), 6.31 (s, 1H), 7.14-7.20 (m, 2H), 7.32-7.35 (m, 2H); LCMS-MS (ESI−) 318.0 (M−H); HPLC (UV=98.99%), (ELSD=100%).

The enantiomers of 4-(3-bromobenzyl)-1,4,5,6-tetrahydrocyclopenta[b]pyrrole-2-carboxylic acid were separated according to General Procedure 8 with a mixture of 80% methanol in $CO_2$ to give 4-(3-bromobenzyl)-1,4,5,6-tetrahydrocyclopenta[b]pyrrole-2-carboxylic acid (64), (peak 1, retention time=2.1 min; 100% ee) and 4-(3-bromobenzyl)-1,4,5,6-tetrahydrocyclopenta[b]pyrrole-2-carboxylic acid (65) (peak 2, retention time=4.8 min; 100% ee).

2.86. Synthesis of 4-(3-methoxybenzyl)-1,4,5,6-tetrahydrocyclopenta[b]pyrrole-2-carboxylic acid (66)

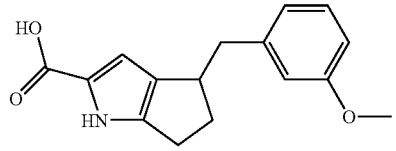

The title compound was synthesized from methyl 4-(3-methoxybenzyl)-1,4,5,6-tetrahydrocyclopenta[b]pyrrole-2-carboxylate (116 mg, 0.40 mmol) and lithium hydroxide (167 mg, 4.00 mmol in 1 mL water), according to General Procedure 7. A 1:1 mixture of methanol (MeOH) and THF (2 mL) was used. The resulting product was purified by chromatography, eluting with heptane-EtOAc, gradient 0 to 50% EtOAc to afford the title compound. 74, mg. $^1$H NMR (400 MHz, CHLOROFORM-d) δ ppm 2.09-2.18 (m, 1H), 2.53-2.65 (m, 1H), 2.65-2.73 (m, 2H), 2.74-2.85 (m, 2H), 3.28-3.37 (m, 1H), 3.81 (s, 3H), 6.56 (d, J=1.46 Hz, 1H), 6.73-6.83 (m, 3H), 7.22 (t, J=7.81 Hz, 1H), 8.85 (br. s, 1H). LCMS m/e 272 (M+H). Purity 99% (HPLC).

The enantiomers of 4-(3-methoxybenzyl)-1,4,5,6-tetrahydrocyclopenta[b]pyrrole-2-carboxylic acid were separated according to General Procedure 8 with a mixture of 70% methanol in $CO_2$ to give 4-(3-methoxybenzyl)-1,4,5,6-tetrahydrocyclopenta[b]pyrrole-2-carboxylic acid (67), (peak 1, retention time=3.4 min; 100% ee) and 4-(3-methoxybenzyl)-1,4,5,6-tetrahydrocyclopenta[b]pyrrole-2-carboxylic acid (68) (peak 2, retention time=4.3 min; 99.4% ee).

2.87. Synthesis of 4-(3,4-dimethoxybenzyl)-1,4,5,6-tetrahydrocyclopenta[b]pyrrole-2-carboxylic acid (69)

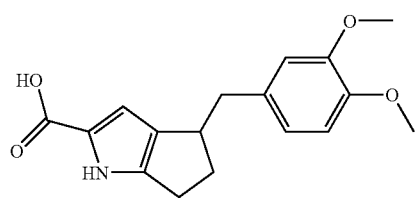

The title compound was synthesized from methyl 4-(3,4-dimethoxybenzyl)-1,4,5,6-tetrahydrocyclopenta[b]pyrrole-2-carboxylate (0.050 g, 0.16 mmol) and lithium hydroxide (0.067 g, 1.6 mmol in 3 mL water), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane) to afford the title compound: 11 mg, 23% yield. $^1$H NMR (400 MHz, METHANOL-$d_4$) δ ppm 2.06-2.18 (m, 1H), 2.50-2.68 (m, 3H), 2.68-2.81 (m, 2H), 3.20-3.35 (m, 1H), 3.77 (s, 3H), 3.81 (s, 3H), 6.35 (s, 1H), 6.72 (m, 2H), 6.86 (d, J=8.0 Hz, 1H); LCMS-MS (ESI–) 300.0 (M–H); HPLC (UV=96%), (ELSD=100%).

2.88. Synthesis of 4-(3-methylbenzyl)-1,4,5,6-tetrahydrocyclopenta[b]pyrrole-2-carboxylic acid (70)

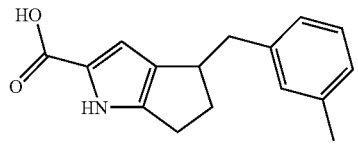

The title compound was synthesized from methyl 4-(3-methylbenzyl)-1,4,5,6-tetrahydrocyclopenta[b]pyrrole-2-carboxylate (85 mg, 0.31 mmol) and lithium hydroxide (129 mg, 3.10 mmol in 3 mL water), according to General Procedure 7. A 1:1 mixture of methanol (MeOH) and THF (6 mL) was used. The resulting product was purified by chromatography, eluting with heptane-EtOAc, gradient 0 to 50% EtOAc to afford the title compound. 45 mg, 57% yield. $^1$H NMR (400 MHz, CHLOROFORM-d) δ ppm 2.07-2.20 (m, J=12.57, 8.44, 6.21, 6.21 Hz, 1H), 2.35 (s, 3H), 2.50-2.84 (m, 5H), 3.26-3.35 (m, 1H), 6.53 (d, J=1.42 Hz, 1H), 6.98-7.07 (m, 2H), 7.17-7.22 (m, 1H), 7.23-7.34 (m, 1H), 8.84 (br. s., 1H). LCMS m/e 256 (M+H). Purity ~100% (HPLC).

2.89. Synthesis of 4-(3,4-dimethylbenzyl)-1,4,5,6-tetrahydrocyclopenta[b]pyrrole-2-carboxylic acid (71)

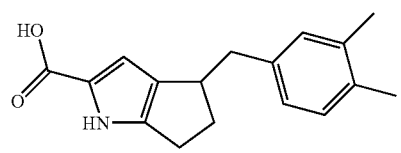

The title compound was synthesized from methyl 4-(3,4-dimethylbenzyl)-1,4,5,6-tetrahydrocyclopenta[b]pyrrole-2-carboxylate (0.050 g, 0.18 mmol) and lithium hydroxide (0.076 g, 1.8 mmol in 3 mL water), according to General Procedure 7. A 1:1 mixture of methanol (MeOH) and THF (6 mL) was used. The resulting product was purified by column chromatography (Isco CombiFlash) eluting with a gradient of 0-100% EtOAc/heptane) to afford the title compound: 27 mg, 56% yield. $^1$H NMR (400 MHz, METHANOL-$d_4$) δ ppm 2.07 (ddt, J=12.40, 8.55, 6.00, 6.00 Hz, 1H), 2.16-2.29 (m, 7H), 2.45-2.73 (m, 5H), 3.22 (quin, J=6.97 Hz, 1H), 6.30 (s, 1H), 6.84-6.92 (m, 1H), 6.95 (s, 1H), 7.01 (d, J=7.61 Hz, 1H); LCMS-MS (ESI–) 268.0 (M–H); HPLC (UV=100%), (ELSD=100%).

2.90. Synthesis of 4-(3,5-dimethylbenzyl)-1,4,5,6-tetrahydrocyclopenta[b]pyrrole-2-carboxylic acid (72)

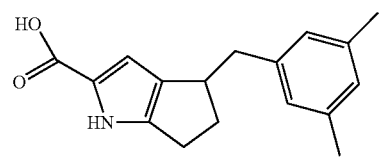

The title compound was synthesized from methyl 4-(3,5-dimethylbenzyl)-1,4,5,6-tetrahydrocyclopenta[b]pyrrole-2-carboxylate (0.066 g, 0.23 mmol) and lithium hydroxide monohydrate (0.049 g, 1.16 mmol), according to General Procedure 7. A 1:1 mixture of methanol (MeOH) and THF was used. The resulting product was purified by chromatography over silica gel (gradient 0 to 100% EtOAc in heptane over 20 min) to afford the title compound. 30 mg. $^1$H NMR (400 MHz, METHANOL-$d_4$) δ ppm 2.06 (ddt, J=12.47, 8.52, 6.03, 6.03 Hz, 1H), 2.26 (s, 6H), 2.44-2.70 (m, 5H), 3.17-3.26

2.91. Synthesis of 4-(3-cyclopropylbenzyl)-1,4,5,6-tetrahydrocyclopenta[b]pyrrole-2-carboxylic acid (73)

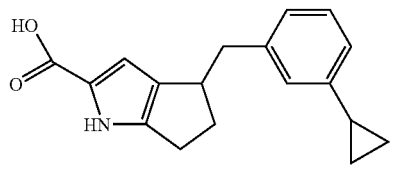

The title compound was synthesized from methyl 4-(3-cyclopropylbenzyl)-1,4,5,6-tetrahydrocyclopenta[b]pyrrole-2-carboxylate (0.020 g, 0.068 mmol) and lithium hydroxide (0.030 g, 0.71 mmol in 1 mL water), according to General Procedure 7. A 1:1 mixture of methanol (MeOH) and THF (2 mL) was used. The resulting product was purified by reverse phase HPLC, eluting with a gradient of 40-100% MeOH: water (with 0.1% formic acid) to afford the title compound: 2.2 mg, 12% yield. $^1$H NMR (400 MHz, METHANOL-$d_4$) δ ppm 0.61-0.66 (m, 2H), 0.92 (s, 2H), 1.86 (s, 1H), 2.06 (s, 1H), 2.49 (s, 1H), 2.59 (s, 2H), 2.72 (d, J=7.03 Hz, 2H), 3.23 (s, 1H), 6.30 (s, 1H), 6.84 (s, 1H), 6.96 (s, 1H), 7.12 (s, 1H); LCMS-MS (ESI−) 280.1 (M−H); HPLC (UV=100%), (ELSD=100%).

2.92. Synthesis of 4-(3-ethynylbenzyl)-1,4,5,6-tetrahydrocyclopenta[b]pyrrole-2-carboxylic acid (74)

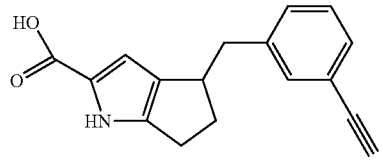

The title compound was synthesized from methyl 4-(3-ethynylbenzyl)-1,4,5,6-tetrahydrocyclopenta[b]pyrrole-2-carboxylate (0.014 g, 0.050 mmol) and lithium hydroxide (0.021 g, 0.50 mmol in 0.5 mL water), according to General Procedure 7. A 1:1 mixture of methanol (MeOH) and THF (1 mL) was used. The resulting product was purified by reverse phase HPLC, eluting with a gradient of 40-100% MeOH: water (with 0.1% formic acid) to afford the title compound: 2.8 mg, 21% yield. $^1$H NMR (400 MHz, METHANOL-$d_4$) δ ppm 2.04-2.13 (m, 1H), 2.48-2.59 (m, 1H), 2.59-2.66 (m, 2H), 2.76 (d, J=7.22 Hz, 2H), 3.22-3.29 (m, 1H), 3.41 (s, 1H), 6.30 (s, 1H), 7.18-7.22 (m, 1H), 7.25 (t, J=7.81 Hz, 1H), 7.28-7.30 (m, 1H), 7.31 (s, 1H); LCMS (ESI−) 264.2 (M−H); HPLC (UV=96.60%), (ELSD=100%).

2.93. Synthesis of 4-(3-cyanobenzyl)-1,4,5,6-tetrahydrocyclopenta[b]pyrrole-2-carboxylic acid (75) and 4-(3-carbamoylbenzyl)-1,4,5,6-tetrahydrocyclopenta[b]pyrrole-2-carboxylic acid (77)

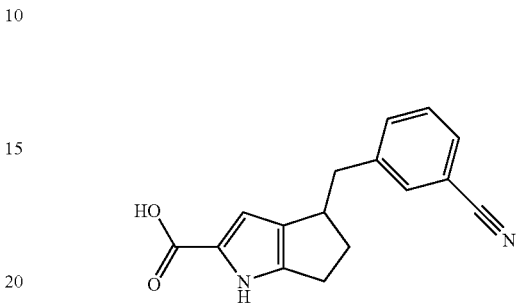

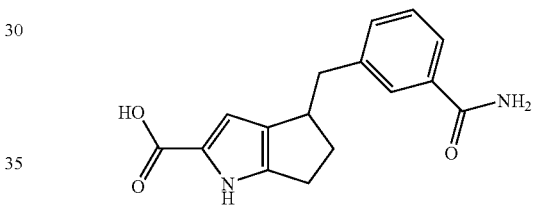

Methyl 4-(3-cyanobenzyl)-1,4,5,6-tetrahydrocyclopenta[b]pyrrole-2-carboxylate (0.065 g, 0.23 mmol) was dissolved in THF (1 mL) and MeOH (1 mL). Then LiOH (0.097 g, 2.31 mmol) in H$_2$O (1 mL) was added and the reaction stirred at 40° C. for 16 h. The solvent was removed under reduced pressure, and the residue re-dissolved in about 5 mL H$_2$O and acidified to pH 2-3 with 1 N HCl. The product was filtered off, and then dissolved in DMSO (about 15 mg/mL) and purified by reverse phase HPLC, eluting with a gradient of 40-80% MeOH: water (with 0.1% formic acid) to afford both 4-(3-carbamoylbenzyl)-1,4,5,6-tetrahydrocyclopenta[b]pyrrole-2-carboxylic acid (77) and 4-(3-cyanobenzyl)-1,4,5,6-tetrahydrocyclopenta[b]pyrrole-2-carboxylic acid (75).

4-(3-carbamoylbenzyl)-1,4,5,6-tetrahydrocyclopenta[b]pyrrole-2-carboxylic acid (77) (0.0017 g): $^1$H NMR (400 MHz, METHANOL-$d_4$) δ ppm 2.05-2.13 (m, 1H), 2.47-2.64 (m, 4H), 2.65 (s, 1H), 2.83-285 (m, 2H), 6.53-6.54 (d, 1H), 6.27 (s, 1H), 6.51-6.52 (d, 1H), 7.43-7.47 (m, 4H); LCMS-MS (ESI−) 283.2 (M−H); HPLC (UV=97.5%), (ELSD=100%).

4-(3-cyanobenzyl)-1,4,5,6-tetrahydrocyclopenta[b]pyrrole-2-carboxylic acid (75) (0.0064 g): $^1$H NMR (400 MHz, METHANOL-$d_4$) δ ppm 2.05-2.13 (m, 1H), 2.51-2.65 (m, 3H), 2.78-2.90 (m, 2H), 3.26-3.29 (m, 1H), 6.27 (s, 1H), 7.43-7.47 (m, 4H); LCMS-MS (ESI−) 265.2 (M−H); HPLC (UV=100%), (ELSD=100%).

2.94. Synthesis of 4-(3-acetylbenzyl)-1,4,5,6-tetrahydrocyclopenta[b]pyrrole-2-carboxylic acid (76)

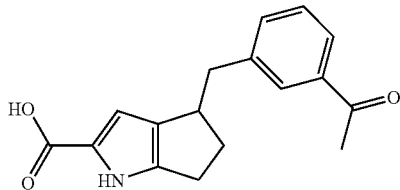

The title compound was synthesized from methyl 4-(3-acetylbenzyl)-1,4,5,6-tetrahydrocyclopenta[b]pyrrole-2-carboxylate (0.006 g, 0.020 mmol) and lithium hydroxide (0.010 g, 0.24 mmol in 0.5 mL water), according to General Procedure 7. A 1:1 mixture of methanol (MeOH) and THF (1 mL) was used. The resulting product was purified by column chromatography (Isco CombiFlash) eluting with a gradient of 0-50% EtOAc/heptane affording the title compound: 0.5 mg, 9% yield. $^1$H NMR (400 MHz, METHANOL-$d_4$) δ ppm 2.56-2.61 (m, 7H), 2.79-2.91 (m, 2H), 6.29 (s, 1H), 7.39-7.44 (m, 1H), 7.44-7.46 (m, 1H), 7.78 (s, 1H), 7.82-7.86 (m, 1H); LCMS-MS (ESI−) 282.2 (M−H); HPLC (UV=100%).

2.95. Synthesis of 4-(naphthalen-2-ylmethyl)-1,4,5,6-tetrahydrocyclopenta[b]pyrrole-2-carboxylic acid (78)

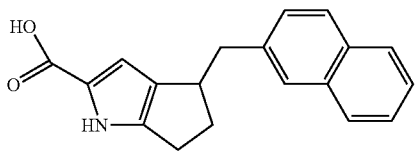

The title compound was synthesized from methyl 4-(naphthalen-2-ylmethyl)-1,4,5,6-tetrahydrocyclopenta[b]pyrrole-2-carboxylate (0.104 g, 0.34 mmol) and lithium hydroxide (0.148 g, 3.53 mmol in 5 mL water), according to General Procedure 7. A 1:1 mixture of methanol (MeOH) and THF (10 mL) was used. The solvent was removed under reduced pressure, and the residue re-dissolved in ca. 5 mL H$_2$O and acidified to pH 7 with 1 N HCl. The solids formed were collected, affording the title compound as a light pink solid: 77 mg, 76% yield. $^1$H NMR (400 MHz, ACETONE-$d_6$) δ ppm 2.16 (ddt, J=12.34, 8.74, 5.98, 5.98 Hz, 1H), 2.50-2.76 (m, 3H), 2.92-3.03 (m, 2H), 3.37-3.47 (m, 1H), 6.31 (d, J=1.71 Hz, 1H), 7.41-7.50 (m, 3H), 7.73 (s, 1H), 7.82-7.90 (m, 3H), 10.39 (br. s, 1H); LCMS-MS (ESI−) 290.0 (M−H); HPLC (UV=93.55%), (ELSD=100%).

The enantiomers of 4-(naphthalen-2-ylmethyl)-1,4,5,6-tetrahydrocyclopenta[b]pyrrole-2-carboxylic acid were separated according to General Procedure 8 with a mixture of 40% [50:50 methanol/isopropanol with 0.1% diethylamine] in CO$_2$ to give 4-(naphthalen-2-ylmethyl)-1,4,5,6-tetrahydrocyclopenta[b]pyrrole-2-carboxylic acid (79), (peak 1, retention time=3.8 min; 89% ee) and 4-(naphthalen-2-ylmethyl)-1,4,5,6-tetrahydrocyclopenta[b]pyrrole-2-carboxylic acid (80) (peak 2, retention time=4.4 min; 90% ee).

2.96. Synthesis of 4-(biphenyl-4-ylmethyl)-1,4,5,6-tetrahydrocyclopenta[b]pyrrole-2-carboxylic acid (81)

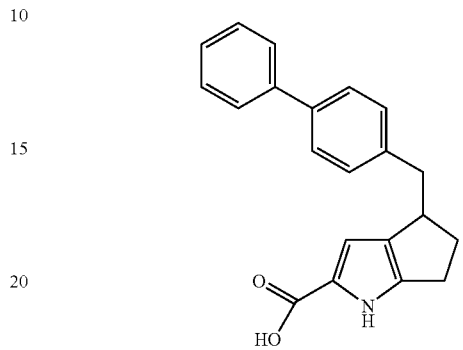

The title compound was synthesized from methyl 4-(biphenyl-4-ylmethyl)-1,4,5,6-tetrahydrocyclopenta[b]pyrrole-2-carboxylate (118 mg, 0.36 mmol) and lithium hydroxide monohydrate (60 mg, 1.42 mmol in 5 mL water), according to General Procedure 7. A 1:1 mixture of methanol (MeOH) and THF (15 mL) was used. The resulting product was purified by flash chromatography (Isco CombiFlash) eluting with a gradient of 0-70% EtOAc/Heptane to give the title compound: 60 mg, 53%. $^1$H NMR (400 MHz, ACETONE-$d_6$) δ ppm 2.06-2.18 (m, 1H), 2.48-2.62 (m, 1H), 2.62-2.75 (m, 2H), 2.78-2.89 (m, 2H), 3.28-3.37 (m, 1H), 6.37 (d, J=1.76 Hz, 1H), 7.29-7.37 (m, 3H), 7.41-7.48 (m, 2H), 7.57-7.63 (m, 2H), 7.63-7.69 (m, 2H), 10.38 (s, 1H); LCMS-MS (ESI−) 316.2 (M−H); HPLC (UV=99.4%), (ELSD=100%).

2.97. Synthesis of 4-(biphenyl-3-ylmethyl)-1,4,5,6-tetrahydrocyclopenta[b]pyrrole-2-carboxylic acid (82)

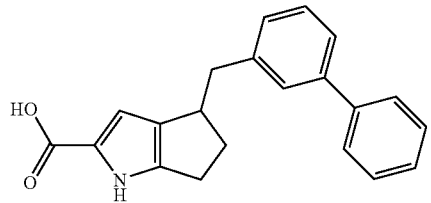

The title compound was synthesized from methyl 4-(biphenyl-3-ylmethyl)-1,4,5,6-tetrahydrocyclopenta[b]pyrrole-2-carboxylate (0.041 g, 0.124 mmol) and lithium hydroxide (0.055 g, 1.31 mmol in 1 mL water), according to General Procedure 7. A 1:1 mixture of methanol (MeOH) and THF (2 mL) was used. The resulting product was purified by reverse phase HPLC, eluting with a gradient of 40-100% MeOH: water (with 0.1% formic acid) to afford the title compound: 24.0 mg, 61% yield. $^1$H NMR (400 MHz, METHANOL-$d_4$) δ ppm 2.08-2.20 (m, 1H), 2.50-2.62 (m, 3H), 2.77-2.90 (m, 2H), 3.27-3.30 (m, 1H), 6.39 (s, 1H), 7.17 (d, J=7.57 Hz, 1H), 7.26-7.44 (m, 6H), 7.53-7.58 (m, 2H); LCMS-MS (ESI−) 316.2 (M−H); HPLC (UV=97.3%), (ELSD=100%).

2.98. Synthesis of 4-(3-(pyridin-3-yl)benzyl)-1,4,5,6-tetrahydrocyclopenta[b]pyrrole-2-carboxylic acid (83)

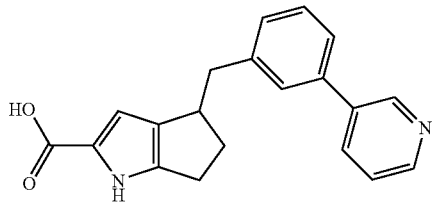

The title compound was synthesized from (E)-methyl 4-(3-(pyridin-3-yl)benzylidene)-1,4,5,6-tetrahydrocyclopenta[b]pyrrole-2-carboxylate (0.051 g, 0.15 mmol) and lithium hydroxide (0.067 g, 1.6 mmol in 1 mL water), according to General Procedure 7. A 1:1 mixture of methanol (MeOH) and THF (2 mL) was used. The resulting product was purified by reverse phase HPLC, eluting with a gradient of 40-100% MeOH: water (with 0.1% formic acid) to afford the title compound. 15.0 mg, 31% yield. $^1$H NMR (400 MHz, METHANOL-$d_4$) δ ppm 2.08-2.21 (m, 1H), 2.52-2.63 (m, 3H), 2.79-2.94 (m, 2H), 3.33-3.36 (m, 1H), 6.34 (s, 1H), 7.28 (d, J=7.57 Hz, 1H), 7.39-7.44 (m, 2H), 7.46-7.51 (m, 2H), 8.04 (dt, J=8.02, 1.90 Hz, 1H), 8.49 (dd, J=4.88, 1.46 Hz, 1H), 8.76 (d, J=2.00 Hz, 1H); LCMS-MS (ESI−) 317.2 (M−H); HPLC (UV=96.4%), (ELSD=100%).

2.99. Synthesis of 4-((4'-(trifluoromethyl)biphenyl-3-yl)methyl)-1,4,5,6-tetrahydrocyclopenta[b]pyrrole-2-carboxylic acid (84)

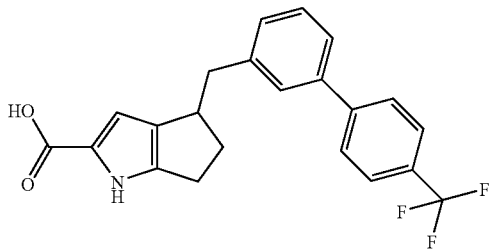

The title compound was synthesized from methyl 4-((4'-(trifluoromethyl)biphenyl-3-yl)methyl)-1,4,5,6-tetrahydrocyclopenta[b]pyrrole-2-carboxylate (0.047 g, 0.12 mmol) and lithium hydroxide (0.052 g, 1.24 mmol in 1 mL water), according to General Procedure 7. A 1:1 mixture of methanol (MeOH) and THF (2 mL) was used. The resulting product was purified by reverse phase HPLC, eluting with a gradient of 40-100% MeOH: water (with 0.1% formic acid) to afford the title compound. 19.4 mg, 43% yield. $^1$H NMR (400 MHz, METHANOL-$d_4$) δ ppm 2.15 (t, J=4.73 Hz, 1H) 2.52-2.62 (m, 3H) 2.78-2.93 (m, 2H) 3.32-3.36 (m, 1H) 6.38 (s, 1H) 7.23-7.27 (m, 1H) 7.36-7.41 (m, 2H) 7.46-7.51 (m, 1H) 7.67-7.77 (m, 4H); LCMS-MS (ESI−) 384.0 (M−H); $^{19}$F NMR (376 MHz, METHANOL-$d_4$) δ ppm −64.30 (s, 3F); HPLC (UV=99.3%), (ELSD=100%).

2.100. Synthesis of 4-((4'-hydroxybiphenyl-3-yl)methyl)-1,4,5,6-tetrahydrocyclopenta[b]pyrrole-2-carboxylic acid (85)

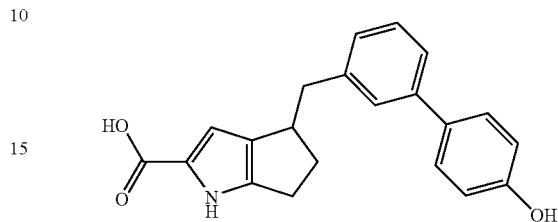

The title compound was synthesized from methyl 4-((4'-hydroxybiphenyl-3-yl)methyl)-1,4,5,6-tetrahydrocyclopenta[b]pyrrole-2-carboxylate (0.044 g, 0.13 mmol) and lithium hydroxide (0.055 g, 1.31 mmol in 1 mL water), according to General Procedure 7. A 1:1 mixture of methanol (MeOH) and THF (2 mL) was used. The resulting product was purified by reverse phase HPLC, eluting with a gradient of 40-100% MeOH: water (with 0.1% formic acid) to afford a light pink solid: 21.7 mg, 51% yield. $^1$H NMR (400 MHz, METHANOL-$d_4$) δ ppm 2.13 (s, 1H), 2.48-2.62 (m, 3H), 2.80 (dd, J=7.05, 3.78 Hz, 2H), 3.25-3.29 (m, 1H), 6.39 (s, 1H), 6.81-6.86 (m, 2H), 7.09 (d, J=7.52 Hz, 1H), 7.25-7.30 (m, 2H), 7.33-7.37 (m, 1H), 7.38-7.42 (m, 2H); LCMS ESI− 332.2 (M−H); HPLC (UV=98.1%), (ELSD=100%).

2.101. Synthesis of 4-((4'-(hydroxymethyl)biphenyl-3-yl)methyl)-1,4,5,6-tetrahydrocyclopenta[b]pyrrole-2-carboxylic acid (86)

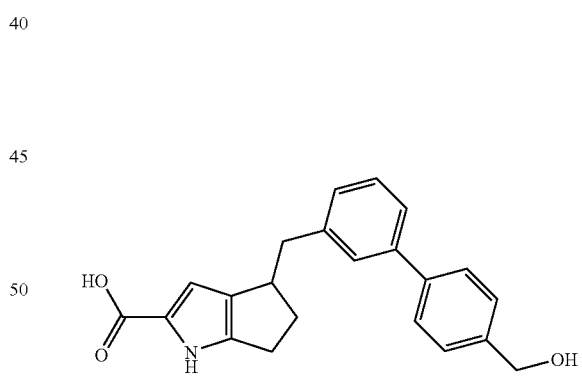

The title compound was synthesized from methyl 4-((4'-(hydroxymethyl)biphenyl-3-yl)methyl)-1,4,5,6-tetrahydrocyclopenta[b]pyrrole-2-carboxylate (0.012 g, 0.033 mmol) and lithium hydroxide (0.016 g, 0.38 mmol in 0.5 mL water), according to General Procedure 7. A 1:1 mixture of methanol (MeOH) and THF (1 mL) was used. The resulting product was purified by reverse phase HPLC, eluting with a gradient of 40-100% MeOH: water (with 0.1% formic acid) to afford the title compound: 4.5 mg, 39% yield. $^1$H NMR (400 MHz, METHANOL-$d_4$) δ ppm 2.10-2.18 (m, 1H), 2.52-2.63 (m, 3H), 2.79-2.91 (m, 2H), 3.33 (d, J=1.61 Hz, 1H), 4.64 (s, 2H), 6.39 (s, 1H), 7.19 (s, 1H), 7.34 (s, 2H), 7.42 (s, 3H), 7.56 (d, J=8.30 Hz, 2H); LCMS-MS (ESI−) 346.2 (M−H); HPLC (UV=93.1%), (ELSD=100%).

2.102. Synthesis of 4-(3-(furan-2-yl)benzyl)-1,4,5,6-tetrahydrocyclopenta[b]pyrrole-2-carboxylic acid (87)

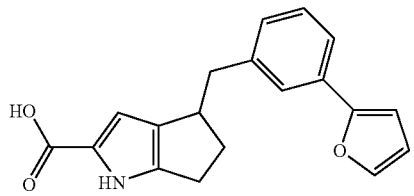

The title compound was synthesized from methyl 4-(3-(furan-2-yl)benzyl)-1,4,5,6-tetrahydrocyclopenta[b]pyrrole-2-carboxylate (0.024 g, 0.075 mmol) and lithium hydroxide (0.032 g, 0.76 mmol), according to General Procedure 7. A 1:1 mixture of methanol (MeOH) and THF (1.5 mL) was used. The resulting product was purified by reverse phase HPLC, eluting with a gradient of 40-100% MeOH: water (with 0.1% formic acid) to afford a light pink solid: 14 mg, 61% yield. LCMS-MS (ESI−) 306.0 (M−H); HPLC (UV=93.7%), (ELSD=100%).

The enantiomers of 4-(3-(furan-2-yl)benzyl)-1,4,5,6-tetrahydrocyclopenta[b]pyrrole-2-carboxylic acid were separated according to General Procedure 8 with a mixture of 72% [50:50 methanol/isopropanol] in $CO_2$ to give 4-(3-(furan-2-yl)benzyl)-1,4,5,6-tetrahydrocyclopenta[b]pyrrole-2-carboxylic acid (88), (peak 1, retention time=1.8 min; 99.2% ee) and 4-(3-(furan-2-yl)benzyl)-1,4,5,6-tetrahydrocyclopenta[b]pyrrole-2-carboxylic acid (89) (peak 2, retention time=2.4 min; 97.9% ee).

2.103. Synthesis of 4-(3-(tetrahydrofuran-3-yl)benzyl)-1,4,5,6-tetrahydrocyclopenta[b]pyrrole-2-carboxylic acid (90)

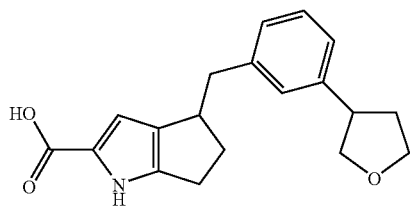

The title compound was synthesized from methyl 4-(3-(tetrahydrofuran-2-yl)benzyl)-1,4,5,6-tetrahydrocyclopenta[b]pyrrole-2-carboxylate (0.028 g, 0.086 mmol) and lithium hydroxide (0.036 g, 0.86 mmol in 0.75 mL water), according to General Procedure 7. THF (0.75 mL) was used to solubilize the starting material. The resulting product was purified by reverse phase HPLC, eluting with a gradient of 40-100% MeOH: water (with 0.1% formic acid) to afford the title compound: 11 mg, 41% yield. $^1$H NMR (400 MHz, METHANOL-$d_4$) δ ppm 1.71-1.83 (m, 1H), 1.96-2.06 (m, 2H), 2.07-2.14 (m, 1H), 2.27-2.36 (m, 1H), 2.49-2.63 (m, 3H), 2.69-2.83 (m, 2H), 3.21-3.28 (m, 1H), 3.87-3.93 (q, 1H), 4.04-4.09 (q, 1H), 4.82-4.83 (m, 1H), 6.26-6.36 (d, 1H), 7.09-7.11 (m, 2H), 7.14-7.18 (m, 1H), 7.21-7.26 (m, 1H); LCMS-MS (ESI−) 310.2 (M−H); HPLC (UV=98.99%).

2.104. Synthesis of 4-(3-(1H-pyrrol-2-yl)benzyl)-1,4,5,6-tetrahydrocyclopenta[b]pyrrole-2-carboxylic acid (91)

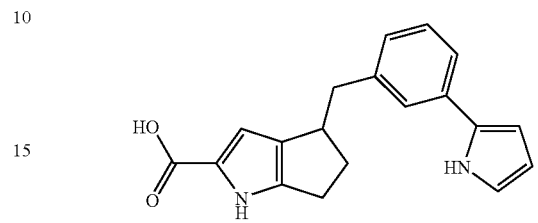

The enantiomers of 4-(3-(1H-pyrrol-2-yl)benzyl)-1,4,5,6-tetrahydrocyclopenta[b]pyrrole-2-carboxylic acid were separated according to General Procedure 8 with a mixture of 55% [50:50 methanol/isopropanol] in $CO_2$ to give 4-(3-(1H-pyrrol-2-yl)benzyl)-1,4,5,6-tetrahydrocyclopenta[b]pyrrole-2-carboxylic acid (92), (peak 1, retention time=2.5 min; 98.9% ee) and 4-(3-(1H-pyrrol-2-yl)benzyl)-1,4,5,6-tetrahydrocyclopenta[b]pyrrole-2-carboxylic acid (93) (peak 2, retention time=3.6 min; 88.3% ee).

2.105. Synthesis of 4-(3-fluorophenyl)-1,4,5,6-tetrahydrocyclopenta[b]pyrrole-2-carboxylic acid (94)

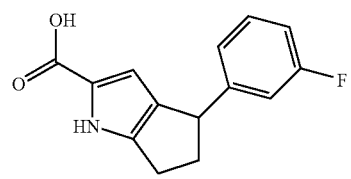

The title compound was synthesized from methyl 4-(3-fluorophenyl)-1,4,5,6-tetrahydrocyclopenta[b]pyrrole-2-carboxylate (0.145 g, 0.56 mmol) and lithium hydroxide (120 mg, 2.8 mmol in 1 mL water), according to General Procedure 7. In this example, methanol was used to solubilize the starting material. The resulting product was purified by chromatography over silica gel (gradient 0 to 100% EtOAc in heptane over 20 min) to give the title compound 78 mg. $^1$H NMR (400 MHz, METHANOL-$d_4$) δ ppm 2.17-2.27 (m, 1H) 2.70-2.98 (m, 3H) 4.20 (t, J=7.17 Hz, 1H) 6.54 (s, 1H) 6.85-6.92 (m, 2H) 7.01 (d, J=7.66 Hz, 1H) 7.22-7.31 (m, 1H). LCMS m/e 244 (M−H). 93% pure by HPLC.

The enantiomers of 4-(3-fluorophenyl)-1,4,5,6-tetrahydrocyclopenta[b]pyrrole-2-carboxylic acid were separated according to General Procedure 8 with a mixture of 30% [50:50 methanol/isopropanol] in $CO_2$ to give 4-(3-fluorophenyl)-1,4,5,6-tetrahydrocyclopenta[b]pyrrole-2-carboxylic acid (95), (peak 1, retention time=2.5 min; 98.7% ee) and 4-(3-fluorophenyl)-1,4,5,6-tetrahydrocyclopenta[b]pyrrole-2-carboxylic acid (96) (peak 2, retention time=4.2 min; 99.0% ee).

2.106. Synthesis of 4-(3,4-difluorophenyl)-1,4,5,6-tetrahydrocyclopenta[b]pyrrole-2-carboxylic acid (97)

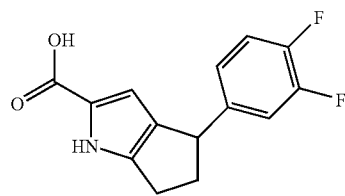

The title compound was synthesized from methyl 4-(3,4-difluorophenyl)-1,4,5,6-tetrahydrocyclopenta[b]pyrrole-2-carboxylate (0.333 g, 1.20 mmol) and lithium hydroxide (0.508 g, 12.1 mmol in 5 mL water), according to General Procedure 7. A 1:1 mixture of water and methanol (4 mL) was used. The resulting product was purified by reverse phase HPLC, eluting with a gradient of 40-100% MeOH: water (with 0.1% formic acid) to afford the title compound. 0.265 g. $^1$H NMR (400 MHz, METHANOL-$d_4$) δ ppm 2.17 (ddt, J=12.70, 8.55, 6.38, 6.38 Hz, 1H), 2.67-2.94 (m, 3H), 4.15 (t, J=7.15 Hz, 1H), 6.53 (s, 1H), 6.93-6.98 (m, 1H), 7.01 (ddd, J=11.87, 7.77, 2.12 Hz, 1H), 7.11 (dt, J=10.59, 8.37 Hz, 1H); $^{19}$F NMR (376 MHz, METHANOL-$d_4$) δ ppm −145.22-−145.11 (m, 1F) −141.41-−141.30 (m, 1F); LCMS (ESI-) 262.0 (M−H); HPLC (UV=99.7%), (ELSD=100%).

2.107. Synthesis of 4-(3,5-difluorophenyl)-1,4,5,6-tetrahydrocyclopenta[b]pyrrole-2-carboxylic acid (98)

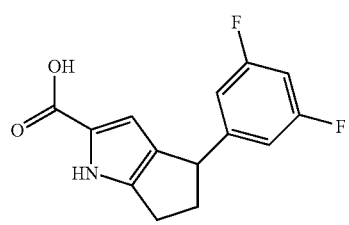

The title compound was synthesized from methyl 4-(3,5-difluorophenyl)-1,4,5,6-tetrahydrocyclopenta[b]pyrrole-2-carboxylate (0.081 g, 0.29 mmol) and lithium hydroxide monohydrate (61 mg, 1.45 mmol), according to General Procedure 7. A 1:6 mixture of water and methanol (MeOH)(3.5 mL) was used. The resulting product was purified by chromatography over silica gel (gradient 0 to 100% EtOAc in heptane over 20 min) to give the title compound 40 mg. $^1$H NMR (400 MHz, METHANOL-$d_4$) δ ppm 2.21 (ddt, 1H), 2.70-2.88 (m, 2H), 2.89-2.99 (m, 1H), 4.20 (dd, J=7.61, 6.64 Hz, 1H), 6.55 (s, 1H), 6.68-6.80 (m, 3H). $^{19}$F NMR (376 MHz, METHANOL-$d_4$) δ ppm −112.87 (t, J=8.58 Hz). LCMS m/e 262 (M−H). 100% pure by HPLC.

The enantiomers of 4-(3,5-difluorophenyl)-1,4,5,6-tetrahydrocyclopenta[b]pyrrole-2-carboxylic acid were separated according to General Procedure 8 with a mixture of 50% methanol in $CO_2$ to give 4-(3,5-difluorophenyl)-1,4,5,6-tetrahydrocyclopenta[b]pyrrole-2-carboxylic acid (99), (peak 1, retention time=1.2 min; 100% ee) and 4-(3,5-difluorophenyl)-1,4,5,6-tetrahydrocyclopenta[b]pyrrole-2-carboxylic acid (100) (peak 2, retention time=1.8 min; 95.2% ee).

2.108. Synthesis of 4-(4-chlorophenyl)-1,4,5,6-tetrahydrocyclopenta[b]pyrrole-2-carboxylic acid (101)

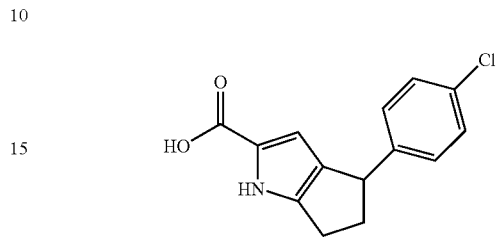

The title compound was synthesized from methyl 4-(4-chlorophenyl)-1,4,5,6-tetrahydrocyclopenta[b]pyrrole-2-carboxylate (0.0492 g, 0.18 mmol) and sodium hydroxide (0.45 mL, 10M, 25 equiv), according to General Procedure 7. A 1:4 mixture of THF and methanol (5 mL) was used. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 minutes) afforded the title compound (22.6 mg, 48%) with purity by HPLC of 93.6% (UV) and 100% (ELSD). LCMS m/e 260 (M−H). $^1$H NMR (400 MHz, METHANOL-$d_4$) δ ppm 7.23-7.28 (m, 2H), 7.15-7.19 (m, 2H), 6.52 (s, 1H), 4.18 (t, J=7.17 Hz, 1H), 2.70-2.97 (m, 3H), 2.20 (dddd, J=12.75, 8.60, 6.53, 6.41 Hz, 1H).

2.109. Synthesis of 4-(3-chlorophenyl)-1,4,5,6-tetrahydrocyclopenta[b]pyrrole-2-carboxylic acid (102)

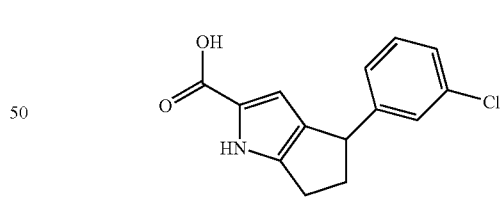

The title compound was synthesized from methyl 4-(3-chlorophenyl)-1,4,5,6-tetrahydrocyclopenta[b]pyrrole-2-carboxylate (0.179 g, 0.65 mmol) and lithium hydroxide (0.272 g, 6.5 mmol), according to General Procedure 7. A 1:1 mixture of THF and methanol (4 mL) was used. The resulting product was purified by reverse phase HPLC, eluting with a gradient of 40-100% MeOH: water (with 0.1% formic acid) to afford the title compound. 0.124 g. $^1$H NMR (400 MHz, METHANOL-$d_4$) δ ppm 2.19 (ddt, J=12.73, 8.52, 6.46, 6.46 Hz, 1H), 2.69-2.97 (m, 3H), 4.17 (t, J=7.13 Hz, 1H), 6.53 (s, 1H), 7.11 (d, J=7.57 Hz, 1H), 7.13-7.18 (m, 2H), 7.20-7.26 (m, 1H); LCMS-MS (ESI−) 260.2 (M−H); HPLC (UV=100%), (ELSD=100%).

2.110. Synthesis of 4-(3-bromophenyl)-1,4,5,6-tetrahydrocyclopenta[b]pyrrole-2-carboxylic acid (103)

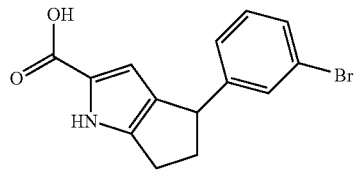

The title compound was synthesized from methyl 4-(3-bromophenyl)-1,4,5,6-tetrahydrocyclopenta[b]pyrrole-2-carboxylate (0.315 g, 0.98 mmol) and lithium hydroxide (0.415 g, 9.9 mmol), according to General Procedure 7. A 1:1 mixture of THF and methanol (8 mL) was used. The resulting product was purified by reverse phase HPLC, eluting with a gradient of 40-100% MeOH: water (with 0.1% formic acid) to afford the title compound. 0.119 g (40% yield). $^1$H NMR (400 MHz, METHANOL-d4) δ ppm 2.16 (ddt, J=12.67, 8.50, 6.30, 6.30 Hz, 1H), 2.67-2.93 (m, 3H), 4.13 (t, J=7.20 Hz, 1H), 6.54 (s, 1H), 7.11-7.17 (m, 2H), 7.26-7.32 (m, 2H); LCMS (ESI+) 328.0 (M+Na); HPLC (UV=93.7%), (ELSD=99.9%).

2.111. Synthesis of 4-(3,5-dimethylphenyl)-1,4,5,6-tetrahydrocyclopenta[b]pyrrole-2-carboxylic acid (104)

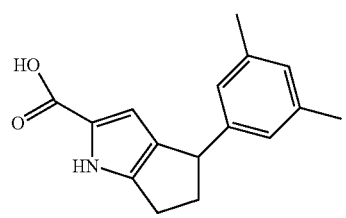

The title compound was synthesized from methyl 4-(3,5-dimethylphenyl)-1,4,5,6-tetrahydrocyclopenta[b]pyrrole-2-carboxylate (150 mg, 0.45 mmol) and lithium hydroxide monohydrate (108 mg, 4.5 mmol), according to General Procedure 7. A 1:1 mixture of THF and methanol (10 mL) was used. The resulting product was purified by chromatography over silica gel (gradient 0 to 100% EtOAc in heptane over 20 min) to give the title compound. $^1$H NMR (400 MHz, METHANOL-d$_4$) δ ppm 2.16-2.22 (m, 1H), 2.24 (s, 6H), 2.66-2.92 (m, 3H), 4.08 (t, J=7.35 Hz, 1H), 6.51 (s, 1H), 6.78 (s, 2H), 6.80 (s, 1H). LCMS m/e 256 (M+H) and 95% pure by HPLC.

2.112. Synthesis of 4-(3-cyanophenyl)-1,4,5,6-tetrahydrocyclopenta[b]pyrrole-2-carboxylic acid (105)

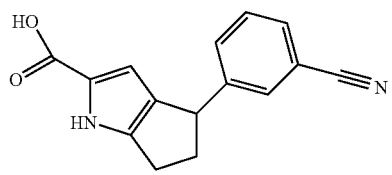

The title compound was synthesized from methyl 4-(3-cyanophenyl)-1,4,5,6-tetrahydrocyclopenta[b]pyrrole-2-carboxylate (0.021 g, 0.079 mmol) and lithium hydroxide (0.035 g, 0.83 mmol), according to General Procedure 7. A 1:1 mixture of THF and methanol (2 mL) was used. The resulting product was purified by reverse phase HPLC, eluting with a gradient of 40-80% MeOH: water (with 0.1% formic acid) to afford a light pink solid: 8.8 mg (44% yield). $^1$H NMR (400 MHz, METHANOL-d$_4$) δ ppm 2.21 (dd, J=6.35, 2.34 Hz, 1H), 2.79 (s, 2H), 2.91-3.02 (m, 1H), 4.26 (s, 1H), 6.52 (s, 1H), 7.42-7.48 (m, 1H), 7.49-7.56 (m, 3H); LCMS (ESI−) 251.2 (M−H); HPLC (UV=100%), (ELSD=100%).

2.113. Synthesis of 4-(biphenyl-4-yl)-1,4,5,6-tetrahydrocyclopenta[b]pyrrole-2-carboxylic acid (106)

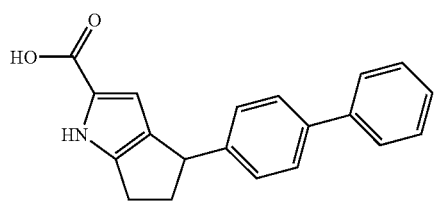

The title compound was synthesized from methyl 4-(biphenyl-4-yl)-1,4,5,6-tetrahydrocyclopenta[b]pyrrole-2-carboxylate (156 mg, 0.49 mmol) and lithium hydroxide monohydrate (83 mg, 1.97 mmol), according to General Procedure 7. A 1:2 mixture of THF and methanol (15 mL) was used. The resulting product was purified by flash chromatography (Isco CombiFlash) eluting with a gradient of 0-80% EtOAc/Heptane to give the title compound: 135 mg, 90.6%. $^1$H NMR (400 MHz, METHANOL-d$_4$) δ ppm 2.22-2.33 (m, 1H), 2.73-2.82 (m, 1H), 2.82-2.91 (m, 1H), 2.91-3.00 (m, 1H), 4.23 (t, J=7.20 Hz, 1H), 6.56 (s, J=1H), 7.24-7.32 (m, 3H) 7.37-7.43

(m, 2H), 7.50-7.55 (m, 2H), 7.57-7.61 (m, 2H); LCMS-MS (ESI+) 304.2 (M+H); HPLC (UV=100%), (ELSD=100%).

2.114. Synthesis of 4-(4-benzylphenyl)-1,4,5,6-tetrahydrocyclopenta[b]pyrrole-2-carboxylic acid (107)

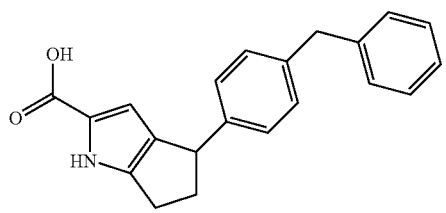

The title compound was synthesized from methyl 4-(4-benzylphenyl)-1,4,5,6-tetrahydrocyclopenta[b]pyrrole-2-carboxylate (150 mg, 0.45 mmol) and lithium hydroxide monohydrate (108 mg, 4.5 mmol), according to General Procedure 7. A 1:1 mixture of methanol (MeOH) and THF (10 mL) was used. The resulting product was purified by chromatography over silica gel (gradient 0 to 100% EtOAc in heptane over 20 min) to give a pure product (50 mg). $^1$H NMR (400 MHz, METHANOL-$d_4$) δ ppm 2.14-2.25 (m, 1H), 2.66-2.94 (m, 3H), 3.91 (s, 2H), 4.14 (t, J=7.30 Hz, 1H), 6.51 (s, 1H), 7.09 (s, 5H), 7.12-7.19 (m, 3H), 7.21-7.28 (m, 2H). LCMS m/e 316 (M−H) and 100% pure by HPLC.

2.115. Synthesis of 4-(4-chlorobenzylamino)-1,4,5,6-tetrahydrocyclopenta[b]pyrrole-2-carboxylic acid (108)

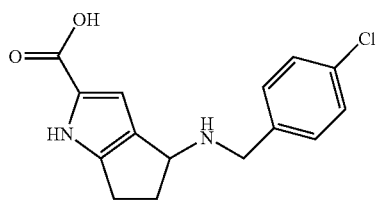

The title compound was synthesized from methyl 4-(4-chlorobenzylamino)-1,4,5,6-tetrahydrocyclopenta[b]pyrrole-2-carboxylate (0.023 g, 0.075 mmol) and lithium hydroxide (0.023 g, 0.55 mmol in 3 mL water), according to General Procedure 7. A 1:1 mixture of methanol (MeOH) and THF (6 mL) was used. The resulting product was purified by reverse phase chromatography, eluting with MeOH in water (0.1% formic acid) a to afford a yellow solid: 3 mg, 14% yield. $^1$H NMR (400 MHz, METHANOL-$d_4$) δ ppm 2.47-2.58 (m, 1H), 2.71-2.83 (m, 1H), 2.87-3.06 (m, 2H), 4.23 (q, J=13.16 Hz, 2H), 4.54-4.67 (m, 1H), 6.81 (s, 1H), 7.38-7.56 (m, 4H), 8.49 (s, 1H); LCMS-MS (ESI−) 289.0 (M−H).

Example 3

Synthesis of Pyrrole Analogs with 5-Substituted Fused Cyclopentanes 3.1. Synthesis of methyl 5,5-difluoro-1,4,5,6-tetrahydrocyclopenta[b]pyrrole-2-carboxylate 3.1.a Synthesis of ethyl 5,5-difluoro-4-oxo-1,4,5,6-tetrahydrocyclopenta[b]pyrrole-2-carboxylate

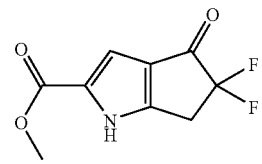

To a solution of methyl 4-oxo-1,4,5,6-tetrahydrocyclopenta[b]pyrrole-2-carboxylate (310 mg, 1.73 mmol) in anhydrous 5:1 THF/Et$_2$O (30 mL) at −78° C. under nitrogen was slowly added a freshly prepared solution of lithium diisopropylamide (0.5M in THF, 12.84 mL, 6.42 mmol). The reaction mixture was stirred at −78° C. for 30 minutes, warmed to −40° C. for a period of 1 h, then cooled again to −78° C. A solution of NFSI (1.20 g, 3.81 mmol, 2.20 eq.) in 3 mL anhydrous THF was added over a period of 15 min while maintaining −78° C. internal temperature. The reaction mixture was kept at −78° C. for 2 h and was then allowed to warm to rt over a period of 12 h. Analysis of the reaction mixture by TLC (9:1 heptane/EtOAc) showed that the reaction had reached completion. Water (10 mL) was carefully added to the reaction mixture followed by 0.5M HCl until the pH was about 2-3. The mixture was extracted with EtOAc (4×100 mL) and the combined extracts were washed with brine, dried (Na$_2$SO$_4$) and concentrated onto Celite. The compound was purified by flash chromatography (0-25% EtOAc/heptane) and reverse-phase chromatography (MeCN/H$_2$O, 0.05% TFA) to afford 111.2 mg of methyl 5,5-difluoro-4-oxo-1,4,5,6-tetrahydrocyclopenta[b]pyrrole-2-carboxylate (31%). $^1$H NMR (400 MHz, acetone-$d_6$) δ ppm 3.59 (t, 2H), 3.87 (s, 3H), 7.01 (s, 1H), 11.89 (bs, 1H); $^{19}$F NMR (400 MHz, ACETONE-$d_6$) δ ppm −107.19; LCMS-MS (ESI+) 216.0 (M+H).

3.1.b Synthesis of methyl 5,5-difluoro-1,4,5,6-tetrahydrocyclopenta[b]pyrrole-2-carboxylate

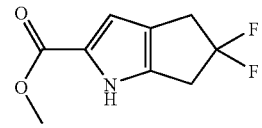

To a solution of methyl 5,5-difluoro-4-oxo-1,4,5,6-tetrahydrocyclopenta[b]pyrrole-2-carboxylate (111.2 mg, 0.517 mmol) in TFA (1 mL) under nitrogen at 25° C. was added triethylsilane (0.25 mL, 1.55 mmol) and the reaction mixture was stirred for 18 h at 25° C. TLC analysis (10% MeOH/DCM) indicated that all starting material had been consumed. The solvent was removed using a nitrogen stream and the residue was taken up in MeCN and purified by reverse-phase chromatography (MeCN/H₂O, 0.05% TFA) to afford 3.9 mg of methyl 5,5-difluoro-1,4,5,6-tetrahydrocyclopenta[b]pyrrole-2-carboxylate in 3.8% yield. ¹H NMR (400 MHz, ACETONE-d₆) δ ppm 3.15 (t, 2H), 3.31 (t, 2H), 3.76 (s, 3H), 6.64 (d, 1H), 10.83 (bs, 1H); ¹⁹F NMR (400 MHz, Acetone-d₆) δ ppm −86.73; LCMS-MS (ESI+) 202.0 (M+H).

3.2. Synthesis of methyl 5-methyl-1,4,5,6-tetrahydrocyclopenta[b]pyrrole-2-carboxylate

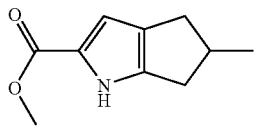

3.2.a) Synthesis of 1-tert-butyl 2-methyl 4-oxo-5,6-dihydrocyclopenta[b]pyrrole-1,2(4H)-dicarboxylate

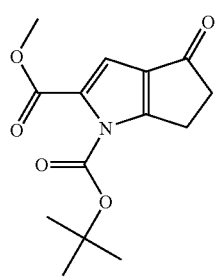

4-(Dimethylamino)pyridine (0.062 g, 0.51 mmol) was added to a stirred solution of methyl 4-oxo-1,4,5,6-tetrahydrocyclopenta[b]pyrrole-2-carboxylate (1.00 g, 5.58 mmol) in CH₂Cl₂ (DCM) (20 mL) at rt under nitrogen. A solution of di-tert-butyl dicarbonate (1.33 g, 6.09 mmol) in CH₂Cl₂ (10 mL) was then added and the solution was stirred for 18 h. The reaction was quenched with a saturated solution of NH₄Cl before extraction with EtOAc (3×50 mL). The combined extracts were washed with brine and dried over Na₂SO₄. Purification by column chromatography (0-50% EtOAc/heptane) gave the title compound as a clear, yellow oil (1.38 g, 88%). R_f (1:1 EtOAc/heptane)=0.40; ¹H NMR (400 MHz, CHLOROFORM-d) δ ppm 1.62 (s, 9H), 2.90-2.92 (m, 2H), 3.14-3.17 (m, 2H), 3.88 (s, 3H), 6.90 (s, 1H).

3.2.b) Synthesis of 1-tert-butyl 2-methyl 5-methyl-4-oxo-5,6-dihydrocyclopenta[b]pyrrole-1,2(4H)-dicarboxylate and methyl 5-methyl-4-oxo-1,4,5,6-tetrahydrocyclopenta[b]pyrrole-2-carboxylate

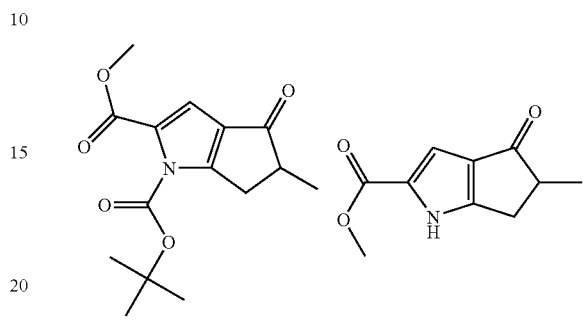

The title compound was synthesized from 1-tert-butyl 2-methyl 4-oxo-5,6-dihydrocyclopenta[b]pyrrole-1,2(4H)-dicarboxylate (0.53 g, 1.9 mmol) and iodomethane (0.297 g, 1.9 mmol) according to General Procedure 4. Purification of the resulting mixture by column chromatography (0-100% EtOAc/heptane), yielded both the BOC-protected product 1-tert-butyl 2-methyl 5-methyl-4-oxo-5,6-dihydrocyclopenta[b]pyrrole-1,2(4H)-dicarboxylate and the deprotected methyl 5-methyl-4-oxo-1,4,5,6-tetrahydrocyclopenta[b]pyrrole-2-carboxylate:

1-tert-butyl 2-methyl 5-methyl-4-oxo-5,6-dihydrocyclopenta[b]pyrrole-1,2(4H)-dicarboxylate was isolated as an orange solid (0.073 g, 13%). R_f (1:1 EtOAc:heptane)=0.54; ¹H NMR (400 MHz, CHLOROFORM-d) δ ppm 1.34 (d, J=7.6 Hz, 3H), 1.62 (s, 9H), 2.65-2.75 (m, 1H), 2.92-3.01 (m, 1H), 3.34-3.45 (m, 1H), 3.88 (s, 3H), 6.90 (s, 1H); LCMS-MS (ESI+) 294.1 (M+H).

Methyl 5-methyl-4-oxo-1,4,5,6-tetrahydrocyclopenta[b]pyrrole-2-carboxylate was isolated as an orange solid (0.045 g, 12%). R_f (1:1 EtOAc:heptane)=0.26; ¹H NMR (400 MHz, CHLOROFORM-d) δ ppm 1.34 (d, J=7.5 Hz, 3H), 2.56-2.61 (m, 1H), 2.98-3.06 (m, 1H), 3.21-3.27 (m, 1H), 3.89 (s, 3H), 6.98 (s, 1H).

3.2.c) Synthesis of ethyl 5-methyl-1,4,5,6-tetrahydrocyclopenta[b]pyrrole-2-carboxylate

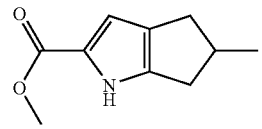

The title compound was synthesized from 1-tert-butyl 2-methyl 5-methyl-4-oxo-5,6-dihydrocyclopenta[b]pyrrole-1,2(4H)-dicarboxylate (0.053 g, 0.181 mmol) according to General Procedure 5.1. Purification by column chromatography (0-30% EtOAc/heptane) yielded methyl 5-methyl-1,4,5,6-tetrahydrocyclopenta[b]pyrrole-2-carboxylate as an off-white solid (0.004 g, 11% yield). R_f (1:1 EtOAc/heptane) =0.64; ¹H NMR (400 MHz, CHLOROFORM-d) δ ppm 1.21

(d, J=6.7 Hz, 3H), 2.20-2.36 (m, 2H), 2.70-3.00 (m, 3H), 3.82 (s, 3H), 6.64 (s, 1H); LCMS-MS (ESI+) 180.1 (M+H).

3.3. Synthesis of methyl 5-benzyl-1,4,5,6-tetrahydrocyclopenta[b]pyrrole-2-carboxylate

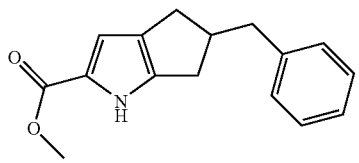

3.3.a) Synthesis of 1-tert-butyl 2-methyl 5-benzyl-4-oxo-5,6-dihydrocyclopenta[b]pyrrole-1,2(4H)-dicarboxylate and methyl 5-benzyl-4-oxo-1,4,5,6-tetrahydrocyclopenta[b]pyrrole-2-carboxylate

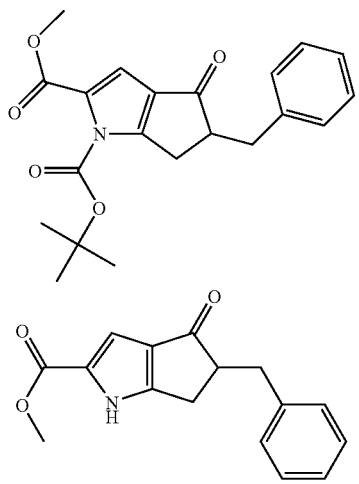

The title compounds were synthesized from 1-tert-butyl 2-methyl 4-oxo-5,6-dihydrocyclopenta[b]pyrrole-1,2(4H)-dicarboxylate (0.53 g, 1.9 mmol) and n-butyllithium in hexanes (10.0 mL, 25.0 mmol, 2.5 M solution) according to General Procedure 4. Purification of the resulting mixture by column chromatography (0-100% EtOAc/heptane), yielded both the BOC-protected product (1-tert-butyl 2-methyl 5-benzyl-4-oxo-5,6-dihydrocyclopenta[b]pyrrole-1,2(4H)-dicarboxylate) and the deprotected methyl 5-benzyl-4-oxo-1,4,5,6-tetrahydrocyclopenta[b]pyrrole-2-carboxylate:

1-tert-Butyl 2-methyl 5-benzyl-4-oxo-5,6-dihydrocyclopenta[b]pyrrole-1,2(4H)-dicarboxylate was isolated as an orange solid (0.098 g, 14% yield). $R_f$ (1:1 EtOAc:heptane)=0.46; $^1$H NMR (400 MHz, CHLOROFORM-d) δ ppm 1.57 (s, 9H), 2.74-2.77 (m, 1H), 2.84-2.89 (m, 1H), 3.11-3.18 (m, 1H), 3.20-3.26 (m, 1H), 3.34-3.45 (m, 1H), 3.87 (s, 3H), 6.90 (s, 1H), 7.20-7.32 (m, 5H); LCMS-MS (ESI+) 370.1 (M+H).

Methyl 5-benzyl-4-oxo-1,4,5,6-tetrahydrocyclopenta[b]pyrrole-2-carboxylate was isolated as an orange solid (0.150 g, 29% yield). $R_f$ (1:1 EtOAc:heptane)=0.30; $^1$H NMR (400 MHz, CHLOROFORM-d) δ ppm 2.67-2.77 (m, 2H), 2.94- 3.01 (m, 1H), 3.20-3.26 (m, 1H), 3.34-3.40 (m, 1H), 3.88 (s, 3H), 6.99 (s, 1H), 7.20-7.32 (m, 5H).

3.3.b) Synthesis of methyl 5-benzyl-1,4,5,6-tetrahydrocyclopenta[b]pyrrole-2-carboxylate

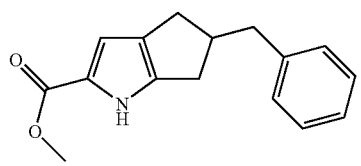

The title compound was synthesized from a mixture of 1-tert-butyl 2-methyl 5-benzyl-4-oxo-5,6-dihydrocyclopenta[b]pyrrole-1,2(4H)-dicarboxylate and methyl 5-benzyl-4-oxo-1,4,5,6-tetrahydrocyclopenta[b]pyrrole-2-carboxylate (0.267 g, 0.99 mmol, using the formula weight of the free pyrrole) according to General Procedure 5.1. Purification by column chromatography (0-30% EtOAc/heptane) yielded methyl 5-benzyl-1,4,5,6-tetrahydrocyclopenta[b]pyrrole-2-carboxylate as an off-white solid (0.017 g, 7% yield). $R_f$ (1:1 EtOAc:heptane)=0.66; $^1$H NMR (400 MHz, CHLOROFORM-d) δ ppm 2.30-2.52 (m, 2H), 2.72-2.90 (m, 4H), 3.10-3.25 (m, 1H), 3.82 (s, 3H), 6.64 (s, 1H), 7.21-7.33 (m, 5H).

3.4. Synthesis of 5,5-difluoro-1,4,5,6-tetrahydrocyclopenta[b]pyrrole-2-carboxylic acid (21)

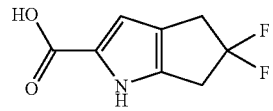

The title compound was synthesized from methyl 5,5-difluoro-1,4,5,6-tetrahydrocyclopenta[b]pyrrole-2-carboxylate and lithium hydroxide monohydrate according to General Procedure 7. The material was purified by reverse-phase chromatography (MeCN/H$_2$O, 0.05% TFA) to afford 1.6 mg of 5,5-difluoro-1,4,5,6-tetrahydrocyclopenta[b]pyrrole-2-carboxylic acid in 45.0% yield. $^{19}$F NMR (400 MHz, acetone-d$_6$) δ ppm −86.73; LCMS-MS (ESI+) 188.0 (M+H).

3.5. Synthesis of 5-methyl-1,4,5,6-tetrahydrocyclopenta[b]pyrrole-2-carboxylic acid (22)

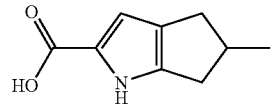

The title compound was synthesized from ethyl 5-methyl-1,4,5,6-tetrahydrocyclopenta[b]pyrrole-2-carboxylate (0.017 g, 0.09 mmol) and lithium hydroxide monohydrate (0.019 g, 0.45 mmol) according to General Procedure 7. The crude was purified by reverse phase HPLC (50-100% MeOH:water, 0.1% formic acid) to give 5-methyl-1,4,5,6-tetrahydrocyclopenta[b]pyrrole-2-carboxylic acid (22) as a light brown solid (2.1 mg, 14%). $R_f$ (1:1 EtOAc:heptane)=0.12; $^1$H NMR (400 MHz, METHANOL-d$_4$) δ ppm 1.19 (d, J=6.6, 3H), 2.17-2.20 (m, 1H), 2.26-2.32 (m, 1H), 2.75-2.80 (m, 1H), 2.84-2.90 (m, 2H), 6.56 (s, 1H); LCMS-MS (ESI+) 166.0 (M+H); HPLC (UV=100%), (ELSD=100%).

3.6. Synthesis of 5-benzyl-1,4,5,6-tetrahydrocyclopenta[b]pyrrole-2-carboxylic acid (23)

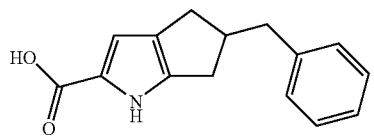

The title compound was synthesized from methyl 5-benzyl-1,4,5,6-tetrahydrocyclopenta[b]pyrrole-2-carboxylate (0.017 g, 0.065 mmol) and lithium hydroxide monohydrate (0.019 g, 0.45 mmol) according to General Procedure 7. The crude product was purified by reverse phase HPLC (40-100% MeOH: water, 0.1% formic acid), to give 5-benzyl-1,4,5,6-tetrahydrocyclopenta[b]pyrrole-2-carboxylic acid (23) as a light brown solid (6.1 mg, 39%). $R_f$ (1:1 EtOAc:heptane)= 0.12; $^1$H NMR (400 MHz, METHANOL-$d_4$) δ ppm 2.30-2.49 (m, 2H), 2.62-2.90 (m, 4H), 3.08-3.20 (m, 1H), 6.57 (s, 1H), 7.16-7.30 (m, 5H); LCMS-MS (ESI+) 242.3 (M+H); HPLC (UV=100%), (ELSD=100%).

Example 4

Synthesis of Pyrrole Analogs with 6-Substituted Fused Cyclopentanes

4.1. Synthesis of ethyl 6-oxo-1,4,5,6-tetrahydrocyclopenta[b]pyrrole-2-carboxylate

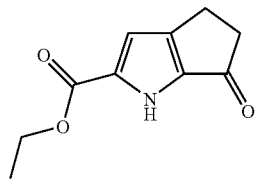

A solution of the ethyl 1,4,5,6-tetrahydrocyclopenta[b]pyrrole-2-carboxylate (1.0 g, 5.58 mmol) in THF/Water (10:1, 11 mL) at 0° C. was deoxygenated by passing a stream of dry nitrogen gas for 10 min. A solution of 2,3-dichloro-5,6-dicyano-1,4-benzochinone (DDQ) in THF (4 mL) was added dropwise over 5 min. After stirring for 1.5 h, the cooling bath was removed and stirring was continued at rt. Silica gel was added, the solvent stripped off and the silica gel-imbedded material was purified by flash chromatography (0-60% EtOAc/Heptane) to afford ethyl 6-oxo-1,4,5,6-tetrahydrocyclopenta[b]pyrrole-2-carboxylate as a taupe solid (270 mg, 25%). $^1$H NMR (400 MHz, CHLOROFORM-d) δ ppm 1.39 (t, J=7.13 Hz, 3H), 2.87-2.95 (m, 4H), 4.39 (q, J=7.13 Hz, 2H), 6.78 (d, J=1.66 Hz, 1H), 9.86 (s, 1H); LCMS-MS (ESI+) 193.9 (M+H).

The inventors have determined that the DDQ oxidation in this experiment yielded the 6-oxo instead of the 4-oxo product (see, e.g., oxidation of a cyclopenta[b]pyrrole as described in Quizon-Colquitt, D. M.; Lash, T. D. *J. Heterocyclic Chemistry* 1993, 30, 477).

4.2. Synthesis of methyl 6-oxo-1,4,5,6-tetrahydrocyclopenta[b]pyrrole-2-carboxylate

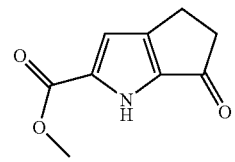

4.2.a) Synthesis of (Z)-methyl 4-(3-tert-butoxy-3-oxoprop-1-enyl)-1H-pyrrole-2-carboxylate and (E)-methyl 4-(3-tert-butoxy-3-oxoprop-1-enyl)-1H-pyrrole-2-carboxylate

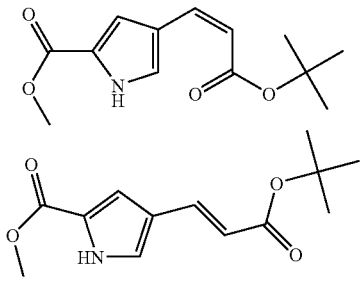

Methyl 5-formyl-1H-pyrrole-2-carboxylate (16.3 g) and its regioisomer methyl 4-formyl-1H-pyrrole-2-carboxylate (6.94 g) were obtained (combined yield of 95%) from a Vilsmeier formylation of 1H-pyrrole-2-carboxylic acid methyl ester via exhaustive extraction of the neutralized aqueous layer with EtOAc to provide a better recovery of the more polar 4-formyl isomer [see, e.g., Charkraborty, T. K. et al., *Tetrahedron Lett.* 2006, 47: 4631 and Denmark, S. E.; Matsuhashi, H. *J. Org. Chem.* 2002, 67: 3479].

To a suspension of NaH (0.54 g, 13.58 mmol; 60% dispersed in oil) in THF (30 mL) at 0° C. was added (tert-butoxycarbonylmethyl)triphenylphosphonium bromide (6.21 g, 13.585 mmol) as a solid in three portions. The cooling bath was removed and the mixture was stirred at rt for 30 min before cooling to 0° C. Methyl 4-formyl-1H-pyrrole-2-carboxylate (1.6 g, 10.45 mmol) in THF (10 mL) was added dropwise over 10 min. The cooling bath was removed, and the reaction mixture was stirred at rt for about 12 h. The crude product was dried onto silica gel and was purified by flash chromatography (0-20% EtOAc/Heptane) to afford two isomeric compounds:

(Z)-methyl 4-(3-tert-butoxy-3-oxoprop-1-enyl)-1H-pyrrole-2-carboxylate (0.81 g, 26.2%) as a white solid; $^1$H NMR (400 MHz, CHLOROFORM-d) δ ppm 1.52 (s, 9H), 3.87 (s, 3H), 5.65 (d, J=12.59 Hz, 1H), 6.67 (d, J=12.64 Hz, 1H), 7.25 (dd, J=2.54, 1.56 Hz, 1H), 7.97 (dd, J=3.10, 1.44 Hz, 1H), 9.14 (br s, 1H); LCMS-MS (ESI+) 195.7 (M-56).

(E)-methyl 4-(3-tert-butoxy-3-oxoprop-1-enyl)-1H-pyrrole-2-carboxylate (1.8 g, 57.8%) as a white solid; $^1$H NMR (400 MHz, CHLOROFORM-d) δ ppm 1.52 (s, 9H), 3.88 (s, 3H), 6.12 (d, J=15.86 Hz, 1H), 7.08 (m, 1H), 7.14 (dd, J=3.03, 1.56 Hz, 1H), 7.49 (d, J=15.86 Hz, 1H), 9.22 (br s, 1H); LCMS-MS (ESI+) 195.8 (M-56).

4.2.b) Synthesis of methyl 4-(3-tert-butoxy-3-oxo-propyl)-1H-pyrrole-2-carboxylate

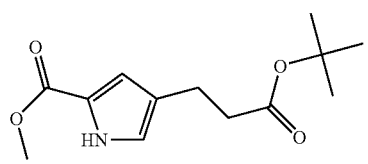

To a solution of methyl 4-(3-tert-butoxy-3-oxoprop-1-enyl)-1H-pyrrole-2-carboxylate (2.0 g, 7.96 mmol) in EtOAc (20 mL) under nitrogen was added 10% Pd/C. The flask was evacuated and refilled with hydrogen three times. The reaction mixture was stirred for 2 h. The catalyst was removed by filtration through Celite and the filtrate was concentrated to give methyl 4-(3-tert-butoxy-3-oxopropyl)-1H-pyrrole-2-carboxylate as a white solid (2.02 g, 100%). $^1$H NMR (400 MHz, CHLOROFORM-d) δ ppm 1.43 (s, 9H), 2.48 (t, J=7.59 Hz, 2H), 2.77 (t, J=7.54 Hz, 2H), 3.84 (s, 3H), 6.77 (dd, J=2.37, 1.93 Hz, 2H), 930 (br s, 1H); LCMS-MS (ESI+) 198.2 (M-isobutylene).

4.2.c) Synthesis of 3-(5-(methoxycarbonyl)-1H-pyrrol-3-yl)propanoic acid

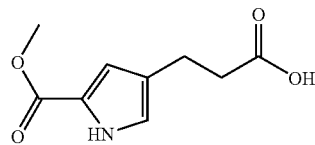

Methyl 4-(3-tert-butoxy-3-oxopropyl)-1H-pyrrole-2-carboxylate (473 g, 1.87 mmol) was treated for about 12 h at rt with 4 N HCl (5 mL). The solvent was removed and the white solid product was dried to give 350 mg (95%) of 3-(5-(methoxycarbonyl)-1H-pyrrol-3-yl)propanoic acid. $^1$H NMR (400 MHz, CHLOROFORM-d) δ ppm 2.64 (t, J=7.35 Hz, 2H), 2.84 (t, J=7.35 Hz, 2H), 3.85 (s, 3H), 6.79 (dd, J=6.66, 2.22 Hz, 2H), 9.08 (br s, 1H); LCMS-MS (ESI+) 198.2 (M+H).

4.2.d) Synthesis of methyl 6-oxo-1,4,5,6-tetrahydro-cyclopenta[b]pyrrole-2-carboxylate

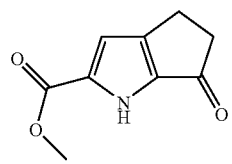

To a polyphosphoric acid (115%, 1.6 g) was added 3-(5-(methoxycarbonyl)-1H-pyrrol-3-yl)propanoic acid (174 mg, 0.88 mmol) and 1,2-dichloroethane (8 mL). The reaction mixture was heated for 1 h at 100° C. Water (20 mL) was added and the mixture was carefully poured into a 50 mL Erlenmeyer flask containing solid sodium bicarbonate and ice. The reaction was neutralized (pH 7) and was then extracted with EtOAc (5×50 mL). The combined organic extracts were washed with water, NaHCO$_3$ and brine, dried (Na$_2$SO$_4$) filtered and concentrated. Purification by flash chromatography (0-40% EtOAc/Heptane) afforded methyl 6-oxo-1,4,5,6-tetrahydrocyclopenta[b]pyrrole-2-carboxylate (106 mg, 67%). $^1$H NMR (400 MHz, CHLOROFORM-d) δ ppm 2.91 (s, 4H), 3.92 (s, 3H), 6.78 (d, J=1.76 Hz, 1H), 9.33 (br s, 1H); LCMS-MS (ESI+) 180.2 (M+H).

4.3. Synthesis of ethyl 6-benzyl-1,4,5,6-tetrahydro-cyclopenta[b]pyrrole-2-carboxylate

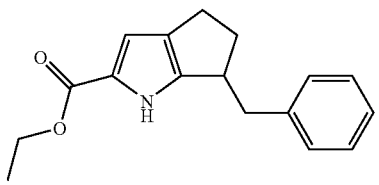

4.3.a) Synthesis of ethyl 6-oxo-1-((2-(trimethylsilyl)ethoxy)methyl)-1,4,5,6-tetrahydrocyclopenta[b]pyrrole-2-carboxylate

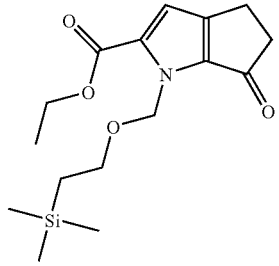

To sodium hydride (60% dispersion in mineral oil) (0.46 g, 11.4 mmol, 1.1 equiv) in anhydrous DMF (10 mL) under a nitrogen atmosphere at 0° C. was added dropwise a solution ethyl 6-oxo-1,4,5,6-tetrahydrocyclopenta[b]pyrrole-2-carboxylate (2.0 g, 10 mmol, 1 equiv) in anhydrous DMF (15 mL). After stirring for 30 min at 0° C., SEM-Cl (2.1 g, 12.4 mmol, 1.2 equiv) was then added dropwise over 5 min and the mixture warmed to rt overnight. The reaction was quenched by pouring the reaction contents into a beaker of ice water. It was extracted with EtOAc (4×50 mL) and the combined organic extracts were washed with brine, dried (Na$_2$SO$_4$), filtered and concentrated. The crude product was purified by flash chromatography (0-30% EtOAc/heptane) to afford 2.9 g of ethyl 6-oxo-1-((2-(trimethylsilyl)ethoxy)methyl)-1,4,5,6-tetrahydrocyclopenta[b]pyrrole-2-carboxylate (86% yield). $^1$H NMR (400 MHz, CHLOROFORM-d) δ ppm 6.84 (s, 1H), 5.87 (s, 2H), 4.35 (q, J=7.13 Hz, 2H), 3.57 (dd, J=8.59, 7.71 Hz, 2H), 2.82-2.92 (m, 4H), 1.38 (t, J=7.14 Hz, 3H), 0.85-0.92 (m, 2H), −0.05 (s, 9H).

4.3.b) Synthesis of (E/Z)-ethyl 6-benzylidene-1-((2-(trimethylsilyl)ethoxy)methyl)-1,4,5,6-tetrahydrocyclopenta[b]pyrrole-2-carboxylate

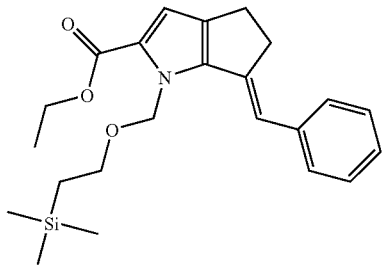

The title compound was synthesized from 6-oxo-1-(2-trimethylsilanyl-ethoxymethyl)-1,4,5,6-tetrahydrocyclopenta[b]pyrrole-2-carboxylic acid ethyl ester (0.2 g, 0.62 mmol) and benzylmagnesium chloride (0.7 mL, 2M in THF, 1.36 mmol) according to General Procedure 3. The crude product was semi-purified by flash chromatography (0-20% EtOAc/heptane) to afford 0.14 g of (E/Z)-ethyl 6-benzylidene-1-((2-(trimethylsilyl)ethoxy)methyl)-1,4,5,6-tetrahydrocyclopenta[b]pyrrole-2-carboxylate, which was used in the next step without further purification.

4.3.c) Synthesis of (E/Z)-ethyl 6-benzylidene-1,4,5,6-tetrahydrocyclopenta[b]pyrrole-2-carboxylate

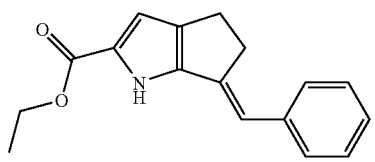

To (E/Z)-ethyl 6-benzylidene-1-((2-(trimethylsilyl)ethoxy)methyl)-1,4,5,6-tetrahydrocyclopenta[b]pyrrole-2-carboxylate (0.12 g, 0.3 mmol) was added a solution of tetrabutylammonium fluoride in THF (4 mL, 1M). The vial was capped tightly and heated to 65° C. for 2 h. The reaction mixture was then diluted with a 1:1 mixture of water and brine (30 mL). The resulting aqueous mixture was extracted with EtOAc (4×30 mL). The combined organic phases were washed with brine, dried (Na₂SO₄), filtered and concentrated. The crude product was purified using reverse phase preparative HPLC (methanol/water with 0.1% formic acid and 1% acetonitrile (70%-100%) to afforded 8.1 mg of a 1:1 mixture of (E)- and (Z)-ethyl 6-benzylidene-1,4,5,6-tetrahydrocyclopenta[b]pyrrole-2-carboxylate (10%). LCMS m/e 268 (M+H); ¹H NMR (400 MHz, CHLOROFORM-d) δ ppm 8.88 (br. s., 1H), 7.40-7.44 (m, 2H), 7.34-7.39 (m, 2H), 7.18-7.24 (m, 1H), 6.73 (d, J=1.64 Hz, 1H), 6.49 (t, J=2.38 Hz, 1H), 4.35 (q, J=7.11 Hz, 2H), 3.36 (td, J=5.52, 2.55 Hz, 2H), 2.82-2.87 (m, 2H), 1.38 (t, J=7.13 Hz, 3H).

4.3.d) Synthesis of ethyl 6-benzyl-1,4,5,6-tetrahydrocyclopenta[b]pyrrole-2-carboxylate

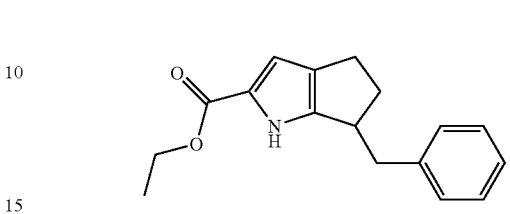

The title compound was synthesized from (E/Z)-ethyl 6-benzylidene-1,4,5,6-tetrahydrocyclopenta[b]pyrrole-2-carboxylate (29.9 mg, 0.11 mmol) according to General Procedure 6 to afford 23.3 mg of ethyl 6-benzyl-1,4,5,6-tetrahydrocyclopenta[b]pyrrole-2-carboxylate in 77% yield. LCMS m/e 292 (M+Na); 268 (M−H); ¹H NMR (400 MHz, CHLOROFORM-d) δ ppm 8.30 (br. s., 1H), 7.32-7.38 (m, 2H), 7.25-7.30 (m, 1H), 7.18-7.24 (m, 2H), 6.63 (d, J=1.73 Hz, 1H), 4.26 (q, J=7.11 Hz, 2H), 3.33-3.43 (m, 1H), 2.96 (dd, J=13.39, 6.55 Hz, 1H), 2.76 (dd, J=13.36, 8.99 Hz, 1H), 2.51-2.68 (m, 3H), 2.09-2.21 (m, 1H), 1.32 (t, J=7.13 Hz, 3H).

4.4. Synthesis of ethyl 6-phenethyl-1,4,5,6-tetrahydrocyclopenta[b]pyrrole-2-carboxylate

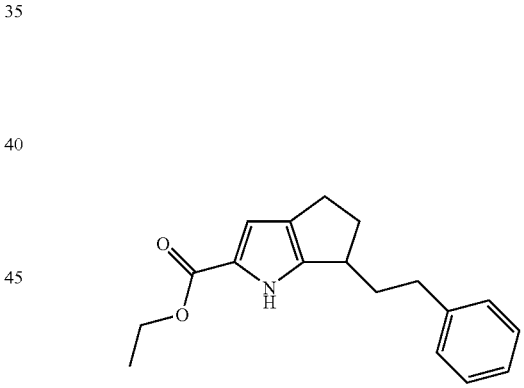

The title compound was synthesized from ethyl 6-oxo-1,4,5,6-tetrahydrocyclopenta[b]pyrrole-2-carboxylate (0.3 g, 1.55 mmol) and phenethylmagnesium bromide (7.5 mL, 0.5 M in THF, 3.7 mmol) according to General Procedure 3 to afford 96.5 mg of (E/Z)-ethyl 6-(2-phenylethylidene)-1,4,5,6-tetrahydrocyclopenta[b]pyrrole-2-carboxylate, followed by General Procedure 6 to give 87.3 mg of ethyl 6-phenethyl-1,4,5,6-tetrahydrocyclopenta[b]pyrrole-2-carboxylate in 90% purity. ¹H NMR (400 MHz, CHLOROFORM-d) δ ppm 8.55 (br. s., 1H), 7.29-7.35 (m, 2H), 7.19-7.26 (m, 3H), 6.64

(d, J=1.59 Hz, 1H), 4.23-4.33 (m, 2H), 3.02-3.13 (m, 1H), 2.51-2.82 (m, 5H), 1.94-2.14 (m, 2H), 1.78-1.90 (m, 1H), 1.34 (t, J=7.13 Hz, 3H).

4.5. Synthesis of 6-oxo-1,4,5,6-tetrahydro-cyclopenta[b]pyrrole-2-carboxylic acid (24)

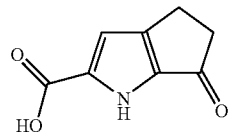

The title compound was synthesized from ethyl 6-oxo-1,4,5,6-tetrahydrocyclopenta[b]pyrrole-2-carboxylate (90 mg, 0.47 mmol) and lithium hydroxide monohydrate (78 mg, 1.86 mmol) according to General Procedure 7 (56 mg, 77%). $^1$H NMR (400 MHz, METHANOL-$d_4$) δ ppm 2.84-2.91 (4H), 6.73 (s, 1H); LCMS-MS (ESI+) 165.8 (M+H); HPLC (UV=100%), (ELSD=100%).

4.6. Synthesis of (E/Z)-6-benzylidene-1,4,5,6-tetrahydrocyclopenta[b]pyrrole-2-carboxylic acid (25)

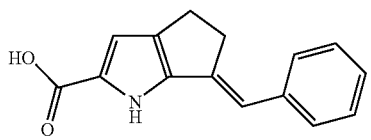

The title compound was synthesized from methyl 6-benzylidene-1,4,5,6-tetrahydrocyclopenta[b]pyrrole-2-carboxylate and NaOH according to General Procedure 7. The crude product was purified using preparative HPLC (40%-100% methanol/water with 1% formic acid and 1% acetonitrile) to afford 2.6 mg of a 1:1 mixture of (E)- and (z)-6-benzylidene-1,4,5,6-tetrahydrocyclopenta[b]pyrrole-2-carboxylic acid (25) in 36% yield. LCMS m/e 240 (M+H). $^1$H NMR (400 MHz, METHANOL-$d_4$) δ ppm 8.43 (br. s., 1H), 7.42 (d, J=7.64 Hz, 2H), 7.32 (t, J=7.75 Hz, 2H), 7.15 (t, J=7.35 Hz, 1H), 6.68 (t, J=2.25 Hz, 1H), 6.64 (s, 1H), 2.78-2.83 (m, 2H).

4.7. Synthesis of 6-benzyl-1,4,5,6-tetrahydrocyclopenta[b]pyrrole-2-carboxylic acid (26)

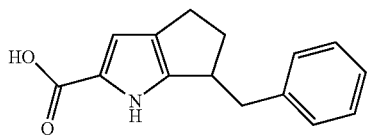

The title compound was synthesized from ethyl 6-benzyl-1,4,5,6-tetrahydrocyclopenta[b]pyrrole-2-carboxylate and NaOH according to General Procedure 7.
The crude product was purified using preparative HPLC (40%-100% methanol/water with 1% formic acid and 1% acetonitrile) to afford 9.9 mg of 6-benzyl-1,4,5,6-tetrahydrocyclopenta[b]pyrrole-2-carboxylic acid (26) in 47% yield. LCMS m/e 264 (M+Na); 240 (M–H). $^1$H NMR (400 MHz, METHANOL-$d_4$) δ ppm 7.22-7.28 (m, 2H), 7.14-7.20 (m, 3H), 6.54 (s, 1H), 3.33-3.38 (m, 1H), 3.03-3.15 (m, 1H), 2.70 (dd, J=13.45, 8.61 Hz, 1H), 2.35-2.46 (m, 3H), 2.04-2.16 (m, 1H).

4.8. Synthesis 6-phenethyl-1,4,5,6-tetrahydrocyclopenta[b]pyrrole-2-carboxylic acid (27)

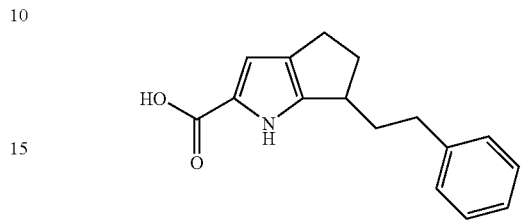

The title compound was synthesized from ethyl 6-phenethyl-1,4,5,6-tetrahydrocyclopenta[b]pyrrole-2-carboxylate (87.3 mg, 0.31 mmol) and NaOH according to General Procedure 7. The crude product was purified by preparative HPLC (50%-100% methanol/water with 1% formic acid and 1% acetonitrile) to afford 22.6 mg of 6-phenethyl-1,4,5,6-tetrahydrocyclopenta[b]pyrrole-2-carboxylic acid (27) in 29% yield. LCMS m/e 254 (M–H); $^1$H NMR (400 MHz, METHANOL-$d_4$) δ ppm 7.18-7.28 (m, 4H), 7.11-7.17 (m, 1H), 6.58 (s, 1H), 3.00-3.10 (m, 1H), 2.48-2.71 (m, 5H), 2.00-2.15 (m, 2H), 1.66-1.79 (m, 1H).

The enantiomers of 6-phenethyl-1,4,5,6-tetrahydrocyclopenta[b]pyrrole-2-carboxylic acid were separated according to General Procedure 8 using 25% of a mixture of 50:50 methanol/isopropanol in $CO_2$ with 0.2% diethylamine to give 6-phenethyl-1,4,5,6-tetrahydrocyclopenta[b]pyrrole-2-carboxylic acid (28) (peak 2, retention time=10.2 min; 97% ee) and 6-phenethyl-1,4,5,6-tetrahydrocyclopenta[b]pyrrole-2-carboxylic acid (29) (peak 1, retention time=9.2 min; 99% ee).

4.9. Synthesis of ethyl 6-methyl-1,4,5,6-tetrahydrocyclopenta[b]pyrrole-2-carboxylate

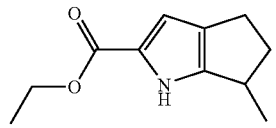

The title compound was synthesized from SEM-protected ethyl 6-oxo-1,4,5,6-tetrahydrocyclopenta[b]pyrrole-2-carboxylate (ethyl 6-oxo-1-((2-(trimethylsilyl)ethoxy)methyl)-1,4,5,6-tetrahydrocyclopenta[b]pyrrole-2-carboxylate) (0.5 g, 2.79 mmol) and methylmagnesium bromide (4.85 mL, 6.8 mmol, 1.4 M in toluene, 2.2 equiv) according to General Procedure 3 to give ethyl 6-methyl-1-((2-(trimethylsilyl)ethoxy)methyl)-1,4-dihydrocyclopenta[b]pyrrole-2-carboxylate. The ethyl 6-methyl-1-((2-(trimethylsilyl)ethoxy)methyl)-1,4-dihydrocyclopenta[b]pyrrole-2-carboxylate was then deprotected according to General Procedure 10.3 to provide ethyl 6-methyl-1,4-dihydrocyclopenta[b]pyrrole-2-carboxylate, which was subjected to hydrogenation according to General Procedure 6. The crude product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 60% methanol and increasing to 100% over 7 minutes) afforded the title compound (20.8 mg, 47%). LCMS m/e 216 (M+Na). $^1$H NMR (400 MHz, CHLOROFORM-d) δ ppm 1.24 (d, J=6.83 Hz, 3H), 1.35 (t, J=7.11 Hz, 3H), 1.90-2.02 (m, 1H), 2.50-2.70 (m, 3H), 3.08-3.20 (m, J=6.92, 6.92, 6.92, 6.92, 6.77 Hz, 1H), 4.30 (qd, J=7.12, 1.39 Hz, 2H), 6.65 (d, J=1.64 Hz, 1H), 8.72 (br. s, 1H).

4.10. Synthesis of methyl 6-propyl-1,4,5,6-tetrahydrocyclopenta[b]pyrrole-2-carboxylate

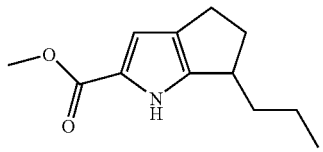

The title compound was synthesized from methyl 6-oxo-1,4,5,6-tetrahydrocyclopenta[b]pyrrole-2-carboxylate (0.5 g, 2.79 mmol) and n-propylmagnesium bromide (3.5 mL, 6.97 mmol, 2.0 M in ether, 2.5 equiv) according to General Procedure 3 to give the exocyclic olefin-containing compound (E)-methyl 6-propylidene-1,4,5,6-tetrahydrocyclopenta[b]pyrrole-2-carboxylate, followed by hydrogenation according to General Procedure 6, and was purified by column chromatography (Isco CombiFlash) eluting with a gradient of 0-100% EtOAc/heptane to give the title compound. $^1$H NMR (400 MHz, CHLOROFORM-d) δ ppm 0.96 (t, J=7.1 Hz, 3H), 1.35-1.53 (m, 3H), 1.57-1.68 (m, 1H), 1.94-2.09 (m, 1H), 2.47-2.69 (m, 3H), 2.98-3.10 (m, 1H), 3.83 (s, 3H), 6.64 (d, J=1.61 Hz, 1H), 8.69 (br. s, 1H).

4.11. Synthesis of methyl 6-(3-fluorophenyl)-1,4,5,6-tetrahydrocyclopenta[b]pyrrole-2-carboxylate

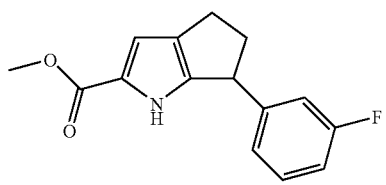

The title compound was synthesized in two steps. First, methyl 6-oxo-1,4,5,6-tetrahydrocyclopenta[b]pyrrole-2-carboxylate (447 mg, 2.5 mmol) was reacted with (3-fluorophenyl)magnesium bromide (0.5 M in hexanes, 13 mL, 6.3 mmol) according to General Procedure 3. The resulting crude product was converted to the title compound by hydrogenation according to General Procedure 6 (with 5% Pd/C). The crude product was purified by chromatography, eluting with heptane-EtOAc, gradient 0 to 40% EtOAc. $^1$H NMR (400 MHz, CHLOROFORM-d) δ ppm 2.24-2.35 (m, 1H), 2.61-2.71 (m, 1H), 2.71-2.81 (m, 1H), 2.87-2.98 (m, 1H), 3.81 (s, 3H), 4.24 (t, J=7.54 Hz, 1H), 6.71 (d, J=1.51 Hz, 1H), 6.81 (dt, J=9.81, 1.85 Hz, 1H), 6.88-6.93 (m, 2H), 7.25 (s, 1H), 8.60 (br. s, 1H).

4.12. Synthesis of ethyl 6-(3,4-difluorophenyl)-1,4,5,6-tetrahydrocyclopenta[b]pyrrole-2-carboxylate

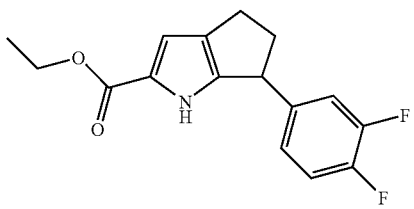

The title compound was synthesized in two steps. First, ethyl 6-oxo-1,4,5,6-tetrahydrocyclopenta[b]pyrrole-2-carboxylate was reacted with (3,4-difluorophenyl)magnesium bromide according to General Procedure 3. The resulting product was converted to the title compound by hydrogenation according to General Procedure 6.

4.13. Synthesis of ethyl 6-(4-chlorophenyl)-1,4,5,6-tetrahydrocyclopenta[b]pyrrole-2-carboxylate

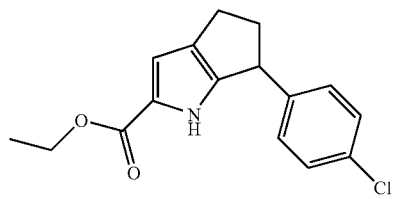

The title compound was synthesized in two steps. First, ethyl 6-oxo-1,4,5,6-tetrahydrocyclopenta[b]pyrrole-2-carboxylate (0.3 g, 1.55 mmol) was reacted with 4-chlorophenyl magnesium bromide (6.2 mL, 1 M in ether, 6.2 mmol, 4 equiv) according to General Procedure 3 to give the endocyclic olefin-containing compound ethyl 6-(4-chlorophenyl)-1,4-dihydrocyclopenta[b]pyrrole-2-carboxylate, followed by hydrogenation according to General Procedure 6, and was purified by column chromatography (Isco CombiFlash) using a 0-30% gradient (EtOAc/Heptane) over 22 minutes. 90.7 mg. LCMS m/e 312 (M+Na). $^1$H NMR (400 MHz, CHLOROFORM-d) δ ppm 1.33 (t, J=7.11 Hz, 3H), 2.27 (dddd, J=12.83, 8.60, 6.36, 6.21 Hz, 1H), 2.58-2.83 (m, 2H), 2.85-3.01 (m, J=12.81, 8.47, 8.47, 4.28 Hz, 1H), 4.27 (tt, J=7.12, 3.63 Hz, 3H), 6.73 (d, J=1.64 Hz, 1H), 7.06 (q, J=4.42 Hz, 2H), 7.28 (d, J=8.35 Hz, 2H), 8.63 (br. s, 1H).

4.14. Synthesis of methyl 6-(3-chlorophenyl)-1,4,5,6-tetrahydrocyclopenta[b]pyrrole-2-carboxylate

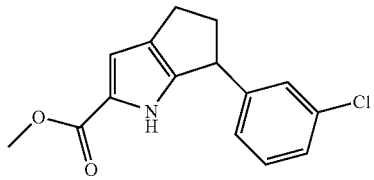

The title compound was synthesized in two steps. First, methyl 6-oxo-1,4,5,6-tetrahydrocyclopenta[b]pyrrole-2-carboxylate (0.508 g, 2.84 mmol) was reacted with 3-chlorophenylmagnesium bromide (0.5 M in THF, 14 mL, 7.0 mmol) according to General Procedure 3 to give the carbinol-containing methyl 6-(3-chlorophenyl)-6-hydroxy-1,4,5,6-tetrahydrocyclopenta[b]pyrrole-2-carboxylate, followed by hydrogenation according to General Procedure 6 (with $Pt_2O$), and was purified by column chromatography (Isco CombiFlash) eluting with a gradient of 0-30% EtOAc/heptane affording the title compound: 0.99 g (29% yield). $^1$H NMR (400 MHz, ACETONE-$d_6$) δ ppm 2.27 (ddt, J=13.17, 8.32, 5.22, 5.22 Hz, 1H), 2.58-2.67 (m, 1H), 2.72-2.79 (m, 1H), 2.90-3.01 (m, 1H), 3.73 (s, 3H), 4.31 (dd, J=8.57, 5.20 Hz, 1H), 6.63-6.65 (m, 1H), 7.06-7.10 (m, 1H), 7.13 (t, J=1.90 Hz, 1H), 7.22 (ddd, J=7.99, 2.16, 1.12 Hz, 1H), 7.30 (t, J=7.79 Hz, 1H), 10.66 (br. s, 1H); LCMS (ESI−) 274.2 (M−H).

4.15. Synthesis of methyl 6-(3-bromophenyl)-1,4,5,6-tetrahydrocyclopenta[b]pyrrole-2-carboxylate

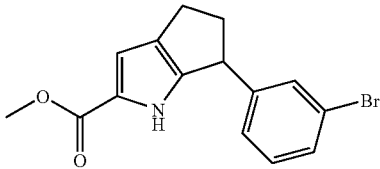

The title compound was synthesized in two steps. First, methyl 6-oxo-1,4,5,6-tetrahydrocyclopenta[b]pyrrole-2-carboxylate (0.503 g, 2.81 mmol) and (3-bromophenyl)magnesium bromide (synthesized in situ) were reacted according to General Procedure 3 to give the carbinol-containing compound methyl 6-(3-bromophenyl)-6-hydroxy-1,4,5,6-tetrahydrocyclopenta[b]pyrrole-2-carboxylate. (Note: (3-Bromophenyl)magnesium bromide was synthesized as follows: Activated magnesium (0.308 g, 12.67 mmol) was placed in a flask and anhydrous THF (50 mL) was added. 1,3-dibromobenzene (1.6 mL, 13.2 mmol) and a catalytic amount of 12 was added. The solution was stirred gently at ambient temperature for 30 min. Additional anhydrous THF (25 mL) was added and the solution refluxed for 3 h, and then allowed to cool to ambient temperature). Methyl 6-(3-bromophenyl)-6-hydroxy-1,4,5,6-tetrahydrocyclopenta[b]pyrrole-2-carboxylate was hydrogenated according to General Procedure 6 (with $Pt_2O$), and was purified by column chromatography (Isco CombiFlash) eluting with a gradient of 0-30% EtOAc/heptane affording the product as a slightly yellow solid: 0.213 g (83% yield). $^1$H NMR (400 MHz, ACETONE-$d_6$) δ ppm 2.27 (ddt, J=13.19, 8.32, 5.23, 5.23 Hz, 1H), 2.58-2.67 (m, 1H), 2.71-2.79 (m, 1H), 2.90-3.01 (m, 1H), 3.73 (s, 3H), 4.30 (dd, J=8.64, 5.17 Hz, 1H), 6.62-6.65 (m, 1H), 7.10-7.14 (m, 1H), 7.21-7.26 (m, 1H), 7.28-7.30 (m, 1H), 7.35-7.40 (m, 1H), 10.67 (br. s, 1H); LCMS (ESI+) 344.0 (M+Na).

4.16. Synthesis of ethyl 6-p-tolyl-1,4,5,6-tetrahydrocyclopenta[b]pyrrole-2-carboxylate

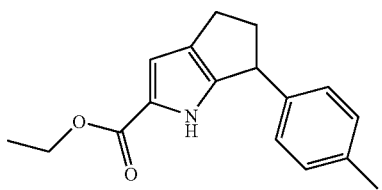

The title compound was synthesized from ethyl 6-oxo-1,4,5,6-tetrahydrocyclopenta[b]pyrrole-2-carboxylate (0.3 g, 1.55 mmol, 1 equiv) and p-tolyl magnesium bromide (6.2 mL, 1M in THF, 6.2 mmol, 4 equiv) according to General Procedure 3 to give the endocyclic olefin-containing compound ethyl 6-p-tolyl-1,4-dihydrocyclopenta[b]pyrrole-2-carboxylate. $^1$H NMR showed a complex mixture but was qualitatively consistent with ethyl 6-p-tolyl-1,4-dihydrocyclopenta[b]pyrrole-2-carboxylate and the corresponding carbinol (ethyl 6-hydroxy-6-p-tolyl-1,4,5,6-tetrahydrocyclopenta[b]pyrrole-2-carboxylate) and was carried on to the next step without further purification. The mixture was hydrogenated according to General Procedure 6, and was purified by column chromatography (Isco CombiFlash) using a 0-30% gradient (EtOAc/Heptane) over 22 minutes. 0.1423 g. LCMS m/e 292 (M+Na). $^1$H NMR (400 MHz, CHLOROFORM-d) δ ppm 1.33 (t, J=7.13 Hz, 3H), 2.30 (dt, J=8.65, 6.43 Hz, 1H), 2.34 (s, 3H), 2.61-2.70 (m, 1H), 2.75 (dd, J=8.79, 4.00 Hz, 1H), 2.86-2.97 (m, J=12.68, 8.41, 8.41, 4.03 Hz, 1H), 4.19-4.32 (m, 3H), 6.73 (d, J=1.61 Hz, 1H), 7.01-7.07 (m, 2H), 7.13 (d, J=7.86 Hz, 2H), 8.60 (br. s, 1H).

4.17. Synthesis of methyl 6-(3-cyanophenyl)-1,4,5,6-tetrahydrocyclopenta[b]pyrrole-2-carboxylate

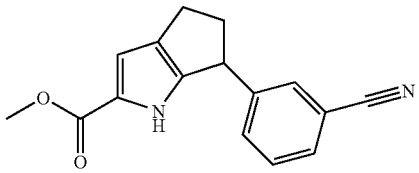

The title compound was synthesized from methyl 6-(3-bromophenyl)-1,4,5,6-tetrahydrocyclopenta[b]pyrrole-2-carboxylate (0.049 g, 0.15 mmol) and zinc cyanide (0.028 g, 0.24 mmol) according to General Procedure 9.4. Purification by (Isco CombiFlash) eluting with a gradient of 0-40% EtOAc/heptane afforded the product as a slightly yellow solid: 0.027 g (68% yield). $^1$H NMR (400 MHz, ACETONE-$d_6$) δ ppm 2.31 (ddt, J=13.26, 8.33, 5.23, 5.23 Hz, 1H), 2.60-2.69 (m, 1H), 2.75-2.83 (m, 2H), 2.94-3.04 (m, 1H), 3.73 (s, 3H), 4.39 (s, 1H), 6.64-6.66 (m, 1H) 7.48 (t, J=1.61

Hz, 1H), 7.51-7.54 (m, 1H), 7.59-7.63 (m, 1H), 10.66 (br s, 1H); LC-MS ESI– 265.2 (m–H).

4.18. Synthesis of ethyl 6-(biphenyl-4-yl)-1,4,5,6-tetrahydrocyclopenta[b]pyrrole-2-carboxylate

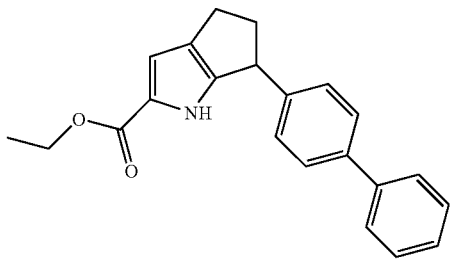

The title compound was synthesized in two steps. Ethyl 6-oxo-1,4,5,6-tetrahydrocyclopenta[b]pyrrole-2-carboxylate (0.3 g, 1.55 mmol) was reacted with 4-biphenyl magnesium bromide (12.4 mL, 0.5M in THF, 6.2 mmol, 4 equiv) according to General Procedure 3 to give the endocyclic olefin-containing compound ethyl 6-(biphenyl-4-yl)-1,4-dihydrocyclopenta[b]pyrrole-2-carboxylate. $^1$H NMR showed a complex mixture but was qualitatively consistent with ethyl 6-(biphenyl-4-yl)-1,4-dihydrocyclopenta[b]pyrrole-2-carboxylate and the corresponding carbinol ethyl 6-(biphenyl-4-yl)-6-hydroxy-1,4,5,6-tetrahydrocyclopenta[b]pyrrole-2-carboxylate and was carried on to the next step without further purification. The mixture was hydrogenated according to General Procedure 6, and was purified by column chromatography (Isco CombiFlash) using a 0-30% gradient (EtOAc/Heptane) over 24 minutes to afford the title compound. 0.1776 g. LCMS m/e 354.2 (M+Na). $^1$H NMR (400 MHz, CHLOROFORM-d) δ ppm 1.34 (t, J=7.11 Hz, 3H), 2.31-2.44 (m, J=12.89, 8.61, 6.42, 6.42 Hz, 1H), 2.65-2.75 (m, 1H), 2.80 (ddd, J=9.07, 4.84, 4.64 Hz, 1H), 2.92-3.03 (m, J=12.74, 8.46, 8.46, 4.15 Hz, 1H), 4.23-4.35 (m, J=7.10, 3.87, 3.54, 3.54 Hz, 3H), 6.76 (d, J=1.44 Hz, 1H), 7.22 (d, J=8.08 Hz, 2H), 7.32-7.38 (m, 1H), 7.45 (t, J=7.57 Hz, 2H), 7.56 (dd, J=15.62, 7.69 Hz, 4H), 8.67 (br. s., 1H).

4.19. Synthesis of methyl 6-(3-chlorobenzyl)-1,4,5,6-tetrahydrocyclopenta[b]pyrrole-2-carboxylate

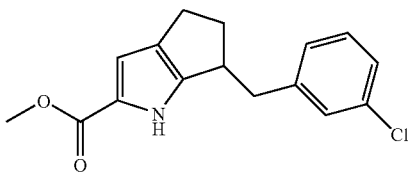

The title compound was synthesized in two steps. Methyl 6-oxo-1,4,5,6-tetrahydrocyclopenta[b]pyrrole-2-carboxylate (447 mg, 2.5 mmol) was reacted with 3-chlorobenzylmagnesium bromide (0.25 M in hexanes, 25 mL, 6.3 mmol) according to General Procedure 3 to give the exocyclic olefin-containing compound (E)-methyl 6-(3-chlorobenzylidene)-1,4,5,6-tetrahydrocyclopenta[b]pyrrole-2-carboxylate, followed by hydrogenation according to General Procedure 6, and was purified by chromatography, eluting with heptane-EtOAc, gradient 0 to 50% EtOAc. 143 mg.

4.20. Synthesis of ethyl 6-(3-chloro-5-fluorobenzyl)-1,4,5,6-tetrahydrocyclopenta[b]pyrrole-2-carboxylate

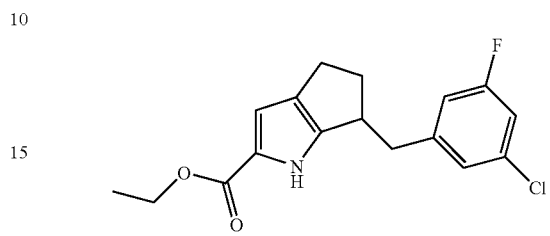

The title compound was synthesized in two steps. Ethyl 6-oxo-1,4,5,6-tetrahydrocyclopenta[b]pyrrole-2-carboxylate (0.40 g, 2.23 mmol) was reacted with 3-chloro-5-fluorobenzylmagnesium chloride (0.25 M in diethyl ether, 23.0 mL, 5.6 mmol) according to General Procedure 3 to give the exocyclic olefin-containing compound (Z)-ethyl 6-(3-chloro-5-fluorobenzylidene)-1,4,5,6-tetrahydrocyclopenta[b]pyrrole-2-carboxylate, followed by hydrogenation according to General Procedure 6 (with Pt$_2$O), and was purified by column chromatography (Isco CombiFlash) eluting with a gradient of 0-20% EtOAc/heptane affording the product as brown solid: 0.055 g (11% yield).

4.21. Synthesis of methyl 6-(3-bromobenzyl)-1,4,5,6-tetrahydrocyclopenta[b]pyrrole-2-carboxylate

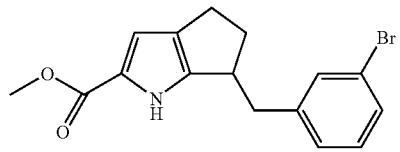

The title compound was synthesized in two steps. First, methyl 6-oxo-1,4,5,6-tetrahydrocyclopenta[b]pyrrole-2-carboxylate (0.502 g, 1.0 mmol) was reacted with 3-bromobenzylmagnesium bromide (28 mL, 2.5 mmol) according to General Procedure 3 to give the carbinol-containing compound methyl 6-(3-bromobenzyl)-6-hydroxy-1,4,5,6-tetrahydrocyclopenta[b]pyrrole-2-carboxylate, followed by hydrogenation with PtO$_2$ (0.045 g, 0.20 mmol) according to General Procedure 6, and was purified by column chromatography (Isco CombiFlash) eluting with a gradient of 0-30% EtOAc/heptane affording the title compound as a slightly yellow solid: 0.257 g (60% yield). $^1$H NMR (400 MHz, ACETONE-d$_6$) δ ppm 2.08-2.13 (m, 1H), 2.37-2.47 (m, 3H), 2.71 (dd, J1=13.47 Hz, J2=8.98 Hz, 1H), 3.19 (dd, J1=13.47 Hz, J2=4.69 Hz, 1H), 3.36-3.42 (m, 1H), 3.74 (s, 3H), 6.53 (d, J=1.9 Hz, 1H), 7.18-7.26 (m, 2H), 7.37-7.39 (m, 2H), 10.50 (s, 1H); LCMS-MS (ESI−) 332.0 (M−H).

4.22. Synthesis of methyl 6-(3-hydroxybenzyl)-1,4,5,6-tetrahydrocyclopenta[b]pyrrole-2-carboxylate

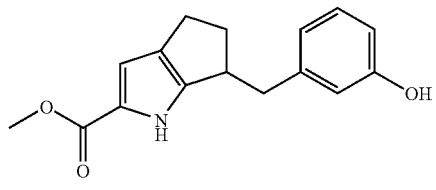

Methyl 6-(3-methoxybenzyl)-1,4,5,6-tetrahydrocyclopenta[b]pyrrole-2-carboxylate (140 mg, 0.50 mmol) in dry $CH_2Cl_2$ (20 mL) was cooled to −78° C., then $BBr_3$, (1.0 M in $CH_2Cl_2$) (0.80 mL, 0.80 mmol) was added. The mixture was allowed to warm slowly to room temperature overnight. The mixture was added to saturated sodium bicarbonate, (100 mL) extracted with $CH_2Cl_2$, (50 mL) (×3), dried ($Na_2SO_4$) and the solvent was evaporated under reduced pressure. The material was purified by chromatography, eluting with heptane-EtOAc, gradient 0 to 50% EtOAc. 50 mg. $^1$H NMR (400 MHz, CHLOROFORM-d) δ ppm 2.07-2.19 (m, 1H), 2.48-2.74 (m, 4H), 2.90 (dd, J=13.42, 6.30 Hz, 1H), 3.26-3.44 (m, 1H), 3.79 (s, 3H), 6.62 (s, 1H), 6.70 (d, J=1.71 Hz, 1H), 6.72-6.80 (m, 2H), 7.21 (t, J=7.81 Hz, 1H), 8.29 (br. s, 1H).

4.23. Synthesis of methyl 6-(3-methoxybenzyl)-1,4,5,6-tetrahydrocyclopenta[b]pyrrole-2-carboxylate

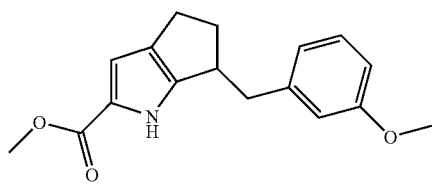

The title compound was synthesized in two steps. First, methyl 6-oxo-1,4,5,6-tetrahydrocyclopenta[b]pyrrole-2-carboxylate (447 mg, 2.5 mmol) was reacted with 3-methoxybenzylmagnesium bromide (0.25 M in hexanes, 25 mL, 6.3 mmol) according to General Procedure 3 to give the exo olefin-containing compound (E)-methyl 6-(3-methoxybenzylidene)-1,4,5,6-tetrahydrocyclopenta[b]pyrrole-2-carboxylate, followed by hydrogenation (with 5% Pd/C) according to General Procedure 6, and was purified by chromatography, eluting with heptane-EtOAc, gradient 0 to 40% EtOAc. The material was carried to the next step without further characterization.

4.24. Synthesis of methyl 6-(2-(naphthalen-1-yl)ethyl)-1,4,5,6-tetrahydrocyclopenta[b]pyrrole-2-carboxylate

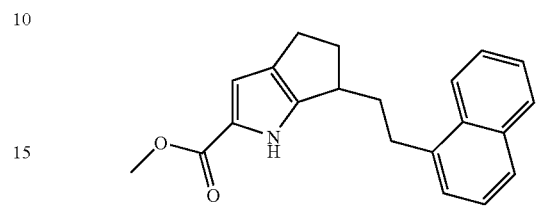

The title compound was synthesized in two steps. First, methyl 6-oxo-1,4,5,6-tetrahydrocyclopenta[b]pyrrole-2-carboxylate (0.50 g, 2.8 mmol) and (2-(naphthalen-1-yl)ethyl) magnesium chloride (synthesized in situ) were reacted according to General Procedure 3 to give the exo olefin-containing compound (E)-methyl 6-(2-(naphthalen-1-yl)ethylidene)-1,4,5,6-tetrahydrocyclopenta[b]pyrrole-2-carboxylate. (Note: (2-(naphthalen-1-yl)ethyl)magnesium chloride was synthesized as follows: Activated magnesium turnings (0.306 g, 12.6 mmol; washed sequentially with 3N HCl, water, THF and diethyl ether) was placed in a flask and anhydrous THF (50 mL). 1-(2-chloroethyl)naphthalene ((0.168 M in THF, 75.0 mL, 12.6 mmol) was added dropwise followed by a few grains of $I_2$ (catalytic). The solution was stirred gently at ambient temperature for 30 min. Additional anhydrous THF (25 mL) was added and the solution refluxed for 3 h, and then allowed to cool to ambient temperature). (E)-methyl 6-(2-(naphthalen-1-yl)ethylidene)-1,4,5,6-tetrahydrocyclopenta[b]pyrrole-2-carboxylate was hydrogenated according to General Procedure 6 (with 5% Pd/C), and was purified by column chromatography (Isco CombiFlash) eluting with a gradient of 0-25% EtOAc/heptane affording the title compound. 0.051 g. $^1$H NMR (400 MHz, CHLOROFORM-d) δ ppm 1.86-2.03 (m, 1H), 2.08-2.29 (m, 2H), 2.55-2.81 (m, 3H), 3.03-3.31 (m, 3H), 3.67-3.86 (m, 3H), 6.54-6.72 (m, 1H), 7.30-7.37 (m, 1H), 7.37-7.45 (m, 1H), 7.45-7.58 (m, 2H), 7.75 (d, J=8.10 Hz, 1H), 7.83-7.93 (m, 1H), 8.01 (d, J=8.25 Hz, 1H), 8.74 (br. s, 1H).

4.25. Synthesis of ethyl 6-(biphenyl-4-ylmethyl)-1,4,5,6-tetrahydrocyclopenta[b]pyrrole-2-carboxylate

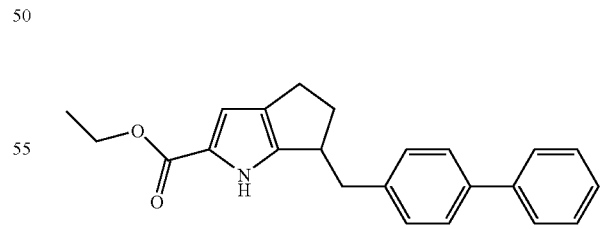

The title compound was synthesized from ethyl 4-oxo-1,4,5,6-tetrahydrocyclopenta[b]pyrrole-2-carboxylate (0.3 g, 1.55 mmol, 1 equiv) and 4-biphenylmethyl magnesium bromide (24.8 mL, 0.25 M in ether, 6.2 mmol, 4 equiv) according to General Procedure 3 to give the endo olefin-containing compound ethyl 6-(biphenyl-4-ylmethyl)-1,4-dihydrocyclopenta[b]pyrrole-2-carboxylate, followed by hydrogenation according to General Procedure 6, and was purified by column chromatography (Isco CombiFlash) using a 0-35% gradient (EtOAc/Heptane) over 26 minutes. 34.3 mg LCMS m/e 368 (M+Na). $^1$H NMR (400 MHz, CHLOROFORM-d) δ ppm 1.30 (t, J=7.13 Hz, 3H), 2.17 (td, J=5.87, 3.90 Hz, 1H), 2.52-2.71 (m, J=15.43, 12.69, 12.69, 12.53 Hz, 3H), 2.80 (dd, J=13.42, 9.03 Hz, 1H), 2.99 (dd, J=13.42, 6.44 Hz, 1H), 3.37-3.47 (m, 1H), 4.25 (q, J=7.11 Hz, 2H), 6.64 (d, J=1.59 Hz, 1H), 7.28 (d, J=8.40 Hz, 2H), 7.33-7.38 (m, 1H), 7.46 (t, J=7.55 Hz, 2H), 7.60 (dd, J=13.59, 7.64 Hz, 4H), 8.25 (br. s, 1H).

4.26. Synthesis of ethyl 6-(3-phenylpropyl)-1,4,5,6-tetrahydrocyclopenta[b]pyrrole-2-carboxylate

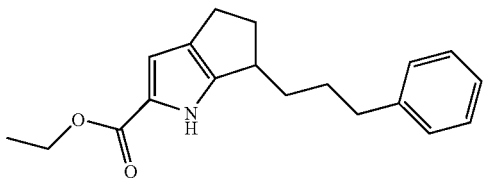

The title compound was synthesized from ethyl 4-oxo-1,4,5,6-tetrahydrocyclopenta[b]pyrrole-2-carboxylate (0.3 g, 1.55 mmol, 1 equiv) and 3-phenyl-propyl magnesium bromide (12.4 mL, 0.5M in THF, 6.2 mmol, 4 equiv) according to General Procedure 3 to give the exo olefin-containing compound (E)-ethyl 6-(3-phenylpropylidene)-1,4,5,6-tetrahydrocyclopenta[b]pyrrole-2-carboxylate, followed by hydrogenation according to General Procedure 6 with 5% Pd on carbon, and was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 60% methanol and increasing to 100% over 7 minutes) afforded the title compound (42.1 mg). $^1$H NMR (400 MHz, CHLOROFORM-d) δ ppm 8.67 (br. s., 1H), 7.28-7.33 (m, 2H), 7.16-7.23 (m, 3H), 6.64 (d, J=1.64 Hz, 1H), 4.25-4.34 (m, 2H), 3.00-3.09 (m, 1H), 2.51-2.68 (m, 5H), 1.97-2.07 (m, 1H), 1.65-1.77 (m, 3H), 1.47-1.55 (m, 1H), 1.34 (t, J=7.13 Hz, 3H).

4.28. Synthesis of 6-methyl-1,4,5,6-tetrahydrocyclopenta[b]pyrrole-2-carboxylic acid (109)

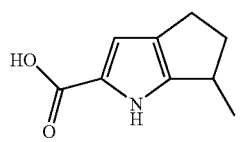

The title compound was synthesized from ethyl 6-methyl-1,4,5,6-tetrahydrocyclopenta[b]pyrrole-2-carboxylate (0.0208 g, 0.11 mmol, 1 equiv) and lithium hydroxide (0.12 mL, 1 M aqueous, 0.12 mmol, 1.1 equiv), according to General Procedure 7. A 1:1 mixture of ethanol (EtOH) and THF (2 mL) was used. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 minutes) afforded the title compound (1.8 mg) with purity by HPLC of 100% (UV). LCMS m/e 164.2 (M−H). $^1$H NMR (400 MHz, METHANOL-d$_4$) δ ppm 1.23 (d, J=6.83 Hz, 3H), 1.81-2.04 (m, 1H), 2.42-2.71 (m, 3H), 3.10 (dd, J=6.69, 1.88 Hz, 1H), 6.55 (s, 1H), 8.48 (br. s, 1H).

4.29. Synthesis of 6-propyl-1,4,5,6-tetrahydrocyclopenta[b]pyrrole-2-carboxylic acid (110)

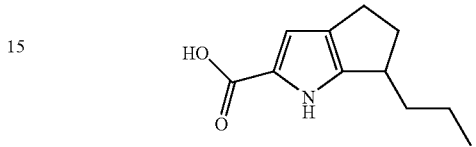

The title compound was synthesized from methyl 6-propyl-1,4,5,6-tetrahydrocyclopenta[b]pyrrole-2-carboxylate (0.15 g, 0.72 mmol) and lithium hydroxide monohydrate (0.3 g, 7.24 mmol), according to General Procedure 7. A 1:1 mixture of methanol (MeOH) and THF (10 mL) was used. The resulting product was purified by chromatography over silica gel (gradient 0 to 100% EtOAc in heptane over 20 min) to give the title compound (75 mg). $^1$H NMR (400 MHz, METHANOL-d$_4$) δ ppm 0.94 (t, J=7.0 Hz, 3H) 1.32-1.49 (m, 3H), 1.62-1.80 (m, 1H), 1.93-2.08 (m, 1H), 2.43-2.65 (m, 3H), 3.01 (br. s, 1H) 6.57 (s, 1H). LCMS m/e 249 (M−H) and 96% pure by HPLC.

4.30. Synthesis of 6-(3-fluorophenyl)-1,4,5,6-tetrahydrocyclopenta[b]pyrrole-2-carboxylic acid (111)

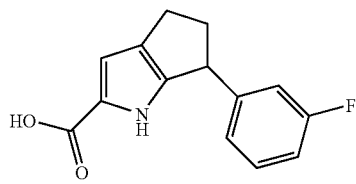

The title compound was synthesized from methyl 6-(3-fluorophenyl)-1,4,5,6-tetrahydrocyclopenta[b]pyrrole-2-carboxylate (116 mg, 0.45 mmol) and lithium hydroxide (188 mg, 4.50 mmol in 1 mL water), according to General Procedure 7. A 1:1 mixture of methanol (MeOH) and THF (2 mL) was used. The resulting product was purified by chromatography. eluting with heptane-EtOAc, gradient 0 to 50% EtOAc. $^1$H NMR (400 MHz, CHLOROFORM-d) δ ppm 2.28-2.39 (m, J=12.87, 8.60, 6.35, 6.35 Hz, 1H), 2.64-2.74 (m, 1H), 2.74-2.85 (m, 1H), 2.90-3.01 (m, J=12.83, 8.48, 8.48, 4.32 Hz, 1H), 4.23-4.31 (m, 1H), 6.80-6.87 (m, 2H), 6.89-6.97 (m, 2H), 7.23-7.32 (m, 1H), 8.74 (br. s, 1H). LCMS m/e 246 (M+H). Purity>98% (HPLC).

4.31. Synthesis of 6-(3,4-difluorophenyl)-1,4,5,6-tetrahydrocyclopenta[b]pyrrole-2-carboxylic acid (112)

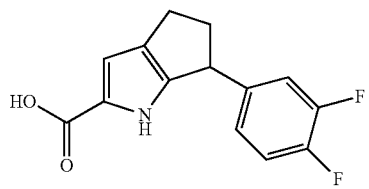

The title compound was synthesized from ethyl 6-(3,4-difluorophenyl)-1,4,5,6-tetrahydrocyclopenta[b]pyrrole-2-carboxylate and lithium hydroxide in water according to General Procedure 7.

4.32. Synthesis of 6-(4-chlorophenyl)-1,4,5,6-tetrahydrocyclopenta[b]pyrrole-2-carboxylic acid (113)

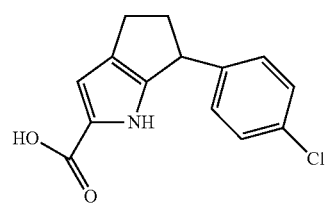

The title compound was synthesized from ethyl 6-(4-chlorophenyl)-1,4,5,6-tetrahydrocyclopenta[b]pyrrole-2-carboxylate (0.0907 g, 0.34 mmol, 1 equiv) and sodium hydroxide (0.86 mL, 8.6 mmol, 10 M, 25 equiv), according to General Procedure 7. A 2-3:1 mixture of methanol (MeOH) and THF (3-4 mL) was used. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 50% methanol and increasing to 100% over 7 minutes) afforded the title compound (48.3 mg, 59%) with purity by HPLC of 94.1% (UV). LCMS m/e 260.2 (M−H). $^1$H NMR (400 MHz, METHANOL-d$_4$) δ ppm 2.16-2.30 (m, J=13.14, 8.19, 5.37, 5.37 Hz, 1H), 2.56- 2.67 (m, 1H), 2.68-2.79 (m, 1H), 2.86-3.01 (m, 1H), 4.26 (dd, J=8.48, 5.28 Hz, 1H), 6.65 (s, 1H), 7.05-7.13 (m, 2H), 7.22-7.31 (m, 2H).

4.33. Synthesis of 6-(3-chlorophenyl)-1,4,5,6-tetrahydrocyclopenta[b]pyrrole-2-carboxylic acid (114)

The title compound was synthesized from methyl 6-(3-chlorophenyl)-1,4,5,6-tetrahydrocyclopenta[b]pyrrole-2-carboxylate (0.099 g, 0.36 mmol) and lithium hydroxide (0.151 g, 3.60 mmol in 2 mL water), according to General Procedure 7. A 1:2 mixture of methanol (MeOH) and THF (3-4 mL) was used. The resulting product was purified by reverse phase HPLC, eluting with a gradient of 40-100% MeOH: water (with 0.1% formic acid) to afford a light pink solid: 0.059 g (63% yield). $^1$H NMR (400 MHz, METHANOL-d$_4$) δ ppm 2.23 (ddt, J=13.18, 8.25, 5.25, 5.25 Hz, 1H), 2.62 (ddd, J=14.31, 8.70, 5.34 Hz, 1H), 2.74 (ddd, J=14.22, 8.63, 5.22 Hz, 1H), 2.89-2.99 (m, 1H), 4.25 (dd, J=8.57, 5.15 Hz, 1H), 6.68 (s, 1H), 7.02-7.05 (m, 1H), 7.10 (t, J=1.83 Hz, 1H), 7.18 (ddd, J=7.97, 2.04, 1.17 Hz, 1H), 7.25 (t, J=7.79 Hz, 1H); LCMS-MS (ESI−) 260.0 (M−H); HPLC (UV=100%), (ELSD=100%).

4.34. Synthesis of 6-(3-bromophenyl)-1,4,5,6-tetrahydrocyclopenta[b]pyrrole-2-carboxylic acid (115)

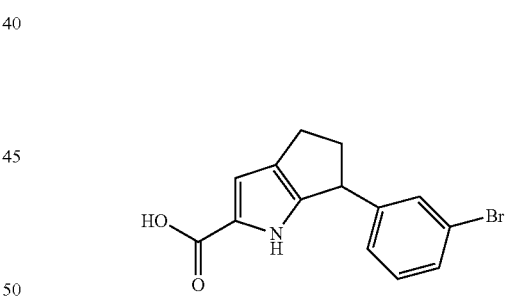

The title compound was synthesized from methyl 6-(3-bromophenyl)-1,4,5,6-tetrahydrocyclopenta[b]pyrrole-2-carboxylate (0.213 g, 0.67 mmol) and lithium hydroxide (0.281 g, 6.70 mmol in 4 mL water), according to General Procedure 7. A 1:2 mixture of methanol (MeOH) and THF (6 mL) was used. The resulting product was purified reverse phase HPLC, eluting with a gradient of 40-100% MeOH: water (with 0.1% formic acid) to afford a light pink solid: 0.098 g (48% yield). $^1$H NMR (400 MHz, METHANOL-d$_4$) δ ppm 2.23 (ddt, J=13.14, 8.21, 5.27, 5.27 Hz, 1H), 2.62 (ddd, J=14.31, 8.65, 5.34 Hz, 1H), 2.69-2.78 (m, 1H), 2.87-2.98 (m, 1H), 4.24 (dd, J=8.40, 5.17 Hz, 1H), 6.67 (s, 1H), 7.07 (d, J=7.61 Hz, 1H), 7.18 (t, J=7.81 Hz, 1H), 7.25 (s, 1H), 7.33 (d, J=7.86 Hz, 1H); LCMS (ESI+) 306.0 (M+H); HPLC (UV=96.1%), (ELSD=99.3%).

4.35. Synthesis of 6-p-tolyl-1,4,5,6-tetrahydrocyclopenta[b]pyrrole-2-carboxylic acid (116)

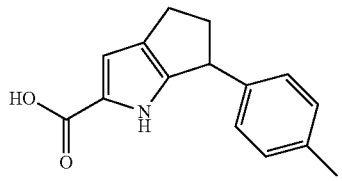

The title compound was synthesized from ethyl 6-p-tolyl-1,4,5,6-tetrahydrocyclopenta[b]pyrrole-2-carboxylate (0.1423 g, 0.56 mmol, 1 equiv) and sodium hydroxide (1.4 mL, 14 mmol, 10M, 25 equiv), according to General Procedure 7. A 4-5:1 mixture of methanol (MeOH) and THF (5-6 mL) was used. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 minutes) afforded the title compound (68.9 mg, 51%) with purity by HPLC of 97.9% (UV). LCMS m/e 240.2 (M–H). $^1$H NMR (400 MHz, METHANOL-$d_4$) δ ppm 2.17-2.26 (m, 1H), 2.29 (s, 3H), 2.62 (ddd, J=14.43, 6.06, 5.84 Hz, 1H), 2.68-2.77 (m, 1H), 2.85-2.96 (m, J=8.63, 8.49, 8.49, 4.20 Hz, 1H), 4.21 (dd, J=8.47, 5.42 Hz, 1H), 6.66 (s, 1H), 6.94-7.03 (m, 2H), 7.09 (d, J=7.91 Hz, 2H).

4.36. Synthesis of 6-(3-cyanophenyl)-1,4,5,6-tetrahydrocyclopenta[b]pyrrole-2-carboxylic acid (117)

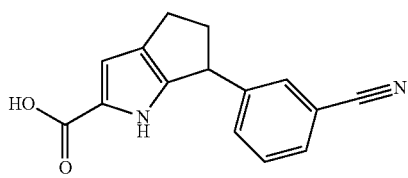

The title compound was synthesized from methyl 6-(3-cyanophenyl)-1,4,5,6-tetrahydrocyclopenta[b]pyrrole-2-carboxylate (0.027 g, 0.10 mmol) and lithium hydroxide (0.044 g, 1.0 mmol in 1 mL water), according to General Procedure 7. A 1:1 mixture of methanol (MeOH) and THF (5-6 mL) was used. The resulting product was purified by reverse phase HPLC, eluting with a gradient of 40-80% MeOH: water (with 0.1% formic acid) to afford a light pink solid: 8.6 mg (34% yield). $^1$H NMR (400 MHz, METHANOL-$d_4$) δ ppm 2.21-2.30 (m, 1H) 2.65 (s, 1H) 2.76 (s, 1H) 2.93-3.03 (m, 1H) 4.33 (s, 1H) 6.68 (s, 1H) 7.40-7.44 (m, 1H) 7.44-7.49 (m, 2H) 7.54-7.58 (m, 1H); LC-MS ESI– 251.2 (m–H); HPLC (UV=97.75%), (ELSD=100%).

4.37. Synthesis of 6-(biphenyl-4-yl)-1,4,5,6-tetrahydrocyclopenta[b]pyrrole-2-carboxylic acid (118)

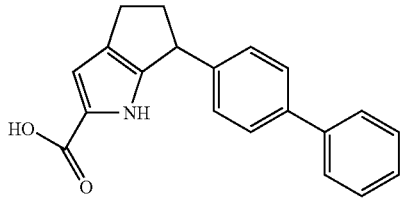

The title compound was synthesized from ethyl 6-(biphenyl-4-yl)-1,4,5,6-tetrahydrocyclopenta[b]pyrrole-2-carboxylate (0.1776 g, 0.54 mmol, 1 equiv) and sodium hydroxide (1.36 mL, 13.6 mmol, 10 M, 25 equiv), according to General Procedure 7. A 4-5:1 mixture of methanol (MeOH) and THF (5-6 mL) was used. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 60% methanol and increasing to 100% over 7 minutes) afforded the title compound (49.3 mg, 30%) with purity by HPLC of 96.6% (UV). LCMS m/e 302.2 (M–H). $^1$H NMR (400 MHz, METHANOL-$d_4$) δ ppm 2.24-2.37 (m, 1H) 2.66 (ddd, J=8.74, 5.64, 5.53 Hz, 1H) 2.72-2.82 (m, 1H) 2.97 (dd, J=12.96, 4.98 Hz, 1H) 4.31 (dd, J=8.44, 5.37 Hz, 1H) 6.68 (s, 1H) 7.20 (d, J=8.20 Hz, 2H) 7.27-7.34 (m, 1H) 7.40 (t, J=7.63 Hz, 2H) 7.56 (dd, J=15.79, 7.71 Hz, 4H).

The enantiomers of 6-(biphenyl-4-yl)-1,4,5,6-tetrahydrocyclopenta[b]pyrrole-2-carboxylic acid were separated according to General Procedure 8 with a mixture of 50% [50:50 methanol/isopropanol] in $CO_2$ to give 6-(biphenyl-4-yl)-1,4,5,6-tetrahydrocyclopenta[b]pyrrole-2-carboxylic acid (119), (peak 1, retention time=6.3 min; 100% ee) and 6-(biphenyl-4-yl)-1,4,5,6-tetrahydrocyclopenta[b]pyrrole-2-carboxylic acid (120) (peak 2, retention time=10.2 min; 100% ee).

4.38. Synthesis of 6-(3-chlorobenzyl)-1,4,5,6-tetrahydrocyclopenta[b]pyrrole-2-carboxylic acid (121)

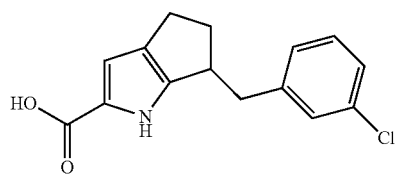

The title compound was synthesized from methyl 6-(3-chlorobenzyl)-1,4,5,6-tetrahydrocyclopenta[b]pyrrole-2-carboxylate (140 mg, 0.48 mmol) and lithium hydroxide (188 mg, 4.50 mmol, in 1 mL water), according to General Procedure 7. A 1:1 mixture of methanol (MeOH) and THF (2 mL) was used. The resulting product was purified by chromatography, eluting with heptane-EtOAc, gradient 0 to 50% EtOAc. 90 mg. $^1$H NMR (400 MHz, CHLOROFORM-d) δ ppm 2.07-2.20 (m, 1H) 2.52-2.68 (m, 3H) 2.74-2.82 (m, 1H) 2.86-2.93 (m, 1H) 3.33-3.43 (m, 1H) 6.75 (d, J=1.61 Hz, 1H) 7.03-7.09 (m, 1H) 7.20-7.23 (m, 1H) 7.25-7.29 (m, 2H) 8.35 (br. s., 1H). LCMS m/e 276 (M+H). Purity>75% (HPLC).

The enantiomers of 6-(3-chlorobenzyl)-1,4,5,6-tetrahydrocyclopenta[b]pyrrole-2-carboxylic acid were separated according to General Procedure 8 with a mixture of 50% methanol in CO$_2$ to give 6-(3-chlorobenzyl)-1,4,5,6-tetrahydrocyclopenta[b]pyrrole-2-carboxylic acid (122), (peak 1, retention time=1.55 min; 100% ee) and 6-(3-chlorobenzyl)-1,4,5,6-tetrahydrocyclopenta[b]pyrrole-2-carboxylic acid (123) (peak 2, retention time=1.95 min; 99% ee).

4.39. Synthesis of 6-(3-chloro-5-fluorobenzyl)-1,4,5,6-tetrahydrocyclopenta[b]pyrrole-2-carboxylic acid (124)

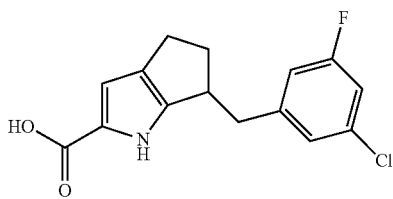

The title compound was synthesized from methyl 6-(3-chloro-5-fluorobenzyl)-1,4,5,6-tetrahydrocyclopenta[b]pyrrole-2-carboxylate (0.055 g, 0.18 mmol) and lithium hydroxide (0.076 g, 1.8 mmol, in 2 mL water), according to General Procedure 7. A 1:1 mixture of methanol (MeOH) and THF (4 mL) was used. The resulting product was purified by reverse phase chromatography from MeOH and water (0.1% formic acid) to afford a light brown solid: 11 mg, 21% yield. $^1$H NMR (400 MHz, METHANOL-d$_4$) δ ppm 1.97-2.17 (m, 1H) 2.30-2.53 (m, 3H) 2.69 (dd, J=13.52, 8.69 Hz, 1H) 3.09 (dd, J=13.52, 4.69 Hz, 1H) 3.33-3.40 (m, 1H) 6.56 (s, 1H) 6.85 (dd, J=9.54, 1.64 Hz, 1H) 6.94-7.07 (m, 2H); $^{19}$F NMR δ ppm −114.14 (t, J=0.8 Hz); LCMS-MS (ESI−) 292.0 (M−H); HPLC (UV=100%), (ELSD=100%).

4.40. Synthesis of 6-(3-bromobenzyl)-1,4,5,6-tetrahydrocyclopenta[b]pyrrole-2-carboxylic acid (125)

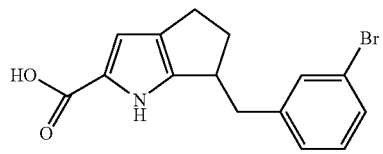

The title compound was synthesized from methyl 6-(3-bromobenzyl)-1,4,5,6-tetrahydrocyclopenta[b]pyrrole-2-carboxylate (0.151 g, 0.45 mmol) and lithium hydroxide (0.193 g, 4.6 mmol in 2 mL water), according to General Procedure 7. A 1:1 mixture of methanol (MeOH) and THF (4 mL) was used. The resulting product was purified by reverse phase HPLC, eluting with a gradient of 40-100% MeOH:water (with 0.1% formic acid) to afford a light pink solid: 0.014 g (10% yield). $^1$H NMR (400 MHz, METHANOL-d$_4$) δ ppm 2.03-2.13 (m, 1H), 2.37-2.46 (m, 4H), 2.68 (dd, J1=13.28 Hz, J2=8.88 Hz, 1H), 3.08 (dd, J1=13.52 Hz, J2=4.73 Hz, 1H), 6.56 (s, 1H), 7.10-7.12 (m, 1H), 7.17 (t, J=7.74 Hz, 1H), 7.32-7.35 (m, 2H); LCMS-MS (ESI−) 318.0 (M−H); HPLC (UV=96.26%), (ELSD=100%).

The enantiomers of 6-(3-bromobenzyl)-1,4,5,6-tetrahydrocyclopenta[b]pyrrole-2-carboxylic acid were separated according to General Procedure 8 with a mixture of 50% [50:50 methanol/isopropanol] in CO$_2$ to give 6-(3-bromobenzyl)-1,4,5,6-tetrahydrocyclopenta[b]pyrrole-2-carboxylic acid (126), (peak 1, retention time=4.9 min; 99.8% ee) and 6-(3-bromobenzyl)-1,4,5,6-tetrahydrocyclopenta[b]pyrrole-2-carboxylic acid (127) (peak 2, retention time=5.8 min; 98.9% ee).

4.41. Synthesis of 6-(3-hydroxybenzyl)-1,4,5,6-tetrahydrocyclopenta[b]pyrrole-2-carboxylic acid (128)

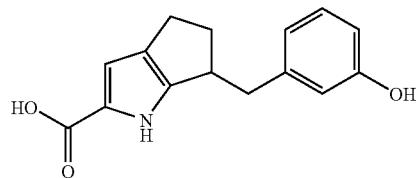

The title compound was synthesized from methyl 6-(3-hydroxybenzyl)-1,4,5,6-tetrahydrocyclopenta[b]pyrrole-2-carboxylate (57 mg, 0.21 mmol) and lithium hydroxide (88 mg, 2.10 mmol in 1 mL water), according to General Procedure 7. A 1:1 mixture of methanol (MeOH) and THF (2 mL) was used. The resulting product was purified by chromatography, eluting with heptane-EtOAc, gradient 0 to 50% EtOAc. $^1$H NMR (400 MHz, METHANOL-d$_4$) δ ppm 2.04-2.16 (m, 1H) 2.36-2.53 (m, 3H) 2.55-2.64 (m, 1H) 2.96-3.04 (m, 1H) 3.31-3.37 (m, 1H) 6.57 (s, 1H) 6.59-6.67 (m, 3H) 7.04-7.11 (m, 1H). LCMS m/e 258 (M+H). Purity 92% (HPLC).

4.42. Synthesis of 6-(3-methoxybenzyl)-1,4,5,6-tetrahydrocyclopenta[b]pyrrole-2-carboxylic acid (129)

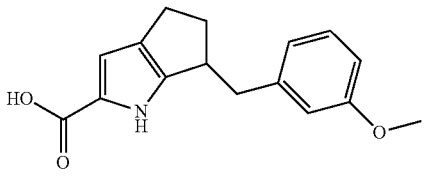

The title compound was synthesized from methyl 6-(3-methoxybenzyl)-1,4,5,6-tetrahydrocyclopenta[b]pyrrole-2-carboxylate (127 mg, 0.45 mmol) and lithium hydroxide (188 mg, 4.50 mmol in 1 mL water), according to General Procedure 7. A 1:1 mixture of methanol (MeOH) and THF (2 mL) was used. The resulting product was purified by chromatography, eluting with heptane-EtOAc, gradient 0 to 50% EtOAc. 80 mg. $^1$H NMR (400 MHz, CHLOROFORM-d) δ ppm 2.10-2.21 (m, 1H) 2.53-2.76 (m, 4H) 2.91-2.99 (m, 1H) 3.34-3.44 (m, 1H) 3.82 (s, 3H) 6.72-6.77 (m, 2H) 6.78-6.86 (m, 2H) 7.24-7.31 (m, 2H) 8.28 (br. s., 1H). LCMS m/e 272 (M+H). Purity>99% (HPLC).

The enantiomers of 6-(3-methoxybenzyl)-1,4,5,6-tetrahydrocyclopenta[b]pyrrole-2-carboxylic acid were separated according to General Procedure 8 with a mixture of 45% methanol in CO$_2$ to give 6-(3-methoxybenzyl)-1,4,5,6-tetrahydrocyclopenta[b]pyrrole-2-carboxylic acid (130), (peak 1, retention time=2.05 min; 100% ee) and 6-(3-methoxybenzyl)-1,4,5,6-tetrahydrocyclopenta[b]pyrrole-2-carboxylic acid (131) (peak 2, retention time=3.55 min; 100% ee).

4.43. Synthesis of 6-(2-(naphthalen-1-yl)ethyl)-1,4,5,6-tetrahydrocyclopenta[b]pyrrole-2-carboxylic acid (132)

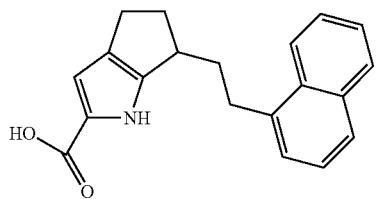

The title compound was synthesized from methyl 6-(2-(naphthalen-1-yl)ethyl)-1,4,5,6-tetrahydrocyclopenta[b]pyrrole-2-carboxylate (0.051 g, 0.16 mmol) and lithium hydroxide (0.067 g, 1.6 mmol in 3 mL water), according to General Procedure 7. A 1:1 mixture of methanol (MeOH) and THF (6 mL) was used. The resulting product was purified by column chromatography (Isco CombiFlash) eluting with a gradient of 0-60% EtOAc/heptane. 17 mg. $^1$H NMR (400 MHz, METHANOL-$d_4$) δ ppm 1.85 (dq, J=13.45, 7.90 Hz, 1H) 2.08-2.27 (m, 2H) 2.46-2.62 (m, 1H) 2.62-2.80 (m, 2H) 3.04-3.22 (m, 3H) 6.61 (s, 1H) 7.29-7.41 (m, 2H) 7.41-7.54 (m, 2H) 7.64-7.73 (m, 1H) 7.80-7.87 (m, 1H) 8.03 (d, J=8.35 Hz, 1H); LCMS-MS (ESI−) 304.0 (M−H); HPLC (UV=95.2%), (ELSD=100%).

4.44. Synthesis of 6-(biphenyl-4-ylmethyl)-1,4,5,6-tetrahydrocyclopenta[b]pyrrole-2-carboxylic acid (133)

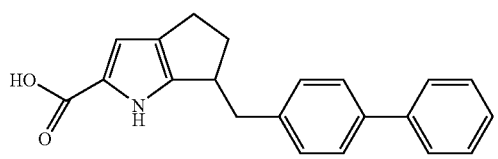

The title compound was synthesized from ethyl 6-(biphenyl-4-ylmethyl)-1,4-dihydrocyclopenta[b]pyrrole-2-carboxylate (0.0343 g, 0.1 mmol, 1 equiv) and sodium hydroxide (0.36 mL, 3.6 mmol, 10 M, 35 equiv), according to General Procedure 7. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 70% methanol and increasing to 100% over 7 minutes) afforded the title compound (15.7 mg, 50%) with purity by HPLC of 93.3% (UV). LCMS m/e 316.2 (M−H). $^1$H NMR (400 MHz, METHANOL-$d_4$) δ ppm 2.08-2.20 (m, 1H) 2.41-2.50 (m, 2H) 2.75 (dd, J=13.62, 8.54 Hz, 1H) 3.06-3.12 (m, 1H) 6.55 (s, 1H) 7.24 (d, J=8.10 Hz, 2H) 7.28-7.33 (m, 1H) 7.41 (t, J=7.61 Hz, 2H) 7.53 (d, J=8.13 Hz, 2H) 7.60 (d, J=7.20 Hz, 2H) 8.50 (s, 1H).

4.45. Synthesis of 6-(3-phenylpropyl)-1,4,5,6-tetrahydrocyclopenta[b]pyrrole-2-carboxylic acid (134)

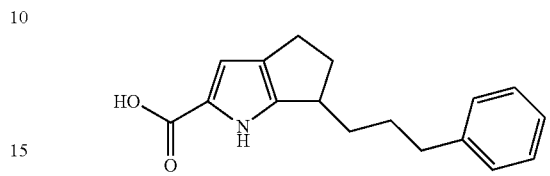

The title compound was synthesized from ethyl 6-(3-phenylpropyl)-1,4,5,6-tetrahydrocyclopenta[b]pyrrole-2-carboxylate (42.1 mg, 0.17 mmol, 1 equiv) and sodium hydroxide (0.42 mL, 10 M, 25 equiv), according to General Procedure 7. The resulting product was purified by preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 minutes) afforded the title compound (24.2 mg, 63%) with purity by HPLC of 93.1% (UV) and 97.4% (ELSD). LCMS m/z 268 (M−H). $^1$H NMR (400 MHz, METHANOL-$d_4$) δ ppm 7.21-7.27 (m, 2H), 7.11-7.19 (m, 3H), 6.56 (s, 1H), 2.98-3.07 (m, 1H), 2.47-2.66 (m, 5H), 1.95-2.05 (m, 1H), 1.64-1.82 (m, 3H), 1.40-1.51 (m, 1H).

The enantiomers of 6-(3-phenylpropyl)-1,4,5,6-tetrahydrocyclopenta[b]pyrrole-2-carboxylic acid were separated according to General Procedure 8 with a mixture of 15% [50:50 methanol/isopropanol with 1% isopropyl amine] in $CO_2$ to give 6-(3-phenylpropyl)-1,4,5,6-tetrahydrocyclopenta[b]pyrrole-2-carboxylic acid (135), (peak 1, retention time=4.3 min; 100% ee) and 6-(3-phenylpropyl)-1,4,5,6-tetrahydrocyclopenta[b]pyrrole-2-carboxylic acid (136) (peak 2, retention time=3.5 min; 97% ee).

Example 5

Synthesis of Pyrrole Analogs with Fused Cyclohexanes

5.1. Synthesis of methyl 4-benzyl-4,5,6,7-tetrahydro-1H-indole-2-carboxylate

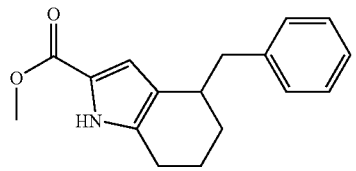

5.1.a) Synthesis of ethyl 4-oxo-4,5,6,7-tetrahydro-1H-indole-2-carboxylate

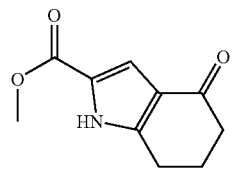

HCl in methanol (60 mL) was added to a solution of 4-oxo-4,5,6,7-tetrahydro-1H-indole-2-carbonitrile (Estep, K. G. Syn. Commun. 1995, 25, 507-514) (0.665 g, 4.15 mmol) in MeOH (10 mL) and the resulting solution was refluxed overnight. The solvent was removed in vacuo and saturated NaHCO$_3$ was added. An approximately equal volume of EtOAc was added. The organic layer was then removed and dried over sodium sulfate, filtered and evaporated to give 0.675 g of a solid consisting of methyl 4-oxo-4,5,6,7-tetrahydro-1H-indole-2-carboxylate (80%) and starting material (20%). $^1$H-NMR (400 MHz, CHLOROFORM-d) δ ppm 2.19 (m, 2H), 2.53 (m, 2H), 2.88 (m, 2H), 3.88 (s, 3H), 7.21 (d, 1H), 9.53 (s broad, 1H); $^{13}$C-NMR (100 MHz, CHLOROFORM-d) δ ppm 22.85, 23.44, 37.96, 51.92, 108.21, 112.38, 161.74, 194.33; DEPT (100 MHz, CDCl$_3$) δ ppm CH$_3$ carbons: 51.92; CH$_2$ carbons: 22.85, 23.44, 37.96; CH carbons: 112.38; LC/MS: 94.09%, m/z=193.

5.1b) Synthesis of methyl 4-oxo-1-((2-(trimethylsilyl)ethoxy)methyl)-4,5,6,7-tetrahydro-1H-indole-2-carboxylate

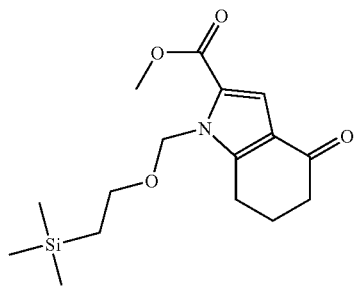

A solution of methyl 4-oxo-4,5,6,7-tetrahydro-1H-indole-2-carboxylate (500 mg, 2.6 mmol) in DMF (3 mL) was added to a cooled (0° C.) suspension of sodium hydride (114 mg, 60% in oil, 2.8 mmol) in DMF (2 mL). After 10 min, 2-(trimethylsilyl)ethoxymethyl chloride (SEM-Cl) (550 μl, 3.1 mmol) was added. The mixture was stirred at rt for 2 h and was then poured into ice-water and extracted with EtOAc. After concentration, methyl 4-oxo-1-((2-(trimethylsilyl)ethoxy)methyl)-4,5,6,7-tetrahydro-1H-indole-2-carboxylate was obtained as a crude oil (930 mg).

5.1.c) Synthesis of (E)-methyl 4-benzylidene-1-((2-(trimethylsilyl)ethoxy)methyl)-4,5,6,7-tetrahydro-1H-indole-2-carboxylate

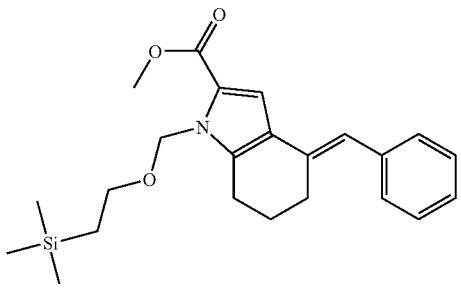

The title compound was synthesized from methyl 4-oxo-1-((2-(trimethylsilyl)ethoxy)methyl)-4,5,6,7-tetrahydro-1H-indole-2-carboxylate (900 mg, 2.78 mmol) and benzylmagnesium chloride (3.4 mL, 2M in THF, 6.8 mmol) according to General Procedure 3. In this example, additional benzylmagnesium chloride (1.7 mL, 2M in THF, 3.4 mmol) was added after 2 h. The crude product (900 mg) was used in the next step without further purification. LC/MS: 50%, m/z=397.

5.1.d) Synthesis of (E)-methyl 4-benzylidene-4,5,6,7-tetrahydro-1H-indole-2-carboxylate

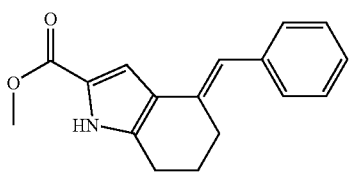

Tetrabutylammonium fluoride (TBAF) (23 mL, 1M in THF, 23 mmol) was added over 5 min to a solution of (E)-methyl 4-benzylidene-1-((2-(trimethylsilyl)ethoxy)methyl)-4,5,6,7-tetrahydro-1H-indole-2-carboxylate (900 mg, 2.26 mmol) in cooled THF (0° C.). The reaction mixture was then heated for 4 h at 80° C. After 48 h at rt, the reaction mixture was partitioned between ether and water. The organic layer was dried over MgSO$_4$ and concentrated under reduced pressure. The crude product was purified by silica gel chromatography (cyclohexane/EtOAc:80/20) to afford the (E)-methyl 4-benzylidene-4,5,6,7-tetrahydro-1H-indole-2-carboxylate (80 mg). LC/MS: 76%, m/z=267.

5.1.e) Synthesis of ethyl 4-benzyl-4,5,6,7-tetrahydro-1H-indole-2-carboxylate

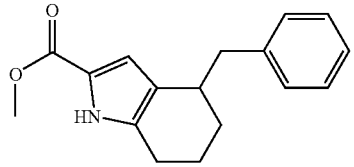

The title compound was synthesized from (E)-methyl 4-benzylidene-4,5,6,7-tetrahydro-1H-indole-2-carboxylate according to General Procedure 6. The crude product was purified by silica gel chromatography (cyclohexane/CH$_2$Cl$_2$: 50/50). LC/MS: 60%, m/z=269.

5.2. Synthesis of 4-benzyl-4,5,6,7-tetrahydro-1H-indole-2-carboxylic acid (32)

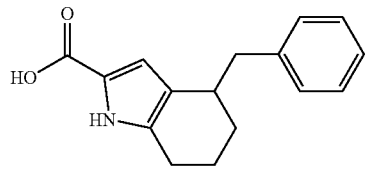

The title compound was synthesized from methyl 4-benzyl-4,5,6,7-tetrahydro-1H-indole-2-carboxylate (20 mg, 0.08 mmol) and aqueous NaOH (1M in H$_2$O, 0.8 mL, 0.8 mmol) according to General Procedure 7. The solid was filtered off, washed with water and dried under vacuum for about 12 h to give 4-benzyl-4,5,6,7-tetrahydro-1H-indole-2-carboxylic acid (32) (19 mg). $^1$H NMR (CHLOROFORM-d 400 MHz) δ ppm 8.8 (1H, br s), 7.3-7.33 (2H, m), 7.2-7.26 (3H, m), 6.81 (1H, s), 3.09 (1H, dd), 2.9 (1H, m), 2.55-2.65 (3H, m), 1.9-2.0 (1H, m), 1.6-1.8 (2H, m), 1.3-1.4 (1H, m); LC/MS: 89%, m/z=255

Example 6

Synthesis of Pyrrole Analogs with Di- or Tri-Substituted Fused Cyclopentanes 6.1. Synthesis of ±(1aS,5aS)-1a,4,5,5a-tetrahydro-1H-4-aza-cyclopropa[a]pentalene-3-carboxylic acid ethyl ester

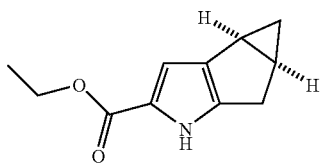

6.1.a) Synthesis of bicyclo[3.1.0]hexan-3-ol

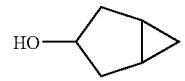

Diethylzinc solution (1.0 M in hexane), 50 mL, 50 mmol) was added to a 0° C. solution of dry CH$_2$Cl$_2$, (250 mL). Diiodomethane, (4.0 mL, 50 mmol) was added and mixture was held for 10 minutes. Then cyclopent-3-enol, (2.1 g, 25 mmol) was added in CH$_2$Cl$_2$ (20 mL). The mixture was held at 0° C. for 3 h and quenched with saturated NH$_4$Cl, (200 mL). After the organic layer was separated, the aqueous phase was extracted with CH$_2$Cl$_2$, (200 mL) (×2), dried (Na$_2$SO$_4$) and the solvent was evaporated carefully under reduced pressure. The material was purified by passing it through a silica plug eluting with diethyl ether and the solvent was evaporated under reduced pressure to provide the title compound. 982 mg.

6.1.b) Synthesis of bicyclo[3.1.0]hexan-3-one

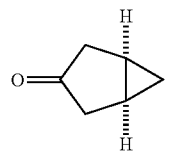

Sodium dichromate dihydrate, (983 mg, 3.3 mmol) was dissolved in water, (5 mL) at room temperature. Then sulphuric acid (97%, 0.6 mL, 5.8 mmol) was added dropwise with stirring. The resulting chromic acid solution was added dropwise to bicyclo[3.1.0]hexan-3-ol, (982 mg, 10 mmol) in 5 mL Et$_2$O, and the mixture was stirred vigorously for 4 h. Water, (20 mL) was added, the upper ethereal layer was separated and the aqueous phase was extracted with Et$_2$O, (20 mL) (×2). The combined ether phases were washed with saturated NaHCO$_3$, (20 mL), brine, (20 mL), dried (Na$_2$SO$_4$) and the solvent was evaporated carefully under reduced pressure. The material was passed through a pad of silica gel eluting with Et$_2$O to provide the title compound. 364 mg.

6.1.c) Synthesis of ±(1S,5S)-3-chlorobicyclo[3.1.0]hex-2-ene-2-carbaldehyde

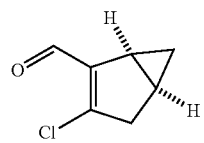

Bicyclo[3.1.0]hexan-3-one (192 mg, 2.0 mmol) was reacted with POCl$_3$, (0.33 mL, 3.6 mmol) and dry DMF (0.31 mL, 4.0 mmol) in dry CH$_2$Cl$_2$ (0.3 mL) according to General Procedure 1.1.A. The material was purified by passing

6.1.d) Synthesis of ±(E)-ethyl 3-((1S,5S)-3-chlorobicyclo[3.1.0]hex-2-en-2-yl)acrylate

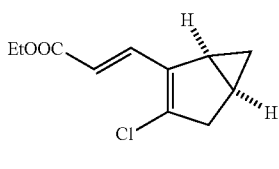

3-Chlorobicyclo[3.1.0]hex-2-ene-2-carbaldehyde (142 mg, 0.67 mmol) was olefinated according to General Procedure 1.1.B with ethoxycarbonylmethylene triphenylphosphorane ((487 mg, 1.4 mmol). The material was purified by chromatography, eluting with heptane-EtOAc, gradient 0 to 10% EtOAc to afford the title compound. 142 mg. $^1$H NMR (CHLOROFORM-d) δ: 7.57 (d, J=15.8 Hz, 1H), 6.11 (d, J=15.7 Hz, 1H), 4.25 (q, J=7.1 Hz, 2H), 3.01 (dd, J=19.1, 7.3 Hz, 1H), 2.65 (dd, J=19.1, 2.9 Hz, 1H), 1.93-2.03 (m, 1H), 1.61 (qd, J=7.3, 4.3 Hz, 1H), 1.33 (t, J=7.1 Hz, 3H), 1.00 (td, J=7.5, 4.7 Hz, 1H), 0.13-0.21 (m, 1H).

6.1.e) Synthesis of ±(1aS,5aS)-1a,4,5,5a-tetrahydro-1H-4-aza-cyclopropa[a]pentalene-3-carboxylic acid ethyl ester

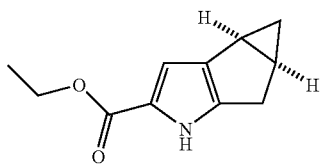

(E)-Ethyl 3-(3-chlorobicyclo[3.1.0]hex-2-en-2-yl)acrylate (142 mg, 0.67 mmol) was reacted with sodium azide (65 mg, 1.00 mmol) according to General Procedure 1.1.C. The product was purified by chromatography eluting with heptane-EtOAc, gradient 0 to 10% EtOAc to afford the title compound. 38 mg. $^1$H NMR (CHLOROFORM-d) δ: 8.67 (br. s., 1H), 6.71 (d, J=1.7 Hz, 1H), 4.28 (q, J=7.1 Hz, 2H), 2.95 (dd, J=16.6, 6.6 Hz, 1H), 2.73 (d, J=16.6 Hz, 1H), 1.87-2.07 (m, 2H), 1.34 (t, J=7.1 Hz, 3H), 1.02 (td, J=7.6, 4.7 Hz, 1H), 0.17 (q, J=4.2 Hz, 1H).

6.2. Synthesis of ±(1S,1aS,5aR)-1-ethyl-1a,4,5,5a-tetrahydro-1H-4-aza-cyclopropa[a]pentalene-3-carboxylic acid ethyl ester

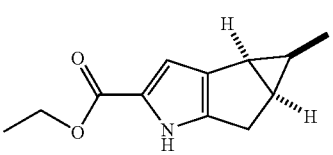

6.2.a) Synthesis of (Z)-trimethyl(3-(tetrahydro-2H-pyran-2-yloxy)hept-5-en-1-ynyl)silane

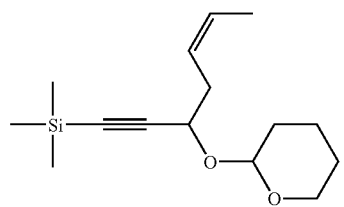

Reaction of trimethyl(3-(tetrahydro-2H-pyran-2-yloxy)prop-1-ynyl)silane (0.157 g, 0.74 mmol) and (Z)-1-bromobut-2-ene (0.12 g, 0.89 mmol) according to General Procedure 11.A provided (Z)-trimethyl(3-(tetrahydro-2H-pyran-2-yloxy)hept-5-en-1-ynyl)silane. The (Z)-1-bromobut-2-ene starting material was synthesized in two steps according to General Procedures 11.F and 11.G.

6.2.b) Synthesis of (Z)-1-(trimethylsilyl)hept-5-en-1-yn-3-ol

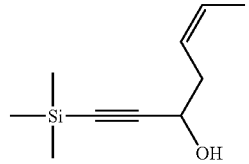

The tetrahydropyran protecting group on (Z)-trimethyl(3-(tetrahydro-2H-pyran-2-yloxy)hept-5-en-1-ynyl)silane was removed according to General Procedure 11.B to afford the title compound.

6.2.c) Synthesis of (Z)-hept-5-en-1-yn-3-ol

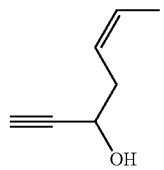

The trimethylsilyl group on (Z)-1-(trimethylsilyl)hept-5-en-1-yn-3-ol was then removed according to General Procedure 11.C to provide the title compound.

6.2.d) Synthesis of ±(1R,5S,6r)-6-methylbicyclo[3.1.0]hexan-3-one

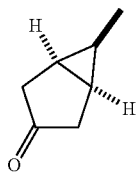

(Z)-hept-5-en-1-yn-3-ol was cyclized in the presence of PtCl$_2$ catalyst (0.31 g, 1.17 mmol) according to General Procedure 11.D to afford the title compound.

6.2.e) Synthesis of ±(1S,5R,6S)-3-chloro-6-methyl-bicyclo[3.1.0]hex-2-ene-2-carbaldehyde

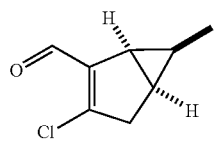

±(1R,5S,6r)-6-Methylbicyclo[3.1.0]hexan-3-one was formylated according to General Procedure 1.1.A to provide the title compound.

6.2.f) Synthesis of ±(E)-ethyl 3-((1S,5R,6S)-3-chloro-6-methylbicyclo[3.1.0]hex-2-en-2-yl)acrylate

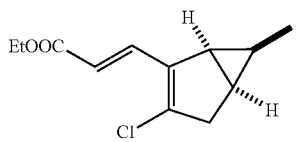

±(1S,5R,6S)-3-Chloro-6-methylbicyclo[3.1.0]hex-2-ene-2-carbaldehyde was olefinated with ethoxycarbonylmethylene triphenylphosphorane according to General Procedure 1.1.B to afford the title compound.

6.2.g) Synthesis of ±(1S,1aS,5aR)-1-ethyl-1a, 4,5,5a-tetrahydro-1H-4-aza-cyclopropa[α]pentalene-3-carboxylic acid ethyl ester

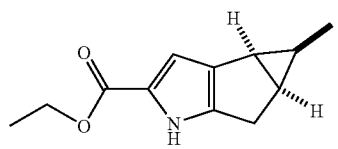

±(E)-Ethyl 3-((1S,5R,6S)-3-chloro-6-methylbicyclo[3.1.0]hex-2-en-2-yl)acrylate was cyclized according to General Procedure 1.1.C. Purification by column chromatography afforded the title compound.

6.3. Synthesis of ±(1S,1aS,5aR)-1-propyl-1a,4,5,5a-tetrahydro-1H-4-aza-cyclopropa[α]pentalene-3-carboxylic acid methyl ester and ±(1R,1aS,5aR)—)-1-propyl-1a,4,5,5a-tetrahydro-1H-4-aza-cyclopropa[α]pentalene-3-carboxylic acid methyl ester

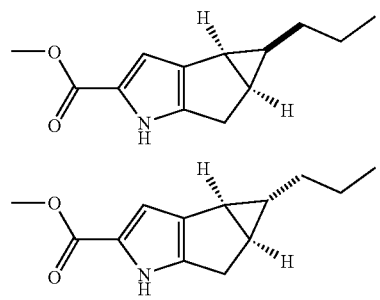

6.3.a) Synthesis of (Z)-trimethyl(3-(tetrahydro-2H-pyran-2-yloxy)non-5-en-1-ynyl)silane

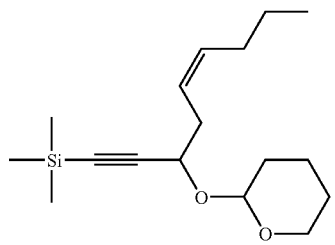

Reaction of trimethyl(3-(tetrahydro-2H-pyran-2-yloxy)prop-1-ynyl)silane and (Z)-1-bromohex-2-ene according to General Procedure 11.A provided (Z)-trimethyl(3-(tetrahydro-2H-pyran-2-yloxy)non-5-en-1-ynyl)silane.

6.3.b) Synthesis of (Z)-1-(trimethylsilyl)non-5-en-1-yn-3-ol

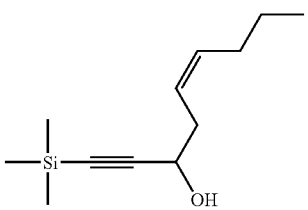

The tetrahydropyran protecting group on (Z)-trimethyl(3-(tetrahydro-2H-pyran-2-yloxy)hept-5-en-1-ynyl)silane was removed according to General Procedure 11.B to afford the title compound.

6.3.c) Synthesis of (Z)-non-5-en-1-yn-3-ol

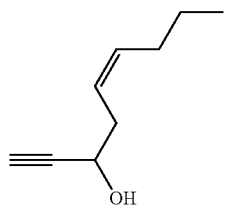

The trimethylsilyl group on (Z)-1-(trimethylsilyl)hept-5-en-1-yn-3-ol was then removed according to General Procedure 11.C to provide the title compound.

6.3.d) Synthesis of a mixture of ±(1R,5S,6r)-6-propylbicyclo[3.1.0]hexan-3-one and ±(1R,5S,6s)-6-propylbicyclo[3.1.0]hexan-3-one

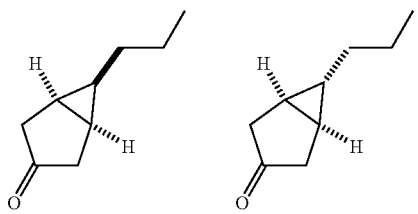

(Z)-Non-5-en-1-yn-3-ol was cyclized in the presence of PtCl₂ catalyst (0.31 g, 1.17 mmol) according to General Procedure 11.D to afford the mixture containing the title compounds.

6.3.e) Synthesis of ±(1S,5R,6S)-3-chloro-6-propyl-bicyclo[3.1.0]hex-2-ene-2-carbaldehyde and (1S,5R,6R)-3-chloro-6-propylbicyclo[3.1.0]hex-2-ene-2-carbaldehyde

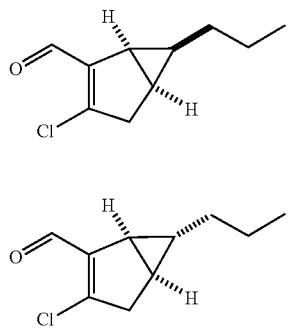

The mixture of ±(1R,5S,6r)-6-propylbicyclo[3.1.0]hexan-3-one and +(1R,5S,6s)-6-propylbicyclo[3.1.0]hexan-3-one was formylated according to General Procedure 1.A to provide the title compounds.

6.3.f) Synthesis of ±3-((1S,5R,6S)-3-chloro-6-propyl-bicyclo[3.1.0]hex-2-en-2-yl)-acrylic acid ethyl ester and ±3-((1S,5R,6R)-3-chloro-6-propyl-bicyclo[3.1.0]hex-2-en-2-yl)-acrylic acid ethyl ester

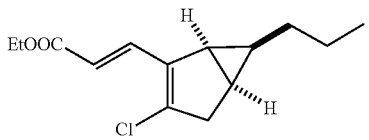

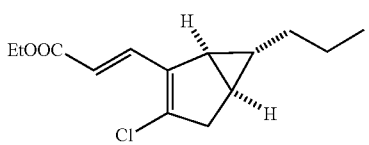

The mixture of ±(1S,5R,6S)-3-chloro-6-propyl-bicyclo[3.1.0]hex-2-ene-2-carbaldehyde and (1S,5R,6R)-3-chloro-6-propylbicyclo[3.1.0]hex-2-ene-2-carbaldehyde was olefinated with ethoxycarbonylmethylene triphenylphosphorane according to General Procedure 1.1.B to afford the title compounds.

6.3.g) Synthesis of ±(1S,1aS,5aR)-1-propyl-1a, 4,5,5a-tetrahydro-1H-4-aza-cyclopropa[α]pentalene-3-carboxylic acid ethyl ester and ±(1R,1aS,5aR)-)-1-propyl-1a,4,5,5a-tetrahydro-1H-4-aza-cyclopropa[α]pentalene-3-carboxylic acid ethyl ester

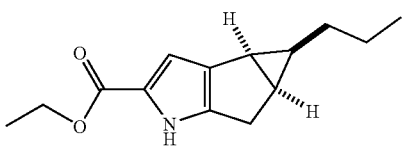

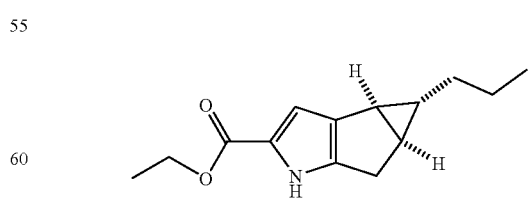

The mixture of ±(±3-((1S,5R,6S)-3-chloro-6-propyl-bicyclo[3.1.0]hex-2-en-2-yl)-acrylic acid ethyl ester and +3-((1S,5R,6R)-3-chloro-6-propyl-bicyclo[3.1.0]hex-2-en-2-yl)-acrylic acid ethyl ester was cyclized according to General Procedure 1.1.C. Purification by column chromatography afforded the title compounds as a mixture of isomers.

6.4. Synthesis of ±(1S,1aS,5aR)-1-Phenethyl-1a,4,5, 5a-tetrahydro-1H-4-aza-cyclopropa[a]pentalene-3-carboxylic acid ethyl ester

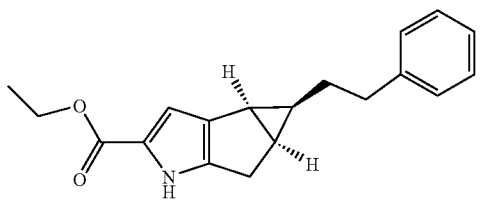

6.4.a) Synthesis of (Z)-trimethyl(8-phenyl-3-(tetrahydro-2H-pyran-2-yloxy)oct-5-en-1-ynyl)silane

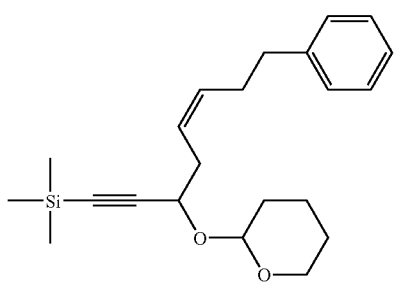

Reaction of trimethyl(3-(tetrahydro-2H-pyran-2-yloxy)prop-1-ynyl)silane (4.6 g, 21.6 mmol 4.6 g, 21.6 mmol) and (z)-5-bromo-pent-3-enyl)-benzene, (4.1 g, 18 mmol)) according to General Procedure 11.A provided the title compound. The material was used in the next step without purification.

6.4.b) Synthesis of (Z)-8-phenyl-1-(trimethylsilyl)oct-5-en-1-yn-3-ol

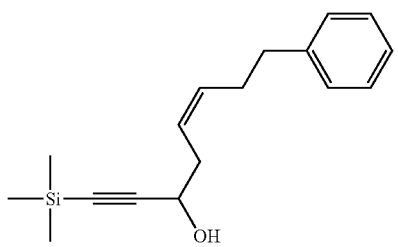

The tetrahydropyran protecting group on (Z)-trimethyl(8-phenyl-3-(tetrahydro-2H-pyran-2-yloxy)oct-5-en-1-ynyl)silane was removed according to General Procedure 11.B to afford the title compound, which was purified by chromatography, eluting with heptane-EtOAc, gradient 0 to 15% EtOAc. 3.0 g. $^1$H NMR (400 MHz, CHLOROFORM-d) δ ppm 0.17 (s, 9H), 1.69-1.76 (m, 1H), 2.35-2.48 (m, 4H), 2.70 (t, J=7.64 Hz, 2H), 4.30 (q, J=6.05 Hz, 1H), 5.46-5.59 (m, 1H), 5.60-5.70 (m, 1H), 7.16-7.23 (m, 3H), 7.26-7.32 (m, 2H).

6.4.c) Synthesis of (Z)-8-phenyloct-5-en-1-yn-3-ol

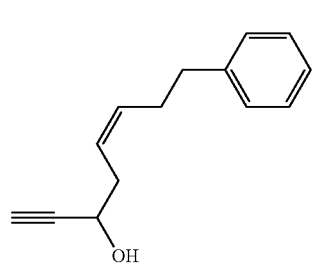

The trimethylsilyl group on (Z)-8-phenyl-1-(trimethylsilyl)oct-5-en-1-yn-3-ol was removed according to General Procedure 11.C to provide the title compound. The material was purified by chromatography, eluting with heptane-EtOAc, gradient 0 to 20% EtOAc. 1.7 g. $^1$H NMR (400 MHz, CHLOROFORM-d) δ ppm 1.74 (d, J=6.15 Hz, 1H), 2.38-2.47 (m, 5H), 2.70 (t, J=7.59 Hz, 2H), 4.29 (qd, J=6.12, 2.05 Hz, 1H), 5.47-5.56 (m, 1H), 5.63-5.72 (m, 1H), 7.17-7.23 (m, 3H), 7.26-7.32 (m, 2H).

6.4.d) Synthesis of ±(1R,5S,6r)-6-phenethylbicyclo[3.1.0]hexan-3-one

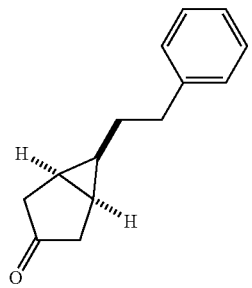

(Z)-8-phenyloct-5-en-1-yn-3-ol (1.7 g, 8.5 mmol) was cyclized in the presence of PtCl$_2$ (113 mg, 0.4 mmol) catalyst according to General Procedure 11.D to afford the title compound. The material purified by chromatography, eluting with heptane-EtOAc, gradient to 0 to 15% EtOAc. 1.6 g. $^1$H NMR (400 MHz, CHLOROFORM-d) δ ppm 1.02 (quin, J=7.81 Hz, 1H), 1.42 (q, J=7.47 Hz, 2H), 1.53-1.59 (m, 2H), 2.00-2.08 (m, 2H), 2.48-2.58 (m, 2H), 2.69 (t, J=7.49 Hz, 2H), 7.15-7.22 (m, 3H), 7.25-7.31 (m, 2H).

6.4.e) Synthesis of ±(1S,5R,6S)-3-chloro-6-phenethylbicyclo[3.1.0]hex-2-ene-2-carbaldehyde

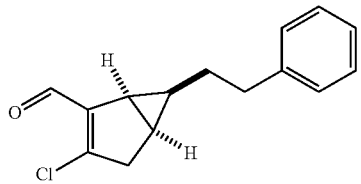

±(1R,5S,6r)-6-phenethylbicyclo[3.1.0]hexan-3-one (2.2 g, 11.0 mmol) was formylated with POCl₃ (1.8 mL, 19.8 mmol) according to General Procedure 1.1.A to provide the title compound. The material was purified by passing through a pad of silica gel eluting with Et₂O.

6.4.f) Synthesis of ±(E)-ethyl 3-((1S,5R,6S)-3-chloro-6-phenethylbicyclo[3.1.0]hex-2-en-2-yl)acrylate

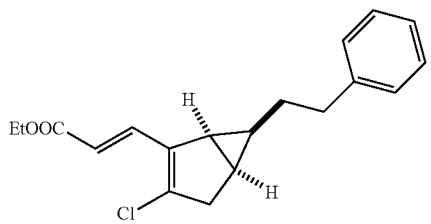

±(1S,5R,6S)-3-chloro-6-phenethylbicyclo[3.1.0]hex-2-ene-2-carbaldehyde (11 mmol crude weight) was olefinated with ethoxycarbonylmethylene triphenylphosphorane (4.6 g, 13.2 mmol) according to General Procedure 1.1.B to afford the title compound. The material was purified by chromatography, eluting with heptane-EtOAc, gradient 0 to 10% EtOAc. 2.2 g. ¹H NMR (400 MHz, CHLOROFORM-d) δ ppm 1.08-1.19 (m, 1H), 1.23-1.31 (m, 1H), 1.30-1.37 (m, 3H), 1.39-1.51 (m, 1H), 1.59-1.68 (m, 1H), 2.14 (td, J=7.25, 3.03 Hz, 1H), 2.38 (dd, J=19.57, 2.68 Hz, 1H), 2.53-2.66 (m, 2H), 2.92 (dd, J=19.55, 7.88 Hz, 1H), 4.20-4.31 (m, 2H), 6.04 (d, J=15.72 Hz, 1H), 7.10-7.22 (m, 3H), 7.23-7.31 (m, 2H), 7.61 (d, J=15.72 Hz, 1H).

6.4.g) Synthesis of ±(1S,1aS,5aR)-1-Phenethyl-1a,4,5,5a-tetrahydro-1H-4-aza-cyclopropa[α]pentalene-3-carboxylic acid ethyl ester

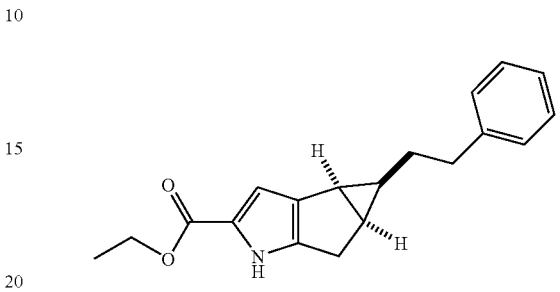

±(E)-ethyl 3-((1S,5R,6S)-3-chloro-6-phenethylbicyclo[3.1.0]hex-2-en-2-yl)acrylate (2.20 g, 0.7.0 mmol) was cyclized according to General Procedure 1.1.C. Purification by column chromatography afforded the title compound. This material was purified by reverse phase HPLC using a water-MeOH, gradient 70 to 90% MeOH. 300 mg. ¹H NMR (400 MHz, CHLOROFORM-d) δ ppm 0.91-1.15 (m, 2H), 1.21-1.32 (m, 1H), 1.35 (t, J=7.13 Hz, 3H), 1.95 (q, J=7.13 Hz, 1H), 2.18 (t, J=7.00 Hz, 1H), 2.47 (d, J=17.03 Hz, 1H), 2.56 (t, J=7.61 Hz, 2H), 2.86 (dd, J=17.06, 7.10 Hz, 1H), 4.29 (q, J=7.13 Hz, 2H), 6.68 (d, J=1.66 Hz, 1H), 7.07 (d, J=8.20 Hz, 2H), 7.12-7.19 (m, 1H), 7.23 (t, J=7.30 Hz, 2H), 8.59 (br. s, 1H).

6.5. Synthesis of ±(1R,1aR,5aR)-1-phenyl-1a,4,5,5a-tetrahydro-1H-4-aza-cyclopropa[α]pentalene-3-carboxylic acid ethyl ester

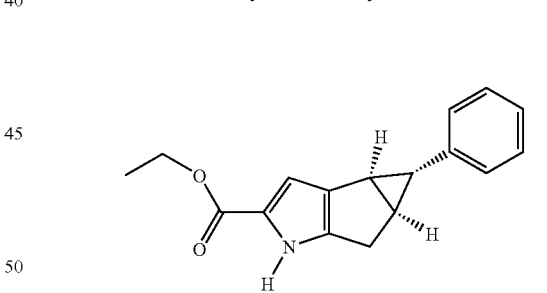

The title compound was synthesized in 7 steps. First, reaction of trimethyl(3-(tetrahydro-2H-pyran-2-yloxy)prop-1-ynyl)silane (6.4 g, 30 mmol) and (E)-(3-bromoprop-1-enyl)benzene (5.3 mL, 36 mmol) according to General Procedure 11.A provided (E)-trimethyl(6-phenyl-3-(tetrahydro-2H-pyran-2-yloxy)hex-5-en-1-ynyl)silane. Tetrahydropyran removal according to General Procedure 11.B afforded (E)-6-phenyl-1-(trimethylsilyl)hex-5-en-1-yn-3-ol. The trimethylsilyl group was then removed according to General Procedure 11.C to provide (E)-6-phenylhex-5-en-1-yn-3-ol, which was then cyclized in the presence of PtCl₂ catalyst (53 mg, 0.2 mmol) according to General Procedure 11.D to afford the cyclopropyl-fused cyclopentanone compound ±(1R,5S,6R)-6-phenylbicyclo[3.1.0]hexan-3-one.

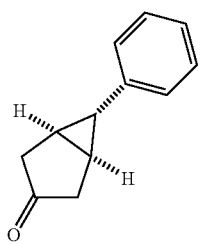

Formylation according to General Procedure 1.1.A afforded the desired ±(1R,5R,6R)-3-chloro-6-phenylbicyclo[3.1.0]hex-2-ene-2-carbaldehyde, which was olefinated according to General Procedure 1.1.B to provide ±(E)-3-((1R,5R,6R)-3-chloro-6-phenyl-bicyclo[3.1.0]hex-2-en-2-yl)-acrylic acid ethyl ester. Cyclization according to General Procedure 1.1. C provided the title compound, which was purified by chromatography, eluting with heptane-EtOAc, gradient 0 to 10% EtOAc. 5 mg.

6.6. Synthesis of (1aS,5aS)-1a,4,5,5a-tetrahydro-1H-2-bromo-4-aza-cyclopropa[a]pentalene-3-carboxylic acid ethyl ester

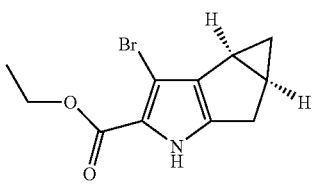

To a solution of ±(1aS,5aS)-1a,4,5,5a-tetrahydro-1H-4-aza-cyclopropa[a]pentalene-2-carboxylic acid ethyl ester (1 g, 5 mmol) in dichloromethane in a 3-neck flask at 2-5° C. was added a solution of TBAF (2.04 g, 7.8 mmol) in THF (3 mL), followed by addition of a suspension of NBS (1.07 g, 6 mmol) in dichloromethane. The reaction mixture was stirred at 2-5° C. for 3 h, warmed up to room temperature, then stirred for additional 1 h. The mixture was poured into water, then extracted with ethyl acetate. After concentration, 0.7 g of the pure title compound was obtained by column chromatography purification. LC-MS: MS m/z: 271 (M+1).

6.7. Synthesis of (1aR,5aR)-1a,2,5,5a-tetrahydro-1H-2-aza-cyclopropa[a]pentalene-3-carboxylic acid ethyl ester

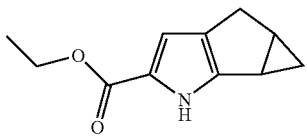

References: *J. Org. Chem.*, 1990, 55, 695.; *Tetrahedron Asymmetry*, 2006, 17, 252.

The title compound was synthesized in 4 steps. First, sodium hydride (60% in mineral oil), (6.0 g, 150 mmol) was placed in a dry 500 mL 3 neck flask equipped with nitrogen inlet, thermometer and septum. The sodium hydride was washed 3 times with dry hexane. Then dry DMSO (150 mL) was added and Me$_3$SOI was added portion-wise allowing for evolution of H$_2$ whilst maintaining the temperature below 30° C. The mixture was allowed 1.5 h and then 2-cyclopentene-1-one, (12 mL, 150 mmol) was added as a solution in DMSO, (20 mL). The reaction was stirred until complete (overnight). The mixture was poured onto ice water, (1000 mL), extracted with Et$_2$O, (200 mL) (×3), the combined Et$_2$O extracts were washed with water (250 mL), washed with brine (250 mL), dried (Na$_2$SO$_4$). Purification by distillation provided bicyclo[3.1.0]hexan-2-one. Next, bicyclo[3.1.0]hexan-2-one (1.44 g, 15 mmol) in dry CH$_2$Cl$_2$, (0.2 mL) was formylated by reaction with POCl$_3$, (2.52 mL, 27 mmol) and DMF (2.32 mL, 30 mmol) according to General Procedure 1.1.A to afford the desired ±(1R,5R,6R)-2-chloro-bicyclo[3.10]hex-2-ene-3-carbaldehyde, which was olefinated according to General Procedure 1.1.B to provide ±(1R,5R,6R)-(E)-3-(2-chloro-bicyclo[3.1.0]hex-2-en-3-yl)-acrylic acid ethyl ester. Cyclization according to General Procedure 1.1.C provided the title compound, which was purified by chromatography eluting with heptane-EtOAc, gradient 0 to 15% EtOAc. 107 mg. $^1$H NMR (400 MHz, CHLOROFORM-d) δ ppm 1.08 (dd, J=15.33, 4.59 Hz, 1H), 1.33 (t, J=7.10 Hz, 3H), 2.01-2.16 (m, 2H), 2.61 (d, J=15.47 Hz, 1H), 2.83 (dd, J=15.55, 6.27 Hz, 1H), 4.28 (q, J=7.14 Hz, 2H), 6.61 (d, J=1.22 Hz, 1H), 8.86 (br. s, 1H).

6.8. Synthesis of 3-bromo-4-phenethyl-1,4,5,6-tetrahydrocyclopenta[b]pyrrole-2-carboxylic acid

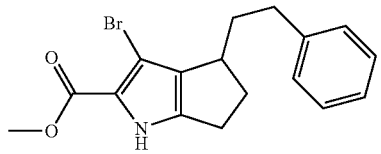

Tetrabutylammonium tribromide (114 mg, 0.24 mmol) was added to a solution of methyl 4-phenethyl-1,4,5,6-tetrahydrocyclopenta[b]pyrrole-2-carboxylate (53 mg, 0.2 mmol) in 5 mL of acetonitrile at room temperature. After reacting overnight, the reaction was diluted with water and extracted with ethyl acetate (3×50 mL). The combined organic extracts were washed with brine, dried (Na$_2$SO$_4$), filtered and concentrated with silica gel. Purification by column chromatography (Isco CombiFlash) eluting with a gradient of 0-30% EtOAc/heptane gave the title compound. 54.2 mg. $^1$H NMR (400 MHz, METHANOL-d$_4$) δ ppm 1.69-1.80 (m, 1H), 2.10-2.22 (m, 2H), 2.56-2.71 (m, 4H), 2.72-2.83 (m, 1H), 3.00-3.09 (m, 1H), 3.80 (s, 3H), 7.11-7.16 (m, 1H), 7.17-7.21 (m, 2H), 7.22-7.27 (m, 2H); LCMS-MS (ESI+) 372.0 (M+Na).

6.10. Synthesis of ±(1aS,5aS)-1a,4,5,5a-tetrahydro-1H-4-aza-cyclopropa[α]pentalene-3-carboxylic acid (138)

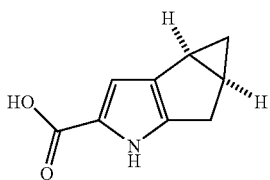

The title compound was synthesized from ±(1aS,5aS)-1a,4,5,5a-tetrahydro-1H-4-aza-cyclopropa[α]pentalene-3-carboxylic acid ethyl ester (65 mg, 0.34 mmol) and lithium hydroxide (143 mg, 3.40 mmol in 5 mL water), according to General Procedure 7. The resulting product was purified by crystallization from Et$_2$O. 35 mg. $^1$H NMR (METHANOL-d$_4$) δ: 6.61 (s, 1H), 2.90 (dd, J=16.7, 6.3 Hz, 1H), 2.69 (d, J=16.7 Hz, 1H), 1.88-2.02 (m, 2H), 0.95-1.04 (m, 1H), 0.07 (q, J=4.0 Hz, 1H). LCMS m/e 164 (M+H). Purity ~100% (HPLC).

The enantiomers of ±(1aS,5aS)-1a,4,5,5a-tetrahydro-1H-4-aza-cyclopropa[α]pentalene-3-carboxylic acid were separated according to General Procedure 8 with a mixture of 60% in CO$_2$ to give 1a,4,5,5a-tetrahydro-1H-4-aza-cyclopropa[α]pentalene-3-carboxylic acid (139), (peak 1, retention time=1.4 min; 99.8% ee) and 1a,4,5,5a-tetrahydro-1H-4-aza-cyclopropa[α]pentalene-3-carboxylic acid (140) (peak 2, retention time=2.0 min; 98.3% ee).

6.11. Synthesis of ±(1S,1aS,5aR)-1-methyl-1a,4,5,5a-tetrahydro-1H-4-aza-cyclopropa[α]pentalene-3-carboxylic acid (141)

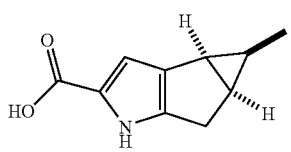

The title compound was synthesized from ±(1S,1aS,5aR)-1-methyl-1a,4,5,5a-tetrahydro-1H-4-aza-cyclopropa[α]pentalene-3-carboxylic acid ethyl ester (0.12 g, 0.585 mmol) and sodium hydroxide (1.5M, 3.1 mL) according to General Procedure 7 to afford the title compound. LC-MS: MS m/z: 178 (M+1).

6.12. Synthesis of the mixture of ±(1S,1aS,5aR)-1-propyl-1a,4,5,5a-tetrahydro-1H-4-aza-cyclopropa[α]pentalene-3-carboxylic acid and ±(1R,1aS,5aR)-1-propyl-1a,4,5,5a-tetrahydro-1H-4-aza-cyclopropa[α]pentalene-3-carboxylic acid (142)

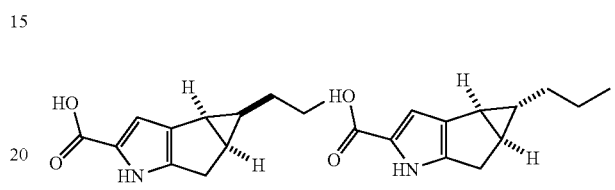

The title compound was synthesized from a mixture of ±(1S,1aS,5aR)-1-propyl-1a,4,5,5a-tetrahydro-1H-4-aza-cyclopropa[α]pentalene-3-carboxylic acid methyl ester and ±(1R,1aS,5aR)—)-1-propyl-1a,4,5,5a-tetrahydro-1H-4-aza-cyclopropa[α]pentalene-3-carboxylic acid methyl ester according to General Procedure 7 to afford the title compound.

6.13. Synthesis of ±(1S,1aS,5aR)-1-phenethyl-1a,4,5,5a-tetrahydro-1H-4-aza-cyclopropa[α]pentalene-3-carboxylic acid (143)

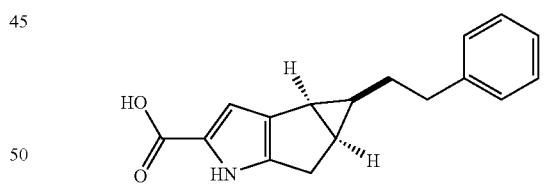

The title compound was synthesized from ±(1S,1aS,5aR)-1-phenethyl-1a,4,5,5a-tetrahydro-1H-4-aza-cyclopropa[α]pentalene-3-carboxylic acid ethyl ester (295 mg, 1.0 mmol) and lithium hydroxide (419 mg, 10.0 mmol in 7 mL water) according to General Procedure 7. A 1:1 mixture of methanol (MeOH) and THF (14 mL) was used. The resulting product was purified by chromatography, eluting with heptane-EtOAc, 0 to 50% EtOAc. 225 mg. $^1$H NMR (400 MHz, CHLOROFORM-d) δ ppm 0.93-1.06 (m, 1H), 1.07-1.17 (m, 1H), 1.24-1.38 (m, 1H), 1.98 (q, J=6.90 Hz, 1H), 2.20 (t, J=6.74 Hz, 1H), 2.50 (d, J=17.33 Hz, 1H), 2.53-2.61 (m, 2H), 2.88 (dd, J=17.23, 7.13 Hz, 1H), 6.80 (d, J=1.51 Hz, 1H), 7.07

(d, J=7.08 Hz, 2H), 7.16 (d, J=7.32 Hz, 1H), 7.24 (t, J=7.39 Hz, 2H), 8.81 (br. s, 1H). LCMS m/e 268 (M+H). Purity 98% (HPLC).

6.14. Synthesis of ±(1R,1aR,5aR)-1-phenyl-1a,4,5,5a-tetrahydro-1H-4-aza-cyclopropa[a]pentalene-3-carboxylic acid (144)

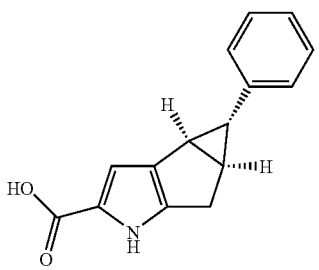

The title compound was synthesized from ±(1R,1aR,5aR)-1-phenyl-1a,4,5,5a-tetrahydro-1H-4-aza-yclopropa[α]pentalene-3-carboxylic acid ethyl ester (5 mg, 0.02 mmol) and lithium hydroxide (8 mg, 0.2 mmol in 1 mL water) according to General Procedure 7. A 1:1 mixture of methanol (MeOH) and THF (2 mL) was used. The resulting product was purified by chromatography, eluting with heptane-EtOAc (1:1). 3 mg. $^1$H NMR (400 MHz, METHANOL-$d_4$) δ ppm 1.54 (t, J=3.27 Hz, 1H) 2.20-2.28 (m, 1H), 2.28-2.35 (m, 1H), 2.85-2.96 (m, 1H), 3.01-3.12 (m, 1H), 6.67 (s, 1H), 7.04 (d, J=8.44 Hz, 2H), 7.12 (d, J=7.42 Hz, 1H), 7.21 (d, J=7.71 Hz, 2H). LCMS m/e 240 (M+H). Purity 88% (HPLC).

6.15. Synthesis of (1aS,5aS)-1a,4,5,5a-tetrahydro-1H-2-bromo-4-aza-cyclopropa[α]pentalene-3-carboxylic acid (145)

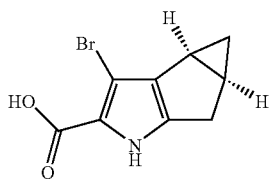

The title compound was synthesized from (1aS,5aS)-1a,4,5,5a-tetrahydro-1H-2-bromo-4-aza-cyclopropa[α]pentalene-3-carboxylic acid ethyl ester according to General Procedure 7. LC-MS: MS m/z: 242 (M+1).

6.16. Synthesis of (1aR,5aR)-1a,2,5,5a-tetrahydro-1H-2-aza-cyclopropa[α]pentalene-3-carboxylic acid (146)

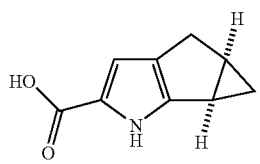

The title compound was synthesized from (1aR,5aR)-1a,2,5,5a-tetrahydro-1H-2-aza-cyclopropa[α]pentalene-3-carboxylic acid ethyl ester (115 mg, 0.6 mmol) and lithium hydroxide (252 mg, 6.0 mmol in 5 mL water) according to General Procedure 7. A 1:1 mixture of methanol (MeOH) and THF (10 mL) was used. The resulting product was purified by chromatography eluting with heptane-EtOAc, gradient 0 to 50% EtOAc. 27 mg. $^1$H NMR (400 MHz, CHLOROFORM-d) δ ppm 0.31-0.39 (m, 1H), 1.06-1.16 (m, 1H), 2.04-2.19 (m, 2H), 2.63 (d, J=15.67 Hz, 1H), 2.84 (dd, J=15.62, 6.35 Hz, 1H), 6.73 (s, 1H), 8.97 (br. s, 1H). LCMS m/e 164 (M+H). Purity>85% (HPLC).

6.17. Synthesis of 3-bromo-4-phenethyl-1,4,5,6-tetrahydrocyclopenta[b]pyrrole-2-carboxylic acid (147)

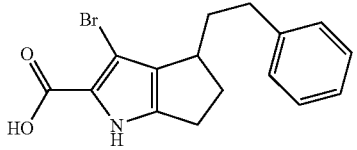

The title compound was synthesized from methyl 3-bromo-4-phenethyl-1,4,5,6-tetrahydrocyclopenta[b]pyrrole-2-carboxylate (68 mg, 0.20 mmol) and lithium hydroxide monohydrate (33 mg, 0.78 mmol in 3 mL water), according to General Procedure 7. A 1:1 mixture of methanol (MeOH) and THF (6 mL) was used. The resulting product was purified by flash chromatography (Isco CombiFlash) eluting with a gradient of 0-80% EtOAc/Heptane to the title compound. 37 mg. $^1$H NMR (400 MHz, METHANOL-$d_4$) δ ppm 1.68-1.80 (m, 1H), 2.08-2.22 (m, 2H), 2.55-2.71 (m, 4H), 2.71-2.83 (m, 1H), 3.00-3.08 (m, 1H), 7.10-7.16 (m, 1H), 7.17-7.28 (m, 4H); LCMS-MS (ESI+) 356.0 (M+Na); HPLC (UV=93.2%), (ELSD=100%).

6.18. Synthesis of 5,5-difluoro-4-methoxy-1,4,5,6-tetrahydrocyclopenta[b]pyrrole-2-carboxylic acid (148)

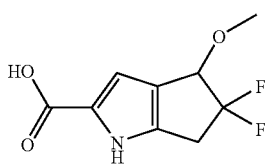

A magnetically-stirred solution/suspension of methyl 5,5-difluoro-4-methoxy-1,4,5,6-tetrahydrocyclopenta[b]pyrrole-2-carboxylate, (17.40 mg, 0.075 mmol) in pH=7 buffer solution, was treated with pig-liver esterase (PLE) (64.44 mg, 100 U/mg), and warmed at 32-37° C. for a period of 18 h after conversion to product appeared to stop. The suspension was diluted with EtOAc (20 mL) and dried onto Celite. The crude was then purified by silica gel chromatography (twice). 7.9 mg. $^1$H NMR (400 MHz, ACETONE-$d_6$) δ ppm 3.17-3.41 (m, 2H), 3.43 (s, 3H), 4.60 (d, J=13.28 Hz, 1H), 6.81 (s, 1H), 10.93 (br. s., 1H); $^{19}$F NMR (400 MHz, ACETONE-$d_6$) δ ppm −105.48 (d, J=0.63 Hz, 1F), −93.65 (d, J=0.65 Hz, 1F); LCMS-MS (ESI−) 216.2 (M-1).

Example 7

D-Amino Acid Oxidase Inhibition

7.1. D-Amino Acid Oxidase Enzyme Assay

DAAO enzyme activity was measured using the substrate D-serine at its Michaelis-Menton $K_m$ of 5 mM. The rate of oxidation is measured as a rate of production of hydrogen peroxide, which was detected using the enzyme horseradish peroxidase (Sigma cat. No. P-8375). This coupled reaction uses the enzyme substrate Amplex Red (Molecular Probes), which is converted to the fluorescent reaction product, resorufin (excitation 530-560 nm; emission ~590 nm). Although DAAO has a higher pH optimum, all reagents were prepared in 50 mM sodium phosphate buffer at pH 7.4 and inhibition curves were generated at this pH.

The final concentrations of components in 200 µl total volume per well (black clear-bottom 96-well plate, Costar) were:
(a) Horseradish peroxidase: 4 Units per mL
(b) D-serine: 5 mM
(c) Test Compound: 100-0.0064 uM for $IC_{50}$s
(d) Amplex Red reagent: 50 uM
(e) DMSO: 1.6%

The reactions were initiated by addition of DAAO enzyme and the fluorescence was monitored. $H_2O_2$ was added at 16 uM final concentration to a control well on each plate to test for compound interference with a coupled enzyme. Inhibition curves were generated in the presence of varying concentrations of the inhibitor and $IC_{50}$ values were calculated for each inhibitor.

7.2. Results of DAAO Inhibition Assay $IC_{50}$ values were determined for compounds 1 through 148, which are summarized in Table 2 below.

TABLE 2

Human and Porcine DAAO Inhibition [$IC_{50}$]

| Compound No. | Compound Name | Human DAAO (µM) |
|---|---|---|
| 1 | 1,4,5,6-tetrahydrocyclopenta[b]pyrrole-2-carboxylic acid | (+++) |
| 2 | 4-oxo-1,4,5,6-tetrahydrocyclopenta[b]pyrrole-2-carboxylic acid | (+) |
| 3 | 3-tert-butyl-4-oxo-1,4,5,6-tetrahydrocyclopenta[b]pyrrole-2-carboxylic acid | (−) |
| 4 | ±4-methyl-1,4,5,6-tetrahydrocyclopenta[b]pyrrole-2-carboxylic acid | (++) |
| 5[a] | Single enantiomer of ±4-methyl-1,4,5,6-tetrahydrocyclopenta[b]pyrrole-2-carboxylic acid (enantiomer 1, peak 2, retention time = 9.7 min.) | (++) |
| 6[b] | Single enantiomer of ±4-methyl-1,4,5,6-tetrahydrocyclopenta[b]pyrrole-2-carboxylic acid (enantiomer 2, peak 1, retention time = 8.1 min.) | (+) |
| 7 | ±4-propyl-1,4,5,6-tetrahydrocyclopenta[b]pyrrole-2-carboxylic acid | (+++) |
| 8[a] | Single enantiomer of ±4-propyl-1,4,5,6-tetrahydrocyclopenta[b]pyrrole-2-carboxylic acid (enantiomer 1, peak 2, retention time = 6.3 min.) | (+++) |
| 9[b] | Single enantiomer of ±4-propyl-1,4,5,6-tetrahydrocyclopenta[b]pyrrole-2-carboxylic acid (enantiomer 2, peak 1, retention time = 3.5 min.) | (+) |
| 10 | 4-isopropyl-1,4,5,6-tetrahydrocyclopenta[b]pyrrole-2-carboxylic acid | (++) |
| 11 | 4-isobutyl-1,4,5,6-tetrahydrocyclopenta[b]pyrrole-2-carboxylic acid | (++) |
| 12 | 4-(cyclohexylmethyl)-1,4,5,6-tetrahydrocyclopenta[b]pyrrole-2-carboxylic acid | (++) |
| 13 | 4-(4-fluorobenzylidene)-1,4,5,6-tetrahydrocyclopenta[b]pyrrole-2-carboxylic acid | (+) |
| 14 | ±4-(4-chlorobenzyl)-1,4,5,6-tetrahydrocyclopenta[b]pyrrole-2-carboxylic acid | (+++) |
| 15[a] | Single enantiomer of ±4-(4-chlorobenzyl)-1,4,5,6-tetrahydrocyclopenta[b]pyrrole-2-carboxylic acid (enantiomer 1, peak 2, retention time = 6.9 min.) | (+++) |
| 16[b] | Single enantiomer of ±4-(4-chlorobenzyl)-1,4,5,6-tetrahydrocyclopenta[b]pyrrole-2-carboxylic acid (enantiomer 2, peak 1, retention time = 4.5 min.) | (+) |
| 17 | 4-benzyl-1,4,5,6-tetrahydrocyclopenta[b]pyrrole-2-carboxylic acid | (+++) |
| 33 | 4-(4-isopropylbenzyl)-1,4,5,6-tetrahydrocyclopenta[b]pyrrole-2-carboxylic acid | (++) |
| 18 | ±4-phenethyl-1,4,5,6-tetrahydrocyclopenta[b]pyrrole-2-carboxylic acid | (++) |
| 19[a] | Single enantiomer of ±4-phenethyl-1,4,5,6-tetrahydrocyclopenta[b]pyrrole-2-carboxylic acid (enantiomer 1, peak 1, retention time = 12.8 min.) | (++) |
| 20[b] | Single enantiomer of ±4-phenethyl-1,4,5,6-tetrahydrocyclopenta[b]pyrrole-2-carboxylic acid (enantiomer 2, peak 2, retention time = 13.8 min.) | (+) |
| 34 | 4-(4-methoxyphenethyl)-1,4,5,6-tetrahydrocyclopenta[b]pyrrole-2-carboxylic acid | (+) |
| 35 | 4-(2-methyl-2-phenylpropyl)-1,4,5,6-tetrahydrocyclopenta[b]pyrrole-2-carboxylic acid | (+) |
| 36 | 4-(3-phenylpropyl)-1,4,5,6-tetrahydrocyclopenta[b]pyrrole-2-carboxylic acid | (++) |
| 37 | 4-p-tolyl-1,4,5,6-tetrahydrocyclopenta[b]pyrrole-2-carboxylic acid | (++) |

TABLE 2-continued

Human and Porcine DAAO Inhibition [$IC_{50}$]

| Compound No. | Compound Name | Human DAAO (μM) |
|---|---|---|
| 38 | 4-(2,2,2-trifluoroethyl)-1,4,5,6-tetrahydrocyclopenta[b]pyrrole-2-carboxylic acid | (+) |
| 39 | ±4-(4-fluorobenzyl)-1,4,5,6-tetrahydrocyclopenta[b]pyrrole-2-carboxylic acid | (+++) |
| 40[a)] | Single enantiomer of ±4-(4-fluorobenzyl)-1,4,5,6-tetrahydrocyclopenta[b]pyrrole-2-carboxylic acid (enantiomer 1, peak 1, retention time = 3.0 min.) | (+++) |
| 41[b)] | Single enantiomer of ±4-(4-fluorobenzyl)-1,4,5,6-tetrahydrocyclopenta[b]pyrrole-2-carboxylic acid (enantiomer 2, peak 2, retention time = 3.6 min.) | (++) |
| 42 | ±4-(3,4-difluorobenzyl)-1,4,5,6-tetrahydrocyclopenta[b]pyrrole-2-carboxylic acid | (+++) |
| 43[b)] | Single enantiomer of ±4-(3,4-difluorobenzyl)-1,4,5,6-tetrahydrocyclopenta[b]pyrrole-2-carboxylic acid (enantiomer 1, peak 1, retention time = 1.7 min.) | (+) |
| 44[a)] | Single enantiomer of ±4-(3,4-difluorobenzyl)-1,4,5,6-tetrahydrocyclopenta[b]pyrrole-2-carboxylic acid (enantiomer 2, peak 2, retention time = 2.3 min.) | (+++) |
| 45 | ±4-(2,4-difluorobenzyl)-1,4,5,6-tetrahydrocyclopenta[b]pyrrole-2-carboxylic acid | (+++) |
| 46[b)] | Single enantiomer of ±4-(2,4-difluorobenzyl)-1,4,5,6-tetrahydrocyclopenta[b]pyrrole-2-carboxylic acid (enantiomer 1, peak 1, retention time = 1.9 min.) | (+) |
| 47[a)] | (Single enantiomer of ±4-(2,4-difluorobenzyl))-1,4,5,6-tetrahydrocyclopenta[b]pyrrole-2-carboxylic acid (enantiomer 2, peak 2, retention time = 3.3 min.) | (+++) |
| 48 | ±4-(3-chloro-4-fluorobenzyl)-1,4,5,6-tetrahydrocyclopenta[b]pyrrole-2-carboxylic acid | (+++) |
| 51 | ±4-(4-fluoro-2-methylbenzyl)-1,4,5,6-tetrahydrocyclopenta[b]pyrrole-2-carboxylic acid | (+++) |
| 52[b)] | Single enantiomer of ±4-(4-fluoro-2-methylbenzyl)-1,4,5,6-tetrahydrocyclopenta[b]pyrrole-2-carboxylic acid (enantiomer 1, peak 1, retention time = 5.1 min.) | (+) |
| 53[a)] | Single enantiomer of ±4-(4-fluoro-2-methylbenzyl)-1,4,5,6-tetrahydrocyclopenta[b]pyrrole-2-carboxylic acid (enantiomer 2, peak 2, retention time = 6.0 min.) | (+++) |
| 54 | 4-(3-fluorobenzyl)-1,4,5,6-tetrahydrocyclopenta[b]pyrrole-2-carboxylic acid | (+++) |
| 55 | 4-(3-chloro-5-fluorobenzyl)-1,4,5,6-tetrahydrocyclopenta[b]pyrrole-2-carboxylic acid | (+++) |
| 56 | 4-(3-chlorobenzyl)-1,4,5,6-tetrahydrocyclopenta[b]pyrrole-2-carboxylic acid | (+++) |
| 57 | ±4-(3,4-dichlorobenzyl)-1,4,5,6-tetrahydrocyclopenta[b]pyrrole-2-carboxylic acid | (+++) |
| 58[b)] | Single enantiomer of ±4-(3,4-dichlorobenzyl)-1,4,5,6-tetrahydrocyclopenta[b]pyrrole-2-carboxylic acid (enantiomer 1, peak 1, retention time = 2.9 min.) | (+) |
| 59[a)] | Single enantiomer of ±4-(3,4-dichlorobenzyl)-1,4,5,6-tetrahydrocyclopenta[b]pyrrole-2-carboxylic acid (enantiomer 2, peak 2, retention time = 4.7 min.) | (+++) |
| 60 | ±4-(4-bromobenzyl)-1,4,5,6-tetrahydrocyclopenta[b]pyrrole-2-carboxylic acid | (+++) |
| 61[b)] | Single enantiomer of ±4-(4-bromobenzyl)-1,4,5,6-tetrahydrocyclopenta[b]pyrrole-2-carboxylic acid (enantiomer 1, peak 1, retention time = 1.8 min.) | (+) |
| 62[a)] | Single enantiomer of ±4-(4-bromobenzyl)-1,4,5,6-tetrahydrocyclopenta[b]pyrrole-2-carboxylic acid (enantiomer 2, peak 2, retention time = 2.7 min.) | (+++) |
| 63 | ±4-(3-bromobenzyl)-1,4,5,6-tetrahydrocyclopenta[b]pyrrole-2-carboxylic acid | (+++) |
| 64[b)] | Single enantiomer of ±4-(3-bromobenzyl)-1,4,5,6-tetrahydrocyclopenta[b]pyrrole-2-carboxylic acid (enantiomer 1, peak 1, retention time = 2.1 min.) | (+++) |
| 65[a)] | Single enantiomer of ±4-(3-bromobenzyl)-1,4,5,6-tetrahydrocyclopenta[b]pyrrole-2-carboxylic acid (enantiomer 2, peak 2, retention time = 4.8 min.) | (+) |
| 66 | ±4-(3-methoxybenzyl)-1,4,5,6-tetrahydrocyclopenta[b]pyrrole-2-carboxylic acid | (+++) |
| 67[b)] | Single enantiomer of ±4-(3-methoxybenzyl)-1,4,5,6-tetrahydrocyclopenta[b]pyrrole-2-carboxylic acid (enantiomer 1, peak 1, retention time = 3.4 min.) | (+) |
| 68[a)] | Single enantiomer of ±4-(3-methoxybenzyl)-1,4,5,6-tetrahydrocyclopenta[b]pyrrole-2-carboxylic acid (enantiomer 2, peak 2, retention time = 4.3 min.) | (+++) |

TABLE 2-continued

Human and Porcine DAAO Inhibition [IC$_{50}$]

| Compound No. | Compound Name | Human DAAO (µM) |
|---|---|---|
| 69 | 4-(3,4-dimethoxybenzyl)-1,4,5,6-tetrahydrocyclopenta[b]pyrrole-2-carboxylic acid | (++) |
| 70 | 4-(3-methylbenzyl)-1,4,5,6-tetrahydrocyclopenta[b]pyrrole-2-carboxylic acid | (+++) |
| 71 | 4-(3,4-dimethylbenzyl)-1,4,5,6-tetrahydrocyclopenta[b]pyrrole-2-carboxylic acid | (++) |
| 72 | 4-(3,5-dimethylphenyl)-1,4,5,6-tetrahydrocyclopenta[b]pyrrole-2-carboxylic acid | (+) |
| 73 | 4-(3-cyclopropylbenzyl)-1,4,5,6-tetrahydrocyclopenta[b]pyrrole-2-carboxylic acid | (+++) |
| 74 | 4-(3-ethynylbenzyl)-1,4,5,6-tetrahydrocyclopenta[b]pyrrole-2-carboxylic acid | (+++) |
| 75 | 4-(3-carbamoylbenzyl)-1,4,5,6-tetrahydrocyclopenta[b]pyrrole-2-carboxylic acid | (+++) |
| 76 | 4-(3-acetylbenzyl)-1,4,5,6-tetrahydrocyclopenta[b]pyrrole-2-carboxylic acid | (++) |
| 77 | 4-(3-carbamoylbenzyl)-1,4,5,6-tetrahydrocyclopenta[b]pyrrole-2-carboxylic acid | (++) |
| 78 | ±4-(naphthalen-2-ylmethyl)-1,4,5,6-tetrahydrocyclopenta[b]pyrrole-2-carboxylic acid | (+++) |
| 79[a)] | Single enantiomer of ±4-(naphthalen-2-ylmethyl)-1,4,5,6-tetrahydrocyclopenta[b]pyrrole-2-carboxylic acid (enantiomer 1, peak 1, retention time = 3.8 min.) | (++) |
| 80[b)] | Single enantiomer of ±4-(naphthalen-2-ylmethyl)-1,4,5,6-tetrahydrocyclopenta[b]pyrrole-2-carboxylic acid (enantiomer 2, peak 2, retention time = 4.4 min.) | (+++) |
| 81 | 4-(biphenyl-4-ylmethyl)-1,4,5,6-tetrahydrocyclopenta[b]pyrrole-2-carboxylic acid | (++) |
| 82 | 4-(biphenyl-3-ylmethyl)-1,4,5,6-tetrahydrocyclopenta[b]pyrrole-2-carboxylic acid | (++) |
| 83 | 4-(3-(pyridin-3-yl)benzyl)-1,4,5,6-tetrahydrocyclopenta[b]pyrrole-2-carboxylic acid | (++) |
| 84 | 4-((4'-(trifluoromethyl)biphenyl-3-yl)methyl)-1,4,5,6-tetrahydrocyclopenta[b]pyrrole-2-carboxylic acid | (++) |
| 85 | 4-((4'-hydroxybiphenyl-3-yl)methyl)-1,4,5,6-tetrahydrocyclopenta[b]pyrrole-2-carboxylic acid | (+) |
| 86 | 4-((4'-(hydroxymethyl)biphenyl-3-yl)methyl)-1,4,5,6-tetrahydrocyclopenta[b]pyrrole-2-carboxylic acid | (++) |
| 87 | ±4-(3-(furan-2-yl)benzyl)-1,4,5,6-tetrahydrocyclopenta[b]pyrrole-2-carboxylic acid | (+) |
| 88[b)] | Single enantiomer of ±4-(3-(furan-2-yl)benzyl)-1,4,5,6-tetrahydrocyclopenta[b]pyrrole-2-carboxylic acid (enantiomer 1, peak 1, retention time = 1.8 min.) | (+) |
| 89[a)] | Single enantiomer of ±4-(3-(furan-2-yl)benzyl)-1,4,5,6-tetrahydrocyclopenta[b]pyrrole-2-carboxylic acid (enantiomer 2, peak 2, retention time = 2.4 min.) | (+++) |
| 90 | 4-(3-(tetrahydrofuran-3-yl)benzyl)-1,4,5,6-tetrahydrocyclopenta[b]pyrrole-2-carboxylic acid | (++) |
| 91 | ±4-(1H-pyrrol-2-yl)benzyl)-1,4,5,6-tetrahydrocyclopenta[b]pyrrole-2-carboxylic acid | (+++) |
| 92[b)] | Single enantiomer of ±4-(1H-pyrrol-2-yl)benzyl)-1,4,5,6-tetrahydrocyclopenta[b]pyrrole-2-carboxylic acid (enantiomer 1, peak 1, retention time = 2.5 min.) | (+) |
| 93[a)] | Single enantiomer of ±4-(1H-pyrrol-2-yl)benzyl)-1,4,5,6-tetrahydrocyclopenta[b]pyrrole-2-carboxylic acid (enantiomer 2, peak 2, retention time = 3.6 min.) | (+++) |
| 94 | ±4-(3-fluorophenyl)-1,4,5,6-tetrahydrocyclopenta[b]pyrrole-2-carboxylic acid | (+++) |
| 95[b)] | Single enantiomer of ±4-(3-fluorophenyl)-1,4,5,6-tetrahydrocyclopenta[b]pyrrole-2-carboxylic acid (enantiomer 1, peak 1, 2.5 min.) | (+) |
| 96[a)] | Single enantiomer of ±4-(3-fluorophenyl)-1,4,5,6-tetrahydrocyclopenta[b]pyrrole-2-carboxylic acid (enantiomer 2, peak 2, retention time = 4.2 min.) | (+++) |
| 97 | 4-(3,4-difluorophenyl)-1,4,5,6-tetrahydrocyclopenta[b]pyrrole-2-carboxylic acid | (+++) |
| 98 | ±4-(3,5-difluorophenyl)-1,4,5,6-tetrahydrocyclopenta[b]pyrrole-2-carboxylic acid | (++) |
| 99[b)] | Single enantiomer of ±4-(3,5-difluorophenyl)-1,4,5,6-tetrahydrocyclopenta[b]pyrrole-2-carboxylic acid (enantiomer 1, peak 1, retention time = 1.2 min.) | (+) |
| 100[a)] | Single enantiomer of ±4-(3,5-difluorophenyl)-1,4,5,6-tetrahydrocyclopenta[b]pyrrole-2-carboxylic acid (enantiomer 2, peak = 2, retention time = 1.8 min.) | (+++) |

TABLE 2-continued

Human and Porcine DAAO Inhibition [IC$_{50}$]

| Compound No. | Compound Name | Human DAAO (μM) |
|---|---|---|
| 101 | 4-(4-chlorophenyl)-1,4,5,6-tetrahydrocyclopenta[b]pyrrole-2-carboxylic acid | (+++) |
| 102 | 4-(3-chlorophenyl)-1,4,5,6-tetrahydrocyclopenta[b]pyrrole-2-carboxylic acid | (+++) |
| 103 | 4-(3-bromophenyl)-1,4,5,6-tetrahydrocyclopenta[b]pyrrole-2-carboxylic acid | (+++) |
| 104 | 4-(3,5-dimethylphenyl)-1,4,5,6-tetrahydrocyclopenta[b]pyrrole-2-carboxylic acid | (+) |
| 105 | 4-(3-cyanophenyl)-1,4,5,6-tetrahydrocyclopenta[b]pyrrole-2-carboxylic acid | (+++) |
| 106 | 4-(biphenyl-4-yl)-1,4,5,6-tetrahydrocyclopenta[b]pyrrole-2-carboxylic acid | (+) |
| 107 | 4-(4-benzylphenyl)-1,4,5,6-tetrahydrocyclopenta[b]pyrrole-2-carboxylic acid | (++) |
| 108 | 4-(4-chlorobenzylamino)-1,4,5,6-tetrahydrocyclopenta[b]pyrrole-2-carboxylic acid | (+) |
| 21 | 5,5-difluoro-1,4,5,6-tetrahydrocyclopenta[b]pyrrole-2-carboxylic acid | (++) |
| 22 | 5-methyl-1,4,5,6-tetrahydrocyclopenta[b]pyrrole-2-carboxylic acid | (++) |
| 23 | 5-benzyl-1,4,5,6-tetrahydrocyclopenta[b]pyrrole-2-carboxylic acid | (+) |
| 24 | 6-oxo-1,4,5,6-tetrahydrocyclopenta[b]pyrrole-2-carboxylic acid | (++) |
| 25 | (E)-6-benzylidene-1,4,5,6-tetrahydrocyclopenta[b]pyrrole-2-carboxylic acid | (+)** |
| 26 | 6-benzyl-1,4,5,6-tetrahydrocyclopenta[b]pyrrole-2-carboxylic acid | (+++) |
| 27 | 6-phenethyl-1,4,5,6-tetrahydrocyclopenta[b]pyrrole-2-carboxylic acid | (++) |
| 28[c)] | Single enantiomer of ±6-phenethyl-1,4,5,6-tetrahydrocyclopenta[b]pyrrole-2-carboxylic acid (enantiomer 1, peak 2, retention time = 10.2 min.) | (++) |
| 29[d)] | Single enantiomer of ±6-phenethyl-1,4,5,6-tetrahydrocyclopenta[b]pyrrole-2-carboxylic acid (enantiomer 2, peak 1, retention time = 9.2 min.) | (+) |
| 109 | 6-methyl-1,4,5,6-tetrahydrocyclopenta[b]pyrrole-2-carboxylic acid | (++) |
| 110 | 6-propyl-1,4,5,6-tetrahydrocyclopenta[b]pyrrole-2-carboxylic acid | (++) |
| 111 | 6-(3-fluorophenyl)-1,4,5,6-tetrahydrocyclopenta[b]pyrrole-2-carboxylic acid | (++) |
| 112 | 6-(3,4-difluorophenyl)-1,4,5,6-tetrahydrocyclopenta[b]pyrrole-2-carboxylic acid | (++) |
| 113 | 6-(4-chlorophenyl)-1,4,5,6-tetrahydrocyclopenta[b]pyrrole-2-carboxylic acid | (++) |
| 114 | 6-(3-chlorophenyl)-1,4,5,6-tetrahydrocyclopenta[b]pyrrole-2-carboxylic acid | (++) |
| 115 | 6-(3-bromophenyl)-1,4,5,6-tetrahydrocyclopenta[b]pyrrole-2-carboxylic acid | (++) |
| 116 | 6-p-tolyl-1,4,5,6-tetrahydrocyclopenta[b]pyrrole-2-carboxylic acid | (++) |
| 117 | 6-(3-cyanophenyl)-1,4,5,6-tetrahydrocyclopenta[b]pyrrole-2-carboxylic acid | (++) |
| 118 | ±6-(biphenyl-4-yl)-1,4,5,6-tetrahydrocyclopenta[b]pyrrole-2-carboxylic acid | (++) |
| 119[d)] | Single enantiomer of ±6-(biphenyl-4-yl)-1,4,5,6-tetrahydrocyclopenta[b]pyrrole-2-carboxylic acid (enantiomer 1, peak 1, retention time = 6.3 min.) | (++) |
| 120[c)] | Single enantiomer of ±6-(biphenyl-4-yl)-1,4,5,6-tetrahydrocyclopenta[b]pyrrole-2-carboxylic acid (enantiomer 2, peak 2, retention time = 10.2 min.) | (−) |
| 121 | ±6-(3-chlorobenzyl)-1,4,5,6-tetrahydrocyclopenta[b]pyrrole-2-carboxylic acid | (+++) |
| 122[d)] | Single enantiomer of ±6-(3-chlorobenzyl)-1,4,5,6-tetrahydrocyclopenta[b]pyrrole-2-carboxylic acid (enantiomer 1, peak 1, retention time = 1.55 min.) | (++) |
| 123[c)] | Single enantiomer of ±6-(3-chlorobenzyl)-1,4,5,6-tetrahydrocyclopenta[b]pyrrole-2-carboxylic acid (enantiomer 2, peak 2, retention time = 1.95 min.) | (+++) |
| 124 | 6-(3-chloro-5-fluorobenzyl)-1,4,5,6-tetrahydrocyclopenta[b]pyrrole-2-carboxylic acid | (+++) |
| 125 | ±6-(3-bromobenzyl)-1,4,5,6-tetrahydrocyclopenta[b]pyrrole-2-carboxylic acid | (+++) |
| 126[d)] | Single enantiomer of ±6-(3-bromobenzyl)-1,4,5,6-tetrahydrocyclopenta[b]pyrrole-2-carboxylic acid (enantiomer 1, peak 1, retention time = 4.9 min.) | (+) |
| 127[c)] | Single enantiomer of ±6-(3-bromobenzyl)-1,4,5,6-tetrahydrocyclopenta[b]pyrrole-2-carboxylic acid (enantiomer 2, peak 2, retention time = 5.8 min.) | (+++) |

TABLE 2-continued

Human and Porcine DAAO Inhibition [IC$_{50}$]

| Compound No. | Compound Name | Human DAAO (µM) |
|---|---|---|
| 128 | 6-(3-hydroxybenzyl)-1,4,5,6-tetrahydrocyclopenta[b]pyrrole-2-carboxylic acid | (+++) |
| 129 | ±6-(3-methoxybenzyl)-1,4,5,6-tetrahydrocyclopenta[b]pyrrole-2-carboxylic acid | (+++) |
| 130[d] | Single enantiomer of ±6-(3-methoxybenzyl)-1,4,5,6-tetrahydrocyclopenta[b]pyrrole-2-carboxylic acid (enantiomer 1, peak 1, retention time = 2.05 min.) | (+) |
| 131[e] | Single enantiomer of ±6-(3-methoxybenzyl)-1,4,5,6-tetrahydrocyclopenta[b]pyrrole-2-carboxylic acid (enantiomer 2, peak 2, retention time = 3.55 min.) | (+++) |
| 132 | 6-(2-(naphthalen-1-yl)ethyl)-1,4,5,6-tetrahydrocyclopenta[b]pyrrole-2-carboxylic acid | (++) |
| 133 | 6-(biphenyl-4-ylmethyl)-1,4,5,6-tetrahydrocyclopenta[b]pyrrole-2-carboxylic acid | (++) |
| 134 | ±6-(3-phenylpropyl)-1,4,5,6-tetrahydrocyclopenta[b]pyrrole-2-carboxylic acid | (++) |
| 135[d] | Single enantiomer of ±6-(3-phenylpropyl)-1,4,5,6-tetrahydrocyclopenta[b]pyrrole-2-carboxylic acid (enantiomer 1, fraction 1, retention time = 4.3 min.) | (+) |
| 136[e] | Single enantiomer of ±6-(3-phenylpropyl)-1,4,5,6-tetrahydrocyclopenta[b]pyrrole-2-carboxylic acid (enantiomer 2, peak 2, retention time = 3.5 min.) | (++) |
| 30 | 4,5,6,7-tetrahydro-1H-indole-2-carboxylic acid | (++) |
| 31 | 3-methyl-4-oxo-4,5,6,7-tetrahydro-1H-indole-2-carboxylic acid | (+) |
| 32 | 4-benzyl-4,5,6,7-tetrahydro-1H-indole-2-carboxylic acid | (+) |
| 137 | ethyl 3-hydroxy-1,4,5,6-tetrahydrocyclopenta[b]pyrrole-2-carboxylate | (−) |
| 138 | ±(1aS,5aS)-1a,4,5,5a-tetrahydro-1H-4-aza-cyclopropa[a]pentalene-3-carboxylic acid | (+++) |
| 139[f] | Single enantiomer of ±(1aS,5aS)-1a,4,5,5a-tetrahydro-1H-4-aza-cyclopropa[a]pentalene-3-carboxylic acid (enantiomer 1, peak 1, retention time = 1.4 min.) | (++) |
| 140[e] | Single enantiomer of ±(1aS,5aS)-1a,4,5,5a-tetrahydro-1H-4-aza-cyclopropa[a]pentalene-3-carboxylic acid (enantiomer 2, peak 2, retention time = 2.0 min.) | (+++) |
| 141 | ±(1S,1aS,5aR)-1-Methyl-1a,4,5,5a-tetrahydro-1H-4-aza-cyclopropa[a]pentalene-3-carboxylic acid | (+++) |
| 142 | Mixture of ±(1S,1aS,5aR)-1-propyl-1a,4,5,5a-tetrahydro-1H-4-aza-cyclopropa[a]pentalene-3-carboxylic acid and ±(1R,1aS,5aR)-1-propyl-1a,4,5,5a-tetrahydro-1H-4-aza-cyclopropa[a]pentalene-3-carboxylic acid | (++) |
| 143 | ±(1S,1aS,5aR)-1-phenethyl-1a,4,5,5a-tetrahydro-1H-4-aza-cyclopropa[a]pentalene-3-carboxylic acid | (+++) |
| 144 | ±(1R,1aR,5aR)-1-phenyl-1a,4,5,5a-tetrahydro-1H-4-aza-cyclopropa[a]pentalene-3-carboxylic acid | (+) |
| 145 | (1aS,5aS)-1a,4,5,5a-tetrahydro-1H-2-bromo-4-aza-cyclopropa[a]pentalene-3-carboxylic acid | (+) |
| 146 | (1aR,5aR)-1a,2,5,5a-tetrahydro-1H-2-aza-cyclopropa[a]pentalene-3-carboxylic acid | (+++) |
| 147 | 3-bromo-4-phenethyl-1,4,5,6-tetrahydrocyclopenta[b]pyrrole-2-carboxylic acid | (++) |
| 148 | 5,5-difluoro-4-methoxy-1,4,5,6-tetrahydrocyclopenta[b]pyrrole-2-carboxylic acid | (+) |

IC$_{50}$ ≤ 100 nM = (+++);
IC$_{50}$ ≤ 1 µM = (++);
IC$_{50}$ ≤ 100 µM = (+);
<50% at 100 µM = (−)
**compound inhibited 30% of the hydrogen peroxide control response without DAAO enzyme present For those compounds of Table 2 marked with a), b), c) or d) absolute stereochemistries are assumed based on docking studies in the D-amino acid oxidase active site (see e.g., *Protein Science* 2006, 15(12), 2708-2717 and *Biochemical and Biophysical Research Communications* 2007, 355(2), 385-391, and references cited within) for crystal structures:

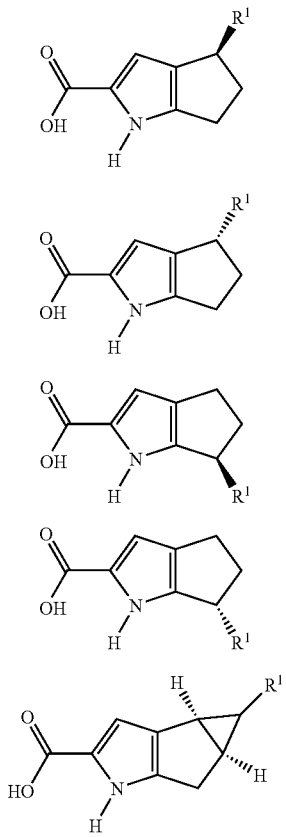

a)
b)
c)
d)
e)

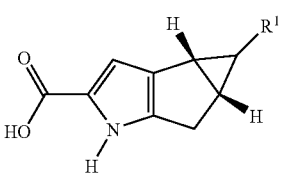

f)

These data demonstrate that the above described method can be used to identify compounds that are DAAO inhibitors. The method can also be used to determine the efficacy of such compounds, e.g., the $IC_{50}$ of such compounds (for example, $IC_{50}$ less than or equal to 100 nM; less than or equal to 1 uM, or less than or equal to 100 uM).

Example 8

In Vivo Elevation of D-Serine Levels in the Cerebellum 8.1. Methods

Mice (C57BL/6, 8-9 weeks of age) are dosed intraperitoneally at 10 mL/kg with 50 mg/kg of compound suspended in 45% (w/v) hydroxy-β-cyclodextrin vehicle. Animals are sacrificed at either 2 or 6 h post compound administration with an N=3 per time point. At sacrifice, trunk blood is collected into tubes containing potassium EDTA, which are then centrifuged to permit isolation of plasma. The cerebellum is dissected from each animal. Plasma and cerebellum samples are stored at −80° C. until samples are analyzed (LC/MS/MS).

8.2. Results

Results obtained for compounds of the invention are summarized in Table 3, below.

TABLE 3

In vivo elevation of D-serine levels in the cerebellum

| Compound No. | Compound Name | Dose (mg/kg) | Cerebellum D-serine at 2 hours | Cerebellum D-serine at 6 hours |
|---|---|---|---|---|
| 1 | 1,4,5,6-tetrahydrocyclopenta[b]pyrrole-2-carboxylic acid | 30* | (++) | (++) |
| 8a) | Single enantiomer of ±4-propyl-1,4,5,6-tetrahydrocyclopenta[b]pyrrole-2-carboxylic acid (enantiomer 1, peak 2, retention time = 6.3 min.) | 30 | (++) | (+) |
| 39 | ±4-(4-fluorobenzyl)-1,4,5,6-tetrahydrocyclopenta[b]pyrrole-2-carboxylic acid | 30 | (+) | (+) |
| 44a) | Single enantiomer of ±4-(3,4-difluorobenzyl)-1,4,5,6-tetrahydrocyclopenta[b]pyrrole-2-carboxylic acid (enantiomer 2, peak 2, retention time = 2.3 min.) | 30 | (+) | (+) |
| 47a) | (Single enantiomer of ±4-(2,4-difluorobenzyl)-1,4,5,6-tetrahydrocyclopenta[b]pyrrole-2-carboxylic acid (enantiomer 2, peak 2, retention time = 3.3 min.) | 30 | (++) | (+) |
| 50a) | Single enantiomer of ±4-(3-chloro-4-fluorobenzyl)-1,4,5,6-tetrahydrocyclopenta[b]pyrrole-2-carboxylic acid (enantiomer 2, peak 2, retention time = 3.3 min.) | 30 | (++) | (+) |

TABLE 3-continued

In vivo elevation of D-serine levels in the cerebellum

| Compound No. | Compound Name | Dose (mg/kg) | Cerebellum D-serine at 2 hours | Cerebellum D-serine at 6 hours |
|---|---|---|---|---|
| 53a) | Single enantiomer of ±4-(4-fluoro-2-methylbenzyl)-1,4,5,6-tetrahydrocyclopenta[b]pyrrole-2-carboxylic acid (enantiomer 2, peak 2, retention time = 6.0 min.) | 10 | (+) | (−) |
| 54 | 4-(3-fluorobenzyl)-1,4,5,6-tetrahydrocyclopenta[b]pyrrole-2-carboxylic acid | 30 | (+) | (+) |
| 59a) | Single enantiomer of ±4-(3,4-dichlorobenzyl)-1,4,5,6-tetrahydrocyclopenta[b]pyrrole-2-carboxylic acid (enantiomer 2, peak 2, retention time = 4.7 min.) | 10 | (+) | (+) |
| 62a) | Single enantiomer of ±4-(4-bromobenzyl)-1,4,5,6-tetrahydrocyclopenta[b]pyrrole-2-carboxylic acid (enantiomer 2, peak 2, retention time = 2.7 min.) | 30 | (+) | (++) |
| 64b) | Single enantiomer of ±4-(3-bromobenzyl)-1,4,5,6-tetrahydrocyclopenta[b]pyrrole-2-carboxylic acid (enantiomer 1, peak 1, retention time = 2.1 min.) | 60 | (−) | |
| 65a) | Single enantiomer of ±4-(3-bromobenzyl)-1,4,5,6-tetrahydrocyclopenta[b]pyrrole-2-carboxylic acid (enantiomer 2, peak 2, retention time = 4.8 min.) | 30 | (++) | (+) |
| 68a) | Single enantiomer of ±4-(3-methoxybenzyl)-1,4,5,6-tetrahydrocyclopenta[b]pyrrole-2-carboxylic acid (enantiomer 2, peak 2, retention time = 4.3 min.) | 30 | (+) | (+) |
| 70 | 4-(3-methylbenzyl)-1,4,5,6-tetrahydrocyclopenta[b]pyrrole-2-carboxylic acid | 60 | (+) | (+) |
| 75 | 4-(3-carbamoylbenzyl)-1,4,5,6-tetrahydrocyclopenta[b]pyrrole-2-carboxylic acid | 60 | (−) | |
| 78 | ±4-(naphthalen-2-ylmethyl)-1,4,5,6-tetrahydrocyclopenta[b]pyrrole-2-carboxylic acid | 30 | (+) | (+) |
| 80b) | Single enantiomer of ±4-(naphthalen-2-ylmethyl)-1,4,5,6-tetrahydrocyclopenta[b]pyrrole-2-carboxylic acid (enantiomer 2, peak 2, retention time = 4.4 min.) | 30 | (+) | (+) |
| 89a) | Single enantiomer of ±4-(3-(furan-2-yl)benzyl)-1,4,5,6-tetrahydrocyclopenta[b]pyrrole-2-carboxylic acid (enantiomer 2, peak 2, retention time = 2.4 min.) | 30 | (−) | |
| 93a) | Single enantiomer of ±4-(1H-pyrrol-2-yl)benzyl)-1,4,5,6-tetrahydrocyclopenta[b]pyrrole-2-carboxylic acid (enantiomer 2, peak 2, retention time = 3.6 min.) | 30 | (+) | (+) |
| 96a) | Single enantiomer of ±4-(3-fluorophenyl)-1,4,5,6-tetrahydrocyclopenta[b]pyrrole-2-carboxylic acid (enantiomer 2, peak 2, retention time = 4.2 min.) | 30 | (+) | (+) |
| 97 | 4-(3,4-difluorophenyl)-1,4,5,6-tetrahydrocyclopenta[b]pyrrole-2-carboxylic acid | 60 | (+) | (+) |
| 100a) | Single enantiomer of ±4-(3,5-difluorophenyl)-1,4,5,6-tetrahydrocyclopenta[b]pyrrole-2-carboxylic acid (enantiomer 2, peak = 2, retention time = 1.8 min.) | 30 | (+) | (+) |
| 105 | 4-(3-cyanophenyl)-1,4,5,6-tetrahydrocyclopenta[b]pyrrole-2-carboxylic acid | 60 | (−) | |
| 123c) | Single enantiomer of ±6-(3-chlorobenzyl)-1,4,5,6-tetrahydrocyclopenta[b]pyrrole-2-carboxylic acid (enantiomer 2, peak 2, retention time = 1.95 min.) | 30 | (+) | (+) |
| 124 | 6-(3-chloro-5-fluorobenzyl)-1,4,5,6-tetrahydrocyclopenta[b]pyrrole-2-carboxylic acid | 60 | (−) | (−) |
| 131c) | Single enantiomer of ±6-(3-methoxybenzyl)-1,4,5,6-tetrahydrocyclopenta[b]pyrrole-2-carboxylic acid (enantiomer 2, peak 2, retention time = 3.55 min.) | 30 | (+) | (+) |
| 137 | ethyl 3-hydroxy-1,4,5,6-tetrahydrocyclopenta[b]pyrrole-2-carboxylate | 30 | (+) | (+) |
| 138 | ±(1aS,5aS)-1a,4,5,5a-tetrahydro-1H-4-aza-cyclopropa[a]pentalene-3-carboxylic acid | 60 | (++) | (++) |
| 140e) | Single enantiomer of ±(1aS,5aS)-1a,4,5,5a-tetrahydro-1H-4-aza-cyclopropa[a]pentalene-3-carboxylic acid | 30* | (++) | (++) |

TABLE 3-continued

In vivo elevation of D-serine levels in the cerebellum

| Compound No. | Compound Name | Dose (mg/kg) | Cerebellum D-serine at 2 hours | Cerebellum D-serine at 6 hours |
|---|---|---|---|---|
| 146 | (enantiomer 2, peak 2, retention time = 2.0 min.) (1aR,5aR)-1a,2,5,5a-tetrahydro-1H-2-aza-cyclopropa[a]pentalene-3-carboxylic acid | 60 | (++) | (++) |

>5 = (++);
2.5-4.9 = (+);
<2.5 = (−);
vehicle 2.1;
values nmol/g tissue wet weight These Data Demonstrate that Compounds of the Invention can be Used to increase the concentration of D-serine in the brain (e.g., cerebellum) of a mammal. In addition, the method can be used to identify compounds that are DAAO inhibitors effective for increasing D-serine in the brain (e.g., cerebellum).

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A compound having a structure according to Formula (Vc):

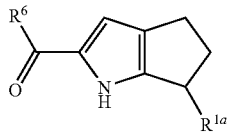

(Vc)

wherein
$R^{1a}$ is a member selected from H, alkyl, and

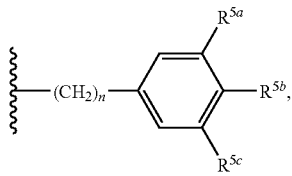

where n is an integer from 0 to 3,
$R^{5a}$, $R^{5b}$ and $R^{5c}$ are members independently selected from H, $C_1$ to $C_4$ alkyl, $C_1$ to $C_4$ alkyne, nitrile, Br, Cl, F, $OR^{18a}$, furan, tetrahydrofuran, and pyrrole,
$R^{18a}$ is a member selected from H and $C_1$ to $C_4$ alkyl,
$R^6$ is a member selected from OH and $O^-X^+$, wherein $X^+$ is a cation,
and any enantiomer, diastereoisomer, racemic mixture, enantiomerically enriched mixture, and enantiomerically pure form thereof.

2. A composition comprising a first stereoisomer and at least one additional stereoisomer of a compound according to claim 1, wherein said first stereoisomer is present in an enantiomeric or diastereomeric excess of at least 90% relative to said at least one additional stereoisomer.

3. A pharmaceutical composition comprising a compound of claim 1, or a pharmaceutically acceptable salt thereof, and a pharmaceutically acceptable carrier.

4. A compound having a structure according to Formula (IVc):

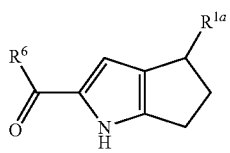

(IVc)

wherein
$R^{1a}$ is a member selected from H, alkyl, and

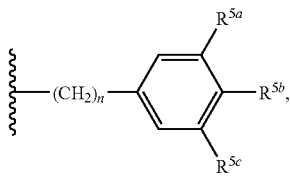

where n is an integer from 0 to 3,
$R^{5a}$, $R^{5b}$ and $R^{5c}$ are members independently selected from H, $C_1$ to $C_4$ alkyl, $C_1$ to $C_4$ alkyne, nitrile, Br, Cl, F, $OR^{18a}$, furan, tetrahydrofuran, and pyrrole,
$R^{18a}$ is a member selected from H and $C_1$ to $C_4$ alkyl,
$R^6$ is a member selected from OH and $O^-X^+$, wherein $X^+$ is a cation,
and any enantiomer, diastereoisomer, racemic mixture, enantiomerically enriched mixture, and enantiomerically pure form thereof.

5. A composition comprising a first stereoisomer and at least one additional stereoisomer of a compound according to claim 4, wherein said first stereoisomer is present in an enantiomeric or diastereomeric excess of at least 90% relative to said at least one additional stereoisomer.

6. A pharmaceutical composition comprising a compound of claim 4, or a pharmaceutically acceptable salt thereof, and a pharmaceutically acceptable carrier.

7. A compound having a structure according to Formula (VIIb):

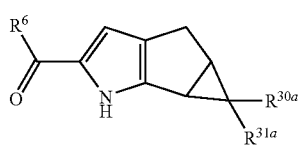

(VIIb)

wherein
R$^{30a}$ and R$^{31a}$ are members independently selected from H, C$_1$ to C$_4$ alkyl, and

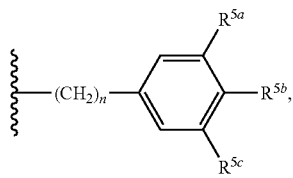

where n is an integer from 0 to 3,
R$^{5a}$, R$^{5b}$ and R$^{5c}$ are members independently selected from H, C$_1$ to C$_4$ alkyl, C$_1$ to C$_4$ alkyne, nitrile, Br, Cl, F, and OR$^{18a}$,
R$^{18a}$ is a member selected from H and C$_1$ to C$_4$ alkyl,
R$^6$ is a member selected from OH and O$^-$X$^+$, wherein X$^+$ is a cation,
and any enantiomer, diastereoisomer, racemic mixture, enantiomerically enriched mixture, and enantiomerically pure form thereof.

8. A composition comprising a first stereoisomer and at least one additional stereoisomer of a compound according to claim 7, wherein said first stereoisomer is present in an enantiomeric or diastereomeric excess of at least 90% relative to said at least one additional stereoisomer.

9. A pharmaceutical composition comprising a compound of claim 7, or a pharmaceutically acceptable salt thereof, and a pharmaceutically acceptable carrier.

10. A compound having a structure according to Formula (VIIIb):

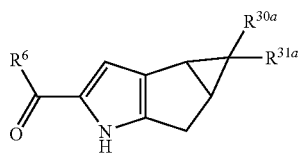

(VIIIb)

wherein
R$^{30a}$ and R$^{31a}$ are members independently selected from H, C$_1$ to C$_4$ alkyl, and

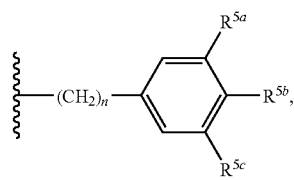

where n is an integer from 0 to 3,
R$^{5a}$, R$^{5b}$ and R$^{5c}$ are members independently selected from H, C$_1$ to C$_4$ alkyl, C$_1$ to C$_4$ alkyne, nitrile, Br, Cl, F, and OR$^{18a}$,
R$^{18a}$ is a member selected from H and C$_1$ to C$_4$ alkyl,
R$^6$ is a member selected from OH and O$^-$X$^+$, wherein X$^+$ is a cation,
and any enantiomer, diastereoisomer, racemic mixture, enantiomerically enriched mixture, and enantiomerically pure form thereof.

11. A composition comprising a first stereoisomer and at least one additional stereoisomer of a compound according to claim 10, wherein said first stereoisomer is present in an enantiomeric or diastereomeric excess of at least 90% relative to said at least one additional stereoisomer.

12. A pharmaceutical composition comprising a compound of claim 10, or a pharmaceutically acceptable salt thereof, and a pharmaceutically acceptable carrier.

* * * * *